(12) United States Patent
Chen et al.

(10) Patent No.: US 10,544,134 B2
(45) Date of Patent: Jan. 28, 2020

(54) 4-SUBSTITUTED COUMARIN DERIVATIVES AND PREPARATION METHODS AND USES THEREOF

(71) Applicants: SI CHUAN UNIVERSITY, Sichua (CN); Lijuan Chen, Sichuan (CN)

(72) Inventors: Lijuan Chen, Sichuan (CN); Yuquan Wei, Sichuan (CN)

(73) Assignee: GUIZHOU BAILING GROUP PHARMACEUTICAL CO., LTD., Anshun (CN)

( * ) Notice: Subject to any disclaimer, the term of this patent is extended or adjusted under 35 U.S.C. 154(b) by 0 days.

(21) Appl. No.: 15/761,885

(22) PCT Filed: Feb. 29, 2016

(86) PCT No.: PCT/CN2016/074796
§ 371 (c)(1),
(2) Date: Mar. 21, 2018

(87) PCT Pub. No.: WO2017/049871
PCT Pub. Date: Mar. 30, 2017

(65) Prior Publication Data
US 2018/0282315 A1    Oct. 4, 2018

(30) Foreign Application Priority Data
Sep. 24, 2015   (CN) .......................... 2015 1 0618234

(51) Int. Cl.
| C07D 409/04 | (2006.01) |
| C07D 311/16 | (2006.01) |
| C07D 405/04 | (2006.01) |
| C07D 409/14 | (2006.01) |
| C07D 409/12 | (2006.01) |
| C07D 407/12 | (2006.01) |
| A61P 35/00  | (2006.01) |

(52) U.S. Cl.
CPC ............ *C07D 409/04* (2013.01); *A61P 35/00* (2018.01); *C07D 311/16* (2013.01); *C07D 405/04* (2013.01); *C07D 407/12* (2013.01); *C07D 409/12* (2013.01); *C07D 409/14* (2013.01)

(58) Field of Classification Search
CPC .... A61K 31/37; A61K 31/4709; A61K 31/55; A61P 35/00; C07D 311/16; C07D 405/04; C07D 407/04; C07D 407/12; C07D 407/14; C07D 409/04; C07D 409/12; C07D 409/14
See application file for complete search history.

(56) References Cited

U.S. PATENT DOCUMENTS 5,527,827 A * 6/1996 Delorme ............... C07C 317/46
514/277

FOREIGN PATENT DOCUMENTS

| CN | 101657443 A | 2/2010 |
| CN | 102627638 A | 8/2012 |
| CN | 102746281 A | 10/2012 |
| DE | 2331438 A1 | 1/1974 |
| WO | 2005103705 A2 | 11/2005 |
| WO | 2012136910 A1 | 10/2012 |
| WO | 2014153533 A1 | 9/2014 |

OTHER PUBLICATIONS

Sanap, et al., Regiospecific inverse electron demand Diels-Alder reactions of 7-methylcoumarin-4-azadienes, RSC Advances, 5(46), 36696-36706 (2015). (Year: 2015).*
Combes et al. (2011). Synthesis and biological evaluation of 4-arylcoumarin analogues of combretastatins. Part 2. Journal of Medical Chemistry, 54, 3153-3162.
Ganina et al. (2008). Synthesis and biological evaluation of polymethoxylated 4-heteroarylcoumarins as tubulin assembly inhibitor. Bioorganic & Medicinal Chemistry, 16, 8806-8812.
Ghate et al. (2003). Synthesis of vanillin ethers from 4-(bromomethyl) coumarins as antiinflammatory agents. European Journal of Medicinal Chemistry, 38, 297-302.
Kasibhatla et al. (2007). A small-molecule inhibitor of microtubule formation that is not a substrate for multidrug resistance pumps. Cancer Research, 67(12), 5865-5871.
Kim et al. (2009). 7-Diethylamino-3(20-benzoxazolyl)-coumarin is a novel microtubule inhibitor with antimitotic activity in multidrug resistant cancer cells. Biochemical Pharmacology, 77, 1773-1779.
Nicolaides et al. (1998). Synthesis and biological evaluation of several coumarin-4-carboxamidoxime and 3 (coumarin-4-yl)-1,2,4-oxadiazole derivatives. European Journal of Medicinal Chemistry, 33, 715-724.
Sasano et al. (2013). Palladium(II)-catalyzed direct carboxylation of alkenyl C—H bonds with CO2. Journal of the American Chemical Society, 135, 10954-10957.

(Continued)

*Primary Examiner* — Erich A Leeser
(74) *Attorney, Agent, or Firm* — Caesar Rivise, PC

(57) ABSTRACT

The present invention pertains to the field of chemical medicine, particularly to 4-substituted coumarin derivatives and preparation methods and applications thereof. The invention provides 4-substituted coumarin derivatives with a structural formula as shown in Formula I. The invention also provides preparation methods and applications for the above 4-substituted coumarin derivatives. The compounds provided in the invention have strong anti-tumor activity with IC50 for plural tumor cell lines between 0.01-5 nM, and it also performs better to inhibit microtubule polymerization and has diversified biological activities and low toxicity, providing new options for drug-sensitive and drug-resistant tumor cells.

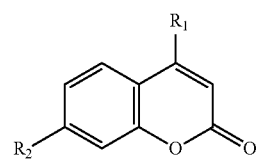

I

21 Claims, 5 Drawing Sheets

(56) References Cited

OTHER PUBLICATIONS

Sheng et al. (2013). Generation of 4-substituted coumarins via C—H bond activation under palladium bromide-copper (I) bromide cooperative catalysis. Tetrahedron, 69, 10230-10234.
Sirisoma et al. (2009). Discovery of N-(4-Methoxyphenyl)-N,2-dimethylquinazolin-4-amine, a potent apoptosis inducer and efficacious anticancer agent with high blood brain barrier penetration. Journal of Medicinal Chemistry, 52 (8), 2341-2351.
Sivakumar. (2004). A fluorogenic 1,3-dipolar cycloaddition reaction of 3-azidocoumarins and acetylenes. Organic Letters, 6(24), 4603-4606.
Soto-Ortega et al. (2011). Inhibition of amyloid-b aggregation by coumarin analogs can be manipulated by functionalization of the aromatic center. Bioorganic & Medicinal Chemistry, 19, 2596-2602.
Vrakas et al. (2005). Retention of substituted coumarins using immobilized artificial membrane (IAM) chromatography: A comparative study with n-octanol partitioning and reversed-phase HPLC and TLC. Journal of Pharmaceutical and Biomedical Analysis, 39, 908-913.
English language Abstract for CN 101657443 A (2010).
English language Abstract for CN 102627638 A (2012).
English language Abstract for CN 102746281 A (2012).
English language Abstract for DE 2331438 A1 (1974).
International Search Report from corresponding PCT/CN2016/074796 dated Jul. 1, 2016.

* cited by examiner

4-SUBSTITUTED COUMARIN DERIVATIVES AND PREPARATION METHODS AND USES THEREOF

CROSS-REFERENCE TO RELATED APPLICATIONS

This application is a U.S. National Phase Application of PCT/CN2016/074796, filed Feb. 29, 2016, which claims priority to CN 201510618234.7, filed Sep. 24, 2015, the contents of which applications are incorporated herein by reference in their entirety for all purposes.

FIELD OF THE INVENTION

The present invention pertains to the field of chemical medicine, particularly to 4-substituted coumarin derivatives and preparation methods and uses thereof.

BACKGROUND OF THE INVENTION

As the main component of cytoskeleton, microtubule has dynamic characteristics of polymerization and depolymerization, and plays an important role in maintaining the morphology of cells, division and proliferation of cells, composition and transport of organelles and conduction of semiochemicals. The antineoplastic drug targeting the microtubule is applied by making use of its dynamic characteristics, either by promoting or inhibiting its polymerization, so as to directly influence mitosis of cells and halt cell division in G2/M phase. Researches show that the microtubule has at least 3 different drug-binding sites: Taxol site, vincristin site and colchicine site. Taxol can inhibit depolymerization of tubulin and stabilize the structure of microtubule; and vinblastine and colchicine can inhibit polymerization of tubulin through respective sites of their actions.

Drugs used to inhibit depolymerization of microtubule, taking Taxol as a representative, are now widely applied for curing breast cancer, ovarian cancer, lung cancer, non-small cell lung cancer, etc. Drugs used to inhibit polymerization of microtubule have two different binding sites: colchicine site and vinblastine site. Drugs acting on the vinblastine site, taking vinblastine, vincristin, etc. as representatives, are now clinically applied to curing leukemia, lymphoma, non-small cell lung cancer, etc. Drugs acting on the colchicine site are represented by colchicine, Podophyllotoxin and Combretastatin (CA-4). Since the cavity volume of colchicine site is relatively small and its corresponding inhibitor structure is relatively simple, researches for its inhibitors have aroused much attention in recent years, and some derivatives for curing tumors have entered into clinical study and have demonstrated promising application prospects, such as E7010

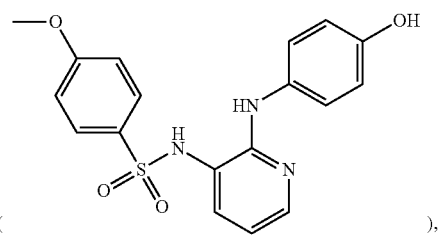 [SMILES: COc1ccc(S(=O)(=O)Nc2cccnc2Nc2ccc(O)cc2)cc1]

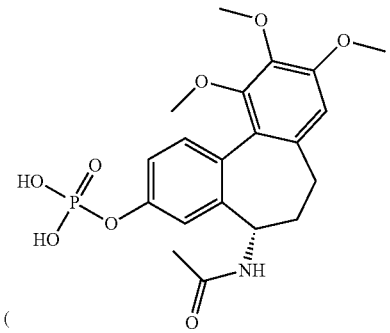

ZD6126 etc. In the treatment of inflammatory diseases, colchicine has been clinically applied to curing acute gout and gouty arthritis. Due to the success achieved by applying taxol and vinblastine compounds for tumor treatment, scientists are rather confident in developing microtubule inhibitors targeting colchicine site.

Compared to the tumor drugs targeting taxol site and vinblastine site, the tumor drugs targeting colchicine site mainly have two important advantages. One advantage is that the chemotherapy drugs targeting colchicine site can not only inhibit polymerization of tubulin, but also generally inhibit generation of new vessels of tumors. Therefore, this kind of drugs can help inhibit generation of vessels of solid tumors, cause insufficient blood supply of tumor tissues and effectively inhibit tumors. In recent years, they are becoming increasingly recognized by scholars. More importantly, the anti-angiogenesis function will not be influenced by multi-drug resistance and can effectively exhibit a long-term antineoplastic activity.

The other advantage is that the chemotherapy drugs targeting colchicine site can effectively overcome drug resistance. Even though the antineoplastic drug targeting microtubule have exhibited strong activity in both separate administration and combined administration, its multi-drug resistance has limited its effect in the chemotherapy for the treatment of tumors. Currently, the resistance mechanism of taxol relates to three aspects: over-expression of MDR-1 gene, point mutations in α, β microtubule genes and expression of β-III tubulin monomer. Recently, US FDA approved epothilone's entry into the market, which is proved necessary to overcome the drug-resistance mechanism of β-III tubulin monomer. The clinical medication has demonstrated that the major drug-resistance mechanisms causing treatment failure of taxol and vinblastine drugs due to drug-resistance are over-expression of P-glycoprotein and altered expression of β-III tubulin monomer.

Structurally regarded as lactone compound generated through dehydration of cis-o-hydroxy cinnamic acid, coumarin compound is a general term for a kind of natural product containing parent nucleus of benzopyrone. Since Vauquelin firstly discovered the coumarin compound daphnin from plant Daphnealpina in 1812, hundreds of coumarin compounds have been obtained. The compounds widely exist in the plant kingdom, and particularly extensively in the Umbelliferae, Rutaceae, Asteraceae, Leguminosae, Solanaceae, etc. This component is contained in Chinese herbs such as Fructus Cnidii, Radix Angelicae Pubescentis, Radix Angelicae Dahuricae, Fructus *Aurantii*, Radix Peucedani, Ash Bark, Herba Artemisiae Scopariae, Fructus Psoraleae and *Euphorbia Lathyris*. Coumarin compounds have many obvious biological activities such as anti-viral, anti-tumor, anti-microbial, anti-cancer and antiinflammatory activities, and have been attached with great importance by domestic and foreign scholars. Based on the difference of the substituent group on the parent nucleus and their locations, it can be divided into four categories: simple coumarins, furocoumarins, pyranocoumarins and other coumarins. Coumarin has fragrance and its representative compounds include *angelica* lactone, angelicone, xanthoxyletin, armillarisin A, etc.

Among the plural reported chemotherapy drugs, coumarin is verified to have minor or no toxicity through tests. Therefore, its action mechanism has aroused interests of many pharmacists. Currently, in the antitumor applications, coumarin is reported to have enzyme inhibitory activity, cell cycle arrest, anti-angiogenesi activity, heat shock protein (HSP90) inhibitory activity, telomerase inhibitory activity, anti-mitotic activity, carbonic anhydrase inhibitory activity, transport protein inhibitory activity, aromatase inhibitory activity and sulfatase inhibitory activity. Furthermore, scholars have conducted in-depth research into the structure-activity relationship of coumarin derivatives.

Tsyganov et al. have studied the anti-mitotic activity of coumarin compounds. They semi-synthesized 3-(4-methoxyphenyl) coumarin substituted by multi-alkoxy, and demonstrated that these compounds have anti-mitotic activity through phenotypic sea urchin embryo test. They also reported a compound A and pointed out that the source of the anti-mitotic activity of the compound A is related with the methoxyl at C5, C6, C7 positions of the parent nucleus of coumarin. The structure of trimethoxy truly appears in many microtubule inhibitors, such as colchicine and CA4. Meanwhile, they concluded from the study that coumarin with substituted aromatic group at 3 position is the characteristic of anti-mitotic drug of coumarins.

*Biochemical Pharmacology*, 2009, 77, 1773-1779 reported a coumarin compound B. The document revealed that the compound B can perform microtubule depolymerization and obviously cause cell arrest in G2/M phase, which conforms to the chemotherapy drugs targeting the colchicine site. Meanwhile, the $IC_{50}$ for inhibiting tumor cells is between 44.8-475.2 nM, and that for inhibiting normal cells is greater than 5 μM. The compound B also demonstrates obvious inhibition for drug-resistant tumor cell strain. The compound B structurally has a diethylamino at C7 position to replace the methoxyl. Furthermore, as the same as compound A, the compound B also has an aromatic substitution structure at C3 position. The substitutive derivative at C3 position is deemed as the characteristic of microtubule inhibition drugs.

J. Med. Chem. 2011, 54, 3153-3162 reported a coumarin derivative compound C. The document revealed that the compound C has strong anti-tumor activity with the $IC_{50}$ value of dozens of nanomolar. Meanwhile, it is discovered that the compound C can perform microtubule depolymerization, similar to colchicine and CA4. More importantly, the compound C still exhibits obvious inhibition to the drug-resistant strain with overexpressed P-glycoprotein. The report for the compound C has aroused everyone's attention to the coumarin with substituted aromatic group at C4 position and has expanded the modifiable scope of coumarin derivatives.

J. Med. Chem. 2009, 52, 2341~2351 reported a compound D (MPC-6827, Azixa), whose $IC_{50}$ value for plural tumor cells is between 1-10 nM. The compound D has entered into clinical phase II for the treatment of multiple neuroglioma and clinical phase I for the treatment of melanoma. Cancer Res. 2007 Jun. 15, 67(12): 5865~71 reported that the functioning mechanism of the compound D is to target the colchicine site and inhibit polymerization of tubulin, so as to stop mitosis and induce cell apoptosis. In the document, the computer simulation results indicated that the 2-substituted functional group of the compound D occupied an important pocket of the colchicine site, and the bigger the 2-substituted group is, the lower the anti-microtubule activity is, wherein, the methyl or halogen atom (such as chlorine atom) substitution makes great contribution for maintaining the anti-microtubule activity of the compound D. No substitution at 2 position of the compound D will lead to total loss of anti-microtubule activity. Furthermore, the 1-position aromatic nitrogen atom and 3-position aromatic nitrogen atom of quinazoline have different functions in maintaining the anti-microtubule activity, wherein, the 1-position aromatic nitrogen atom forms hydrogen bond with the hydrogen bond donor in tubulin, which contributes to maintaining the activity of tubulin, while the 3-position aromatic nitrogen atom has no such function. Meanwhile, the substituent methyl of the nitrogen atom at 4 position of quinazoline is also important in inhibiting activity of tubulin. If the methyl is substituted by other groups, such as hydrogen, the anti-microtubule activity will lose as well. Although the compound D has demonstrated good anti-tumor activity, the phase I and II clinical trials have revealed great toxicity, which may limit its efficacy.

The structural formulas of the above compounds A, B, C and D are as follows:

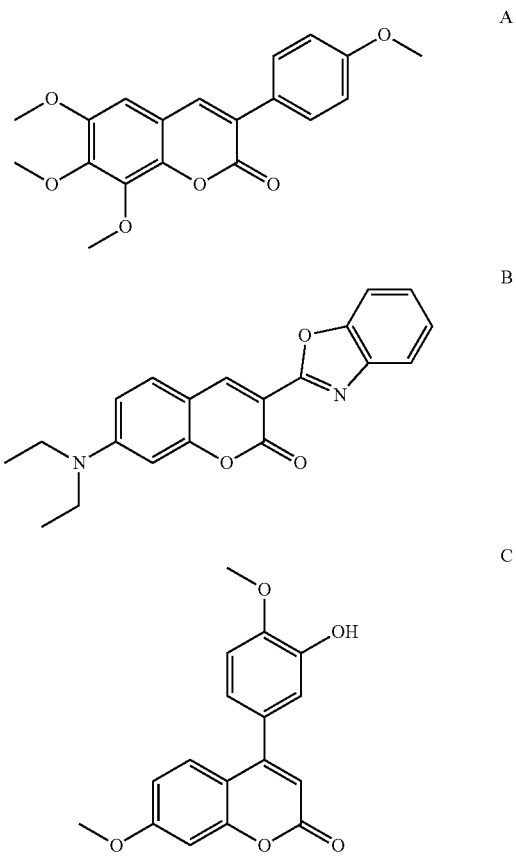

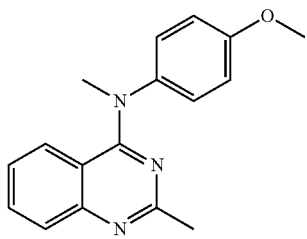

D(MPC-6827)

Currently, it is of urgent need to develop safe and low toxic compounds which may effectively resist drug-resistance.

SUMMARY OF THE INVENTION

In order to solve the above problems, the Invention provides 4-substituted coumarin derivatives with a structural formula as shown in Formula I:

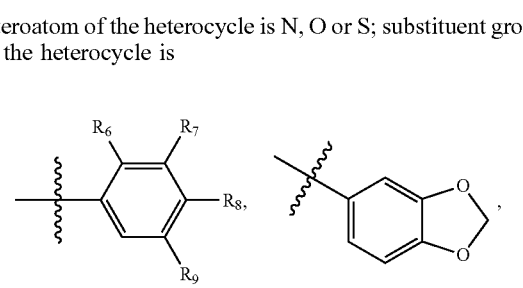

I wherein, $R_1$ is a substituted saturated or unsaturated 5-12-membered heterocycle or

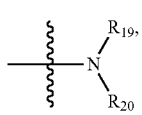

heteroatom of the heterocycle is N, O or S; substituent group on the heterocycle is

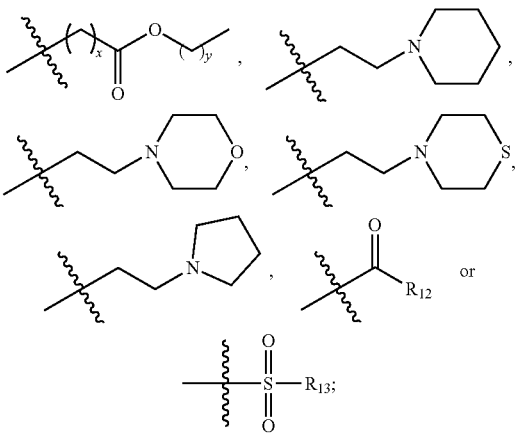

C1-C8 alkoxy, C1-C8 alkyl, halogen or C3-C8 cycloalkyl; $R_2$ is C1-C8 alkoxy, —H,

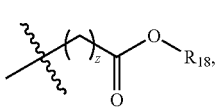

C1-C8 alkyl, halogen or C3-C8 cycloalkyl;

$R_3$-$R_5$ are independently —H, C1-C8 alkoxy, C1-C8 alkyl, halogen, C3-C8 cycloalkyl,

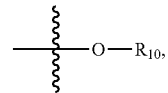

C2-C8 alkenyl, C1-C8 alkyl substituted by halogen, —NH$_2$ or

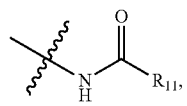

and are not —H at the same time;

$R_6$-$R_9$ are independently —H, C1-C8 alkoxy, halogen, C1-C8 alkyl,

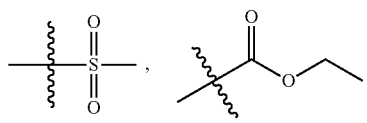

or C1-C8 alkyl substituted by halogen;

$R_{10}$ is

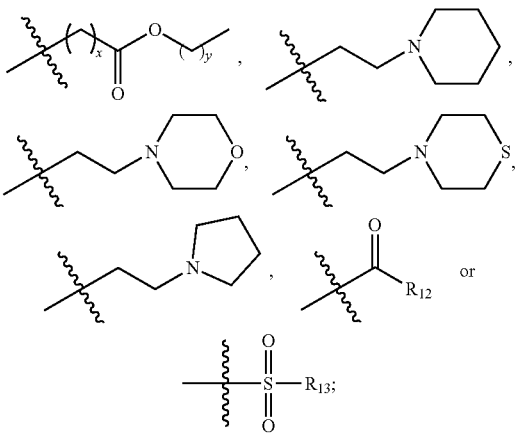

x=1-4, y=1-4;

$R_{11}$ is C1-C10 alkyl,

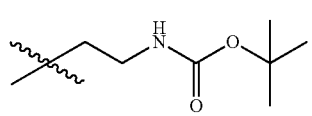 [SMILES: *CCNC(=O)OC(C)(C)C]

C2-C8 alkenyl, C1-C8 alkyl substituted by halogen, C3-C8 cycloalkyl,

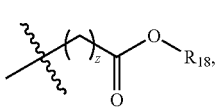

or —NH$_2$; z=1-10;

$R_{12}$ is C1-C10 alkyl,

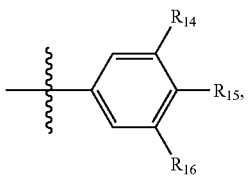

halogen, C2-C8 alkenyl, C1-C8 alkyl substituted by halogen, C3-C8 cycloalkyl,

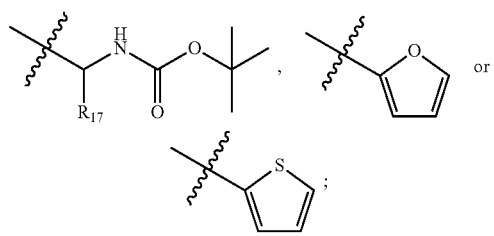

$R_{13}$ is C1-C8 alkyl, phenyl substituted by C1-C8 alkyl or phenyl substituted by halogen;

$R_{14}$-$R_{16}$ are each independently C1-C8 alkyl, halogen, —H, C1-C8 alkoxy or —NH$_2$, and are not —H at the same time;

$R_{17}$ is C1-C8 alkyl, halogen, —H or

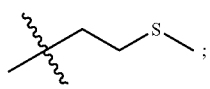 [SMILES: *CCSC]

$R_{18}$ is C1-C8 alkyl, halogen or —H;

$R_{19}$ and $R_{20}$ are each independently C1-C8 alkyl, halogen or —H.

As a preferred scheme of the Invention, $R_1$ is a substituted saturated or unsaturated 5-12-membered heterocycle or

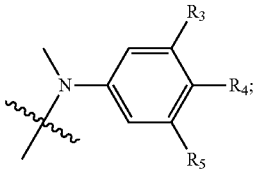

heteroatom of the heterocycle is N, O or S; substituent group on the heterocycle is

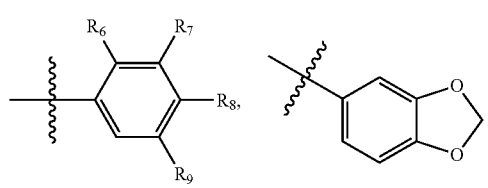

or C1-C4 alkoxy; $R_2$ is C1-C4 alkoxy, —H,

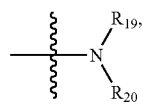

C1-C4 alkyl, halogen or C3-C8 cycloalkyl; $R_3$-$R_5$ are each independently —H, C1-C4 alkoxy, C1-C4 alkyl, halogen, C3-C8 cycloalkyl,

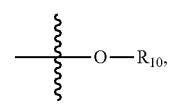

C2-C4 alkenyl, C1-C4 alkyl substituted by halogen, —NH$_2$ or

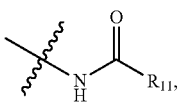

and are not —H at the same time; $R_6$-$R_9$ are each independently —H, C1-C4 alkoxy, halogen, C1-C4 alkyl,

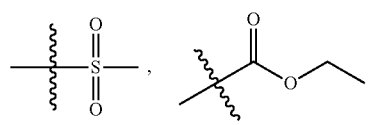

or C1-C4 alkyl substituted by halogen; $R_{10}$ is

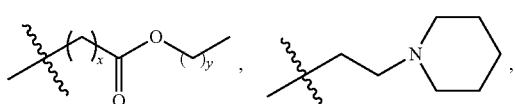

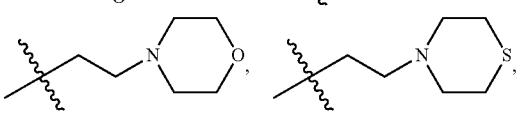

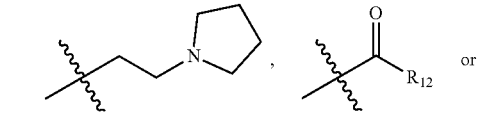

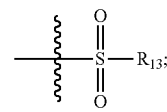

x=1-4, y=1-4; $R_{11}$ is C1-C10 alkyl,

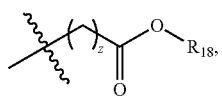

C2-C8 alkenyl, C1-C4 alkyl substituted by halogen, C3-C8 cycloalkyl,

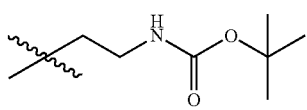 [SMILES: *CCNC(=O)OC(C)(C)C]

or —NH₂; z=1-10; $R_{12}$ is C1-C10 alkyl,

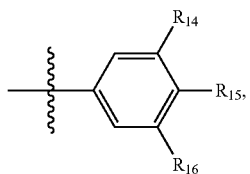

halogen, C2-C8 alkenyl, C1-C4 alkyl substituted by halogen, C3-C8 cycloalkyl,

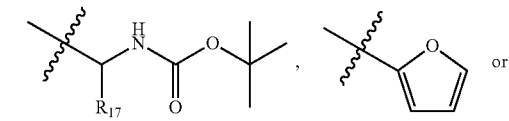

$R_{13}$ is C1-C4 alkyl, phenyl substituted by C1-C4 alkyl or phenyl substituted by halogen; $R_{14}$-$R_{16}$ are each independently C1-C4 alkyl, halogen, —H, C1-C4 alkoxy or —NH₂, and are not —H at the same time;

$R_{17}$ is C1-C4 alkyl, halogen, —H or

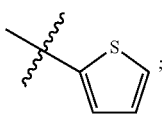

$R_{18}$ is C1-C4 alkyl, halogen or —H; $R_{19}$ and $R_{20}$ are each independently C1-C4 alkyl, halogen or —H.

Preferably, $R_1$ is

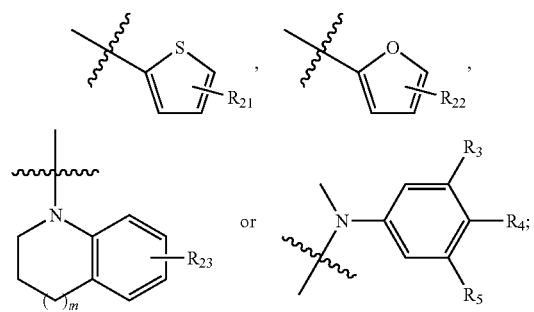

$R_{21}$-$R_{23}$ are each independently

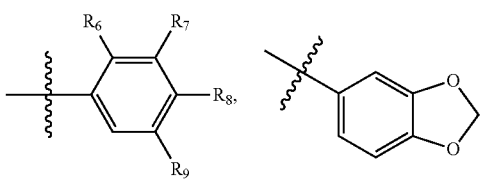

or C1-C4 alkoxy; $R_2$ is C1-C4 alkoxy, —H,

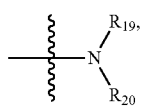

C1-C4 alkyl, halogen or C3-C8 cycloalkyl; $R_3$-$R_5$ are each independently —H, C1-C4 alkoxy, C1-C4 alkyl, halogen, C3-C8 cycloalkyl,

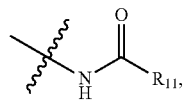

C2-C4 alkenyl, C1-C4 alkyl substituted by halogen, —NH₂ or

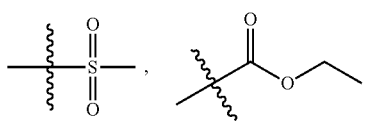

and are not —H at the same time; $R_6$-$R_9$ are each independently —H, C1-C4 alkoxy, halogen, C1-C4 alkyl,

or C1-C4 alkyl substituted by halogen; $R_{10}$ is

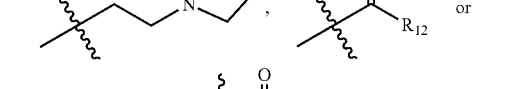

x=1-4, y=1-4; $R_{11}$ is C1-C10 alkyl,

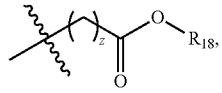

C2-C8 alkenyl, C1-C4 alkyl substituted by halogen, C3-C8 cycloalkyl,

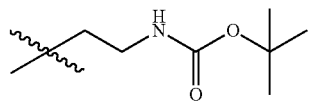 [SMILES: *CCNC(=O)OC(C)(C)C]

or —NH$_2$; z=1-10; $R_{12}$ is C1-C10 alkyl,

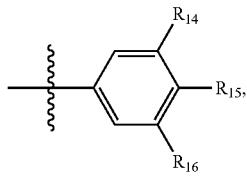

halogen, C2-C8 alkenyl, C1-C4 alkyl substituted by halogen, C3-C8 cycloalkyl,

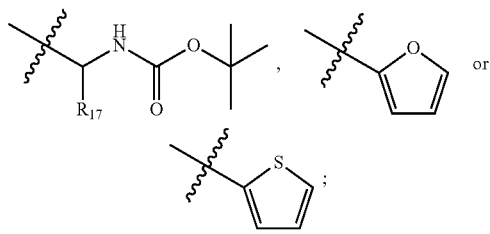

$R_{13}$ is C1-C4 alkyl, phenyl substituted by C1-C4 alkyl or phenyl substituted by halogen; $R_{14}$-$R_{16}$ are each independently C1-C4 alkyl, halogen, —H, C1-C4 alkoxy or —NH$_2$, and are not —H at the same time; $R_{17}$ is C1-C4 alkyl, halogen, —H or

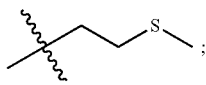 [SMILES: *CCSC]

$R_{18}$ is C1-C4 alkyl, halogen or —H; $R_{19}$ and $R_{20}$ are each independently C1-C4 alkyl, halogen or —H.

Further preferably, $R_1$ is

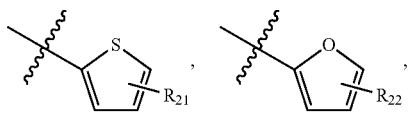

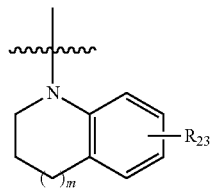 or 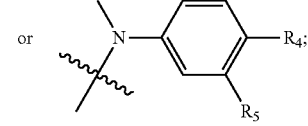

$R_{21}$ and $R_{22}$ are each independently

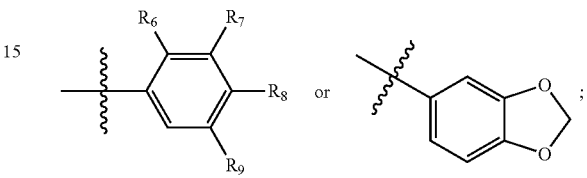

$R_{23}$ is C1-C4 alkoxy; $R_2$ is C1-C4 alkoxy, —H,

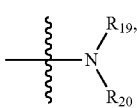

C1-C4 alkyl, halogen or C3-C8 cycloalkyl; $R_3$-$R_5$ are each independently —H, C1-C4 alkoxy, C1-C4 alkyl, halogen, C3-C8 cycloalkyl,

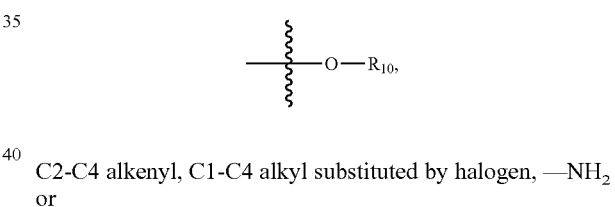

C2-C4 alkenyl, C1-C4 alkyl substituted by halogen, —NH$_2$ or

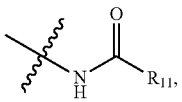

and are not —H at the same time; $R_6$-$R_9$ are each independently —H, C1-C4 alkoxy, halogen, C1-C4 alkyl,

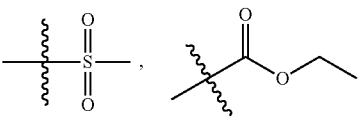

or C1-C4 alkyl substituted by halogen; $R_{10}$ is

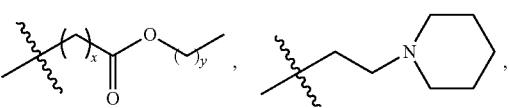

-continued

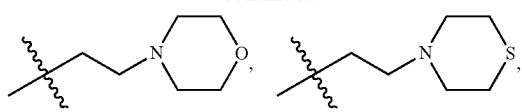

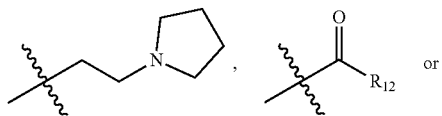

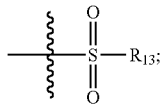

x=1-4, y=1-4; R$_{11}$ is C1-C10 alkyl,

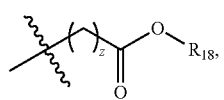

or —NH$_2$; z=1-10; R$_{12}$ is C1-C10 alkyl,

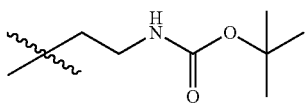 [SMILES: *CCNC(=O)OC(C)(C)C]

halogen, C2-C8 alkenyl, C1-C4 alkyl substituted by halogen, C3-C8 cycloalkyl,

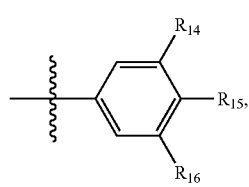

R$_{13}$ is C1-C4 alkyl, phenyl substituted by C1-C4 alkyl or phenyl substituted by halogen; R$_{14}$-R$_{16}$ are each independently C1-C4 alkyl, halogen, —H, C1-C4 alkoxy or —NH$_2$, and are not —H at the same time; R$_{17}$ is C1-C4 alkyl, halogen, —H or

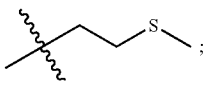 [SMILES: *CCSC]

R$_{18}$ is C1-C4 alkyl, halogen or —H; R$_{19}$ and R$_{20}$ are each independently C1-C4 alkyl, halogen or —H.

Preferably, R$_1$ is

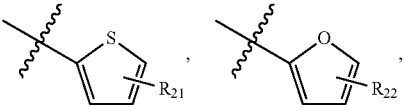

R$_{21}$-R$_{23}$ are each independently

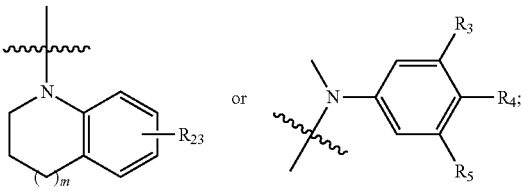

or C1-C4 alkoxy; R$_2$ is C1-C4 alkoxy, —H,

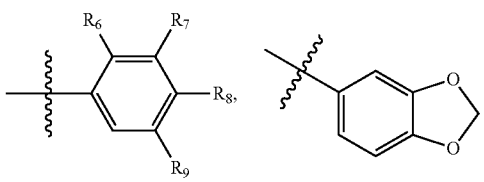

or C1-C4 alkyl; R$_3$-R$_5$ are each independently —H, C1-C4 alkoxy, C1-C4 alkyl, halogen, C3-C8 cycloalkyl,

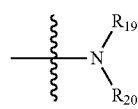

C2-C4 alkenyl, C1-C4 alkyl substituted by halogen, —NH$_2$ or

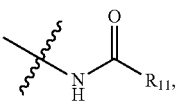

and are not —H at the same time; R$_6$-R$_9$ are each independently —H, C1-C4 alkoxy, halogen, C1-C4 alkyl,

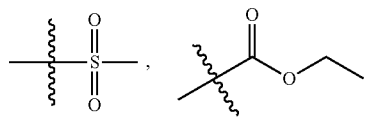

or C1-C4 alkyl substituted by halogen; $R_{10}$ is

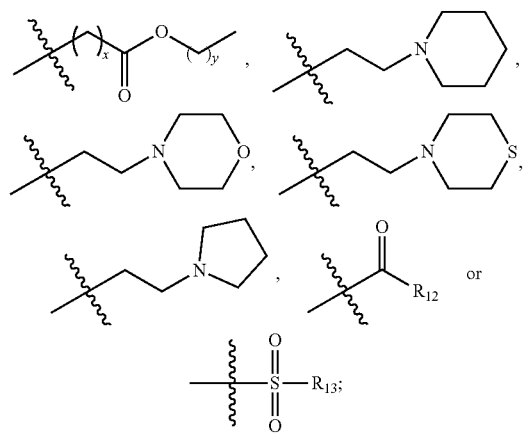

x=1-4, y=1-4; $R_{11}$ is C1-C10 alkyl,

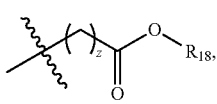

C2-C8 alkenyl, C1-C4 alkyl substituted by halogen, C3-C8 cycloalkyl,

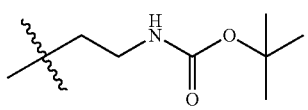 [SMILES: *CCNC(=O)OC(C)(C)C]

or —$NH_2$; z=1-10; $R_{12}$ is C1-C10 alkyl,

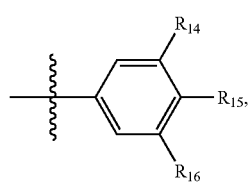

halogen, C2-C8 alkenyl, C1-C4 alkyl substituted by halogen, C3-C8 cycloalkyl,

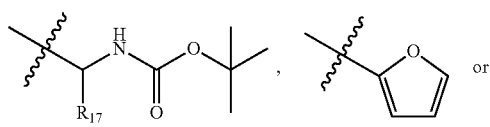

-continued

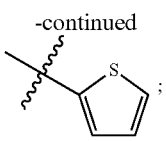

$R_{13}$ is C1-C4 alkyl, phenyl substituted by C1-C4 alkyl or phenyl substituted by halogen; $R_{14}$-$R_{16}$ are each independently C1-C4 alkyl, halogen, —H, C1-C4 alkoxy or —$NH_2$, and are not —H at the same time; $R_{17}$ is C1-C4 alkyl, halogen, —H or

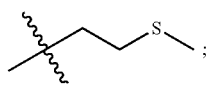 [SMILES: *CCSC]

$R_{18}$ is C1-C4 alkyl, halogen or —H; $R_{19}$ and $R_{20}$ are each independently C1-C4 alkyl, halogen or —H.

Further preferably, $R_1$ is

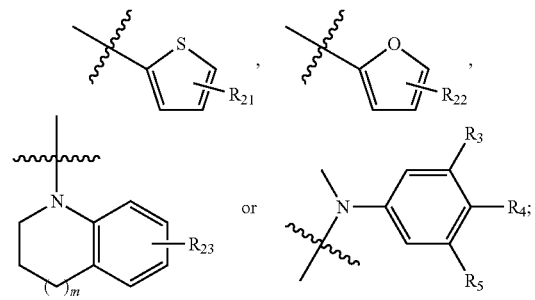

$R_{21}$-$R_{23}$ are each independently

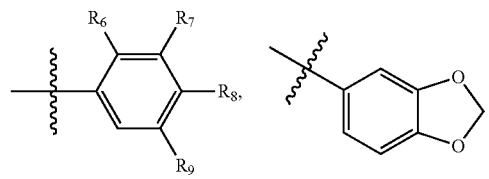

or C1-C4 alkoxy; $R_2$ is C1-C4 alkoxy, —H or

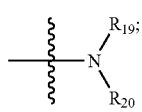

$R_3$-$R_5$ are each independently —H, C1-C4 alkoxy, C1-C4 alkyl, halogen, C3-C8 cycloalkyl,

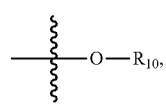

C2-C4 alkenyl, C1-C4 alkyl substituted by halogen, —$NH_2$ or

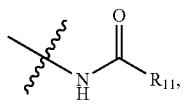

and are not —H at the same time; $R_6$-$R_9$ are each independently —H, C1-C4 alkoxy, halogen, C1-C4 alkyl,

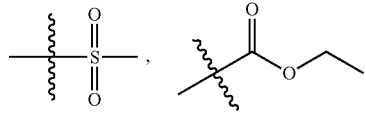

or C1-C4 alkyl substituted by halogen; $R_{10}$ is

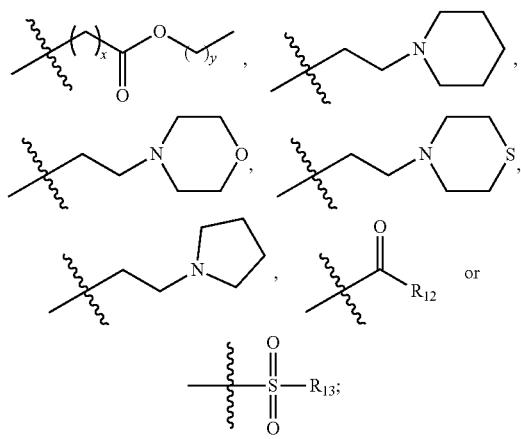

x=1-4, y=1-4; $R_{11}$ is C1-C10 alkyl,

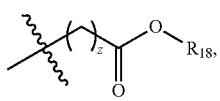

C2-C8 alkenyl, C1-C4 alkyl substituted by halogen, C3-C8 cycloalkyl,

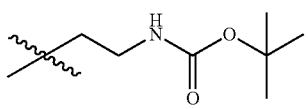 [SMILES: *CCNC(=O)OC(C)(C)C]

or —NH$_2$; z=1-10; $R_{12}$ is C1-C10 alkyl,

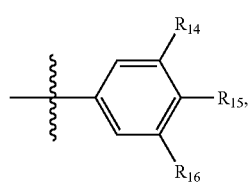

halogen, C2-C8 alkenyl, C1-C4 alkyl substituted by halogen, C3-C8 cycloalkyl,

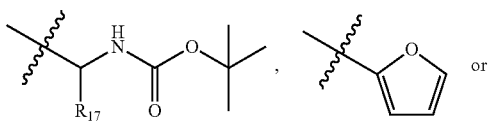

$R_{13}$ is C1-C4 alkyl, phenyl substituted by C1-C4 alkyl or phenyl substituted by halogen; $R_{14}$-$R_{16}$ are each independently C1-C4 alkyl, halogen, —H, C1-C4 alkoxy or —NH$_2$, and are not —H at the same time; $R_{17}$ is C1-C4 alkyl, halogen, —H or

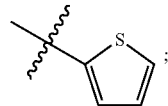

$R_{18}$ is C1-C4 alkyl, halogen or —H; $R_{19}$ and $R_{20}$ are each independently C1-C4 alkyl, halogen or —H.

Preferably, $R_1$ is

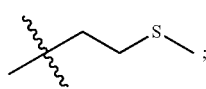 [SMILES: *CCSC]

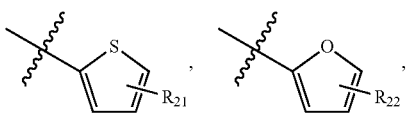

$R_{21}$-$R_{23}$ are each independently

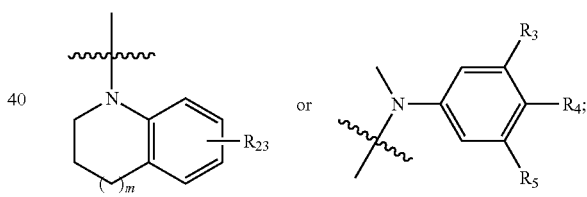

or C1-C4 alkoxy; $R_2$ is C1-C4 alkoxy, —H or

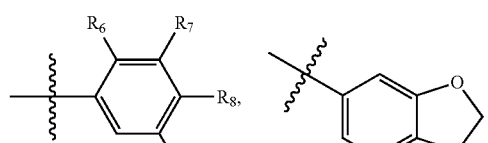

$R_3$-$R_5$ are each independently —H, C1-C4 alkoxy, C1-C4 alkyl, halogen, C3-C8 cycloalkyl,

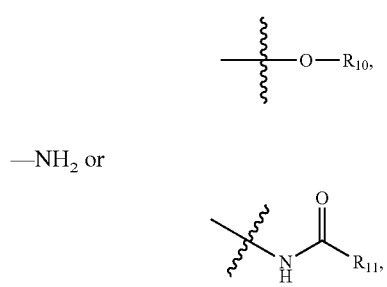

—NH₂ or

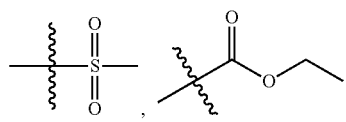

and are not —H at the same time; $R_6$-$R_9$ are each independently —H, C1-C4 alkoxy, halogen, C1-C4 alkyl,

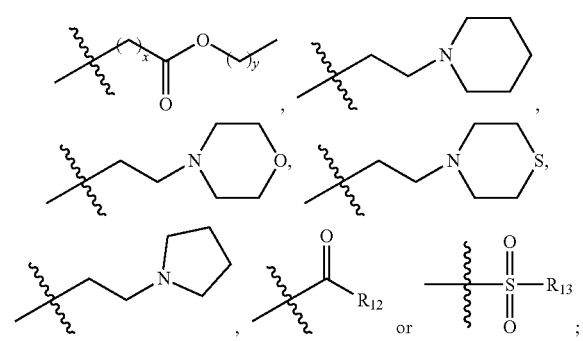

or C1-C4 alkyl substituted by halogen; $R_{10}$ is

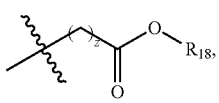

x=1-4, y=1-4; $R_{11}$ is C1-C10 alkyl,

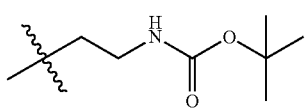 [SMILES: *CCNC(=O)OC(C)(C)C]

C2-C8 alkenyl, C1-C4 alkyl substituted by halogen, C3-C8 cycloalkyl,

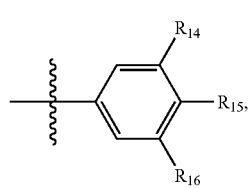

or —NH₂; z=1-10; $R_{12}$ is C1-C10 alkyl,

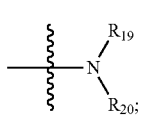

halogen, C2-C8 alkenyl, C1-C4 alkyl substituted by halogen, C3-C8 cycloalkyl,

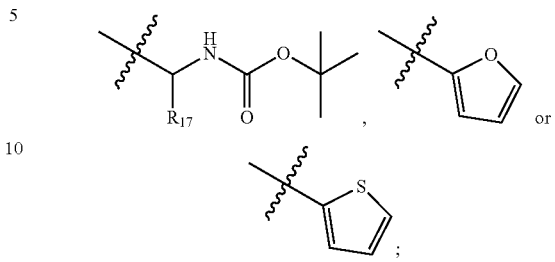

$R_{13}$ is C1-C4 alkyl, phenyl substituted by C1-C4 alkyl or phenyl substituted by halogen; $R_{14}$-$R_{16}$ are each independently C1-C4 alkyl, halogen, —H, C1-C4 alkoxy or —NH₂, and are not —H at the same time; $R_{17}$ is C1-C4 alkyl, halogen, —H or

$R_{18}$ is C1-C4 alkyl, halogen or —H; $R_{19}$ and $R_{20}$ are each independently C1-C4 alkyl, halogen or —H.

Further preferably, $R_1$ is

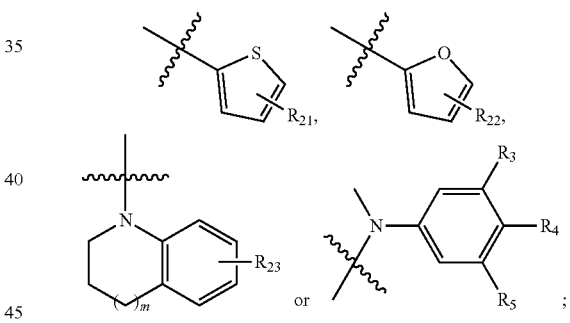

$R_{21}$-$R_{23}$ are each independently

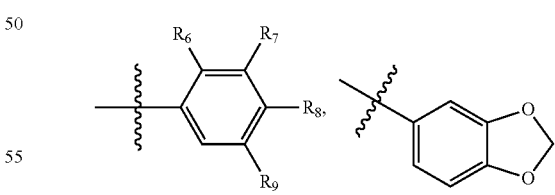

or C1-C4 alkoxy; $R_2$ is C1-C4 alkoxy, —H or

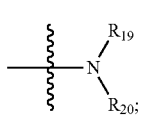

$R_3$-$R_5$ are each independently —H, C1-C4 alkoxy,

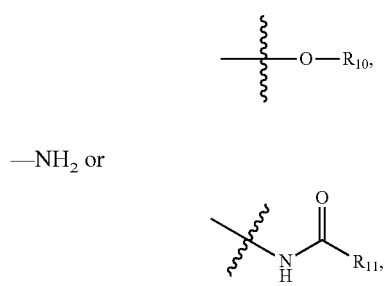

—NH$_2$ or

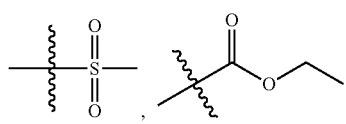

and are not —H at the same time; $R_6$-$R_9$ are each independently —H, C1-C4 alkoxy, halogen, C1-C4 alkyl,

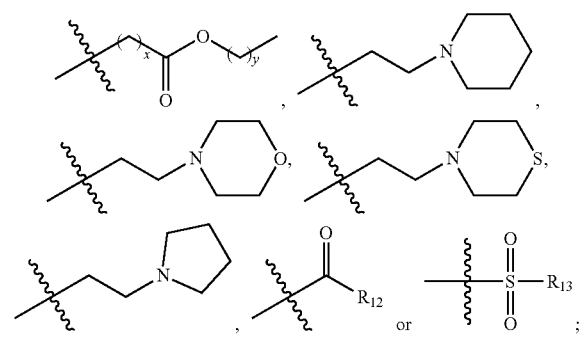

or C1-C4 alkyl substituted by halogen; $R_{10}$ is

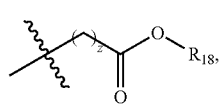

x=1-4, y=1-4; $R_{11}$ is C1-C10 alkyl,

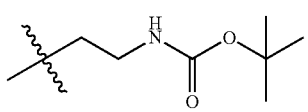 [SMILES: *CCNC(=O)OC(C)(C)C]

C2-C8 alkenyl, C1-C4 alkyl substituted by halogen, C3-C8 cycloalkyl,

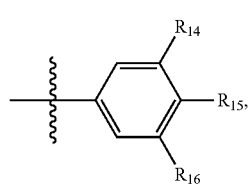

or —NH$_2$; z=1-10; $R_{12}$ is C1-C10 alkyl, halogen, C2-C8 alkenyl, C1-C4 alkyl substituted by halogen, C3-C8 cycloalkyl,

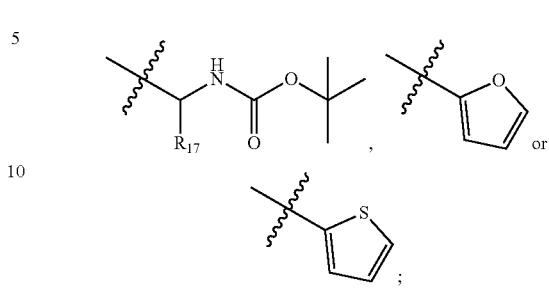

$R_{13}$ is C1-C4 alkyl, phenyl substituted by C1-C4 alkyl or phenyl substituted by halogen; $R_{14}$-$R_{16}$ are each independently C1-C4 alkyl, halogen, —H, C1-C4 alkoxy or —NH$_2$, and are not —H at the same time; $R_{17}$ is C1-C4 alkyl, halogen, —H or

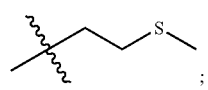 [SMILES: *CCSC]

$R_{18}$ is C1-C4 alkyl, halogen or —H; $R_{19}$ and $R_{20}$ are each independently C1-C4 alkyl, halogen or —H.

Preferably, $R_1$ is

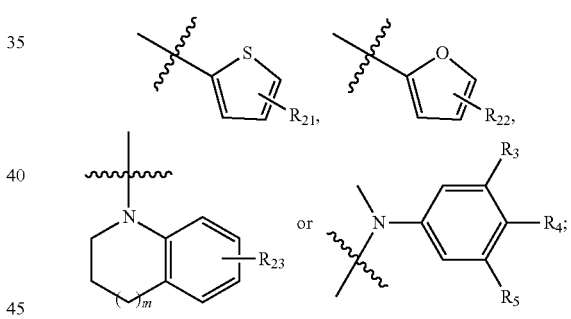

$R_{21}$-$R_{23}$ are each independently

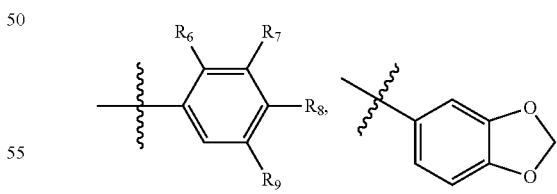

or C1-C4 alkoxy; $R_2$ is C1-C4 alkoxy, —H or

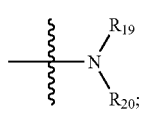

$R_3$-$R_5$ are each independently —H, C1-C4 alkoxy,

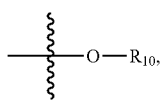

—NH$_2$ or

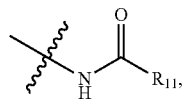

and are not —H at the same time; $R_6$-$R_9$ are each independently —H, C1-C4 alkoxy, halogen, C1-C4 alkyl,

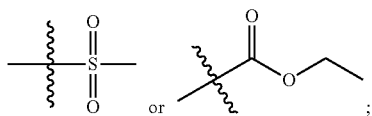

$R_{10}$ is

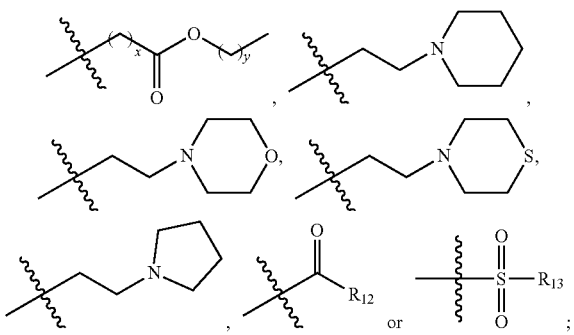

x=1-4, y=1-4; $R_{11}$ is C1-C10 alkyl,

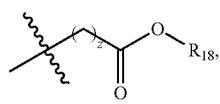

C2-C8 alkenyl, C1-C4 alkyl substituted by halogen, C3-C8 cycloalkyl,

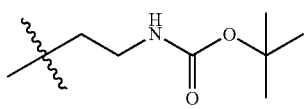 [SMILES: *CCNC(=O)OC(C)(C)C]

or —NH$_2$; z=1-10; $R_{12}$ is C1-C10 alkyl,

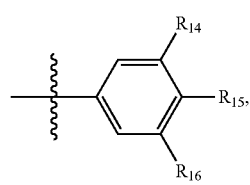

halogen, C2-C8 alkenyl, C1-C4 alkyl substituted by halogen, C3-C8 cycloalkyl,

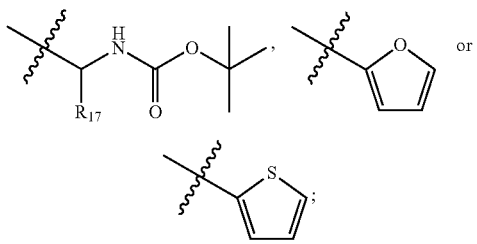

$R_{13}$ is C1-C4 alkyl, phenyl substituted by C1-C4 alkyl or phenyl substituted by halogen; $R_{14}$-$R_{16}$ are each independently C1-C4 alkyl, halogen, —H, C1-C4 alkoxy or —NH$_2$, and are not —H at the same time; $R_{17}$ is C1-C4 alkyl, halogen, —H or

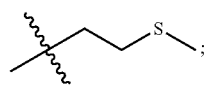 [SMILES: *CCSC]

$R_{18}$ is C1-C4 alkyl, halogen or —H; $R_{19}$ and $R_{20}$ are each independently C1-C4 alkyl, halogen or —H.

Preferably, $R_1$ is

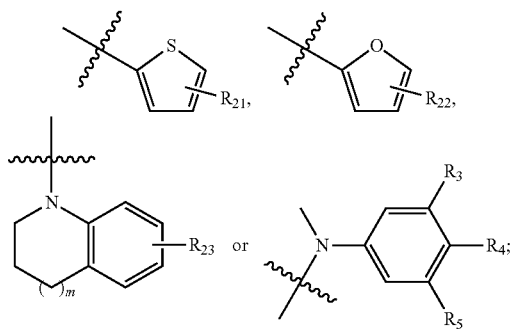

$R_{21}$-$R_{23}$ are each independently

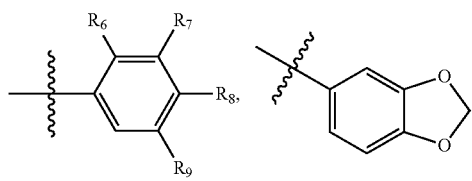

or C1-C4 alkoxy; $R_2$ is C1-C4 alkoxy, —H or

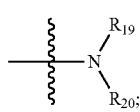

$R_3$-$R_5$ are each independently —H, C1-C4 alkoxy,

—NH$_2$ or

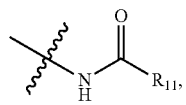

and are not —H at the same time; $R_6$-$R_9$ are each independently —H, C1-C4 alkoxy, halogen, C1-C4 alkyl,

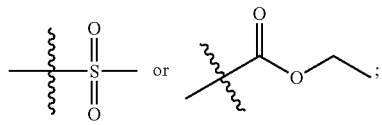

$R_{10}$ is

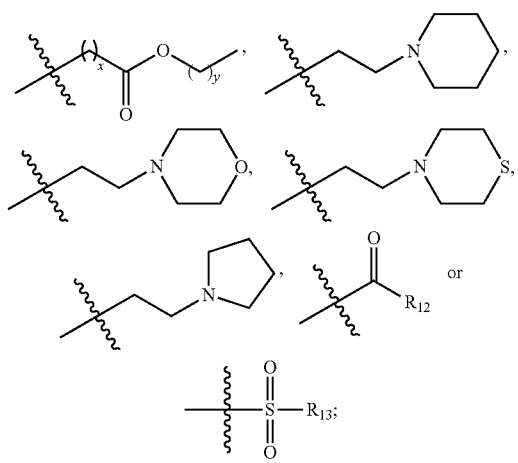

x=1-2, y=1-2; $R_{11}$ is C1-C10 alkyl,

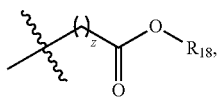

C2-C8 alkenyl, C1-C4 alkyl substituted by halogen, C3-C8 cycloalkyl or

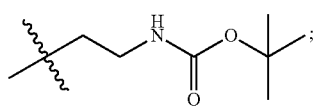 [SMILES: *CCNC(=O)OC(C)(C)C]

z=1-10; $R_{12}$ is C1-C10 alkyl,

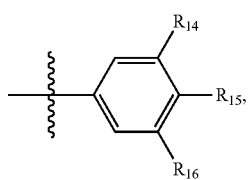

halogen, C2-C8 alkenyl, C1-C4 alkyl substituted by halogen, C3-C8 cycloalkyl,

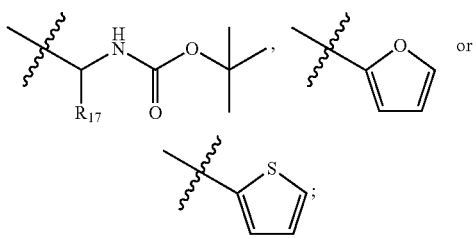

$R_{13}$ is C1-C4 alkyl, phenyl substituted by C1-C4 alkyl or phenyl substituted by halogen; $R_{14}$-$R_{16}$ are each independently C1-C4 alkyl, halogen, —H or C1-C4 alkoxy, and are not —H at the same time; $R_{17}$ is C1-C4 alkyl, —H or

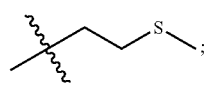 [SMILES: *CCSC]

$R_{18}$ is C1-C4 alkyl or —H; $R_{19}$ and $R_{20}$ are each independently C1-C4 alkyl or —H.

Most preferably, $R_1$ is

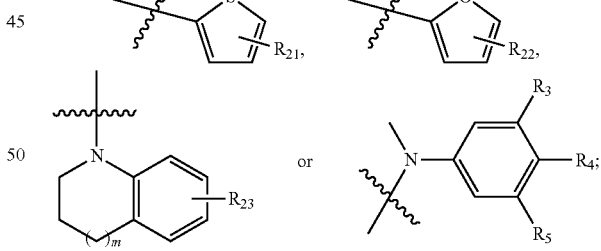

$R_{21}$ and $R_{22}$ are each independently

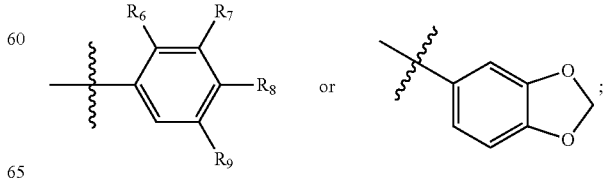

$R_{23}$ is C1-C4 alkoxy; $R_2$ is C1-C4 alkoxy, —H or

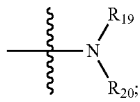

$R_3$-$R_5$ are each independently —H, C1-C4 alkoxy,

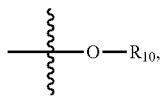

—NH$_2$ or

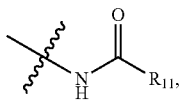

and are not —H at the same time; $R_6$-$R_9$ are each independently —H, C1-C4 alkoxy, halogen, C1-C4 alkyl,

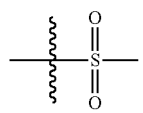 or 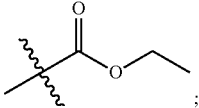;

$R_{10}$ is

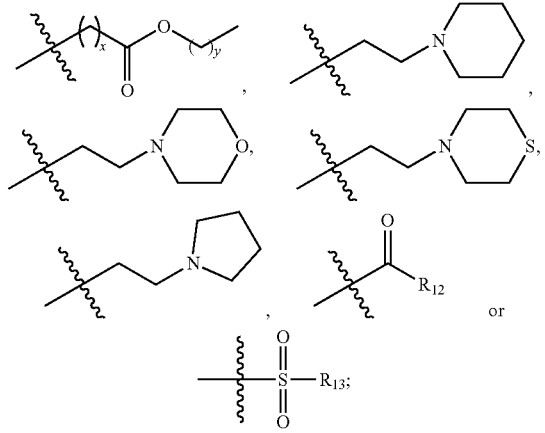

$R_{11}$ is C1-C10 alkyl,

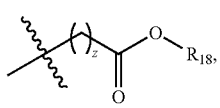

C2-C8 alkenyl, C1-C4 alkyl substituted by halogen, C3-C8 cycloalkyl or

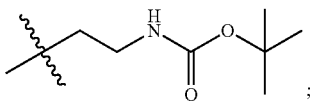 [SMILES: *CCNC(=O)OC(C)(C)C];

z=1-10; $R_{12}$ is C1-C10 alkyl,

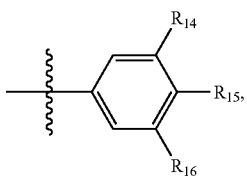

halogen, C2-C8 alkenyl, C1-C4 alkyl substituted by halogen, C3-C8 cycloalkyl,

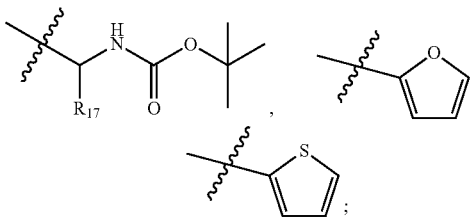

$R_{13}$ is C1-C4 alkyl, phenyl substituted by C1-C4 alkyl or phenyl substituted by halogen; $R_{14}$-$R_{16}$ are each independently C1-C4 alkyl, halogen, —H or C1-C4 alkoxy, and are not —H at the same time; $R_{17}$ is C1-C4 alkyl, —H or

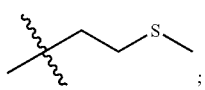 [SMILES: *CCSC];

$R_{18}$ is C1-C4 alkyl or —H; $R_{19}$ and $R_{20}$ are each independently C1-C4 alkyl or —H.

The structural formula of the above 4-substituted coumarin derivatives is shown in Formula II when $R_1$ is a substituted unsaturated 5-membered heterocycle:

II

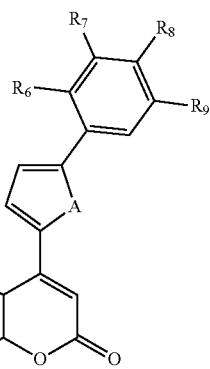

wherein, A is O or S;
$R_2$ is C1-C8 alkoxy, —H,

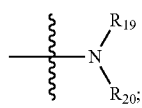

C1-C8 alkyl, halogen or C3-C8 cycloalkyl;
$R_6$-$R_9$ are independently —H, C1-C8 alkoxy, halogen, C1-C8 alkyl,

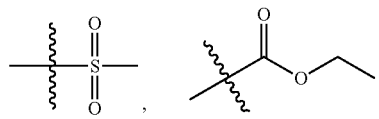

or C1-C8 alkyl substituted by halogen;
$R_{19}$ and $R_{20}$ are each independently C1-C8 alkyl, halogen or —H.

As a preferred scheme of the Invention, A is O or S; $R_2$ is C1-C4 alkoxy, —H,

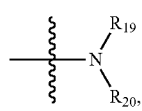

C1-C4 alkyl, halogen or C3-C8 cycloalkyl; $R_6$-$R_9$ are each independently —H, C1-C4 alkoxy, halogen, C1-C4 alkyl,

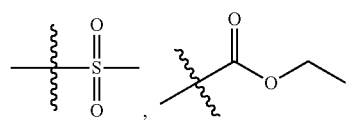

or C1-C4 alkyl substituted by halogen; $R_{19}$ and $R_{20}$ are each independently C1-C4 alkyl, halogen or —H.

Preferably, A is O or S; $R_2$ is C1-C4 alkoxy, —H,

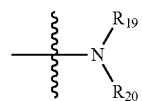

or C1-C4 alkyl; $R_6$-$R_9$ are each independently —H, C1-C4 alkoxy, halogen, C1-C4 alkyl,

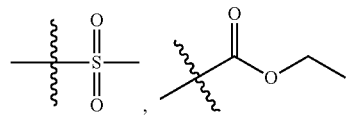

or C1-C4 alkyl substituted by halogen; $R_{19}$ and $R_{20}$ are each independently C1-C4 alkyl, halogen or —H.

Further preferably, A is O or S; $R_2$ is C1-C4 alkoxy or —H; $R_6$-$R_9$ are each independently —H, C1-C4 alkoxy, halogen, C1-C4 alkyl,

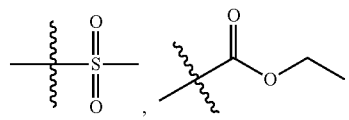

or C1-C4 alkyl substituted by halogen; $R_{19}$ and $R_{20}$ are each independently C1-C4 alkyl, halogen or —H.

Furthermore preferably, A is O or S; $R_2$ is C1-C4 alkoxy or —H; $R_6$-$R_9$ are each independently —H, C1-C4 alkoxy, halogen, C1-C4 alkyl,

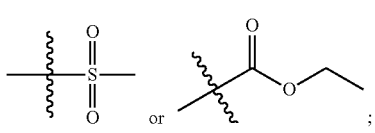

$R_{19}$ and $R_{20}$ are each independently C1-C4 alkyl, halogen or —H.

Most preferably, A is O or S; $R_2$ is C1-C4 alkoxy or —H; $R_6$-$R_9$ are each independently —H, C1-C4 alkoxy, halogen, C1-C4 alkyl,

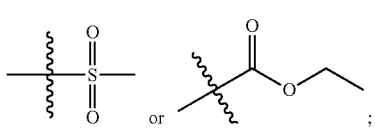

$R_{19}$ and $R_{20}$ are each independently C1-C4 alkyl or —H.

The structural formula of the above 4-substituted coumarin derivatives is shown in Formula III when $R_1$ is

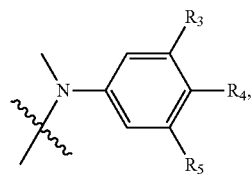

$R_3$ is —H, $R_4$ is methoxyl and $R_5$ is

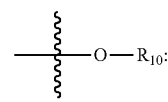

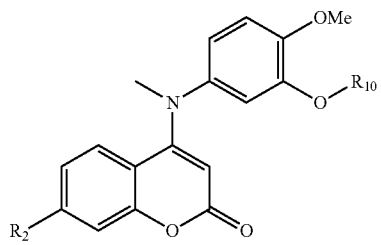

III

Wherein, $R_2$ is C1-C8 alkoxy, —H,

31

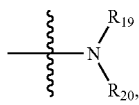

C1-C8 alkyl, halogen or C3-C8 cycloalkyl;
$R_{10}$ is

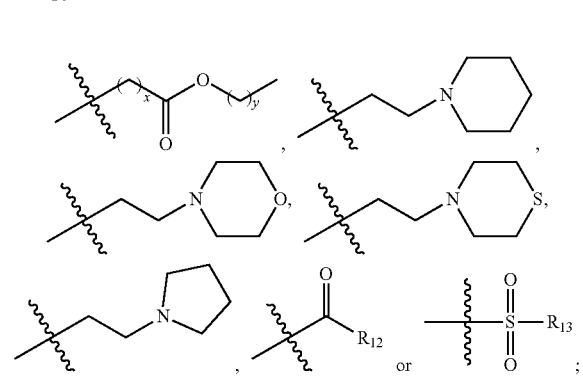

x=1-4, y=1-4;
$R_{12}$ is C1-C10 alkyl,

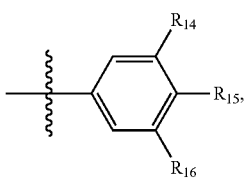

halogen, C2-C8 alkenyl, C1-C8 alkyl substituted by halogen, C3-C8 cycloalkyl,

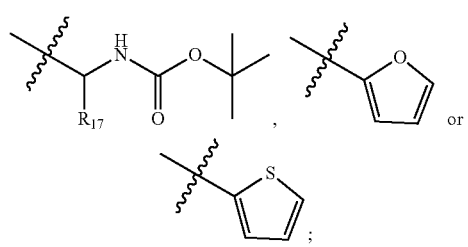

$R_{13}$ is C1-C8 alkyl, phenyl substituted by C1-C8 alkyl or phenyl substituted by halogen;

$R_{14}$-$R_{16}$ are each independently C1-C8 alkyl, halogen, —H, C1-C8 alkoxy or —NH$_2$, and are not —H at the same time;

$R_{17}$ is C1-C8 alkyl, halogen, —H or

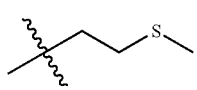

As a preferred scheme of the Invention, $R_2$ is C1-C4 alkoxy, —H,

32

C1-C4 alkyl, halogen or C3-C8 cycloalkyl; $R_{10}$ is

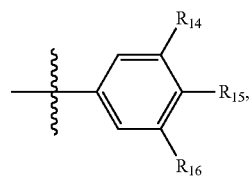

x=1-4, y=1-4; $R_{12}$ is C1-C10 alkyl,

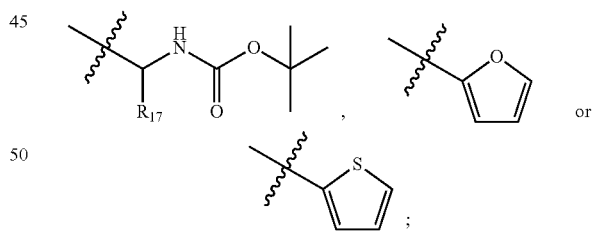

halogen, C2-C8 alkenyl, C1-C4 alkyl substituted by halogen, C3-C8 cycloalkyl, $R_{13}$ is C1-C4 alkyl, phenyl substituted by C1-C4 alkyl or phenyl substituted by halogen; $R_{14}$-$R_{16}$ are each independently C1-C4 alkyl, halogen, —H, C1-C4 alkoxy or —NH$_2$, and are not —H at the same time; $R_{17}$ is C1-C4 alkyl, halogen, —H or

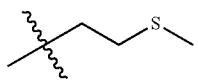

Preferably, $R_2$ is C1-C4 alkoxy, —H or

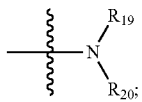

$R_{10}$ is

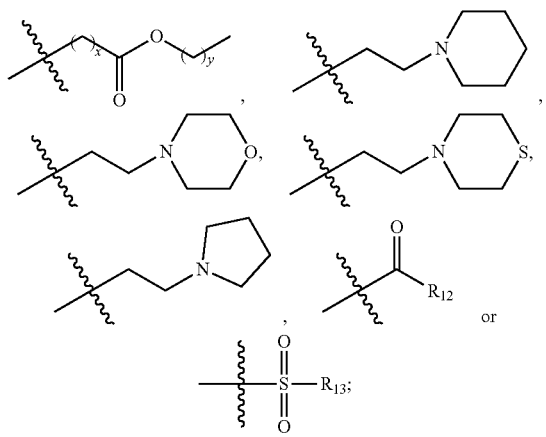

x=1-4, y=1-4; $R_{12}$ is C1-C10 alkyl,

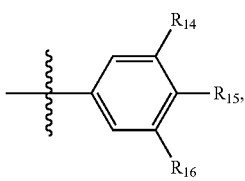

halogen, C2-C8 alkenyl, C1-C4 alkyl substituted by halogen, C3-C8 cycloalkyl,

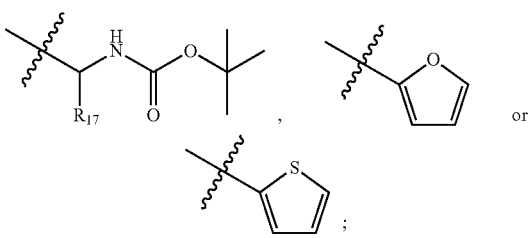

$R_{13}$ is C1-C4 alkyl, phenyl substituted by C1-C4 alkyl or phenyl substituted by halogen; $R_{14}$-$R_{16}$ are each independently C1-C4 alkyl, halogen, —H, C1-C4 alkoxy or —NH$_2$, and are not —H at the same time; $R_{17}$ is C1-C4 alkyl, halogen, —H or

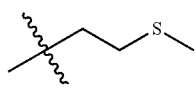

Further preferably, $R_2$ is C1-C4 alkoxy, —H or

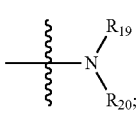

$R_{10}$ is

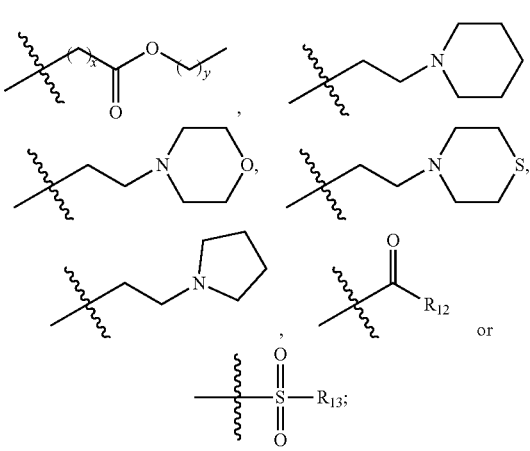

x=1-2, y=1-2; $R_{12}$ is C1-C10 alkyl,

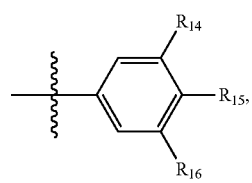

halogen, C2-C8 alkenyl, C1-C4 alkyl substituted by halogen, C3-C8 cycloalkyl,

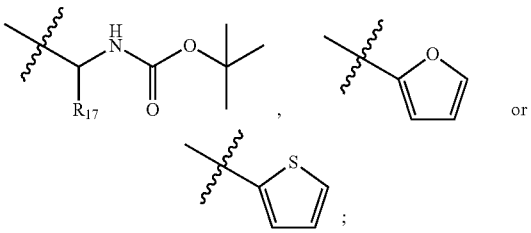

$R_{13}$ is C1-C4 alkyl, phenyl substituted by C1-C4 alkyl or phenyl substituted by halogen; $R_{14}$-$R_{16}$ are each independently C1-C4 alkyl, halogen, —H or C1-C4 alkoxy, and are not —H at the same time; $R_{17}$ is C1-C4 alkyl, —H or

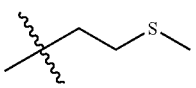

Most preferably, $R_2$ is C1-C4 alkoxy, —H or

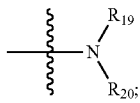

$R_{10}$ is

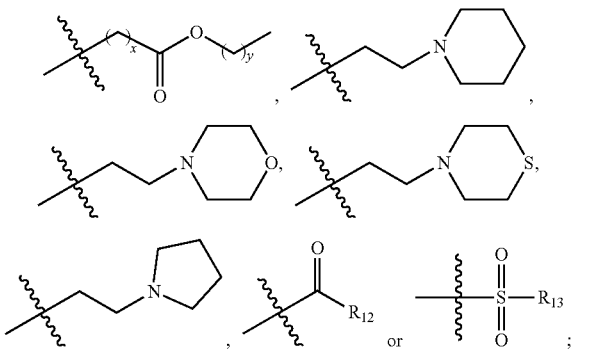

$R_{12}$ is C1-C10 alkyl,

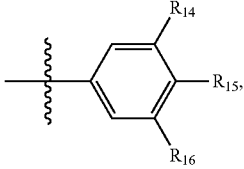

halogen, C2-C8 alkenyl, C1-C4 alkyl substituted by halogen, C3-C8 cycloalkyl,

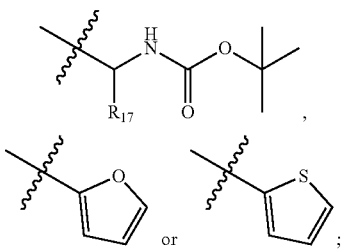

$R_{13}$ is C1-C4 alkyl, phenyl substituted by C1-C4 alkyl or phenyl substituted by halogen; $R_{14}$-$R_{16}$ are each independently C1-C4 alkyl, halogen, —H or C1-C4 alkoxy, and are not —H at the same time; $R_{17}$ is C1-C4 alkyl, —H or

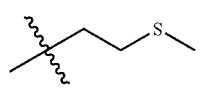

The structural formula of the above 4-substituted coumarin derivatives is shown in Formula IV when $R_1$ is

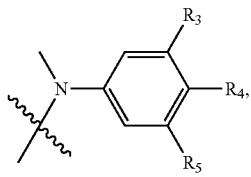

$R_3$ is —H, $R_4$ is methoxyl and $R_5$ is

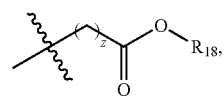

IV

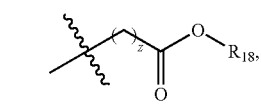

wherein, $R_{11}$ is C1-C10 alkyl,

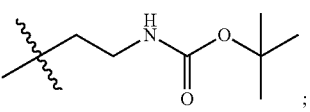

C2-C8 alkenyl, C1-C4 alkyl substituted by halogen, C3-C8 cycloalkyl, or —NH$_2$; z=1-10;

$R_{18}$ is C1-C4 alkyl, halogen or —H.

As a preferred scheme of the Invention, $R_{11}$ is C1-C10 alkyl,

C2-C8 alkenyl, C1-C4 alkyl substituted by halogen, C3-C8 cycloalkyl or z=1-10; $R_{18}$ is C, 1-C4 alkyl, halogen or —H;

Preferably, R$_{11}$ is C1-C10 alkyl,
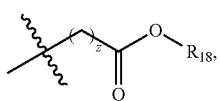
C2-C8 alkenyl, C1-C4 alkyl substituted by halogen, C3-C8 cycloalkyl or
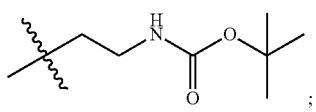 [SMILES: *CCNC(=O)OC(C)(C)C]
z=1-10; R$_{18}$ is C1-C4 alkyl or —H.
The above 4-substituted coumarin derivatives are with a structural formula of:
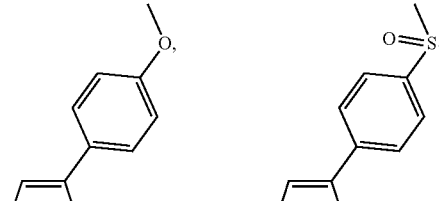
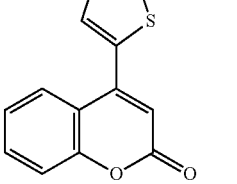
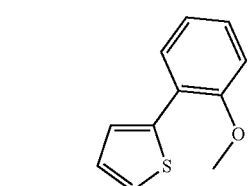
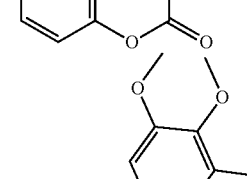
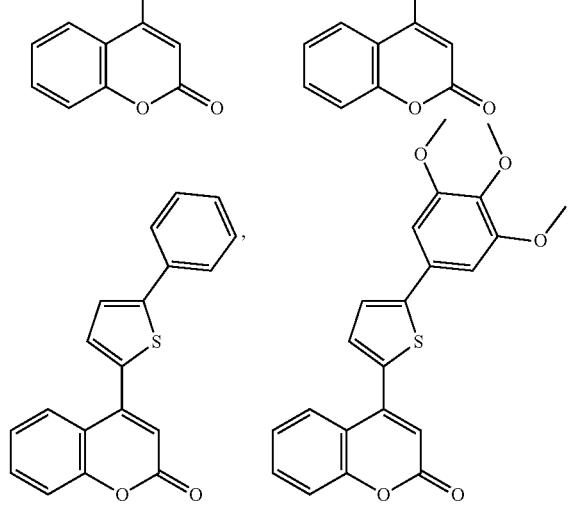
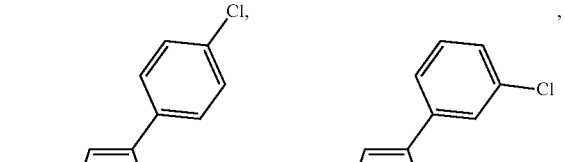
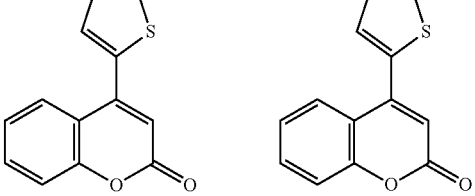
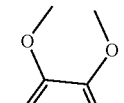
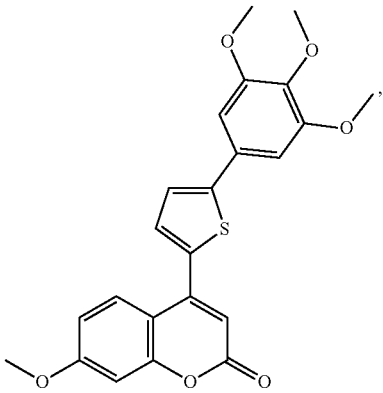
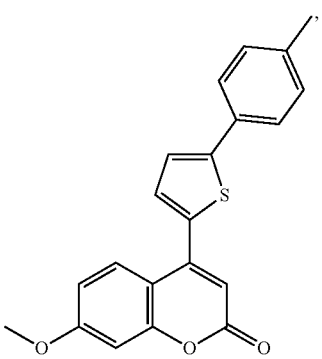
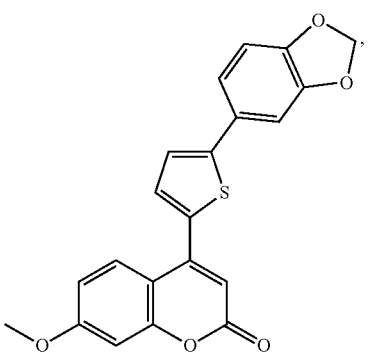

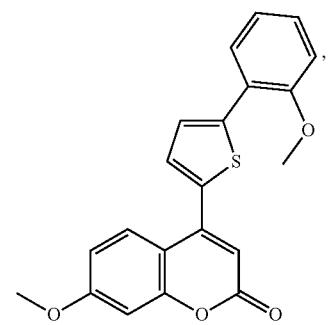
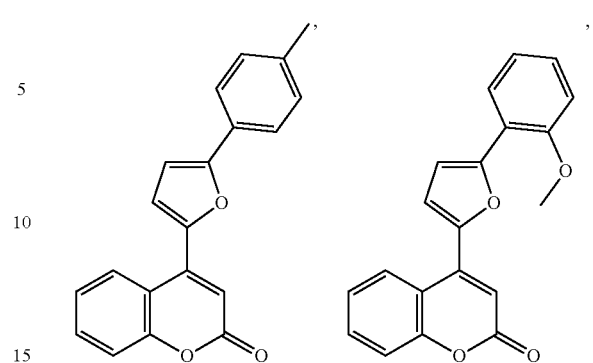
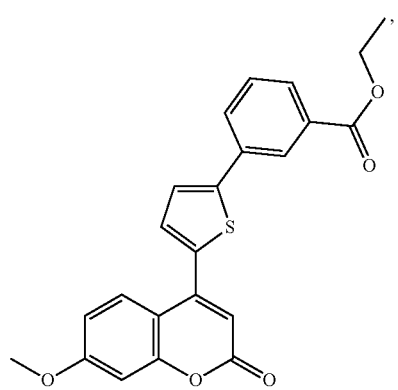
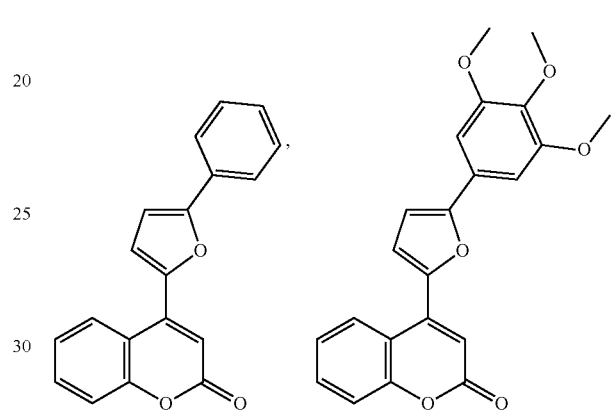
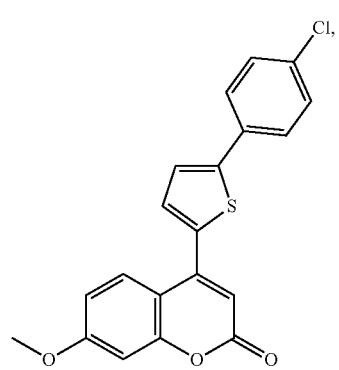
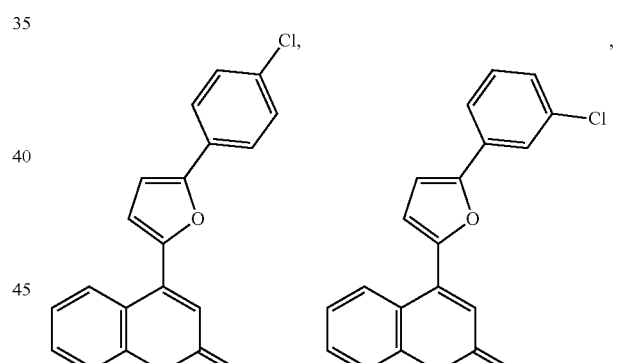
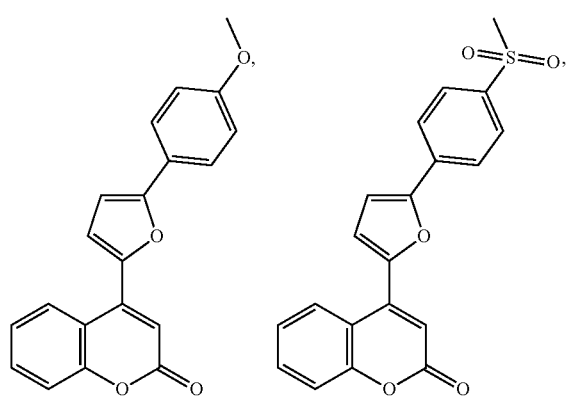
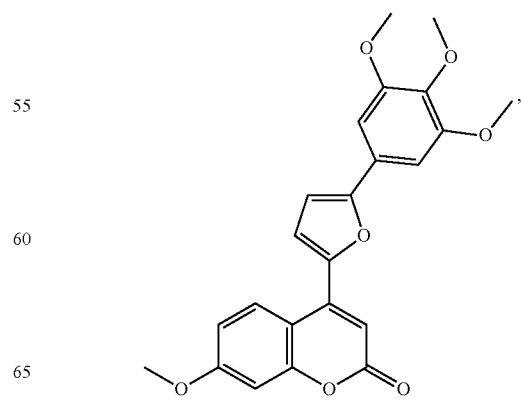

-continued
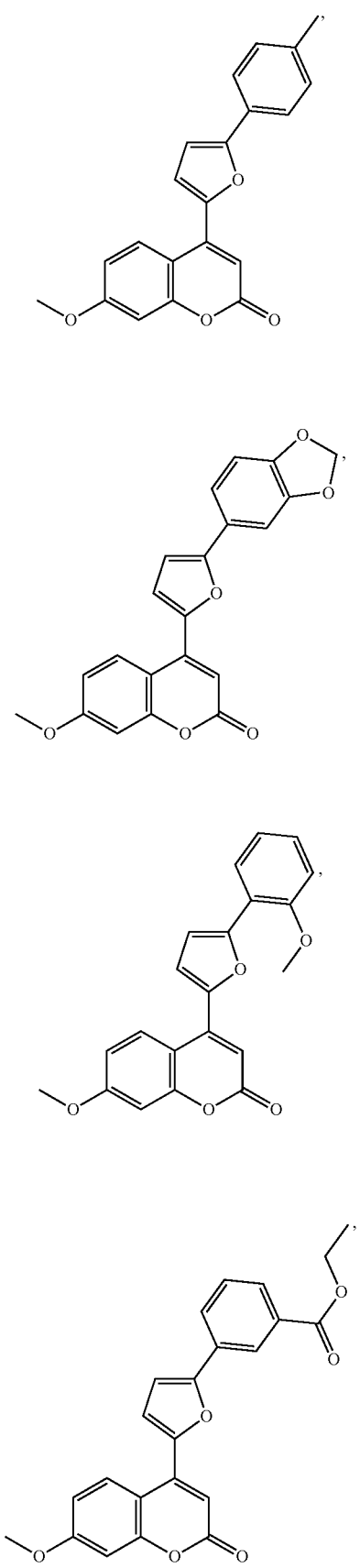
-continued
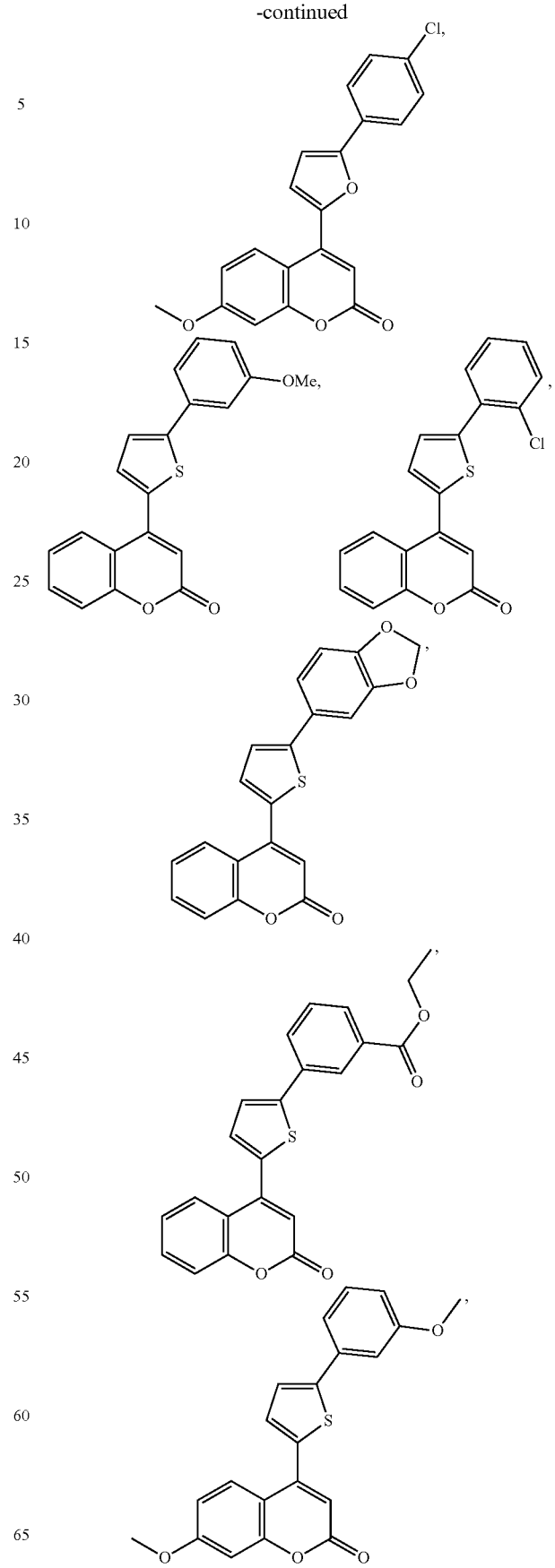

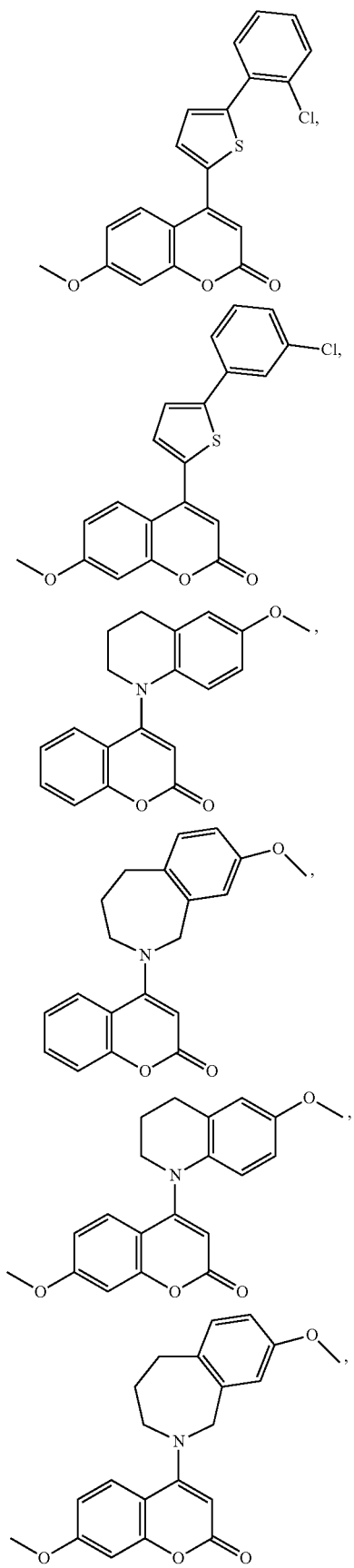
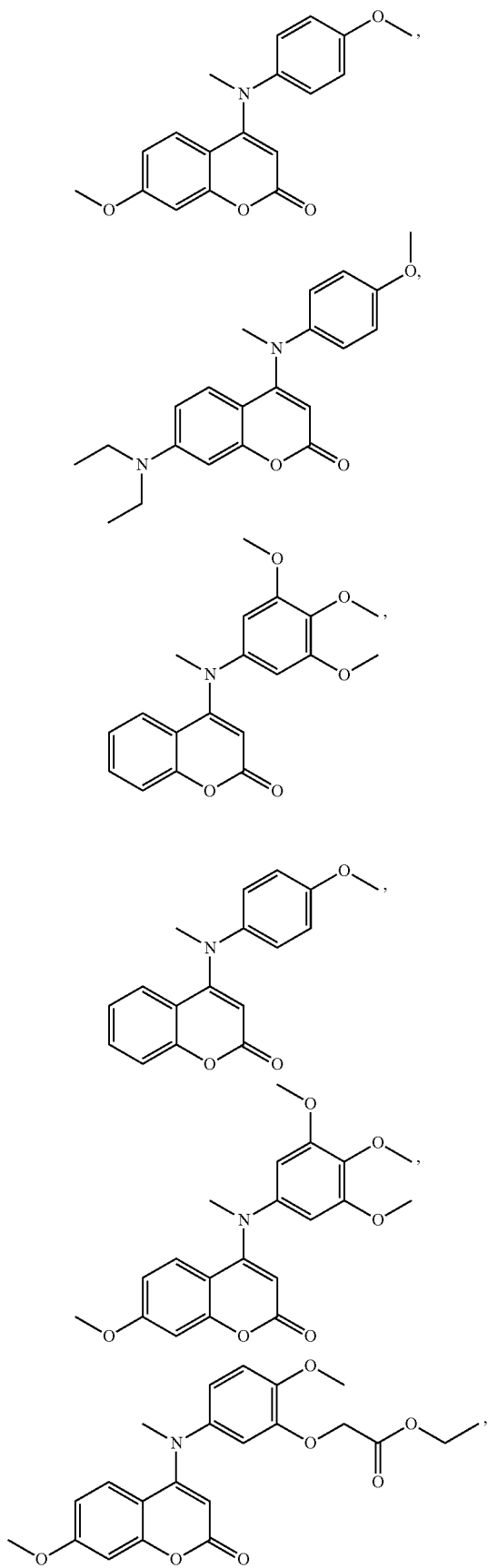

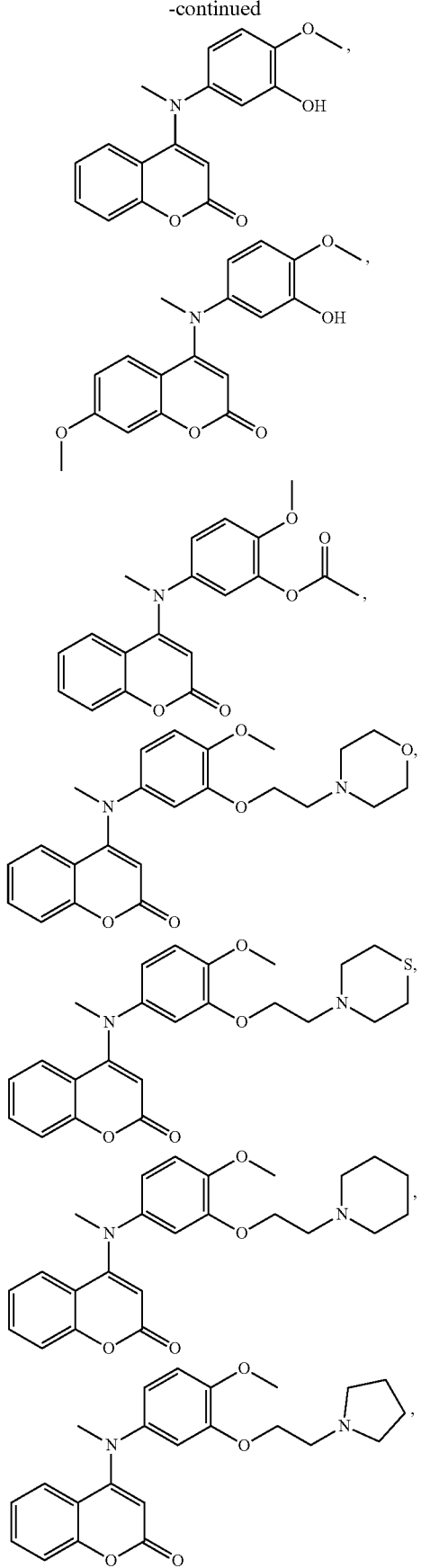
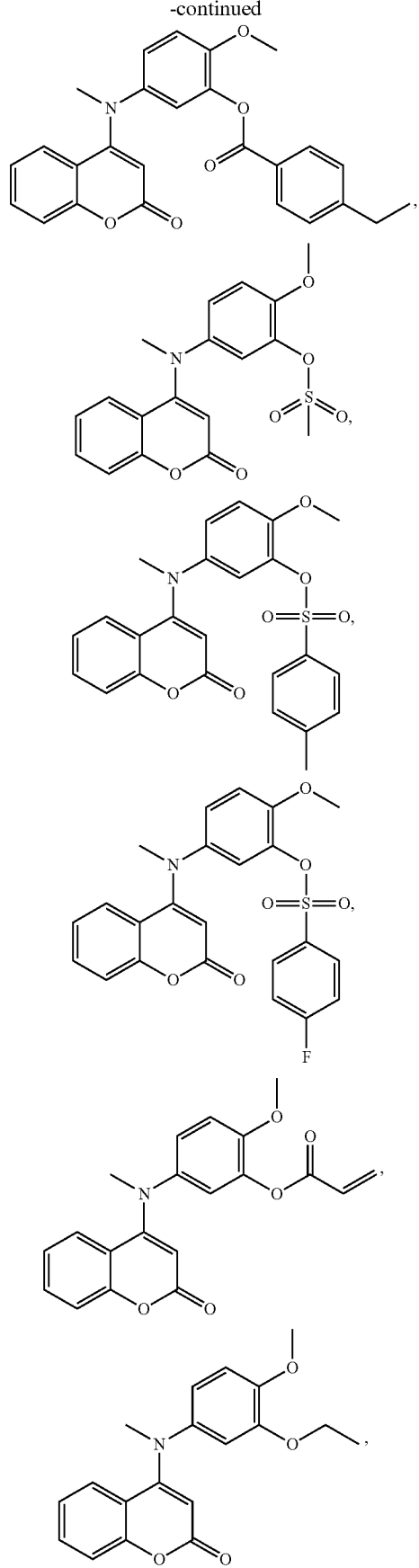

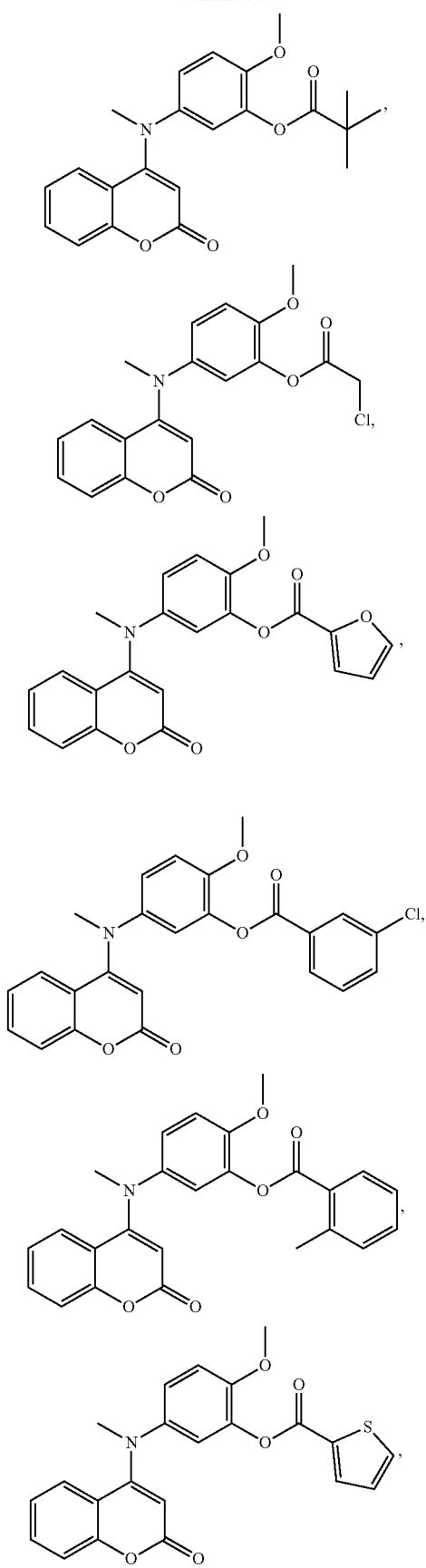
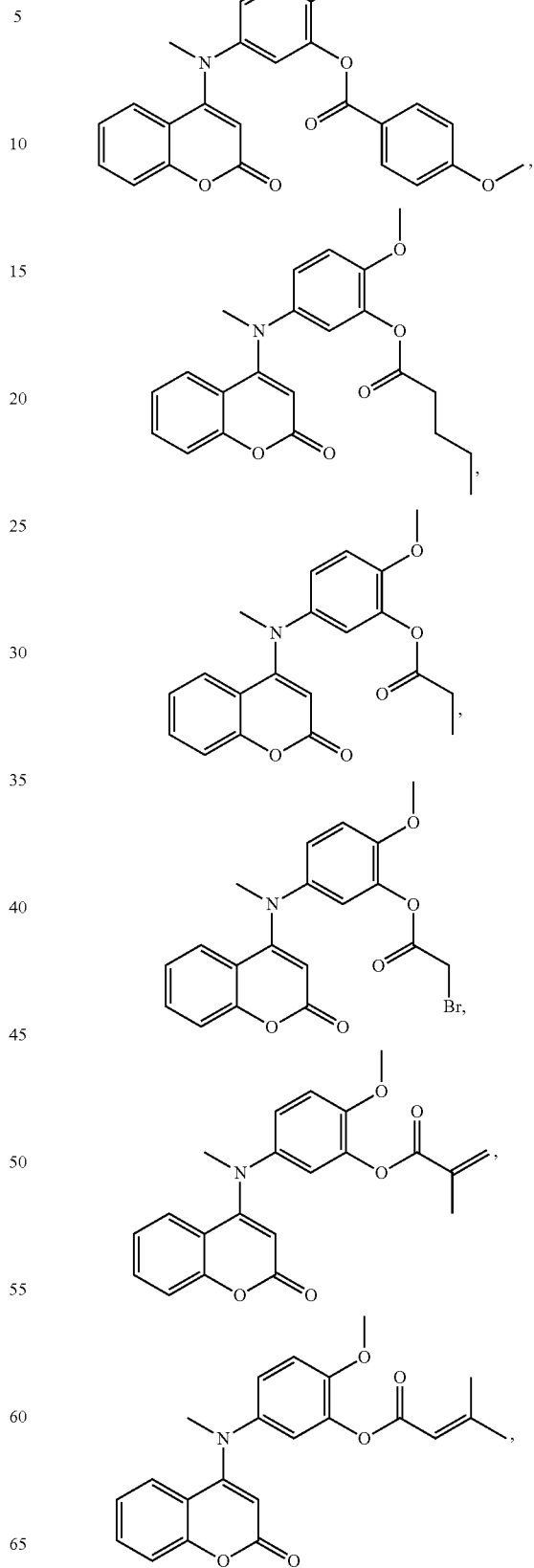

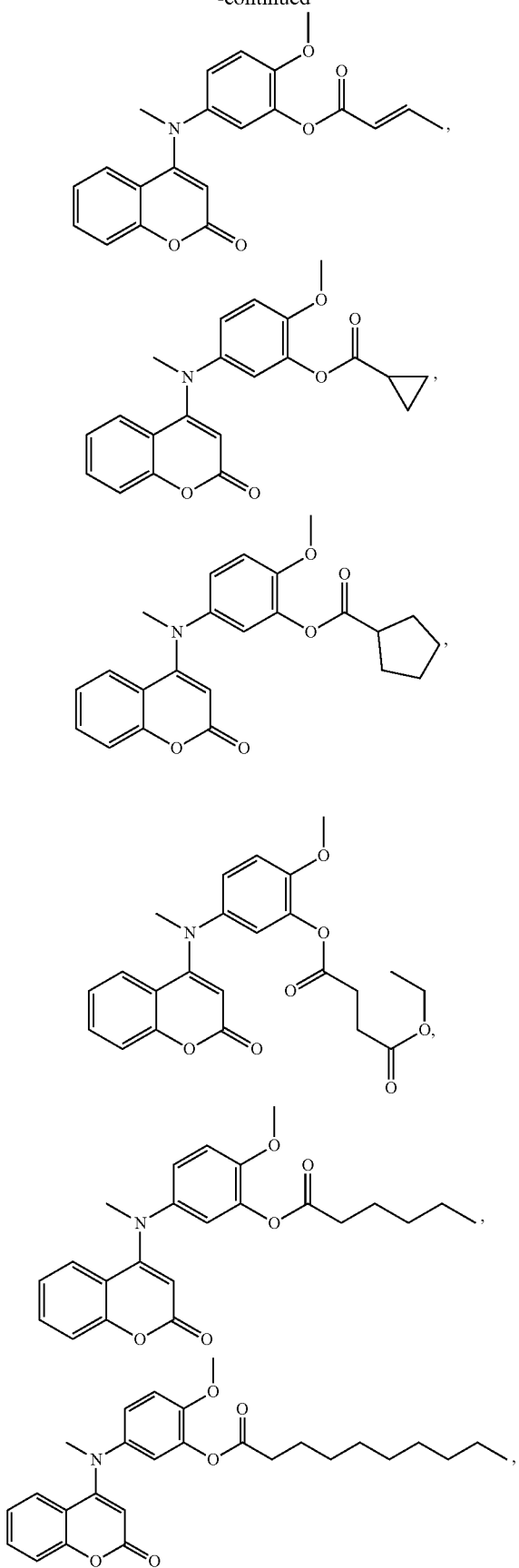
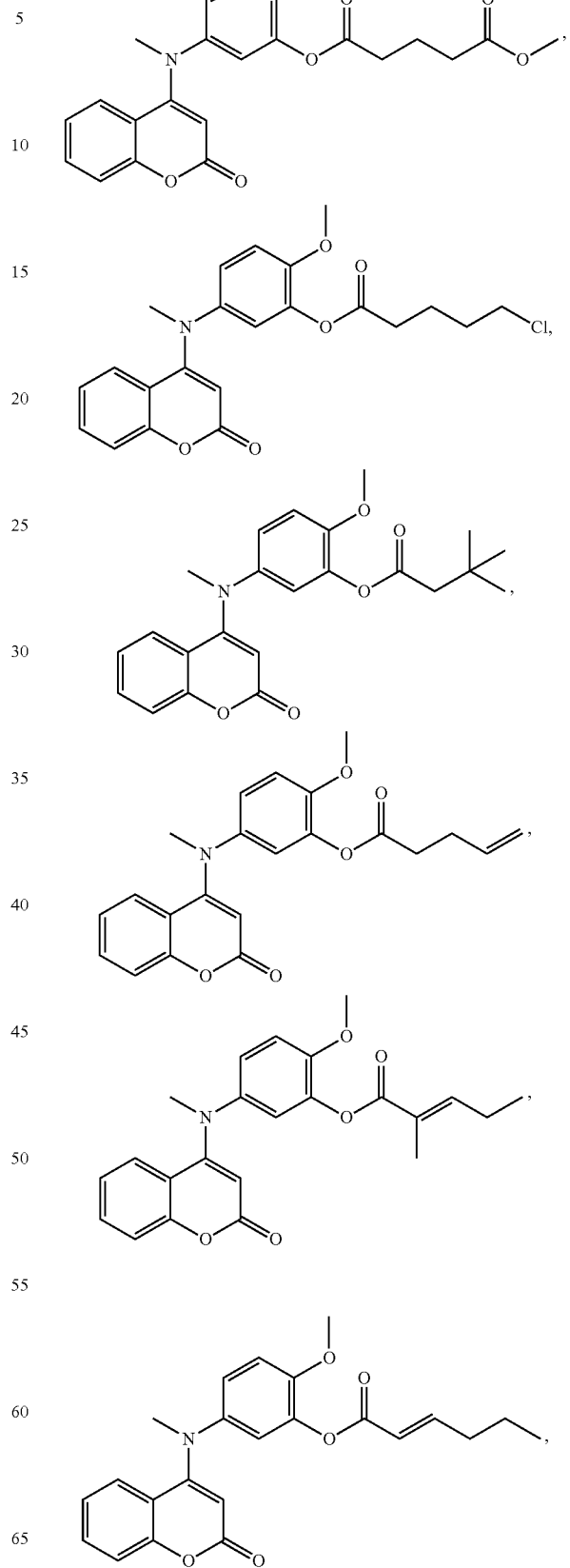

51
-continued
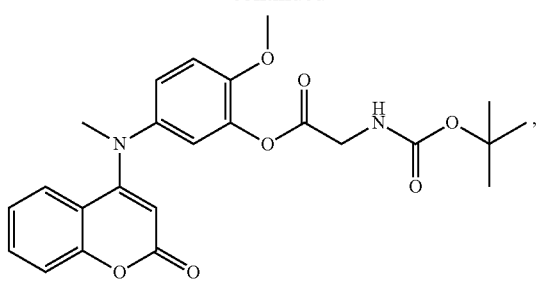
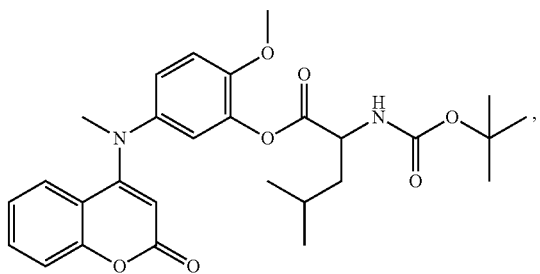
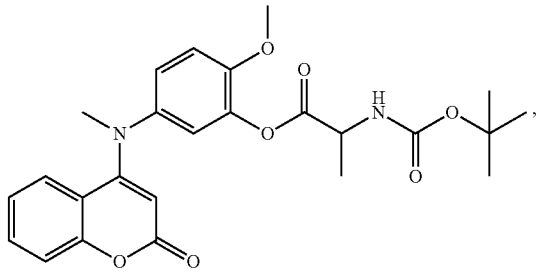
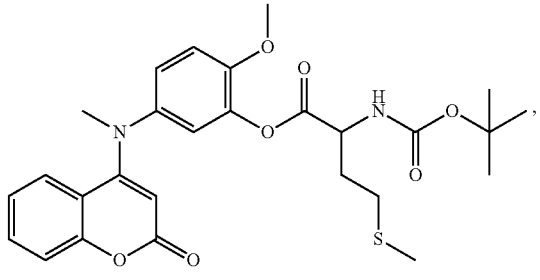
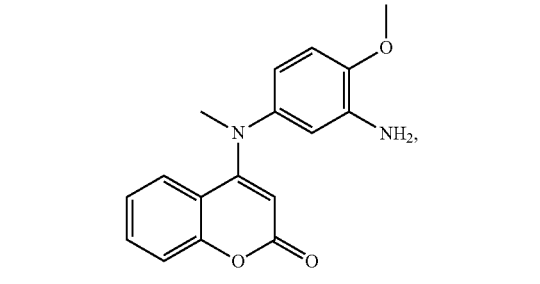
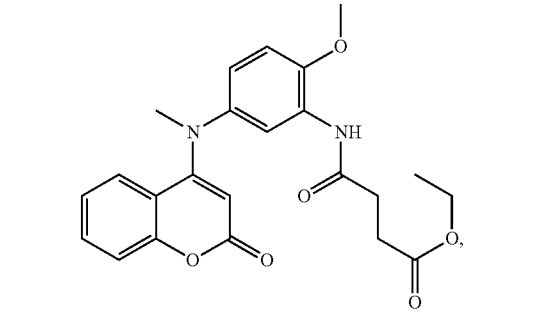
52
-continued
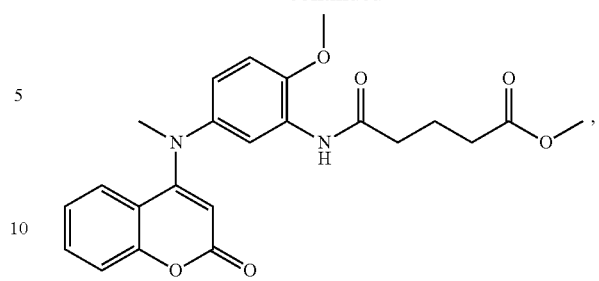
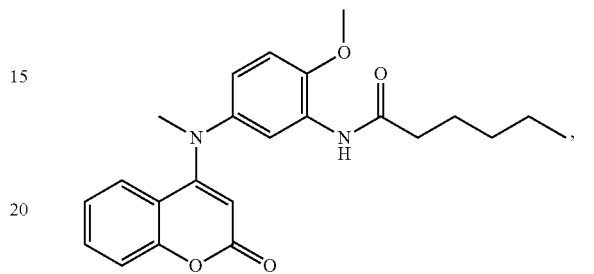
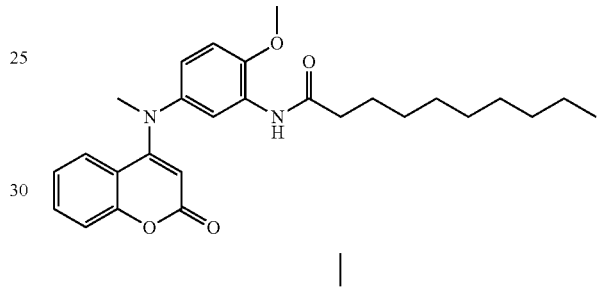
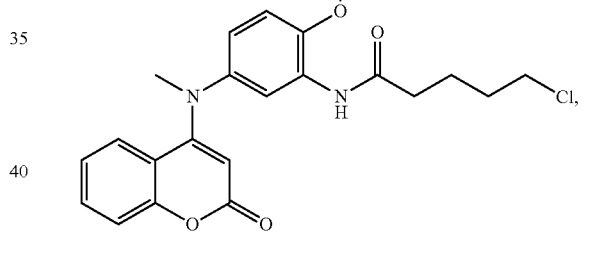
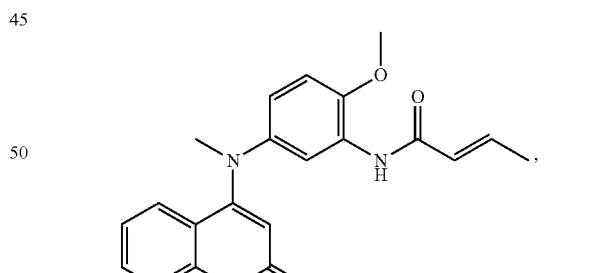
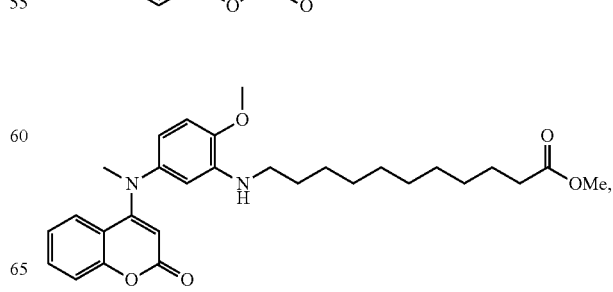

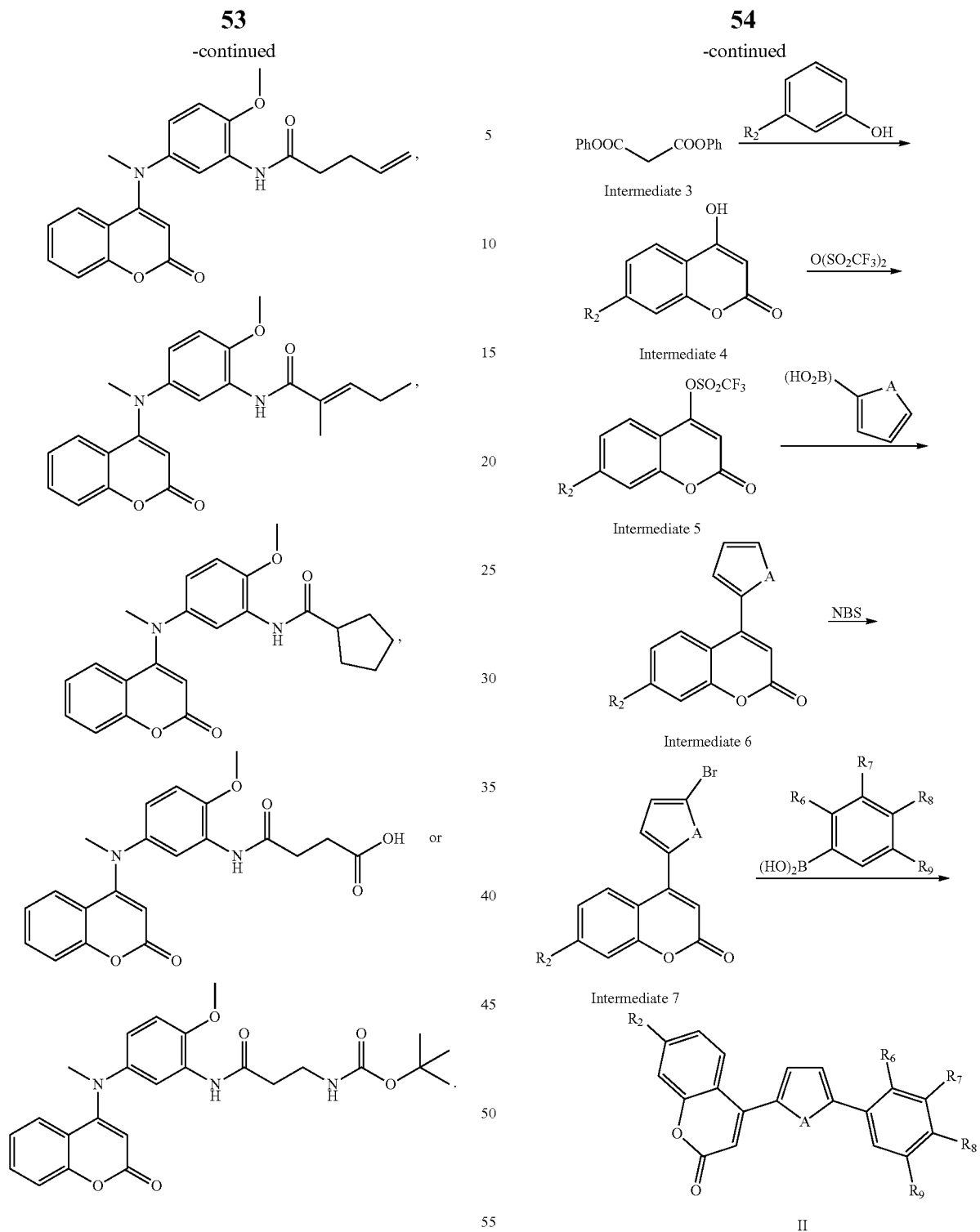
The Invention also provides preparation methods for the above 4-substituted coumarin derivatives.
wherein, A is O or S; $R_2$ is C1-C8 alkoxy, —H,
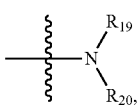
C1-C8 alkyl, halogen or C3-C8 cycloalkyl; $R_6$-$R_9$ are each independently —H, C1-C8 alkoxy, halogen, C1-C8 alkyl,
Reaction route I:
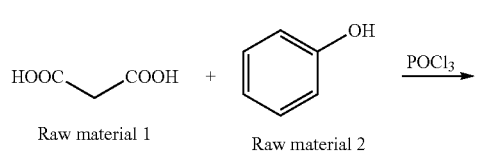

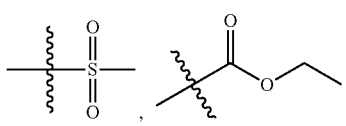

or C1-C8 alkyl substituted by halogen; $R_{19}$ and $R_{20}$ are each independently C1-C8 alkyl, halogen or —H.

Specific steps of the above reaction route I are as follows:

1) Firstly, make 10-20 equivalents of phosphorus oxychloride and 1 equivalent of raw material 1 (malonic acid) react for 2 hours under 80-100° C., remove the unreacted phosphorus oxychloride, then make it react with 2-3 equivalents of raw material 2 (phenol) for 6-8 hours under 25-50° C. in organic solvent to obtain intermediate 3; the organic solvent is any one selected from N,N-dimethyl formamide (DMF), methyl alcohol, ethyl alcohol, methylbenzene, ethyl acetate, pyridine, tetrahydrofuran, dichloromethane or carbon tetrachloride.

2) Put 1 equivalent of intermediate 3, 1-2 equivalents of

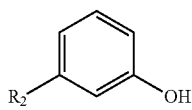

and 3-5 equivalents of alkali in organic solvent for reaction by reflux technique for 6-12 hours to obtain intermediate 4; the alkali is any one selected from triethylamine, diisopropyl ethylamine (DIPEA), pyridine, potassium carbonate, sodium carbonate, potassium hydroxide, sodium hydroxide or sodium hydride; the organic solvent is any one selected from N,N-dimethyl formamide (DMF), methyl alcohol, ethyl alcohol, methylbenzene, ethyl acetate, pyridine, tetrahydrofuran, dichloromethane or carbon tetrachloride;

3) Dissolve 1 equivalent of intermediate 4 and 2-4 equivalents of trifluoromethanesulfonic anhydride in organic solvent for reaction for 2-8 hours under 0-50° C. to obtain intermediate 5; the organic solvent is any one selected from N,N-dimethyl formamide (DMF), methyl alcohol, ethyl alcohol, methylbenzene, ethyl acetate, pyridine, tetrahydrofuran, dichloromethane or carbon tetrachloride;

4) Dissolve 1 equivalent of intermediate 5 and 1 equivalent of

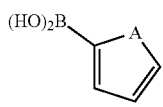

in organic solvent and add 2-5 equivalents of alkali and 0.3%-0.8% equivalents of catalyst for reaction by reflux technique to obtain intermediate 6; the alkali is any one selected from triethylamine, diisopropyl ethylamine (DIPEA), pyridine, potassium carbonate, sodium carbonate, potassium hydroxide, sodium hydroxide or sodium hydride; the organic solvent is any one selected from N,N-dimethyl formamide (DMF), methyl alcohol, ethyl alcohol, methylbenzene, ethyl acetate, pyridine, tetrahydrofuran, dichloromethane or carbon tetrachloride; the catalyst is any one selected from palladium acetate, palladium dichloride, palladium on activated carbon (10% Pd) and tetrakis (triphenylphosphine) palladium;

5) Dissolve 1 equivalent of intermediate 6 in organic solvent to react with 1-2 equivalents of NBS (N-bromosuccinimide) to obtain intermediate 7; the organic solvent is any one selected from N,N-dimethyl formamide (DMF), methyl alcohol, ethyl alcohol, methylbenzene, ethyl acetate, pyridine, tetrahydrofuran, dichloromethane or carbon tetrachloride; the reaction temperature is 0-50° C. and the reaction time is 2-8 hours;

6) Dissolve 1 equivalent of intermediate 7 and 1 equivalent of

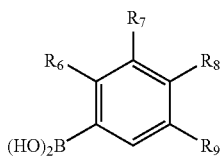

in organic solvent and add 2-5 equivalents of alkali and 0.3%-0.8% equivalents of catalyst for reaction by reflux technique to obtain compound of Formula II; the alkali is any one selected from triethylamine, diisopropyl ethylamine (DIPEA), pyridine, potassium carbonate, sodium carbonate, potassium hydroxide, sodium hydroxide or sodium hydride; the organic solvent is any one selected from N,N-dimethyl formamide (DMF), methyl alcohol, ethyl alcohol, methylbenzene, ethyl acetate, pyridine, tetrahydrofuran, dichloromethane or carbon tetrachloride; the catalyst is any one selected from palladium acetate, palladium dichloride, palladium on activated carbon (10% Pd) and tetrakis (triphenylphosphine) palladium; the reaction time is 2-24 hours.

Reaction route II:

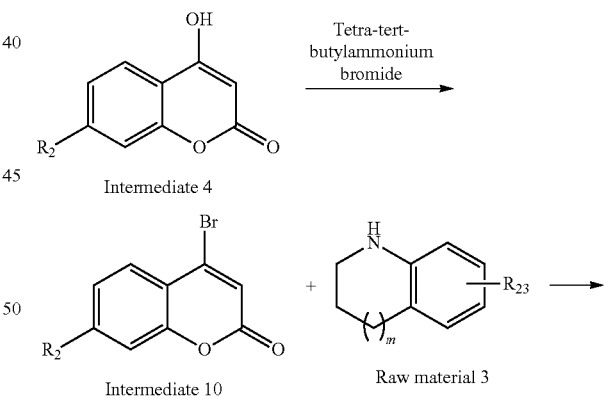

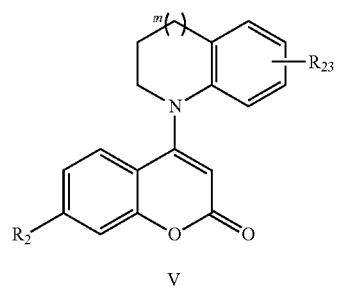

wherein, $R_2$ is C1-C8 alkoxy, —H,

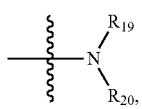

C1-C8 alkyl, halogen or C3-C8 cycloalkyl; $R_{19}$ and $R_{20}$ are each independently C1-C8 alkyl, halogen or —H; $R_{23}$ is C1-C4 alkoxy.

Specific steps of the above reaction route II are as follows:

1) Put 1 equivalent of intermediate 4 and 2-3 equivalents of tetra-tert-butylammonium bromide in organic solvent for reaction by reflux technique to obtain intermediate 10; the organic solvent is any one selected from N,N-dimethyl formamide (DMF), methyl alcohol, ethyl alcohol, methylbenzene, ethyl acetate, pyridine, tetrahydrofuran, dichloromethane or carbon tetrachloride; the reaction time is 2-8 hours;

2) Dissolve 1 equivalent of intermediate 10 in organic solvent, add 2-5 equivalents of alkali and 1 equivalent of

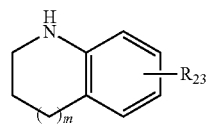

for reaction by reflux technique to obtain compound of Formula V; the alkali is any one selected from triethylamine, diisopropyl ethylamine (DIPEA), pyridine, potassium carbonate, sodium carbonate, potassium hydroxide, sodium hydroxide or sodium hydride; the organic solvent is any one selected from N,N-dimethyl formamide (DMF), methyl alcohol, ethyl alcohol, methylbenzene, ethyl acetate, pyridine, tetrahydrofuran, dichloromethane or carbon tetrachloride; the reaction time is 2-24 hours.

Reaction route III:

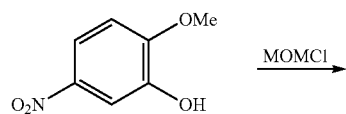

Raw material 4

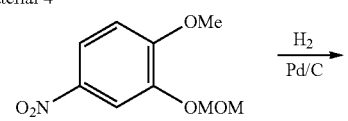

Intermediate 11

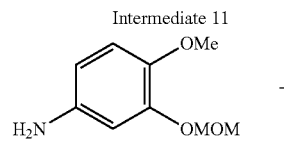

Intermediate 12

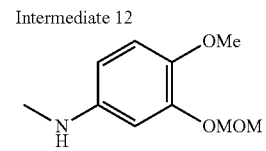

Intermediate 13

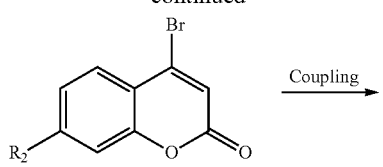

Intermediate 10

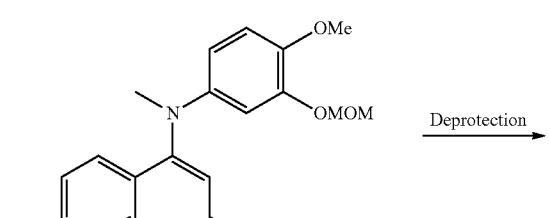

Intermediate 14

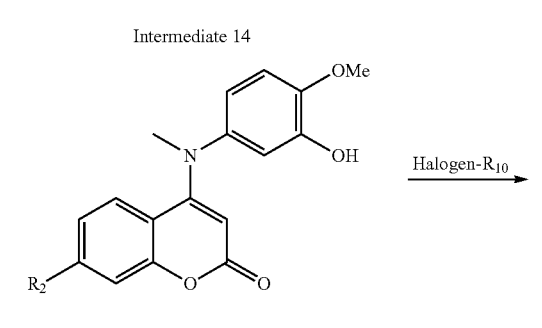

Intermediate 15

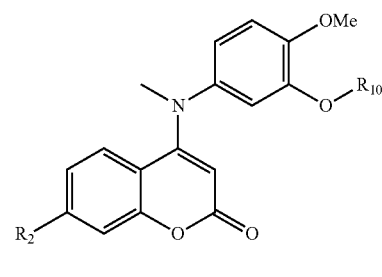

III wherein, $R_2$ is C1-C8 alkoxy, —H,

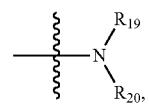

C1-C8 alkyl, halogen or C3-C8 cycloalkyl; $R_{10}$ is

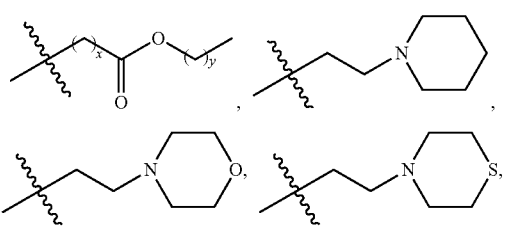

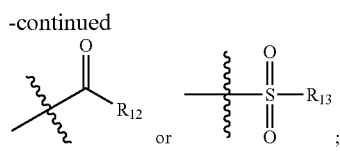

x=1-4, y=1-4; R$_{12}$ is C1-C10 alkyl,

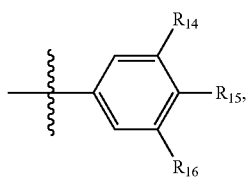

halogen, C2-C8 alkenyl, C1-C8 alkyl substituted by halogen, C3-C8 cycloalkyl,

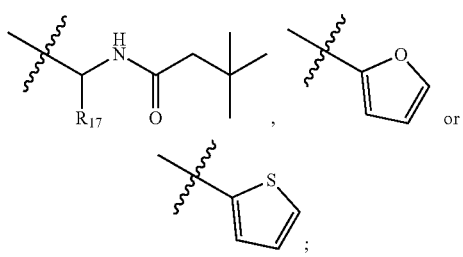

R$_{13}$ is C1-C8 alkyl, phenyl substituted by C1-C8 alkyl or phenyl substituted by halogen; R$_{14}$-R$_{16}$ are each independently C1-C8 alkyl, halogen, —H, C1-C8 alkoxy or —NH$_2$, and are not —H at the same time; R$_{17}$ is C1-C8 alkyl, halogen, —H or

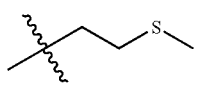

Specific steps of the above reaction route III are as follows:

1) Dissolve 1 equivalent of raw material 4 in organic solvent, dropwise add 3-5 equivalents of chloromethyl methyl ether (MOMCl) for reaction to obtain intermediate 11; the organic solvent is any one selected from N,N-dimethyl formamide (DMF), methyl alcohol, ethyl alcohol, methylbenzene, ethyl acetate, pyridine, tetrahydrofuran, dichloromethane or carbon tetrachloride; the reaction temperature is 0-80° C. and the reaction time is 2-12 hours;

2) Dissolve 1 equivalent of intermediate 11 in organic solvent, add 1%-2% equivalents of palladium-activated carbon catalyst, feed 5-20 equivalents of hydrogen for reduction reaction to obtain intermediate 12; the palladium catalyst is palladium on activated carbon with 10% Pd; the organic solvent is any one selected from N,N-dimethyl formamide (DMF), methyl alcohol, ethyl alcohol, methylbenzene, ethyl acetate, pyridine, tetrahydrofuran, dichloromethane or carbon tetrachloride; the reaction temperature is 0-40° C. and the reaction time is 2-12 hours;

3) Dissolve 1 equivalent of intermediate 12 in organic solvent, add 3-5 equivalents of sodium methoxide, add 1-3 equivalents of paraformaldehyde, stir for reaction overnight, add 1-2 equivalents of sodium borohydride in the reaction substrate for reaction by reflux technique to obtain compound 13; the organic solvent is any one selected from N,N-dimethyl formamide (DMF), methyl alcohol, ethyl alcohol, methylbenzene, ethyl acetate, pyridine, tetrahydrofuran, dichloromethane or carbon tetrachloride; the reflux temperature is 0-80° C. and the reflux time is 2-12 hours;

4) Dissolve 1 equivalent of compound 13 and 1 equivalent of intermediate 10 in organic solvent, add 2-3 equivalents of alkali for reaction by reflux technique to obtain intermediate 14; the alkali is any one selected from triethylamine, diisopropyl ethylamine (DIPEA), pyridine, potassium carbonate, sodium carbonate, potassium hydroxide, sodium hydroxide or sodium hydride; the organic solvent is any one selected from N,N-dimethyl formamide (DMF), methyl alcohol, ethyl alcohol, methylbenzene, ethyl acetate, pyridine, tetrahydrofuran, dichloromethane or carbon tetrachloride; the reaction time is 2-24 hours;

5) Dissolve 1 equivalent of intermediate 14 in organic solvent, add 2-3 equivalents of acids for reaction to obtain intermediate 15; the acid is any one selected from concentrated hydrochloric acid, hydrogen chloride-ethyl acetate solution, trifluoroacetic acid, methanesulfonic acid or sulfuric acid; the organic solvent is any one selected from N,N-dimethyl formamide (DMF), methyl alcohol, ethyl alcohol, methylbenzene, ethyl acetate, pyridine, tetrahydrofuran, dichloromethane or carbon tetrachloride; the reaction temperature is 40-100° C. and the reaction time is 2-24 hours;

6) Dissolve 1 equivalent of intermediate 15 in organic solvent, add 2-3 equivalents of alkali, add 1-3 equivalents of halogen-R$_{10}$ for reaction to obtain compound of Formula III; the alkali used in the reaction is any one selected from triethylamine, diisopropyl ethylamine (DIPEA), pyridine, potassium carbonate, sodium carbonate, potassium hydroxide, sodium hydroxide or sodium hydride; the organic solvent is any one selected from N,N-dimethyl formamide (DMF), methyl alcohol, ethyl alcohol, methylbenzene, ethyl acetate, pyridine, tetrahydrofuran, dichloromethane or carbon tetrachloride; the reaction temperature is 0-60° C. and the reaction time is 1-12 hours.

Reaction route IV:

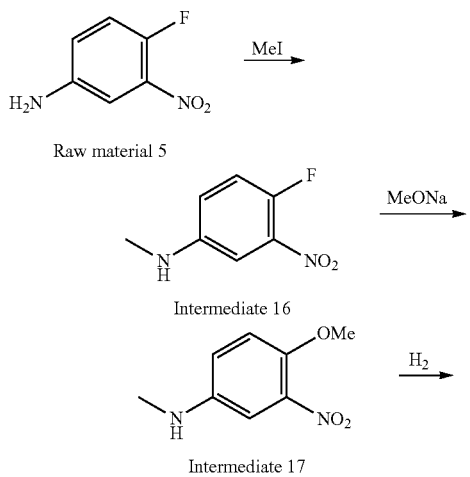

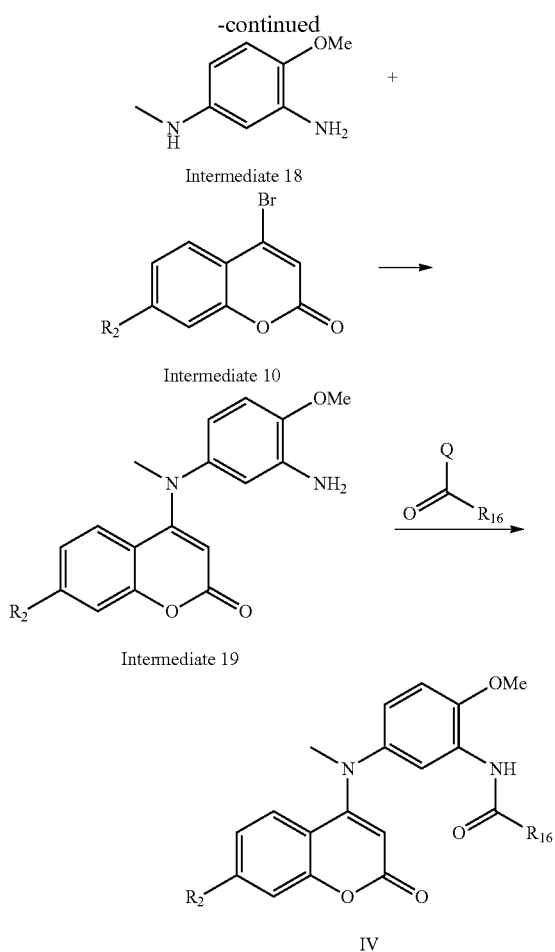

Intermediate 18

Intermediate 10

Intermediate 19

IV wherein, Q is halogen; $R_{11}$ is C1-C10 alkyl,

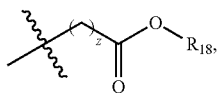

C2-C8 alkenyl, C1-C4 alkyl substituted by halogen, C3-C8 cycloalkyl,

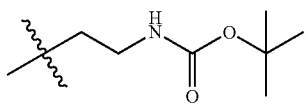 [SMILES: *CCNC(=O)OC(C)(C)C]

or —$NH_2$; z=1-10; $R_{18}$ is C1-C4 alkyl, halogen or —H.

Specific steps of the above reaction route IV are as follows:

1) Dissolve 1 equivalent of raw material 5 in organic solvent, add 2-3 equivalents of alkali, dropwise add 2-3 equivalents of iodomethane for reaction to obtain intermediate 16; the alkali is any one selected from triethylamine, diisopropyl ethylamine (DIPEA), pyridine, potassium carbonate, sodium carbonate, potassium hydroxide, sodium hydroxide or sodium hydride; the organic solvent is any one selected from N,N-dimethyl formamide (DMF), methyl alcohol, ethyl alcohol, methylbenzene, ethyl acetate, pyridine, tetrahydrofuran, dichloromethane or carbon tetrachloride; the reaction temperature is 0-60° C. and the reaction time is 1-12 hours;

2) Dissolve 1 equivalent of intermediate 16 in organic solvent, add 3-5 equivalents of sodium methoxide for reaction by reflux technique to obtain intermediate 17; the organic solvent is any one selected from N,N-dimethyl formamide (DMF), methyl alcohol, ethyl alcohol, methylbenzene, ethyl acetate, pyridine, tetrahydrofuran, dichloromethane or carbon tetrachloride; the reaction time is 2-24 hours;

3) Dissolve 1 equivalent of intermediate 17 in organic solvent, add 1%-2% equivalents of palladium on activated carbon, feed 5-20 equivalents of hydrogen for reduction reaction to obtain intermediate 18; the organic solvent is any one selected from N,N-dimethyl formamide (DMF), methyl alcohol, ethyl alcohol, methylbenzene, ethyl acetate, pyridine, tetrahydrofuran, dichloromethane or carbon tetrachloride; the reaction temperature can be 20-100° C. and the reaction time is 2-24 hours;

4) Dissolve 1 equivalent of intermediate 18 and 1 equivalent of intermediate 10 in organic solvent, add 2-5 equivalents of alkali for reaction by reflux technique to obtain intermediate 19; the alkali is any one selected from triethylamine, diisopropyl ethylamine (DIPEA), pyridine, potassium carbonate, sodium carbonate, potassium hydroxide, sodium hydroxide or sodium hydride; the organic solvent is any one selected from N,N-dimethyl formamide (DMF), methyl alcohol, ethyl alcohol, methylbenzene, ethyl acetate, pyridine, tetrahydrofuran, dichloromethane or carbon tetrachloride; the reaction time is 2-24 hours;

5) Dissolve intermediate 19 in organic solvent, add 2-5 equivalents of alkali, add 1-3 equivalents of

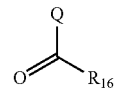

for reaction by reflux technique to obtain compound of Formula IV; the alkali is any one selected from triethylamine, diisopropyl ethylamine (DIPEA), pyridine, potassium carbonate, sodium carbonate, potassium hydroxide, sodium hydroxide or sodium hydride; the organic solvent is any one selected from N,N-dimethyl formamide (DMF), methyl alcohol, ethyl alcohol, methylbenzene, ethyl acetate, pyridine, tetrahydrofuran, dichloromethane or carbon tetrachloride; the reaction temperature can be 0-60° C. and the reaction time is 1-12 hours.

The Invention also provides the pharmaceutically acceptable salts of the above 4-substituted coumarin derivatives.

The Invention also provides the drug combinations composed of active ingredients, i.e., the 4-substituted coumarin derivatives as shown in Formula I-IV and their salts, plus a pharmaceutically acceptable carrier.

The Invention also provides the uses of the above 4-substituted coumarin derivatives and their salts in the preparation of antineoplastic drugs.

Preferably, the antineoplastic drugs are drugs which antagonize lung cancer, colon cancer, prostate cancer, ovarian cancer and breast cancer.

The targets of the antineoplastic drugs are human non-small cell lung carcinoma NCI-H460, human small cell lung cancer cell NCI-H446, human hepatocellular carcinoma cell strain HepG2, human colon carcinoma cell strain HCT116, human prostate cancer PC-3 and human melanoma A375.

The Invention also provides the uses of the above 4-substituted coumarin derivatives and their salts in the preparation of drugs for curing sensitive and drug-resistant cancer cells.

The Invention also provides the uses of the above 4-substituted coumarin derivatives and their salts in the preparation of drugs for curing inflammations.

The Invention also provides the above 4-substituted coumarin derivatives and their salts existing in form of pharmaceutically acceptable preparations including tablets, oral agents, suppositories, dripping pills, infusion solutions, injection solutions, freeze-dried powders for injections, capsules, aerosols, dispersible tablets, ointments, and including various sustained-release/controlled-release preparations or nano preparations. Administration of the above 4-substituted coumarin derivatives and their salts adopts the form of unit dose, and the injection includes intravenous injection, intramuscular injection, subcutaneous injection and intraperitoneal injection.

The above tablets and capsules can contain: binding agent (such as gum arabic, corn starch or gelatin), excipient (such as dicalcium phosphate); disintegrating agent (such as corn starch, potato starch, alginic acid, etc.), lubricant (such as magnesium stearate), sweetener (such as sucrose, fructose, lactose, etc.) or flavoring agent (such as mint, etc.). When the preparation is capsule, it can also contain liquid carrier (such as vegetable oil or polyethylene glycol).

In addition, the active compounds based on the 4-substituted coumarin derivatives and their salts provided in the Invention can be incorporated in sustained-release preparations and devices.

The active compounds based on the 4-substituted coumarin derivatives and their salts provided in the Invention can also be administrated through infusion or injection into veins or peritonea.

The active compounds based on the 4-substituted coumarin derivatives and their salts provided in the Invention can also be used to prepare their aqueous solutions, or to mix with non-toxic surfactants, and can also be used to prepare at least one of dispersants from glycerin, liquid macrogol and triglyceride. The above preparations also contain preservatives to prevent growth of microorganisms.

The drug preparations for injection or infusion can contain aseptic aqueous solution, dispersant or sterile powder of the active compounds based on the 4-substituted coumarin derivatives and their salts provided in the Invention. The liquid carrier of the dispersant can be solvent or liquid dispersion medium, including at least one selected from water, ethyl alcohol, polyol (such as glycerin, propylene glycol, liquid macrogol, etc.), vegetable oil or non-toxic glyceride.

In addition, it also includes drugs prepared by application of new drug preparations such as liposome, fat emulsion, microsphere and nanosphere, for example, by applying particle dispersion system, including polymericmicelles, nanoemulsion, submicroemuls, microcapsule, microsphere, liposome and niosomes, etc.

The compounds provided in the Invention have strong anti-tumor activity with the $IC_{50}$ value of plural tumor cell strains between 0.01-5 nM, and it also has relatively good effect in inhibition of microtubule polymerization and has diversified biological activities and low toxicity, providing new options for preparing drugs for curing sensitive and drug-resistant cancer cells.

DETAILED DESCRIPTION OF THE PREFERRED EMBODIMENTS

Figure 1:
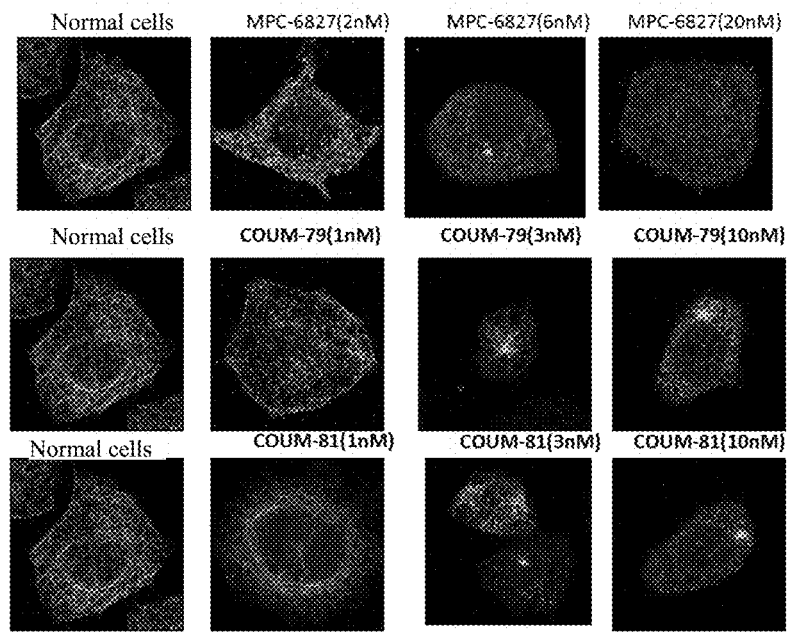
FIG. 1 Depolymerization of some compounds on microtubule.

Preparation methods for the 4-substituted coumarin derivatives.

Reaction route I:

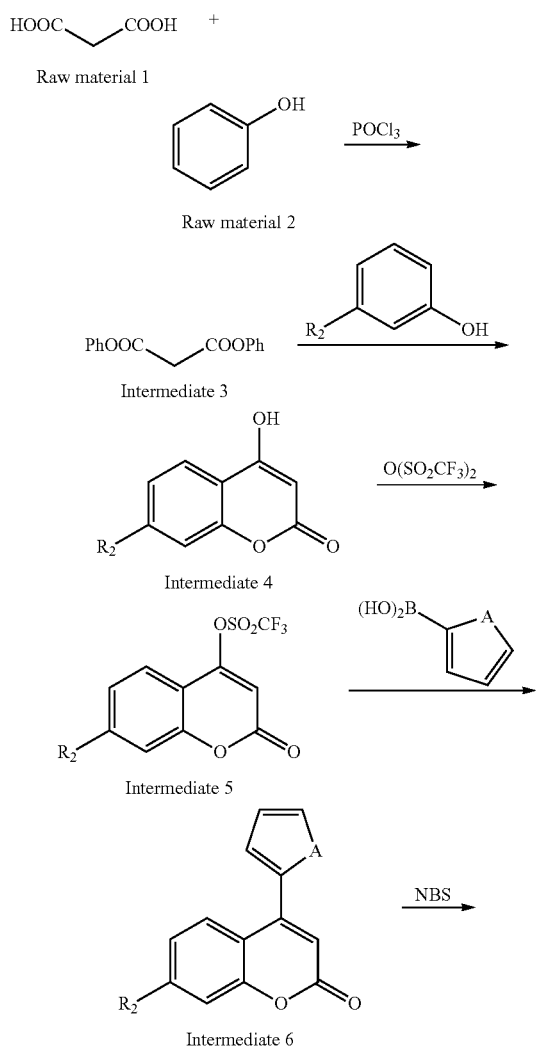

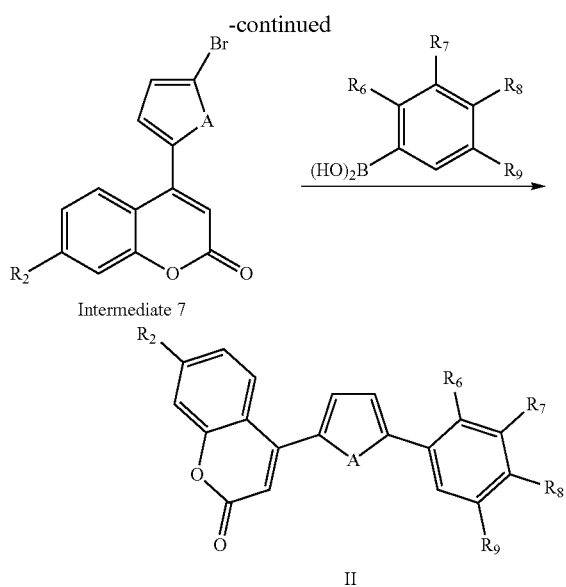

Intermediate 7

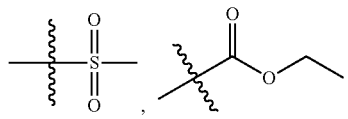

II wherein, A is O or S; R$_2$ is C1-C8 alkoxy, —H,

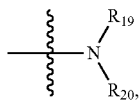

C1-C8 alkyl, halogen or C3-C8 cycloalkyl; R$_6$-R$_9$ are each independently —H, C1-C8 alkoxy, halogen, C1-C8 alkyl,

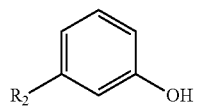

or C1-C8 alkyl substituted by halogen; R$_{19}$ and R$_{20}$ are each independently C1-C8 alkyl, halogen or —H.

Specific steps of the above reaction route I are as follows:

1) Firstly, make 10-20 equivalents of phosphorus oxychloride and 1 equivalent of raw material 1 (malonic acid) react for 2 hours under 80-100° C., remove the unreacted phosphorus oxychloride, then make it react with 2-3 equivalents of raw material 2 (phenol) for 6-8 hours under 25-50° C. in organic solvent to obtain intermediate 3; the organic solvent is any one selected from N,N-dimethyl formamide (DMF), methyl alcohol, ethyl alcohol, methylbenzene, ethyl acetate, pyridine, tetrahydrofuran, dichloromethane or carbon tetrachloride.

2) Put 1 equivalent of intermediate 3, 1-2 equivalents of and 3-5 equivalents of alkali in organic solvent for reaction by reflux technique for 6-12 hours to obtain intermediate 4; the alkali is any one selected from triethylamine, diisopropyl ethylamine (DIPEA), pyridine, potassium carbonate, sodium carbonate, potassium hydroxide, sodium hydroxide or sodium hydride; the organic solvent is any one selected from N,N-dimethyl formamide (DMF), methyl alcohol, ethyl alcohol, methylbenzene, ethyl acetate, pyridine, tetrahydrofuran, dichloromethane or carbon tetrachloride;

3) Dissolve 1 equivalent of intermediate 4 and 2-4 equivalents of trifluoromethanesulfonic anhydride in organic solvent for reaction for 2-8 hours under 0-50° C. to obtain intermediate 5; the organic solvent is any one selected from N,N-dimethyl formamide (DMF), methyl alcohol, ethyl alcohol, methylbenzene, ethyl acetate, pyridine, tetrahydrofuran, dichloromethane or carbon tetrachloride;

4) Dissolve 1 equivalent of intermediate 5 and 1 equivalent of

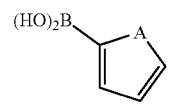

in organic solvent and add 2-5 equivalents of alkali and 0.3%-0.8% equivalents of catalyst for reaction by reflux technique to obtain intermediate 6; the alkali is any one selected from triethylamine, diisopropyl ethylamine (DIPEA), pyridine, potassium carbonate, sodium carbonate, potassium hydroxide, sodium hydroxide or sodium hydride; the organic solvent is any one selected from N,N-dimethyl formamide (DMF), methyl alcohol, ethyl alcohol, methylbenzene, ethyl acetate, pyridine, tetrahydrofuran, dichloromethane or carbon tetrachloride; the catalyst is any one selected from palladium acetate, palladium dichloride, palladium on activated carbon (10% Pd) and tetrakis (triphenylphosphine) palladium;

5) Dissolve 1 equivalent of intermediate 6 in organic solvent to react with 1-2 equivalents of NBS (N-bromosuccinimide) to obtain intermediate 7; the organic solvent is any one selected from N,N-dimethyl formamide (DMF), methyl alcohol, ethyl alcohol, methylbenzene, ethyl acetate, pyridine, tetrahydrofuran, dichloromethane or carbon tetrachloride; the reaction temperature is 0-50° C. and the reaction time is 2-8 hours;

6) Dissolve 1 equivalent of intermediate 7 and 1 equivalent of

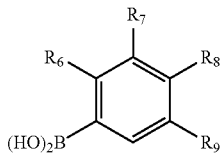

in organic solvent and add 2-5 equivalents of alkali and 0.3%-0.8% equivalents of catalyst for reaction by reflux technique to obtain compound of Formula II; the alkali is any one selected from triethylamine, diisopropyl ethylamine (DIPEA), pyridine, potassium carbonate, sodium carbonate, potassium hydroxide, sodium hydroxide or sodium hydride; the organic solvent is any one selected from N,N-dimethyl formamide (DMF), methyl alcohol, ethyl alcohol, methylbenzene, ethyl acetate, pyridine, tetrahydrofuran, dichloromethane or carbon tetrachloride; the catalyst is any one selected from palladium acetate, palladium dichloride, palladium on activated carbon (10% Pd) and tetrakis (triphenylphosphine) palladium; the reaction time is 2-24 hours.

Reaction route II:

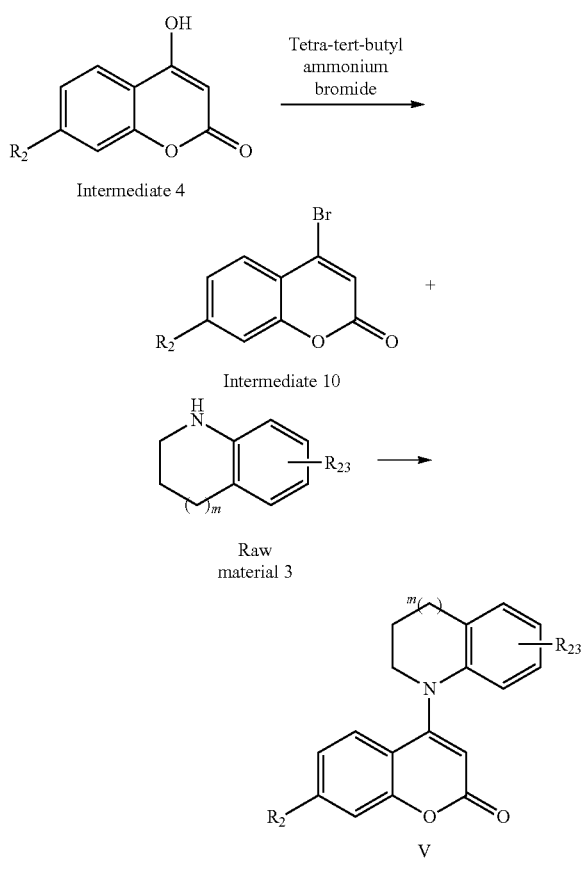

wherein, $R_2$ is C1-C8 alkoxy, —H,

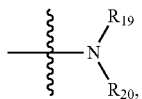

C1-C8 alkyl, halogen or C3-C8 cycloalkyl; $R_{19}$ and $R_{20}$ are each independently C1-C8 alkyl, halogen or —H; $R_{23}$ is C1-C4 alkoxy.

Specific steps of the above reaction route II are as follows:

1) Put 1 equivalent of intermediate 4 and 2-3 equivalents of tetra-tert-butylammonium bromide in organic solvent for reaction by reflux technique to obtain intermediate 10; the organic solvent is any one selected from N,N-dimethyl formamide (DMF), methyl alcohol, ethyl alcohol, methylbenzene, ethyl acetate, pyridine, tetrahydrofuran, dichloromethane or carbon tetrachloride; the reaction time is 2-8 hours;

2) Dissolve 1 equivalent of intermediate 10 in organic solvent, add 2-5 equivalents of alkali and 1 equivalent of

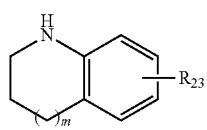

for reaction by reflux technique to obtain compound of Formula V; the alkali is any one selected from triethylamine, diisopropyl ethylamine (DIPEA), pyridine, potassium carbonate, sodium carbonate, potassium hydroxide, sodium hydroxide or sodium hydride; the organic solvent is any one selected from N,N-dimethyl formamide (DMF), methyl alcohol, ethyl alcohol, methylbenzene, ethyl acetate, pyridine, tetrahydrofuran, dichloromethane or carbon tetrachloride; the reaction time is 2-24 hours.

Reaction route III:

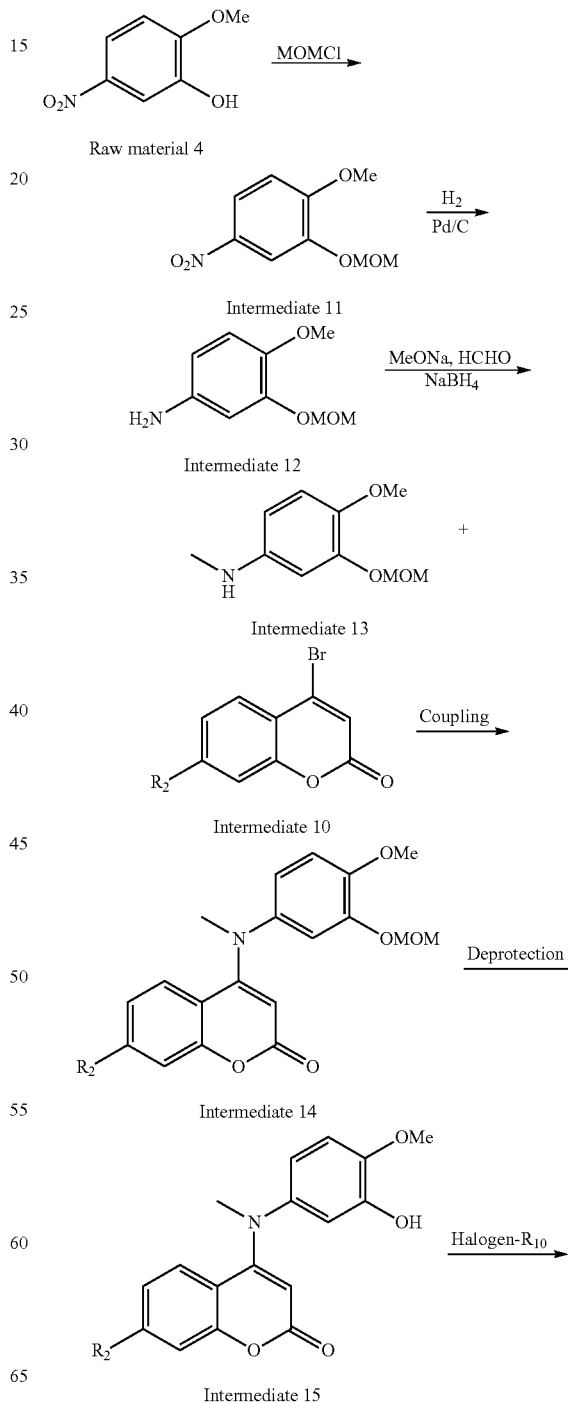

-continued

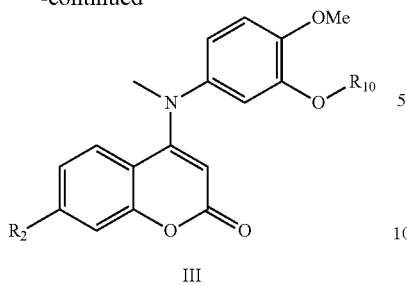

III wherein, R₂ is C1-C8 alkoxy, —H,

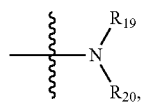

C1-C8 alkyl, halogen or C3-C8 cycloalkyl; R₁₀ is

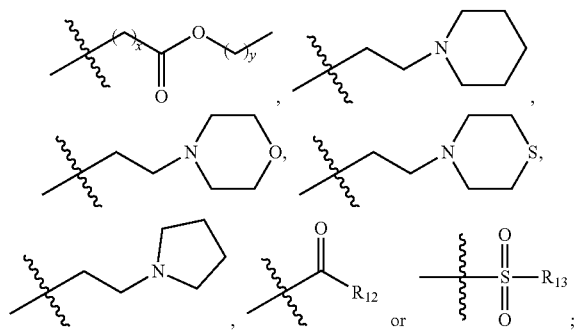

x=1-4, y=1-4; R₁₂ is C1-C10 alkyl,

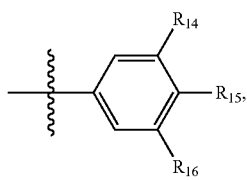

halogen, C2-C8 alkenyl, C1-C8 alkyl substituted by halogen, C3-C8 cycloalkyl,

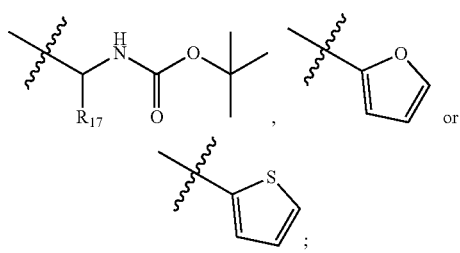

R₁₃ is C1-C8 alkyl, phenyl substituted by C1-C8 alkyl or phenyl substituted by halogen; R₁₄-R₁₆ are each independently C1-C8 alkyl, halogen, —H, C1-C8 alkoxy or —NH₂, and are not —H at the same time; R₁₇ is C1-C8 alkyl, halogen, —H or

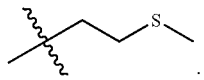

Specific steps of the above reaction route III are as follows:

1) Dissolve 1 equivalent of raw material 4 in organic solvent, dropwise add 3-5 equivalents of chloromethyl methyl ether (MOMC1) for reaction to obtain intermediate 11; the organic solvent is any one selected from N,N-dimethyl formamide (DMF), methyl alcohol, ethyl alcohol, methylbenzene, ethyl acetate, pyridine, tetrahydrofuran, dichloromethane or carbon tetrachloride; the reaction temperature is 0-80° C. and the reaction time is 2-12 hours;

2) Dissolve 1 equivalent of intermediate 11 in organic solvent, add 1%-2% equivalents of palladium-activated carbon catalyst, feed 5-20 equivalents of hydrogen for reduction reaction to obtain intermediate 12; the palladium catalyst is palladium on activated carbon with 10% Pd; the organic solvent is any one selected from N,N-dimethyl formamide (DMF), methyl alcohol, ethyl alcohol, methylbenzene, ethyl acetate, pyridine, tetrahydrofuran, dichloromethane or carbon tetrachloride; the reaction temperature is 0-40° C. and the reaction time is 2-12 hours;

3) Dissolve 1 equivalent of intermediate 12 in organic solvent, add 3-5 equivalents of sodium methoxide, add 1-3 equivalents of paraformaldehyde, stir for reaction overnight, add 1-2 equivalents of sodium borohydride in the reaction substrate for reaction by reflux technique to obtain compound 13; the organic solvent is any one selected from N,N-dimethyl formamide (DMF), methyl alcohol, ethyl alcohol, methylbenzene, ethyl acetate, pyridine, tetrahydrofuran, dichloromethane or carbon tetrachloride; the reflux temperature is 0-80° C. and the reflux time is 2-12 hours;

4) Dissolve 1 equivalent of compound 13 and 1 equivalent of intermediate 10 in organic solvent, add 2-3 equivalents of alkali for reaction by reflux technique to obtain intermediate 14; the alkali is any one selected from triethylamine, diisopropyl ethylamine (DIPEA), pyridine, potassium carbonate, sodium carbonate, potassium hydroxide, sodium hydroxide or sodium hydride; the organic solvent is any one selected from N,N-dimethyl formamide (DMF), methyl alcohol, ethyl alcohol, methylbenzene, ethyl acetate, pyridine, tetrahydrofuran, dichloromethane or carbon tetrachloride; the reaction time is 2-24 hours;

5) Dissolve 1 equivalent of intermediate 14 in organic solvent, add 2-3 equivalents of acids for reaction to obtain intermediate 15; the acid is any one selected from concentrated hydrochloric acid, hydrogen chloride-ethyl acetate solution, trifluoroacetic acid, methanesulfonic acid or sulfuric acid; the organic solvent is any one selected from N,N-dimethyl formamide (DMF), methyl alcohol, ethyl alcohol, methylbenzene, ethyl acetate, pyridine, tetrahydrofuran, dichloromethane or carbon tetrachloride; the reaction temperature is 40-100° C. and the reaction time is 2-24 hours;

6) Dissolve 1 equivalent of intermediate 15 in organic solvent, add 2-3 equivalents of alkali, add 1-3 equivalents of halogen-R₁₀ for reaction to obtain compound of Formula III; the alkali used in the reaction is any one selected from triethylamine, diisopropyl ethylamine (DIPEA), pyridine, potassium carbonate, sodium carbonate, potassium hydroxide, sodium hydroxide or sodium hydride; the organic solvent is any one selected from N,N-dimethyl formamide (DMF), methyl alcohol, ethyl alcohol, methylbenzene, ethyl acetate, pyridine, tetrahydrofuran, dichloromethane or carbon tetrachloride; the reaction temperature is 0-60° C. and the reaction time is 1-12 hours.

Reaction route IV:

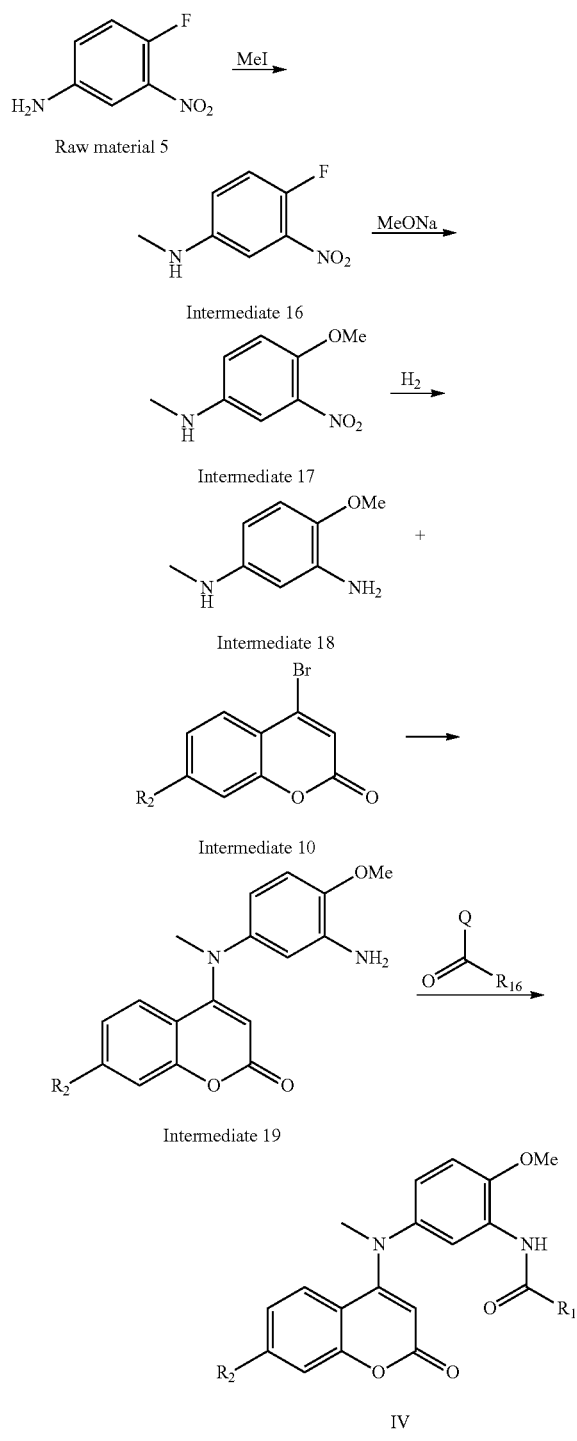

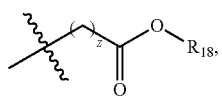

C2-C8 alkenyl, C1-C4 alkyl substituted by halogen, C3-C8 cycloalkyl,

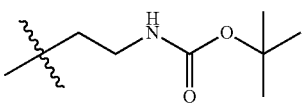 [SMILES: *CCNC(=O)OC(C)(C)C]

or —$NH_2$; z=1-10; $R_{18}$ is C1-C4 alkyl, halogen or —H.

Specific steps of the above reaction route IV are as follows:

1) Dissolve 1 equivalent of raw material 5 in organic solvent, add 2-3 equivalents of alkali, dropwise add 2-3 equivalents of iodomethane for reaction to obtain intermediate 16; the alkali is any one selected from triethylamine, diisopropyl ethylamine (DIPEA), pyridine, potassium carbonate, sodium carbonate, potassium hydroxide, sodium hydroxide or sodium hydride; the organic solvent is any one selected from N,N-dimethyl formamide (DMF), methyl alcohol, ethyl alcohol, methylbenzene, ethyl acetate, pyridine, tetrahydrofuran, dichloromethane or carbon tetrachloride; the reaction temperature is 0-60° C. and the reaction time is 1-12 hours;

2) Dissolve 1 equivalent of intermediate 16 in organic solvent, add 3-5 equivalents of sodium methoxide for reaction by reflux technique to obtain intermediate 17; the organic solvent is any one selected from N,N-dimethyl formamide (DMF), methyl alcohol, ethyl alcohol, methylbenzene, ethyl acetate, pyridine, tetrahydrofuran, dichloromethane or carbon tetrachloride; the reaction time is 2-24 hours;

3) Dissolve 1 equivalent of intermediate 17 in organic solvent, add 1%-2% equivalents of palladium on activated carbon, feed 5-20 equivalents of hydrogen for reduction reaction to obtain intermediate 18; the organic solvent is any one selected from N,N-dimethyl formamide (DMF), methyl alcohol, ethyl alcohol, methylbenzene, ethyl acetate, pyridine, tetrahydrofuran, dichloromethane or carbon tetrachloride; the reaction temperature can be 20-100° C. and the reaction time is 2-24 hours;

4) Dissolve 1 equivalent of intermediate 18 and 1 equivalent of intermediate 10 in organic solvent, add 2-5 equivalents of alkali for reaction by reflux technique to obtain intermediate 19; the alkali is any one selected from triethylamine, diisopropyl ethylamine (DIPEA), pyridine, potassium carbonate, sodium carbonate, potassium hydroxide, sodium hydroxide or sodium hydride; the organic solvent is any one selected from N,N-dimethyl formamide (DMF), methyl alcohol, ethyl alcohol, methylbenzene, ethyl acetate, pyridine, tetrahydrofuran, dichloromethane or carbon tetrachloride; the reaction time is 2-24 hours;

5) Dissolve intermediate 19 in organic solvent, add 2-5 equivalents of alkali, add 1-3 equivalents of

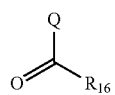

wherein, Q is halogen; $R_{11}$ is C1-C10 alkyl, for reaction by reflux technique to obtain compound of Formula IV; the alkali is any one selected from triethylamine, diisopropyl ethylamine (DIPEA), pyridine, potassium carbonate, sodium carbonate, potassium hydroxide, sodium hydroxide or sodium hydride; the organic solvent is any one selected from N,N-dimethyl formamide (DMF), methyl alcohol, ethyl alcohol, methylbenzene, ethyl acetate, pyridine, tetrahydrofuran, dichloromethane or carbon tetrachloride; the reaction temperature can be 0-60° C. and the reaction time is 1-12 hours.

The following detailed description of preferred embodiments intends to further illustrate the above-mentioned contents of the Invention in detail but not to limit the Invention.

Embodiment 1: Preparation of 4-(5-(4-methoxyphenyl) thiophene-2-yl)-coumarin (COUM-1)

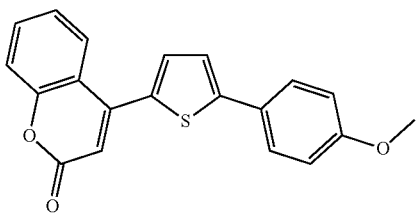 [SMILES: COc1ccc(-c2ccc(-c3cc(=O)oc4ccccc34)s2)cc1]

Under protection of nitrogen gas, dissolve corresponding intermediate 7a (4-(5-bromothiophene-2-yl)-coumarin), 4-methoxyphenylboronic acid, tetrakis (triphenylphosphine) palladium and cesium carbonate anhydrous in anhydrous DMF solution. Reflux for 12 hours under anhydrous and anaerobic conditions. Cool it to room temperature after the reaction is completed, dilute with large amount of water, and perform ethyl acetate extraction for three times. Combine organic phases, wash successively with water and saturated salt water, dry with anhydrous sodium sulfate for 30 min, and remove organic solvent to obtain crude product. Carry out flash column chromatography with ethyl acetate: petroleum ether of 1:10 to obtain a light yellow solid product, with a yield of 58%.

$^1$H NMR (400 MHz, DMSO) δ 7.65 (dd, J=11.0, 3.9 Hz, 2H), 7.51 (d, J=8.0 Hz, 1H), 7.36 (dt, J=14.3, 6.8 Hz, 2H), 7.18~7.08 (m, 4H), 6.81 (d, J=8.7 Hz, 2H), 3.72 (s, 3H). MS (ESI, m/z): 357.1 [M+Na]$^+$.

Embodiment 2: Preparation of 4-(5-(4-methylsulfonyl phenyl) thiophene-2-yl)-coumarin (COUM-2)

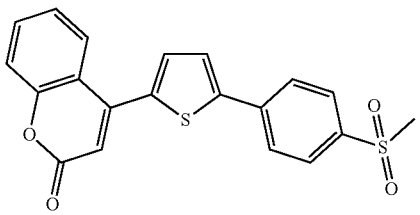 [SMILES: CS(=O)(=O)c1ccc(-c2ccc(-c3cc(=O)oc4ccccc34)s2)cc1]

Under protection of nitrogen gas, dissolve corresponding intermediate 7a (4-(5-bromothiophene-2-yl)-coumarin), 4-methyl sulfonyl phenylboronic acid, tetrakis (triphenylphosphine) palladium and cesium carbonate anhydrous in anhydrous DMF solution. Reflux for 12 hours under anhydrous and anaerobic conditions. Cool it to room temperature after the reaction is completed, dilute with large amount of water, and perform ethyl acetate extraction for three times. Combine organic phases, wash successively with water and saturated salt water, dry with anhydrous sodium sulfate for 30 min, and remove organic solvent to obtain crude product. Carry out flash column chromatography with ethyl acetate: petroleum ether of 1:10 to obtain a light yellow solid product, with a yield of 56%.

$^1$H NMR (400 MHz, CDCl$_3$) δ 7.84 (d, J=8.4 Hz, 2H), 7.61 (t, J=7.8 Hz, 1H), 7.5~97.54 (m, 1H), 7.50~7.39 (m, 4H), 7.29 (t, J=7.7 Hz, 1H), 7.03 (dd, J=5.0, 3.7 Hz, 1H), 6.99~6.95 (m, 1H), 3.04 (s, 3H). MS (ESI, m/z): 405.0 [M+Na]$^+$.

Embodiment 3: Preparation of 4-(5-(4-methylphenyl) thiophene-2-yl)-coumarin (COUM-3)

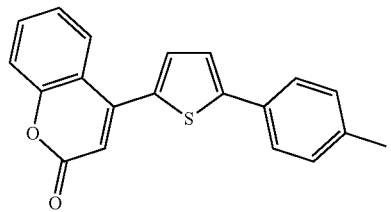 [SMILES: Cc1ccc(-c2ccc(-c3cc(=O)oc4ccccc34)s2)cc1]

Under protection of nitrogen gas, dissolve corresponding intermediate 7a, 4-methylphenyl boronic acid, tetrakis (triphenylphosphine) palladium and cesium carbonate anhydrous in anhydrous DMF solution. Reflux for 12 hours under anhydrous and anaerobic conditions. Cool it to room temperature after the reaction is completed, dilute with large amount of water, and perform ethyl acetate extraction for three times. Combine organic phases, wash successively with water and saturated salt water, dry with anhydrous sodium sulfate for 30 min, and remove organic solvent to obtain crude product. Carry out flash column chromatography with ethyl acetate: petroleum ether of 1:10 to obtain a light yellow solid product, with a yield of 59%.

$^1$H NMR (400 MHz, CDCl$_3$) δ 7.58~7.50 (m, 2H), 7.42 (d, J=8.2 Hz, 1H), 7.37 (dd, J=5.0, 1.0 Hz, 1H), 7.23 (d, J=7.1 Hz, 1H), 7.08 (q, J=8.3 Hz, 4H), 7.05~7.01 (m, 1H), 7.0~16.97 (m, 1H), 2.30 (s, 3H). MS (ESI, m/z): 341.1 [M+Na]$^+$.

Embodiment 4: Preparation of 4-(5-(2-methoxyphenyl) thiophene-2-yl)-coumarin (COUM-4)

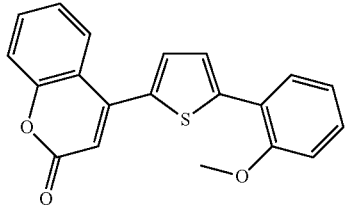

Under protection of nitrogen gas, dissolve corresponding intermediate 7a, 2-methoxyphenylboronic acid, tetrakis (triphenylphosphine) palladium and cesium carbonate anhydrous in anhydrous DMF solution. Reflux for 12 hours under anhydrous and anaerobic conditions. Cool it to room temperature after the reaction is completed, dilute with large amount of water, and perform ethyl acetate extraction for three times. Combine organic phases, wash successively with water and saturated salt water, dry with anhydrous sodium sulfate for 30 min, and remove organic solvent to obtain crude product. Carry out flash column chromatography with ethyl acetate: petroleum ether of 1:10 to obtain a light yellow solid product, with a yield of 52%.

$^1$H NMR (400 MHz, DMSO) δ 7.73~7.65 (m, 1H), 7.63 (dd, J=4.9, 1.2 Hz, 1H), 7.52 (d, J=8.3 Hz, 1H), 7.44~7.33 (m, 2H), 7.29~7.23 (m, 1H), 7.11~7.01 (m, 3H), 6.96 (d, J=8.3 Hz, 1H), 6.83 (t, J=7.4 Hz, 1H), 3.68 (s, 3H). MS (ESI, m/z): 357.1 [M+Na]$^+$.

Embodiment 5: Preparation of
4-(5-phenylthiophene-2-yl)-coumarin (COUM-5)

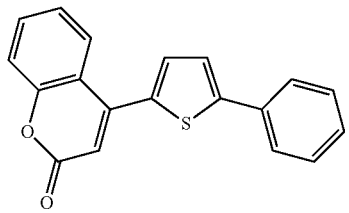 [SMILES: O=c1cc(-c2ccc(-c3ccccc3)s2)c2ccccc2o1]

Under protection of nitrogen gas, dissolve corresponding intermediate 7a, phenylboronic acid, tetrakis (triphenylphosphine) palladium and cesium carbonate anhydrous in anhydrous DMF solution. Reflux for 12 hours under anhydrous and anaerobic conditions. Cool it to room temperature after the reaction is completed, dilute with large amount of water, and perform ethyl acetate extraction for three times. Combine organic phases, wash successively with water and saturated salt water, dry with anhydrous sodium sulfate for 30 min, and remove organic solvent to obtain crude product. Carry out flash column chromatography with ethyl acetate: petroleum ether of 1:10 to obtain a light yellow solid product, with a yield of 62%.

$^1$H NMR (400 MHz, DMSO) δ 7.68 (d, J=7.0 Hz, 1H), 7.65 (dd, J=5.0, 1.0 Hz, 1H), 7.52 (d, J=8.2 Hz, 1H), 7.43~7.39 (m, 1H), 7.35 (t, J=7.5 Hz, 1H), 7.29~7.19 (m, 5H), 7.15~7.12 (m, 1H), 7.08 (dd, J=4.9, 3.6 Hz, 1H). MS (ESI, m/z): 327.1 [M+Na]$^+$.

Embodiment 6: Preparation of 4-(5-(3,4,5-trimethoxyphenyl) thiophene-2-yl)-coumarin (COUM-6)

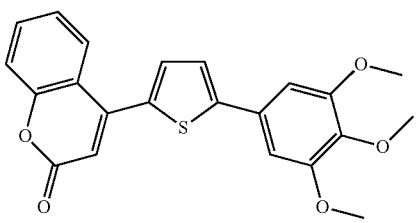 [SMILES: COc1cc(-c2ccc(-c3cc(=O)oc4ccccc34)s2)cc(OC)c1OC]

Under protection of nitrogen gas, dissolve corresponding intermediate 7a, 3,4,5-trimethoxyphenylboronic acid, tetrakis (triphenylphosphine) palladium and cesium carbonate anhydrous in anhydrous DMF solution. Reflux for 12 hours under anhydrous and anaerobic conditions. Cool it to room temperature after the reaction is completed, dilute with large amount of water, and perform ethyl acetate extraction for three times. Combine organic phases, wash successively with water and saturated salt water, dry with anhydrous sodium sulfate for 30 min, and remove organic solvent to obtain crude product. Carry out flash column chromatography with ethyl acetate: petroleum ether of 1:10 to obtain a light yellow solid product, with a yield of 48%.

$^1$H NMR (400 MHz, DMSO) δ 7.70 (d, J=4.9 Hz, 1H), 7.68~7.64 (m, 1H), 7.52 (d, J=7.9 Hz, 1H), 7.42 (d, J=6.8 Hz, 1H), 7.36 (t, J=7.3 Hz, 1H), 7.17 (d, J=2.4 Hz, 1H), 7.15~7.11 (m, 1H), 6.55 (s, 2H), 6.05 (s, 1H), 3.64 (s, 3H), 3.61 (s, 5H). MS (ESI, m/z): 417.1 [M+Na]$^+$.

Embodiment 7: Preparation of 4-(5-(4-chlorobenzene) thiophene-2-yl)-coumarin (COUM-7)

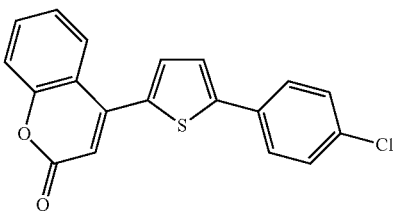 [SMILES: O=c1cc(-c2ccc(-c3ccc(Cl)cc3)s2)c2ccccc2o1]

Under protection of nitrogen gas, dissolve corresponding intermediate 7a, 4-chlorophenyl boronic acid, tetrakis (triphenylphosphine) palladium and cesium carbonate anhydrous in anhydrous DMF solution. Reflux for 12 hours under anhydrous and anaerobic conditions. Cool it to room temperature after the reaction is completed, dilute with large amount of water, and perform ethyl acetate extraction for three times. Combine organic phases, wash successively with water and saturated salt water, dry with anhydrous sodium sulfate for 30 min, and remove organic solvent to obtain crude product. Carry out flash column chromatography with ethyl acetate: petroleum ether of 1:10 to obtain a light yellow solid product, with a yield of 52%.

$^1$H NMR (400 MHz, DMSO) δ 7.7-27.64 (m, 2H), 7.53 (d, J=8.2 Hz, 1H), 7.40 (dd, J=8.7, 7.4 Hz, 2H), 7.37~7.30 (m, 3H), 7.25 (d, J=8.5 Hz, 2H), 7.17~7.14 (m, 1H), 7.1~37.09 (m, 1H). MS (ESI, m/z): 361.1 [M+Na]$^+$.

Embodiment 8: Preparation of 4-(5-(3-chlorobenzene) thiophene-2-yl)-coumarin (COUM-8)

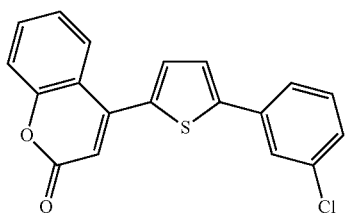 [SMILES: O=c1cc(-c2ccc(-c3cccc(Cl)c3)s2)c2ccccc2o1]

Under protection of nitrogen gas, dissolve corresponding intermediate 7a, 3-chlorophenyl boronic acid, tetrakis (triphenylphosphine) palladium and cesium carbonate anhydrous in anhydrous DMF solution. Reflux for 12 hours under anhydrous and anaerobic conditions. Cool it to room temperature after the reaction is completed, dilute with large amount of water, and perform ethyl acetate extraction for three times. Combine organic phases, wash successively with water and saturated salt water, dry with anhydrous sodium sulfate for 30 min, and remove organic solvent to obtain crude product. Carry out flash column chromatography with ethyl acetate: petroleum ether of 1:10 to obtain a light yellow solid product, with a yield of 53%.

$^1$H NMR (400 MHz, DMSO) δ 7.72~7.64 (m, 2H), 7.56~7.50 (m, 1H), 7.45~7.39 (m, 1H), 7.37 (d, J=7.8 Hz, 1H), 7.36~7.26 (m, 3H), 7.18 (dd, J=12.5, 5.1 Hz, 2H), 7.12 (dd, J=4.9, 3.6 Hz, 1H). MS (ESI, m/z): 361.1 [M+Na]$^+$.

Embodiment 9: Preparation of 4-(5-(3,4,5-trimethoxybenzene) thiophene-2-yl)-7-methoxyl-coumarin (COUM-9)

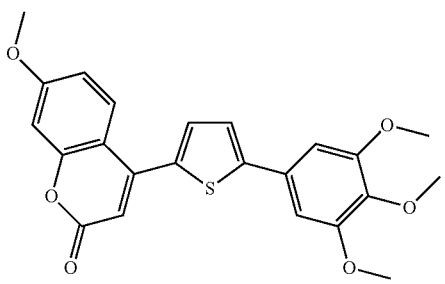 [SMILES: COc1ccc2c(-c3ccc(-c4cc(OC)c(OC)c(OC)c4)s3)cc(=O)oc2c1]

Under protection of nitrogen gas, dissolve corresponding intermediate 7b (4-(5-bromothiophene-2-yl)-7-methoxyl-coumarin), 3,4,5-trimethoxyphenylboronic acid, tetrakis (triphenylphosphine) palladium and cesium carbonate anhydrous in anhydrous DMF solution. Reflux for 12 hours under anhydrous and anaerobic conditions. Cool it to room temperature after the reaction is completed, dilute with large amount of water, and perform ethyl acetate extraction for three times. Combine organic phases, wash successively with water and saturated salt water, dry with anhydrous sodium sulfate for-min, and remove organic solvent to obtain crude product. Carry out flash column chromatography with ethyl acetate: petroleum ether of 1:10 to obtain a light yellow solid product, with a yield of 51%.

$^1$H NMR (400 MHz, DMSO) δ 7.71~7.66 (m, 1H), 7.32 (d, J=8.9 Hz, 1H), 7.17~7.09 (m, 3H), 6.96 (dd, J=8.9, 2.4 Hz, 1H), 6.51 (s, 2H), 3.89 (s, 3H), 3.63 (s, 3H), 3.60 (s, 5H). MS (ESI, m/z): 447.1 [M+Na]$^+$.

Embodiment 10: Preparation of 4-(5-(4-methyl benzene) thiophene-2-yl)-7-methoxyl-coumarin (COUM-10)

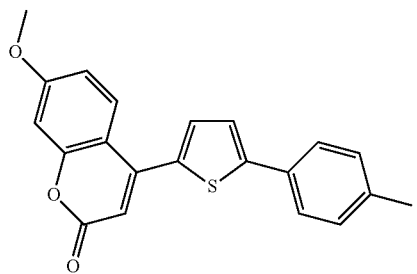 [SMILES: COc1ccc2c(-c3ccc(-c4ccc(C)cc4)s3)cc(=O)oc2c1]

Under protection of nitrogen gas, dissolve corresponding intermediate 7b, 4-methylphenyl boronic acid, tetrakis (triphenylphosphine) palladium and cesium carbonate anhydrous in anhydrous DMF solution. Reflux for 12 hours under anhydrous and anaerobic conditions. Cool it to room temperature after the reaction is completed, dilute with large amount of water, and perform ethyl acetate extraction for three times. Combine organic phases, wash successively with water and saturated salt water, dry with anhydrous sodium sulfate for 30 min, and remove organic solvent to obtain crude product. Carry out flash column chromatography with ethyl acetate: petroleum ether of 1:10 to obtain a light yellow solid product, with a yield of 59%.

$^1$H NMR (400 MHz, CDCl$_3$) δ 7.64 (d, J=4.4 Hz, 1H), 7.28 (d, J=8.9 Hz, 1H), 7.15~7.01 (m, 7H), 6.95 (dd, J=8.9, 2.0 Hz, 1H), 3.88 (s, 3H), 2.50 (s, 2H). MS (ESI, m/z): 371.1 [M+Na]$^+$.

Embodiment 11: Preparation of 4-(5-(3,4-(methylenedioxy) benzene) thiophene-2-yl)-7-methoxyl-coumarin (COUM-11)

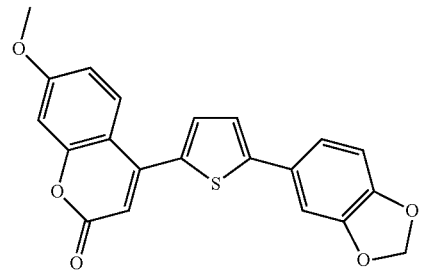 [SMILES: COc1ccc2c(-c3ccc(-c4ccc5c(c4)OCO5)s3)cc(=O)oc2c1]

Under protection of nitrogen gas, dissolve corresponding intermediate 7b, 3,4-(methylenedioxy) phenylboronic acid, tetrakis (triphenylphosphine) palladium and cesium carbonate anhydrous in anhydrous DMF solution. Reflux for 12 hours under anhydrous and anaerobic conditions. Cool it to room temperature after the reaction is completed, dilute with large amount of water, and perform ethyl acetate extraction for three times. Combine organic phases, wash successively with water and saturated salt water, dry with anhydrous sodium sulfate for 30 min, and remove organic solvent to obtain crude product. Carry out flash column chromatography with ethyl acetate: petroleum ether of 1:10 to obtain a light yellow solid product, with a yield of 50%.

$^1$H NMR (400 MHz, DMSO) δ 7.72~7.65 (m, 1H), 7.29 (d, J=8.9 Hz, 1H), 7.17~7.13 (m, 1H), 7.11 (d, J=4.8 Hz, 2H), 6.95 (dd, J=8.9, 2.3 Hz, 1H), 6.81~6.74 (m, 2H), 6.62 (dd, J=8.0, 1.3 Hz, 1H), 5.99 (s, 2H), 3.88 (s, 3H). MS (ESI, m/z): 401.1 [M+Na]$^+$.

Embodiment 12: Preparation of 4-(5-(2-methoxybenzene) thiophene-2-yl)-7-methoxyl-coumarin (COUM-12)

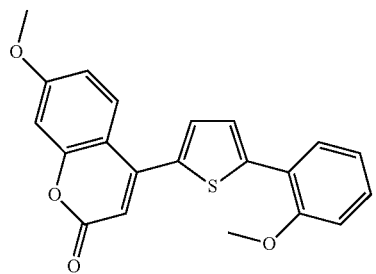 [SMILES: COc1ccc2c(-c3ccc(-c4ccccc4OC)s3)cc(=O)oc2c1]

Under protection of nitrogen gas, dissolve corresponding intermediate 7b, 2-methoxyphenyl boronic acid, tetrakis (triphenylphosphine) palladium and cesium carbonate anhydrous in anhydrous DMF solution. Reflux for 12 hours under anhydrous and anaerobic conditions. Cool it to room temperature after the reaction is completed, dilute with large amount of water, and perform ethyl acetate extraction for three times. Combine organic phases, wash successively with water and saturated salt water, dry with anhydrous sodium sulfate for 30 min, and remove organic solvent to obtain crude product. Carry out flash column chromatography with ethyl acetate: petroleum ether of 1:10 to obtain a light yellow solid product, with a yield of 55%.

$^1$H NMR (400 MHz, CDCl$_3$) δ 7.61 (dd, J=3.7, 2.3 Hz, 1H), 7.31 (d, J=8.9 Hz, 1H), 7.25 (t, J=7.8 Hz, 1H), 7.12 (d, J=2.1 Hz, 1H), 7.05 (d, J=2.3 Hz, 2H), 7.01 (d, J=7.4 Hz, 1H), 6.95 (dd, J=8.3, 3.3 Hz, 2H), 6.81 (t, J=7.4 Hz, 1H), 3.89 (s, 3H), 3.67 (s, 3H). MS (ESI, m/z): 387.1 [M+Na]$^+$.

Embodiment 13: Preparation of 4-(5-(3-ethoxycarbonyl benzene) thiophene-2-yl)-7-methoxyl-coumarin (COUM-13)

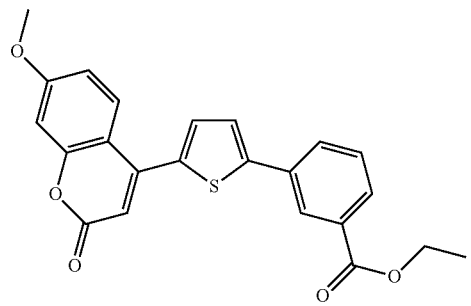 [SMILES: CCOC(=O)c1cccc(-c2ccc(-c3cc(=O)oc4cc(OC)ccc34)s2)c1]

Under protection of nitrogen gas, dissolve corresponding intermediate 7b, 3-ethoxycarbonylphenyl boronic acid, tetrakis (triphenylphosphine) palladium and cesium carbonate anhydrous in anhydrous DMF solution. Reflux for 12 hours under anhydrous and anaerobic conditions. Cool it to room temperature after the reaction is completed, dilute with large amount of water, and perform ethyl acetate extraction for three times. Combine organic phases, wash successively with water and saturated salt water, dry with anhydrous sodium sulfate for 30 min, and remove organic solvent to obtain crude product. Carry out flash column chromatography with ethyl acetate: petroleum ether of 1:10 to obtain a light yellow solid product, with a yield of 52%.

$^1$H NMR (400 MHz, DMSO) δ 7.82 (d, J=7.1 Hz, 2H), 7.65 (d, J=4.5 Hz, 1H), 7.45 (d, J=7.7 Hz, 1H), 7.40 (d, J=7.8 Hz, 1H), 7.32 (d, J=9.0 Hz, 1H), 7.13 (dd, J=6.4, 2.5 Hz, 2H), 7.10~7.05 (m, 1H), 6.97 (dd, J=8.9, 2.3 Hz, 1H), 4.28 (q, J=7.1 Hz, 2H), 3.90 (s, 3H), 1.30 (t, J=7.1 Hz, 3H). MS (ESI, m/z): 429.1 [M+Na]$^+$.

Embodiment 14: Preparation of 4-(5-(4-chlorobenzene) thiophene-2-yl)-7-methoxyl-coumarin (COUM-14)

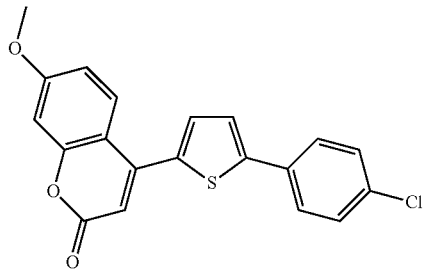 [SMILES: COc1ccc2c(-c3ccc(-c4ccc(Cl)cc4)s3)cc(=O)oc2c1]

Under protection of nitrogen gas, dissolve corresponding intermediate 7b, 4-chlorophenyl boronic acid, tetrakis (triphenylphosphine) palladium and cesium carbonate anhydrous in anhydrous DMF solution. Reflux for 12 hours under anhydrous and anaerobic conditions. Cool it to room temperature after the reaction is completed, dilute with large amount of water, and perform ethyl acetate extraction for three times. Combine organic phases, wash successively with water and saturated salt water, dry with anhydrous sodium sulfate for 30 min, and remove organic solvent to obtain crude product. Carry out flash column chromatography with ethyl acetate: petroleum ether of 1:10 to obtain a light yellow solid product, with a yield of 55%.

$^1$H NMR (400 MHz, DMSO) δ 3.93 (s, 3H), 7.72~7.64 (m, 2H), 7.53 (d, J=8.2 Hz, 1H), 7.40 (dd, J=8.7, 7.4 Hz, 2H), 7.37~7.30 (m, 2H), 7.25 (d, J=8.5 Hz, 2H), 7.17~7.14 (m, 1H), 7.13~7.09 (m, 1H). MS (ESI, m/z): 391.1 [M+Na]$^+$.

Embodiment 15: Preparation of 4-(5-(4-methoxyphenyl) furan-2-yl)-coumarin (COUM-15)

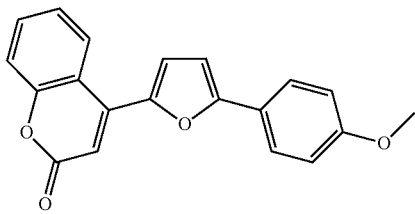 [SMILES: COc1ccc(-c2ccc(-c3cc(=O)oc4ccccc34)o2)cc1]

Under protection of nitrogen gas, dissolve corresponding intermediate 7c (4-(5-bromofuran-2-yl)-coumarin), 4-methoxyphenylboronic acid, tetrakis (triphenylphosphine) palladium and cesium carbonate anhydrous in anhydrous DMF solution. Reflux for 12 hours under anhydrous and anaerobic conditions. Cool it to room temperature after the reaction is completed, dilute with large amount of water, and perform ethyl acetate extraction for three times. Combine organic phases, wash successively with water and saturated salt water, dry with anhydrous sodium sulfate for 30 min, and remove organic solvent to obtain crude product. Carry out flash column chromatography with ethyl acetate: petroleum ether of 1:10 to obtain a light yellow solid product, with a yield of 58%.

$^1$H NMR (400 MHz, DMSO) δ 7.65 (dd, J=11.0, 3.9 Hz, 2H), 7.51 (d, J=8.0 Hz, 1H), 7.36 (dt, J=14.3, 6.8 Hz, 2H), 7.18~7.08 (m, 4H), 6.81 (d, J=8.7 Hz, 2H), 3.72 (s, 3H). MS (ESI, m/z): 341.1 [M+Na]$^+$.

Embodiment 16: Preparation of 4-(5-(4-methylsulfonyl phenyl) furan-2-yl)-coumarin (COUM-16)

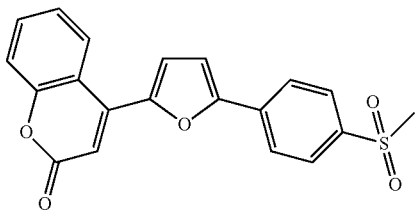 [SMILES: CS(=O)(=O)c1ccc(-c2ccc(-c3cc(=O)oc4ccccc34)o2)cc1]

Under protection of nitrogen gas, dissolve corresponding intermediate 7c, 4-methylsulfonyl phenylboronic acid, tetrakis (triphenylphosphine) palladium and cesium carbonate anhydrous in anhydrous DMF solution. Reflux for 12 hours under anhydrous and anaerobic conditions. Cool it to room temperature after the reaction is completed, dilute with large amount of water, and perform ethyl acetate extraction for three times. Combine organic phases, wash successively with water and saturated salt water, dry with anhydrous sodium sulfate for 30 min, and remove organic solvent to obtain crude product. Carry out flash column chromatography with ethyl acetate: petroleum ether of 1:10 to obtain a light yellow solid product, with a yield of 56%.

$^1$H NMR (400 MHz, CDCl$_3$) δ 7.84 (d, J=8.4 Hz, 2H), 7.61 (t, J=7.8 Hz, 1H), 7.59~7.54 (m, 1H), 7.50~7.39 (m, 4H), 7.29 (t, J=7.7 Hz, 1H), 7.03 (dd, J=5.0, 3.7 Hz, 1H), 6.99~6.95 (m, 1H), 3.04 (s, 3H). MS (ESI, m/z): 489.0 [M+Na]$^+$.

Embodiment 17: Preparation of 4-(5-(4-methylphenyl) furan-2-yl)-coumarin (COUM-17)

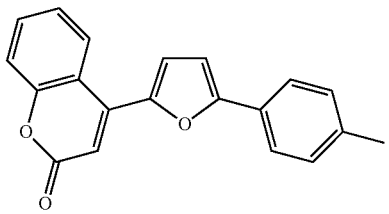 [SMILES: Cc1ccc(-c2ccc(-c3cc(=O)oc4ccccc34)o2)cc1]

Under protection of nitrogen gas, dissolve corresponding intermediate 7c, 4-methylphenyl boronic acid, tetrakis (triphenylphosphine) palladium and cesium carbonate anhydrous in anhydrous DMF solution. Reflux for 12 hours under anhydrous and anaerobic conditions. Cool it to room temperature after the reaction is completed, dilute with large amount of water, and perform ethyl acetate extraction for three times. Combine organic phases, wash successively with water and saturated salt water, dry with anhydrous sodium sulfate for 30 min, and remove organic solvent to obtain crude product. Carry out flash column chromatography with ethyl acetate: petroleum ether of 1:10 to obtain a light yellow solid product, with a yield of 59%.

$^1$H NMR (400 MHz, CDCl$_3$) δ 7.5-87.50 (m, 2H), 7.42 (d, J=8.2 Hz, 1H), 7.37 (dd, J=5.0, 1.0 Hz, 1H), 7.23 (d, J=7.1 Hz, 1H), 7.08 (q, J=8.3 Hz, 4H), 7.05~7.01 (m, 1H), 7.01~6.97 (m, 1H), 2.30 (s, 3H). MS (ESI, m/z): 325.1 [M+Na]$^+$.

Embodiment 18: Preparation of 4-(5-(2-methoxyphenyl) furan-2-yl)-coumarin (COUM-18)

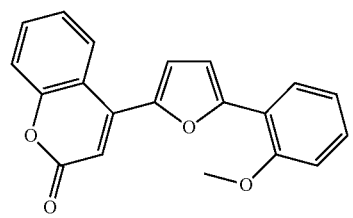 [SMILES: COc1ccccc1-c1ccc(-c2cc(=O)oc3ccccc23)o1]

Under protection of nitrogen gas, dissolve corresponding intermediate 7c, 2-methoxyphenyl boronic acid, tetrakis (triphenylphosphine) palladium and cesium carbonate anhydrous in anhydrous DMF solution. Reflux for 12 hours under anhydrous and anaerobic conditions. Cool it to room temperature after the reaction is completed, dilute with large amount of water, and perform ethyl acetate extraction for three times. Combine organic phases, wash successively with water and saturated salt water, dry with anhydrous sodium sulfate for 30 min, and remove organic solvent to obtain crude product. Carry out flash column chromatography with ethyl acetate: petroleum ether of 1:10 to obtain a light yellow solid product, with a yield of 52%.

$^1$H NMR (400 MHz, DMSO) δ 7.73~7.65 (m, 1H), 7.63 (dd, J=4.9, 1.2 Hz, 1H), 7.52 (d, J=8.3 Hz, 1H), 7.44~7.33 (m, 2H), 7.29~7.23 (m, 1H), 7.11~7.01 (m, 3H), 6.96 (d, J=8.3 Hz, 1H), 6.83 (t, J=7.4 Hz, 1H), 3.68 (s, 3H). MS (ESI, m/z): 341.1 [M+Na]$^+$.

Embodiment 19: Preparation of 4-(5-phenylfuran-2-yl)-coumarin (COUM-19)

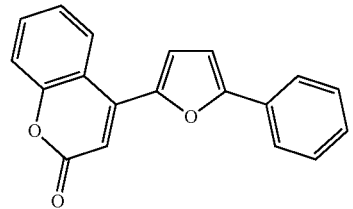 [SMILES: O=c1cc(-c2ccc(-c3ccccc3)o2)c2ccccc2o1]

Under protection of nitrogen gas, dissolve corresponding intermediate 7c, phenylboronic acid, tetrakis (triphenylphosphine) palladium and cesium carbonate anhydrous in anhydrous DMF solution. Reflux for 12 hours under anhydrous and anaerobic conditions. Cool it to room temperature after the reaction is completed, dilute with large amount of water, and perform ethyl acetate extraction for three times. Combine organic phases, wash successively with water and saturated salt water, dry with anhydrous sodium sulfate for 30 min, and remove organic solvent to obtain crude product. Carry out flash column chromatography with ethyl acetate: petroleum ether of 1:10 to obtain a light yellow solid product, with a yield of 62%.

¹H NMR (400 MHz, DMSO) δ 7.68 (d, J=7.0 Hz, 1H), 7.65 (dd, J=5.0, 1.0 Hz, 1H), 7.52 (d, J=8.2 Hz, 1H), 7.43~7.39 (m, 1H), 7.35 (t, J=7.5 Hz, 1H), 7.29~7.19 (m, 5H), 7.15~7.12 (m, 1H), 7.08 (dd, J=4.9, 3.6 Hz, 1H). MS (ESI, m/z): 311.1 [M+Na]⁺.

Embodiment 20: Preparation of 4-(5-(3,4,5-trimethoxyphenyl) furan-2-yl)-coumarin (COUM-20)

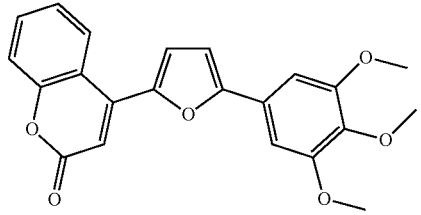 [SMILES: COc1cc(-c2ccc(-c3cc(=O)oc4ccccc34)o2)cc(OC)c1OC]

Under protection of nitrogen gas, dissolve corresponding intermediate 7c, 3,4,5-trimethoxyphenylboronic acid, tetrakis (triphenylphosphine) palladium and cesium carbonate anhydrous in anhydrous DMF solution. Reflux for 12 hours under anhydrous and anaerobic conditions. Cool it to room temperature after the reaction is completed, dilute with large amount of water, and perform ethyl acetate extraction for three times. Combine organic phases, wash successively with water and saturated salt water, dry with anhydrous sodium sulfate for 30 min, and remove organic solvent to obtain crude product. Carry out flash column chromatography with ethyl acetate: petroleum ether of 1:10 to obtain a light yellow solid product, with a yield of 48%.

¹H NMR (400 MHz, DMSO) δ 7.70 (d, J=4.9 Hz, 1H), 7.68~7.64 (m, 1H), 7.52 (d, J=7.9 Hz, 1H), 7.42 (d, J=6.8 Hz, 1H), 7.36 (t, J=7.3 Hz, 1H), 7.17 (d, J=2.4 Hz, 1H), 7.15~7.11 (m, 1H), 6.55 (s, 2H), 6.05 (s, 1H), 3.64 (s, 3H), 3.61 (s, 5H). MS (ESI, m/z): 401.1 [M+Na]⁺.

Embodiment 21: Preparation of 4-(5-(4-chlorobenzene) furan-2-yl)-coumarin (COUM-21)

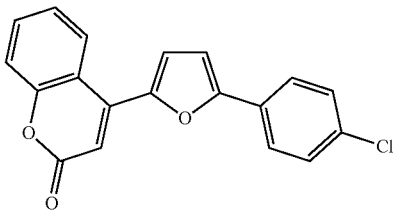 [SMILES: O=c1cc(-c2ccc(-c3ccc(Cl)cc3)o2)c2ccccc2o1]

Under protection of nitrogen gas, dissolve intermediate 7c, 4-chlorophenyl boronic acid, tetrakis (triphenylphosphine) palladium and cesium carbonate anhydrous in anhydrous DMF solution. Reflux for 12 hours under anhydrous and anaerobic conditions. Cool it to room temperature after the reaction is completed, dilute with large amount of water, and perform ethyl acetate extraction for three times. Combine organic phases, wash successively with water and saturated salt water, dry with anhydrous sodium sulfate for 30 min, and remove organic solvent to obtain crude product. Carry out flash column chromatography with ethyl acetate: petroleum ether of 1:10 to obtain a light yellow solid product, with a yield of 52%.

¹H NMR (400 MHz, DMSO) δ 7.72~7.64 (m, 2H), 7.53 (d, J=8.2 Hz, 1H), 7.40 (dd, J=8.7, 7.4 Hz, 2H), 7.37-7.30 (m, 3H), 7.25 (d, J=8.5 Hz, 2H), 7.17~7.14 (m, 1H), 7.13~7.09 (m, 1H). MS (ESI, m/z): 345.1 [M+Na]⁺.

Embodiment 22: Preparation of 4-(5-(3-chlorobenzene) furan-2-yl)-coumarin (COUM-22)

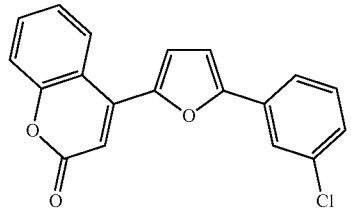 [SMILES: O=c1cc(-c2ccc(-c3cccc(Cl)c3)o2)c2ccccc2o1]

Under protection of nitrogen gas, dissolve intermediate 7c, 3-chlorophenyl boronic acid, tetrakis (triphenylphosphine) palladium and cesium carbonate anhydrous in anhydrous DMF solution. Reflux for 12 hours under anhydrous and anaerobic conditions. Cool it to room temperature after the reaction is completed, dilute with large amount of water, and perform ethyl acetate extraction for three times. Combine organic phases, wash successively with water and saturated salt water, dry with anhydrous sodium sulfate for 30 min, and remove organic solvent to obtain crude product. Carry out flash column chromatography with ethyl acetate: petroleum ether of 1:10 to obtain a light yellow solid product, with a yield of 53%.

¹H NMR (400 MHz, DMSO) δ 7.72~7.64 (m, 2H), 7.56~7.50 (m, 1H), 7.45~7.39 (m, 1H), 7.37 (d, J=7.8 Hz, 1H), 7.36~7.26 (m, 3H), 7.18 (dd, J=12.5, 5.1 Hz, 2H), 7.12 (dd, J=4.9, 3.6 Hz, 1H). MS (ESI, m/z): 345.1 [M+Na]⁺.

Embodiment 23: Preparation of 4-(5-(3,4,5-trimethoxybenzene) furan-2-yl)-7-methoxyl-coumarin (COUM-23)

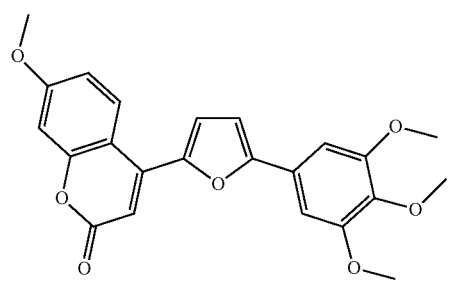 [SMILES: COc1ccc2c(-c3ccc(-c4cc(OC)c(OC)c(OC)c4)o3)cc(=O)oc2c1]

Under protection of nitrogen gas, dissolve intermediate 7d (4-(5-bromofuran-2-yl)-7-methoxyl-coumarin), 3,4,5-trimethoxyphenylboronic acid, tetrakis (triphenylphosphine) palladium and cesium carbonate anhydrous in anhydrous DMF solution. Reflux for 12 hours under anhydrous and anaerobic conditions. Cool it to room temperature after the reaction is completed, dilute with large amount of water, and perform ethyl acetate extraction for three times. Combine organic phases, wash successively with water and saturated salt water, dry with anhydrous sodium sulfate for 30 min, and remove organic solvent to obtain crude product. Carry out flash column chromatography with ethyl acetate: petroleum ether of 1:10 to obtain a light yellow solid product, with a yield of 51%.

¹H NMR (400 MHz, DMSO) δ 7.7-17.66 (m, 1H), 7.32 (d, J=8.9 Hz, 1H), 7.17~7.09 (m, 3H), 6.96 (dd, J=8.9, 2.4 Hz, 1H), 6.51 (s, 2H), 3.89 (s, 3H), 3.63 (s, 3H), 3.60 (s, 5H). MS (ESI, m/z): 431.1 [M+Na]⁺.

Embodiment 24: Preparation of 4-(5-(4-methyl benzene) furan-2-yl)-7-methoxyl-coumarin (COUM-24)

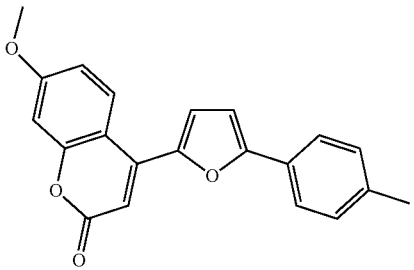 [SMILES: COc1ccc2c(-c3ccc(-c4ccc(C)cc4)o3)cc(=O)oc2c1]

Under protection of nitrogen gas, dissolve intermediate 7d, 4-methylphenyl boronic acid, tetrakis (triphenylphosphine) palladium and cesium carbonate anhydrous in anhydrous DMF solution. Reflux for 12 hours under anhydrous and anaerobic conditions. Cool it to room temperature after the reaction is completed, dilute with large amount of water, and perform ethyl acetate extraction for three times. Combine organic phases, wash successively with water and saturated salt water, dry with anhydrous sodium sulfate for 30 min, and remove organic solvent to obtain crude product. Carry out flash column chromatography with ethyl acetate: petroleum ether of 1:10 to obtain a light yellow solid product, with a yield of 59%.

H NMR (400 MHz, CDCl₃) δ 7.64 (d, J=4.4 Hz, 1H), 7.28 (d, J=8.9 Hz, 1H), 7.15~7.01 (m, 7H), 6.95 (dd, J=8.9, 2.0 Hz, 1H), 3.88 (s, 3H), 2.50 (s, 2H). MS (ESI, m/z): 355.1 [M+Na]⁺.

Embodiment 25: Preparation of 4-(5-(3,4-(methylenedioxy) benzene) furan-2-yl)-7-methoxyl-coumarin (COUM-25)

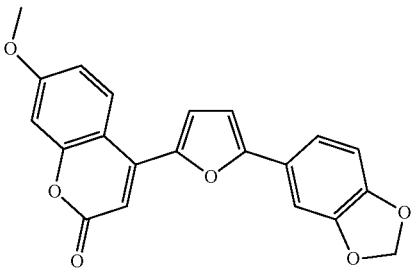 [SMILES: COc1ccc2c(-c3ccc(-c4ccc5c(c4)OCO5)o3)cc(=O)oc2c1]

Under protection of nitrogen gas, dissolve intermediate 7d, 3,4-(methylenedioxy) phenylboronic acid, tetrakis (triphenylphosphine) palladium and cesium carbonate anhydrous in anhydrous DMF solution. Reflux for 12 hours under anhydrous and anaerobic conditions. Cool it to room temperature after the reaction is completed, dilute with large amount of water, and perform ethyl acetate extraction for three times. Combine organic phases, wash successively with water and saturated salt water, dry with anhydrous sodium sulfate for 30 min, and remove organic solvent to obtain crude product. Carry out flash column chromatography with ethyl acetate: petroleum ether of 1:10 to obtain a light yellow solid product, with a yield of 50%.

¹H NMR (400 MHz, DMSO) δ 7.72~7.65 (m, 1H), 7.29 (d, J=8.9 Hz, 1H), 7.17~7.13 (m, 1H), 7.11 (d, J=4.8 Hz, 2H), 6.95 (dd, J=8.9, 2.3 Hz, 1H), 6.81~6.74 (m, 2H), 6.62 (dd, J=8.0, 1.3 Hz, 1H), 5.99 (s, 2H), 3.88 (s, 3H). MS (ESI, m/z): 485.1 [M+Na]⁺.

Embodiment 26: Preparation of 4-(5-(2-methoxybenzene) furan-2-yl)-7-methoxyl-coumarin (COUM-26)

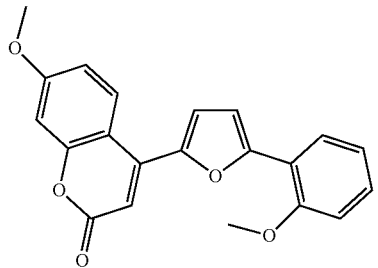 [SMILES: COc1ccc2c(-c3ccc(-c4ccccc4OC)o3)cc(=O)oc2c1]

Under protection of nitrogen gas, dissolve intermediate 7d, 2-methoxyphenylboronic acid, tetrakis (triphenylphosphine) palladium and cesium carbonate anhydrous in anhydrous DMF solution. Reflux for 12 hours under anhydrous and anaerobic conditions. Cool it to room temperature after the reaction is completed, dilute with large amount of water, and perform ethyl acetate extraction for three times. Combine organic phases, wash successively with water and saturated salt water, dry with anhydrous sodium sulfate for 30 min, and remove organic solvent to obtain crude product. Carry out flash column chromatography with ethyl acetate: petroleum ether of 1:10 to obtain a light yellow solid product, with a yield of 55%.

¹H NMR (400 MHz, CDCl₃) δ 7.61 (dd, J=3.7, 2.3 Hz, 1H), 7.31 (d, J=8.9 Hz, 1H), 7.25 (t, J=7.8 Hz, 1H), 7.12 (d, J=2.1 Hz, 1H), 7.05 (d, J=2.3 Hz, 2H), 7.01 (d, J=7.4 Hz, 1H), 6.95 (dd, J=8.3, 3.3 Hz, 2H), 6.81 (t, J=7.4 Hz, 1H), 3.89 (s, 3H), 3.67 (s, 3H). MS (ESI, m/z): 371.1 [M+Na]⁺.

Embodiment 27: Preparation of 4-(5-(3-ethoxycarbonyl benzene) furan-2-yl)-7-methoxyl-coumarin (COUM-27)

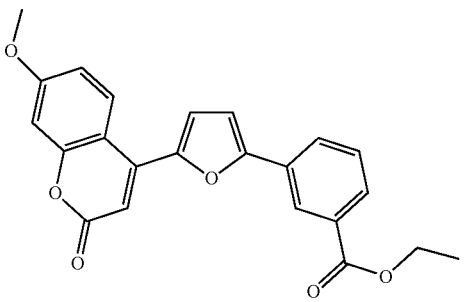 [SMILES: CCOC(=O)c1cccc(-c2ccc(-c3cc(=O)oc4cc(OC)ccc34)o2)c1]

Under protection of nitrogen gas, dissolve intermediate 7d, 3-ethoxycarbonylphenyl boronic acid, tetrakis (triphenylphosphine) palladium and cesium carbonate anhydrous in anhydrous DMF solution. Reflux for 12 hours under anhydrous and anaerobic conditions. Cool it to room temperature after the reaction is completed, dilute with large amount of water, and perform ethyl acetate extraction for three times. Combine organic phases, wash successively with water and saturated salt water, dry with anhydrous sodium sulfate for 30 min, and remove organic solvent to obtain crude product. Carry out flash column chromatography with ethyl acetate: petroleum ether of 1:10 to obtain a light yellow solid product, with a yield of 52%.

$^1$H NMR (400 MHz, DMSO) δ 7.82 (d, J=7.1 Hz, 2H), 7.65 (d, J=4.5 Hz, 1H), 7.45 (d, J=7.7 Hz, 1H), 7.40 (d, J=7.8 Hz, 1H), 7.32 (d, J=9.0 Hz, 1H), 7.13 (dd, J=6.4, 2.5 Hz, 2H), 7.10~7.05 (m, 1H), 6.97 (dd, J=8.9, 2.3 Hz, 1H), 4.28 (q, J=7.1 Hz, 2H), 3.90 (s, 3H), 1.30 (t, J=7.1 Hz, 3H). MS (ESI, m/z): 413.1 [M+Na]$^+$.

Embodiment 28: Preparation of 4-(5-(4-chlorobenzene) furan-2-yl)-7-methoxyl-coumarin (COUM-28)

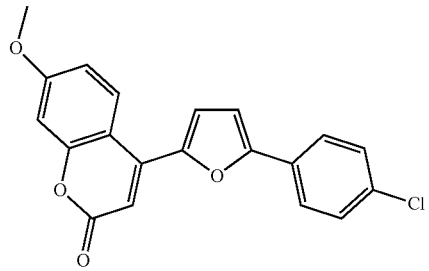 [SMILES: COc1ccc2c(-c3ccc(-c4ccc(Cl)cc4)o3)cc(=O)oc2c1]

Under protection of nitrogen gas, dissolve intermediate 7d, 4-chlorophenyl boronic acid, tetrakis (triphenylphosphine) palladium and cesium carbonate anhydrous in anhydrous DMF solution. Reflux for 12 hours under anhydrous and anaerobic conditions. Cool it to room temperature after the reaction is completed, dilute with large amount of water, and perform ethyl acetate extraction for three times. Combine organic phases, wash successively with water and saturated salt water, dry with anhydrous sodium sulfate for 30 min, and remove organic solvent to obtain crude product. Carry out flash column chromatography with ethyl acetate: petroleum ether of 1:10 to obtain a light yellow solid product, with a yield of 55%.

$^1$H NMR (400 MHz, DMSO) δ 3.93 (s, 3H), 7.72~7.64 (m, 2H), 7.53 (d, J=8.2 Hz, 1H), 7.40 (dd, J=8.7, 7.4 Hz, 2H), 7.37-7.30 (m, 2H), 7.25 (d, J=8.5 Hz, 2H), 7.17~7.14 (m, 1H), 7.13~7.09 (m, 1H). MS (ESI, m/z): 375.1 [M+Na]$^+$.

Embodiment 29: Preparation of 4-(5-(3-methoxyphenyl) thiophene-2-yl)-coumarin (COUM-29)

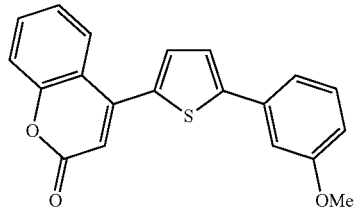 [SMILES: COc1cccc(-c2ccc(-c3cc(=O)oc4ccccc34)s2)c1]

Under protection of nitrogen gas, dissolve corresponding intermediate 7a, 3-methoxyphenylboronic acid, tetrakis (triphenylphosphine) palladium and cesium carbonate anhydrous in anhydrous DMF solution. Reflux for 12 hours under anhydrous and anaerobic conditions. Cool it to room temperature after the reaction is completed, dilute with large amount of water, and perform ethyl acetate extraction for three times. Combine organic phases, wash successively with water and saturated salt water, dry with anhydrous sodium sulfate for 30 min, and remove organic solvent to obtain crude product. Carry out flash column chromatography with ethyl acetate: petroleum ether of 1:10 to obtain a light yellow solid product, with a yield of 52%.

$^1$H NMR (400 MHz, DMSO) δ 7.73~7.65 (m, 1H), 7.63 (dd, J=4.9, 1.2 Hz, 1H), 7.52 (d, J=8.3 Hz, 1H), 7.44~7.33 (m, 2H), 7.29-7.23 (m, 1H), 7.11-7.01 (m, 3H), 6.96 (d, J=8.3 Hz, 1H), 6.83 (t, J=7.4 Hz, 1H), 3.68 (s, 3H). MS (ESI, m/z): 357.1 [M+Na]$^+$.

Embodiment 30: Preparation of 4-(5-(2-chlorobenzene) thiophene-2-yl)-coumarin (COUM-30)

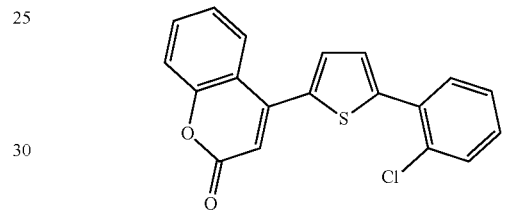

Under protection of nitrogen gas, dissolve corresponding intermediate 7a, 2-chlorophenyl boronic acid, tetrakis (triphenylphosphine) palladium and cesium carbonate anhydrous in anhydrous DMF solution. Reflux for 12 hours under anhydrous and anaerobic conditions. Cool it to room temperature after the reaction is completed, dilute with large amount of water, and perform ethyl acetate extraction for three times. Combine organic phases, wash successively with water and saturated salt water, dry with anhydrous sodium sulfate for 30 min, and remove organic solvent to obtain crude product. Carry out flash column chromatography with ethyl acetate: petroleum ether of 1:10 to obtain a light yellow solid product, with a yield of 52%.

$^1$H NMR (400 MHz, DMSO) δ 7.72~7.64 (m, 2H), 7.53 (d, J=8.2 Hz, 1H), 7.40 (dd, J=8.7, 7.4 Hz, 2H), 7.37~7.30 (m, 3H), 7.25 (d, J=8.5 Hz, 2H), 7.17~7.14 (m, 1H), 7.13~7.09 (m, 1H). MS (ESI, m/z): 361.1 [M+Na]$^+$.

Embodiment 31: Preparation of 4-(5-(3,4-(methylenedioxy) benzene) thiophene-2-yl)-coumarin (COUM-31)

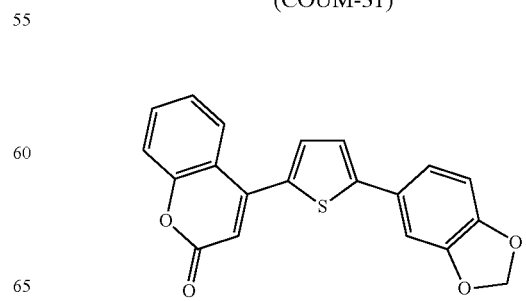

Under protection of nitrogen gas, dissolve corresponding intermediate 7a, 3,4-(methylenedioxy) phenylboronic acid, tetrakis (triphenylphosphine) palladium and cesium carbonate anhydrous in anhydrous DMF solution. Reflux for 12 hours under anhydrous and anaerobic conditions. Cool it to room temperature after the reaction is completed, dilute with large amount of water, and perform ethyl acetate extraction for three times. Combine organic phases, wash successively with water and saturated salt water, dry with anhydrous sodium sulfate for 30 min, and remove organic solvent to obtain crude product. Carry out flash column chromatography with ethyl acetate: petroleum ether of 1:10 to obtain a light yellow solid product, with a yield of 50%.

$^1$H NMR (400 MHz, DMSO) δ 7.72-7.65 (m, 1H), 7.29 (d, J=8.9 Hz, 1H), 7.17~7.13 (m, 1H), 7.11 (d, J=4.8 Hz, 2H), 6.95 (dd, J=8.9, 2.3 Hz, 1H), 6.81~6.74 (m, 2H), 6.62 (dd, J=8.0, 1.3 Hz, 1H), 5.99 (s, 2H). MS (ESI, m/z): 371.1 [M+Na]$^+$.

Embodiment 32: Preparation of 4-(5-(3-ethoxycarbonyl benzene) furan-2-yl)-coumarin (COUM-32)

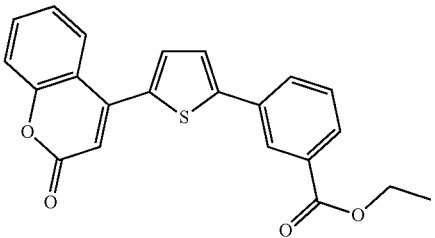 [SMILES: CCOC(=O)c1cccc(-c2ccc(-c3cc(=O)oc4ccccc34)s2)c1]

Under protection of nitrogen gas, dissolve intermediate 7a, 3-ethoxycarbonylphenyl boronic acid, tetrakis (triphenylphosphine) palladium and cesium carbonate anhydrous in anhydrous DMF solution. Reflux for 12 hours under anhydrous and anaerobic conditions. Cool it to room temperature after the reaction is completed, dilute with large amount of water, and perform ethyl acetate extraction for three times. Combine organic phases, wash successively with water and saturated salt water, dry with anhydrous sodium sulfate for 30 min, and remove organic solvent to obtain crude product. Carry out flash column chromatography with ethyl acetate: petroleum ether of 1:10 to obtain a light yellow solid product, with a yield of 52%.

$^1$H NMR (400 MHz, DMSO) δ 7.82 (d, J=7.1 Hz, 2H), 7.65 (d, J=4.5 Hz, 1H), 7.45 (d, J=7.7 Hz, 1H), 7.40 (d, J=7.8 Hz, 1H), 7.32 (d, J=9.0 Hz, 1H), 7.13 (dd, J=6.4, 2.5 Hz, 2H), 7.10~7.05 (m, 1H), 6.97 (dd, J=8.9, 2.3 Hz, 1H), 4.28 (q, J=7.1 Hz, 2H), 1.30 (t, J=7.1 Hz, 3H). MS (ESI, m/z): 399.1 [M+Na]$^+$.

Embodiment 33: Preparation of 4-(5-(3-methoxybenzene) thiophene-2-yl)-7-methoxyl-coumarin (COUM-33)

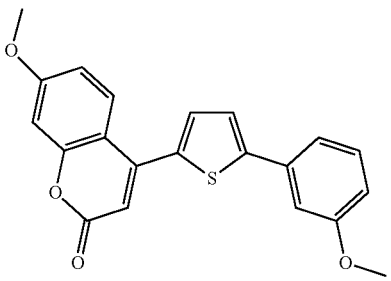 [SMILES: COc1cccc(-c2ccc(-c3cc(=O)oc4cc(OC)ccc34)s2)c1]

Under protection of nitrogen gas, dissolve corresponding intermediate 7b, 3-methoxyphenyl boronic acid, tetrakis (triphenylphosphine) palladium and cesium carbonate anhydrous in anhydrous DMF solution. Reflux for 12 hours under anhydrous and anaerobic conditions. Cool it to room temperature after the reaction is completed, dilute with large amount of water, and perform ethyl acetate extraction for three times. Combine organic phases, wash successively with water and saturated salt water, dry with anhydrous sodium sulfate for 30 min, and remove organic solvent to obtain crude product. Carry out flash column chromatography with ethyl acetate: petroleum ether of 1:10 to obtain a light yellow solid product, with a yield of 55%.

$^1$H NMR (400 MHz, CDCl$_3$) δ 7.61 (dd, J=3.7, 2.3 Hz, 1H), 7.31 (d, J=8.9 Hz, 1H), 7.25 (t, J=7.8 Hz, 1H), 7.12 (d, J=2.1 Hz, 1H), 7.05 (d, J=2.3 Hz, 2H), 7.01 (d, J=7.4 Hz, 1H), 6.95 (dd, J=8.3, 3.3 Hz, 2H), 6.81 (t, J=7.4 Hz, 1H), 3.89 (s, 3H), 3.67 (s, 3H). MS (ESI, m/z): 387.1 [M+Na]$^+$.

Embodiment 34: Preparation of 4-(5-(2-chlorobenzene) thiophene-2-yl)-7-methoxyl-coumarin (COUM-34)

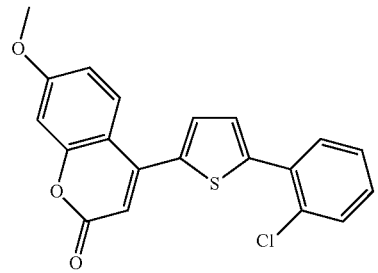 [SMILES: COc1ccc2c(-c3ccc(-c4ccccc4Cl)s3)cc(=O)oc2c1]

Under protection of nitrogen gas, dissolve corresponding intermediate 7b, 2-chlorophenyl boronic acid, tetrakis (triphenylphosphine) palladium and cesium carbonate anhydrous in anhydrous DMF solution. Reflux for 12 hours under anhydrous and anaerobic conditions. Cool it to room temperature after the reaction is completed, dilute with large amount of water, and perform ethyl acetate extraction for three times. Combine organic phases, wash successively with water and saturated salt water, dry with anhydrous sodium sulfate for 30 min, and remove organic solvent to obtain crude product. Carry out flash column chromatography with ethyl acetate: petroleum ether of 1:10 to obtain a light yellow solid product, with a yield of 55%.

$^1$H NMR (400 MHz, DMSO) δ 3.93 (s, 3H), 7.72~7.64 (m, 2H), 7.53 (d, J=8.2 Hz, 1H), 7.40 (dd, J=8.7, 7.4 Hz, 2H), 7.37~7.30 (m, 2H), 7.25 (d, J=8.5 Hz, 2H), 7.17~7.14 (m, 1H), 7.13~7.09 (m, 1H). MS (ESI, m/z): 391.1 [M+Na]$^+$.

Embodiment 35: Preparation of 4-(5-(3-chlorobenzene) thiophene-2-yl)-7-methoxyl-coumarin (COUM-35)

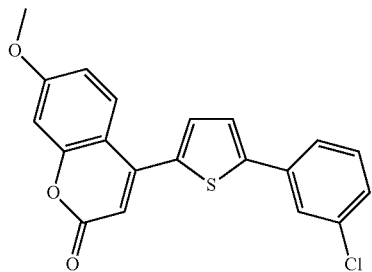 [SMILES: COc1ccc2c(-c3ccc(-c4cccc(Cl)c4)s3)cc(=O)oc2c1]

Under protection of nitrogen gas, dissolve corresponding intermediate 7b, 3-chlorophenyl boronic acid, tetrakis (triphenylphosphine) palladium and cesium carbonate anhydrous in anhydrous DMF solution. Reflux for 12 hours under anhydrous and anaerobic conditions. Cool it to room temperature after the reaction is completed, dilute with large amount of water, and perform ethyl acetate extraction for three times. Combine organic phases, wash successively with water and saturated salt water, dry with anhydrous sodium sulfate for 30 min, and remove organic solvent to obtain crude product. Carry out flash column chromatography with ethyl acetate: petroleum ether of 1:10 to obtain a light yellow solid product, with a yield of 55%.

$^1$H NMR (400 MHz, DMSO) δ 3.93 (s, 3H), 7.72~7.64 (m, 2H), 7.53 (d, J=8.2 Hz, 1H), 7.40 (dd, J=8.7, 7.4 Hz, 2H), 7.37-7.30 (m, 2H), 7.25 (d, J=8.5 Hz, 2H), 7.17~7.14 (m, 1H), 7.13~7.09 (m, 1H). MS (ESI, m/z): 391.1 [M+Na]$^+$.

Embodiment 36: Preparation of 4-(6-methoxy-3,4-dihydroquinoline-1(2H)-yl) coumarin (COUM-36)

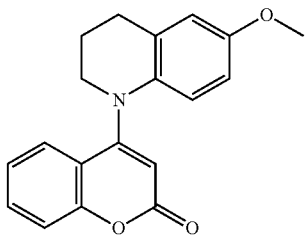 [SMILES: COc1ccc2c(c1)CCCN2c1cc(=O)oc2ccccc12]

Under protection of nitrogen gas, dissolve intermediate 10a (4-bromo-coumarin), 6-methoxy-1,2,3,4-tetrahydroquinoline and N,N-diisopropyl ethylamine in anhydrous DMF to reflux for 24 hours. Cool it to room temperature after the reaction is completed, dilute with large amount of water, and perform ethyl acetate extraction for three times. Combine organic phases, dry with anhydrous sodium sulfate, remove organic solvent, and carry out flash column chromatography with petroleum ether: ethyl acetate of 4:1 for separation of residual substrate to obtain a white solid, with a yield of 70%.

$^1$H NMR (400 MHz, CDCl$_3$) δ 7.73 (d, J=7.5 Hz, 1H), 7.57 (d, J=7.2 Hz, 1H), 7.35 (d, J=7.8 Hz, 1H), 7.28 (d, J=7.8 Hz, 1H), 7.15 (d, J=8.2 Hz, 1H), 6.81 (d, J=2.3 Hz, 1H), 6.77 (dd, J=8.2, 2.5 Hz, 1H), 5.59 (s, 1H), 4.03 (q, J=7.1 Hz, 2H), 3.75 (s, 3H), 3.70 (t, J=5.6 Hz, 2H), 2.99~2.85 (m, 2H), 1.99 (s, 4H), 1.17 (t, J=7.1 Hz, 3H).

Embodiment 37: Preparation of 4-(8-methoxy-1,3,4,5-tetrahydro-2H-benzoazepine-2-yl) Coumarin (COUM-37)

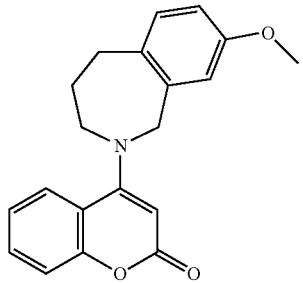 [SMILES: COc1ccc2c(c1)CN(c1cc(=O)oc3ccccc13)CCC2]

Under protection of nitrogen gas, dissolve intermediate 10a, intermediate 15 and N,N-diisopropyl ethylamine in anhydrous DMF to reflux for 24 hours. Cool it to room temperature after the reaction is completed, dilute with large amount of water, and perform ethyl acetate extraction for three times. Combine organic phases, dry with anhydrous sodium sulfate, remove organic solvent, and carry out flash column chromatography with petroleum ether: ethyl acetate of 4:1 for separation of residual substrate to obtain a white solid, with a yield of 70%.

$^1$H NMR (400 MHz, CDCl$_3$) δ 7.73 (d, J=7.5 Hz, 1H), 7.57 (d, J=7.2 Hz, 1H), 7.35 (d, J=7.8 Hz, 1H), 7.28 (d, J=7.8 Hz, 1H), 7.15 (d, J=8.2 Hz, 1H), 6.81 (d, J=2.3 Hz, 1H), 6.77 (dd, J=8.2, 2.5 Hz, 1H), 5.59 (s, 1H), 4.55 (s, 2H), 4.03 (q, J=7.1 Hz, 2H), 3.75 (s, 3H), 3.70 (t, J=5.6 Hz, 2H), 2.99~2.85 (m, 2H), 1.99 (s, 4H), 1.17 (t, J=7.1 Hz, 3H).

Embodiment 38: Preparation of 4-(6-methoxy-3,4-dihydroquinoline-1(211)-yl)-7 methoxycoumarin (COUM-38)

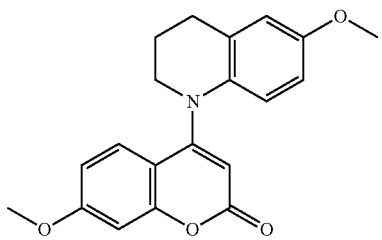

Under protection of nitrogen gas, dissolve intermediate 10b (4-bromo-7-methoxycoumarin), 6-methoxy-1,2,3,4-tetrahydroquinoline and N,N-diisopropyl ethylamine in anhydrous DMF to reflux for 24 hours. Cool it to room temperature after the reaction is completed, dilute with large amount of water, and perform ethyl acetate extraction for three times. Combine organic phases, dry with anhydrous sodium sulfate, remove organic solvent, and carry out flash column chromatography with petroleum ether: ethyl acetate of 4:1 for separation of residual substrate to obtain a white solid, with a yield of 70%.

$^1$H NMR (400 MHz, CDCl$_3$) δ 7.73 (d, J=7.5 Hz, 1H), 7.57 (d, J=7.2 Hz, 1H), 7.35 (d, J=7.8 Hz, 1H), 7.28 (d, J=7.8

Hz, 1H), 7.15 (d, J=8.2 Hz, 1H), 6.81 (d, J=2.3 Hz, 1H), 6.77 (dd, J=8.2, 2.5 Hz, 1H), 5.59 (s, 1H), 4.03 (q, J=7.1 Hz, 2H), 3.85 (s, 3H), 3.75 (s, 3H), 3.70 (t, J=5.6 Hz, 2H), 2.99~2.85 (m, 2H), 1.99 (s, 4H), 1.17 (t, J=7.1 Hz, 3H).

Embodiment 39: Preparation of 4-(8-methoxy-1,3,4, 5-tetrahydro-2H-benzoazepine-2-yl)-7-methoxycoumarin (COUM-39)

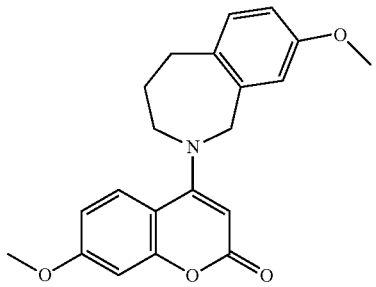

Under protection of nitrogen gas, dissolve intermediate 10b, intermediate 15 and N,N-diisopropyl ethylamine in anhydrous DMF to reflux for 24 hours. Cool it to room temperature after the reaction is completed, dilute with large amount of water, and perform ethyl acetate extraction for three times. Combine organic phases, dry with anhydrous sodium sulfate, remove organic solvent, and carry out flash column chromatography with petroleum ether: ethyl acetate of 4:1 for separation of residual substrate to obtain a white solid, with a yield of 70%.

$^1$H NMR (400 MHz, CDCl$_3$) δ 7.73 (d, J=7.5 Hz, 1H), 7.57 (d, J=7.2 Hz, 1H), 7.35 (d, J=7.8 Hz, 1H), 7.28 (d, J=7.8 Hz, 1H), 7.15 (d, J=8.2 Hz, 1H), 6.81 (d, J=2.3 Hz, 1H), 6.77 (dd, J=8.2, 2.5 Hz, 1H), 5.59 (s, 1H), 4.55 (s, 2H), 4.03 (q, J=7.1 Hz, 2H), 3.85 (s, 3H), 3.75 (s, 3H), 3.70 (t, J=5.6 Hz, 2H), 2.99~2.85 (m, 2H), 1.99 (s, 4H), 1.17 (t, J=7.1 Hz, 3H).

Embodiment 40: Preparation of 4-(N-methyl-N-(4-methoxybenzene)-amino)-7-methoxycoumarin (COUM-40)

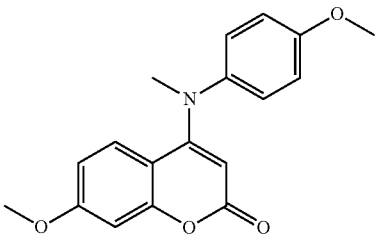

Under protection of nitrogen gas, dissolve intermediate 10b, N-methyl-4-methoxyaniline and N,N-diisopropyl ethylamine in anhydrous DMF to reflux for 24 hours. Cool it to room temperature after the reaction is completed, dilute with large amount of water, and perform ethyl acetate extraction for three times. Combine organic phases, dry with anhydrous sodium sulfate, remove organic solvent, and carry out flash column chromatography with petroleum ether: ethyl acetate of 4:1 for separation of residual substrate to obtain a white solid, with a yield of 72%.

$^1$H NMR (400 MHz, DMSO) δ 7.42 (dd, J=10.5, 4.1 Hz, 1H), 7.32 (d, J=8.1 Hz, 1H), 7.15 (d, J=8.7 Hz, 2H), 6.94 (t, J=10.4 Hz, 4H), 5.83 (s, 1H), 3.85 (s, 3H), 3.75 (s, 3H), 3.32 (s, 3H).

Embodiment 41: Preparation of 4-(N-methyl-N-(4-methoxybenzene)-amino)-7-diethylaminocoumarin (COUM-41)

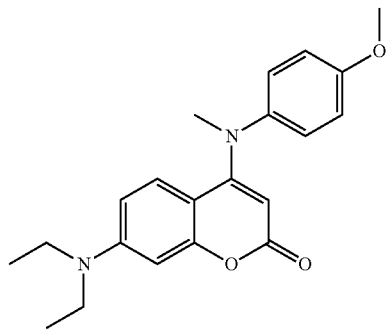 [SMILES: CCN(CC)c1ccc2c(N(C)c3ccc(OC)cc3)cc(=O)oc2c1]

Under protection of nitrogen gas, dissolve intermediate 10c (4-bromo-7-diethylaminocoumarin), N-methyl-4-methoxyaniline and N,N-diisopropyl ethylamine in anhydrous DMF to reflux for 24 hours. Cool it to room temperature after the reaction is completed, dilute with large amount of water, and perform ethyl acetate extraction for three times. Combine organic phases, dry with anhydrous sodium sulfate, remove organic solvent, and carry out flash column chromatography with petroleum ether: ethyl acetate of 4:1 for separation of residual substrate to obtain a white solid, with a yield of 72%.

$^1$H NMR (400 MHz, DMSO) δ 7.42 (dd, J=10.5, 4.1 Hz, 1H), 7.32 (d, J=8.1 Hz, 1H), 7.15 (d, J=8.7 Hz, 2H), 6.94 (t, J=10.4 Hz, 4H), 5.83 (s, 1H), 3.75 (s, 3H), 3.38 (m, 4H), 3.32 (s, 3H), 1.20 (m, 6H).

Embodiment 42: Preparation of 4-(N-methyl-N-(3, 4,5-trimethoxybenzene)-amino) coumarin (COUM-42)

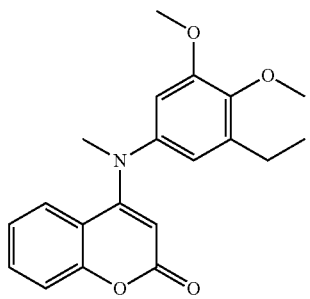 [SMILES: CCc1cc(N(C)c2cc(=O)oc3ccccc23)cc(OC)c1OC]

Under protection of nitrogen gas, dissolve intermediate 10a, N-methyl-3,4,5-methoxyaniline and N,N-diisopropyl ethylamine in anhydrous DMF to reflux for 24 hours. Cool it to room temperature after the reaction is completed, dilute with large amount of water, and perform ethyl acetate extraction for three times. Combine organic phases, dry with anhydrous sodium sulfate, remove organic solvent, and carry out flash column chromatography with petroleum ether: ethyl acetate of 4:1 for separation of residual substrate to obtain a white solid, with a yield of 72%.

¹H NMR (400 MHz, DMSO) δ 7.42 (dd, J=10.5, 4.1 Hz, 1H), 7.32 (d, J=8.1 Hz, 1H), 7.15 (d, J=8.7 Hz, 2H), 6.94 (t, J=10.4 Hz, 4H), 5.83 (s, 1H), 3.75 (s, 3H), 3.72 (s, 6H), 3.32 (s, 3H).

Embodiment 43: preparation of 4-(N-methyl-N-(4-methoxybenzene)-amino) coumarin (COUM-43)

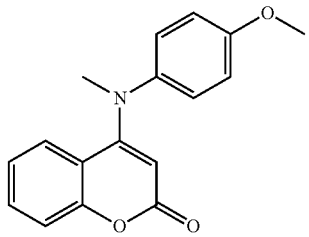 [SMILES: COc1ccc(N(C)c2cc(=O)oc3ccccc23)cc1]

Under protection of nitrogen gas, dissolve intermediate 10a, N-methyl-4-methoxyaniline and N,N-diisopropyl ethylamine in anhydrous DMF to reflux for 24 hours. Cool it to room temperature after the reaction is completed, dilute with large amount of water, and perform ethyl acetate extraction for three times. Combine organic phases, dry with anhydrous sodium sulfate, remove organic solvent, and carry out flash column chromatography with petroleum ether: ethyl acetate of 4:1 for separation of residual substrate to obtain a white solid, with a yield of 72%.

¹H NMR (400 MHz, DMSO) δ 7.42 (dd, J=10.5, 4.1 Hz, 1H), 7.32 (d, J=8.1 Hz, 1H), 7.15 (d, J=8.7 Hz, 2H), 6.94 (t, J=10.4 Hz, 4H), 5.83 (s, 1H), 3.75 (s, 3H), 3.32 (s, 3H). MS (ESI, m/z): 304.1 [M+Na]⁺.

Embodiment 44: Preparation of 4-(N-methyl-N-(3,4,5-trimethoxybenzene)-amino) coumarin (COUM-44)

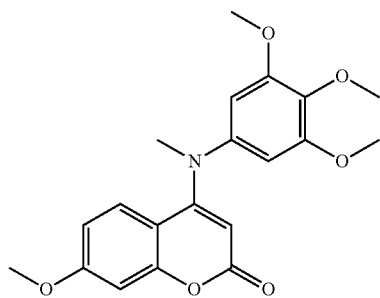

Under protection of nitrogen gas, dissolve intermediate 10b, N-methyl-3,4,5-methoxyaniline and N,N-diisopropyl ethylamine in anhydrous DMF to reflux for 24 hours. Cool it to room temperature after the reaction is completed, dilute with large amount of water, and perform ethyl acetate extraction for three times. Combine organic phases, dry with anhydrous sodium sulfate, remove organic solvent, and carry out flash column chromatography with petroleum ether: ethyl acetate of 4:1 for separation of residual substrate to obtain a white solid, with a yield of 72%.

¹H NMR (400 MHz, DMSO) δ 7.42 (dd, J=10.5, 4.1 Hz, 1H), 7.32 (d, J=8.1 Hz, 1H), 7.15 (d, J=8.7 Hz, 2H), 6.94 (t, J=10.4 Hz, 4H), 5.83 (s, 1H), 3.85 (s, 3H), 3.75 (s, 3H), 3.72 (s, 6H), 3.32 (s, 3H).

Embodiment 45: Preparation of 4-(N-methyl-N-(4-methoxy-3-(2-ethoxy-2-carbonylethoxy)-benzene)-amino) coumarin (COUM-45)

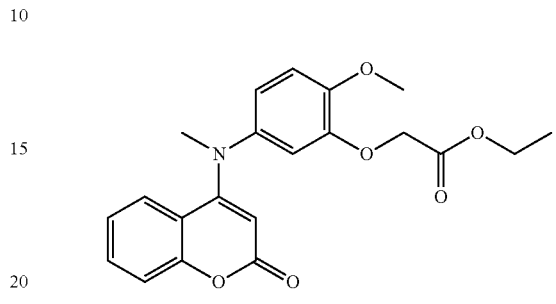

Under protection of nitrogen gas, dissolve intermediate 15a (4-(N-methyl-N-(3-hydroxy-4-methoxybenzene)-amino) coumarin) and N,N-diisopropyl ethylamine in anhydrous dichloromethane, and slowly dropwise add ethyl bromoacetate while stirring in an ice bath. Then, increase to room temperature to stir overnight. On the next day, remove organic solvent, and carry out flash column chromatography with petroleum ether: ethyl acetate of 6:1 for separation of residual substrate to obtain a light yellow solid, with a yield of 76%.

¹H NMR (400 MHz, CDCl₃) δ 7.39~7.32 (m, 1H), 7.29 (s, 1H), 6.96 (dd, J=8.2, 1.1 Hz, 1H), 6.90~6.85 (m, 1H), 6.83 (d, J=8.6 Hz, 1H), 6.70 (dd, J=8.6, 2.5 Hz, 1H), 6.65 (d, J=2.5 Hz, 1H), 5.83 (s, 1H), 4.63 (s, 2H), 4.17 (q, J=7.1 Hz, 2H), 3.89 (s, 3H), 3.34 (s, 3H), 1.25 (t, J=7.1 Hz, 3H).

Embodiment 46: Preparation of 4-(N-methyl-N-(4-methoxy-3-hydroxy-benzene)-amino) Coumarin (COUM-46)

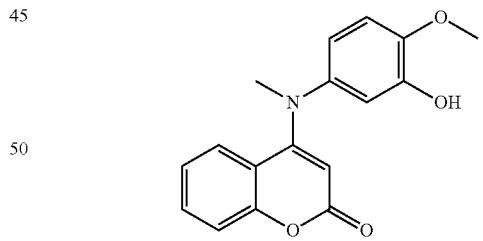

Under protection of nitrogen gas, dissolve intermediate 14a (4-(N-methyl-N-(3-methoxymethoxy-4-methoxybenzene)-amino) coumarin) in anhydrous ethyl acetate, feed hydrogen chloride gas and stir for 24 hours under room temperature. After the reaction is completed, add large amount of saturated sodium bicarbonate solution for neutralization, and perform ethyl acetate extraction for three times. Combine organic phases, dry with anhydrous sodium sulfate, remove organic solvent, and carry out flash column chromatography with petroleum ether: ethyl acetate of 3:1 for separation of residual substrate to obtain a yellow solid, with a yield of 82%.

¹H NMR (400 MHz, CDCl₃) δ 7.34 (m, 1H), 7.29 (m, 1H), 7.05 (d, J=8.2 Hz, 1H), 6.88 (t, J=7.6 Hz, 1H), 6.81 (d, J=2.5 Hz, 1H), 6.75 (d, J=8.5 Hz, 1H), 6.51 (dd, J=8.5, 2.5 Hz, 1H), 5.83 (s, 1H), 3.90 (s, 3H), 3.34 (s, 3H). MS (ESI, m/z): 298.3 [M+H]⁺.

Embodiment 47: Preparation of 4-(N-methyl-N-(4-methoxy-3-hydroxybenzene)-amino)-7-methoxycoumarin (COUM-47)

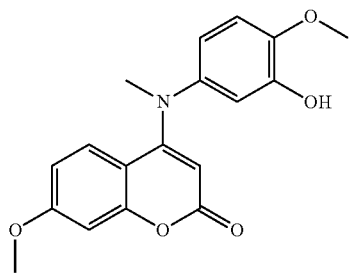 [SMILES: COc1ccc2c(N(C)c3ccc(OC)c(O)c3)cc(=O)oc2c1]

Under protection of nitrogen gas, dissolve intermediate 14b (4-(N-methyl-N-(3-methoxymethoxy-4-methoxybenzene)-amino)-7-methoxycoumarin) in anhydrous ethyl acetate, feed hydrogen chloride gas and stir for 24 hours under room temperature. After the reaction is completed, add large amount of saturated sodium bicarbonate solution for neutralization, and perform ethyl acetate extraction for three times. Combine organic phases, dry with anhydrous sodium sulfate, remove organic solvent, and carry out flash column chromatography with petroleum ether: ethyl acetate of 3:1 for separation of residual substrate to obtain a yellow solid, with a yield of 85%.

¹H NMR (400 MHz, CDCl₃) δ 6.91 (d, J=9.1 Hz, 1H), 6.77 (d, J=18.8 Hz, 3H), 6.52 (d, J=7.3 Hz, 1H), 6.45 (d, J=8.2 Hz, 1H), 5.71 (s, 1H), 3.90 (s, 3H), 3.79 (s, 3H), 3.32 (s, 3H). MS (ESI, m/z): 328.1156 [M+H]⁺.

Embodiment 48: Preparation of 4-(N-methyl-N-(4-methoxy-3-acetoxy-benzene)-amino) Coumarin (COUM-48)

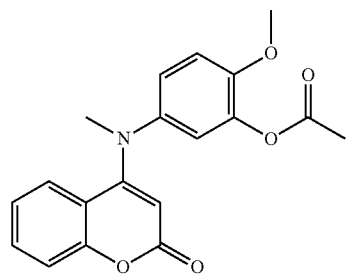 [SMILES: COc1ccc(N(C)c2cc(=O)oc3ccccc23)cc1OC(C)=O]

Under protection of nitrogen gas, dissolve intermediate 15a and N,N-diisopropyl ethylamine in anhydrous dichloromethane, slowly dropwise add acetyl chloride while stirring in an ice bath. Then, increase to room temperature to stir overnight. On the next day, remove organic solvent, and carry out flash column chromatography with petroleum ether: ethyl acetate of 6:1 for separation of residual substrate to obtain a light yellow solid, with a yield of 83%.

¹H NMR (400 MHz, CDCl₃) δ 7.36 (t, J=7.6 Hz, 1H), 7.28 (d, J=8.5 Hz, 1H), 7.01 (d, J=8.2 Hz, 1H), 6.95-6.86 (m, 4H), 5.86 (s, 1H), 3.84 (s, 3H), 3.36 (s, 3H), 2.30 (s, 3H). MS (ESI, m/z): 340.1156 [M+H]⁺.

Embodiment 49: Preparation of 4-(N-methyl-N-(4-methoxy-3-(2-morpholinoethoxy)-benzene)-amino) Coumarin (COUM-49)

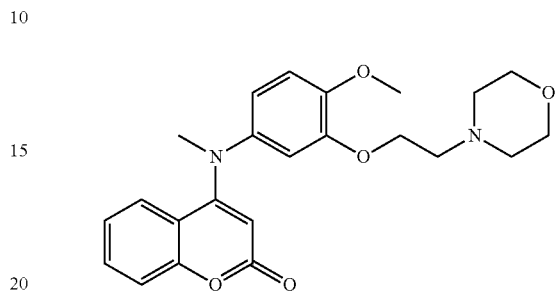

Under protection of nitrogen gas, dissolve intermediate 15a and N,N-diisopropyl ethylamine in anhydrous dichloromethane, add chloroethyl morpholine hydrochloride in batches while stirring in an ice bath. Then, increase to room temperature to stir overnight. On the next day, remove organic solvent, and carry out flash column chromatography with petroleum ether: ethyl acetate of 3:1 for separation of residual substrate to obtain a light yellow solid, with a yield of 53%.

¹H NMR (400 MHz, CDCl₃) δ 7.35 (t, J=7.6 Hz, 1H), 7.29 (m, 1H), 6.98 (d, J=8.2 Hz, 1H), 6.87 (t, J=7.7 Hz, 1H), 6.81 (d, J=8.5 Hz, 1H), 6.74-6.64 (m, 2H), 5.83 (s, 1H), 4.11 (m, 2H), 3.86 (s, 3H), 3.76 (m, 4H), 3.35 (s, 3H), 2.73 (m, 6H). MS (ESI, m/z): 411.1912 [M+H]⁺.

Embodiment 50: Preparation of 4-(N-methyl-N-(4-methoxy-3-(2-thiomorpholinoethoxy)-benzene)-amino) Coumarin (COUM-50)

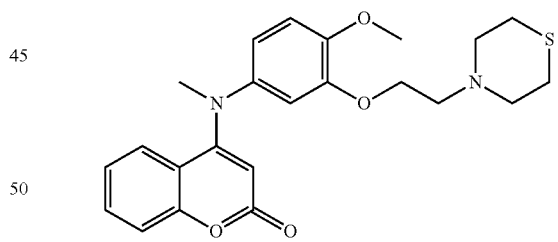

Under protection of nitrogen gas, dissolve intermediate 15a and N,N-diisopropyl ethylamine in anhydrous dichloromethane, add chloroethyl thiomorpholine hydrochloride in batches while stirring in an ice bath. Then, increase to room temperature to stir overnight. On the next day, remove organic solvent, and carry out flash column chromatography with petroleum ether: ethyl acetate of 3:1 for separation of residual substrate to obtain a light yellow solid, with a yield of 53%.

¹H NMR (400 MHz, CDCl₃) δ 7.35 (t, J=7.6 Hz, 1H), 7.29 (m, 1H), 6.98 (d, J=8.2 Hz, 1H), 6.87 (t, J=7.7 Hz, 1H), 6.81 (d, J=8.5 Hz, 1H), 6.74-6.64 (m, 2H), 5.83 (s, 1H), 4.11 (m, 2H), 3.86 (s, 3H), 3.76 (m, 4H), 3.35 (s, 3H), 2.73 (m, 6H).

Embodiment 51: Preparation of 4-(N-methyl-N-(4-methoxy-3-(2-piperidinoethoxy)-benzene)-amino) Coumarin (COUM-51)

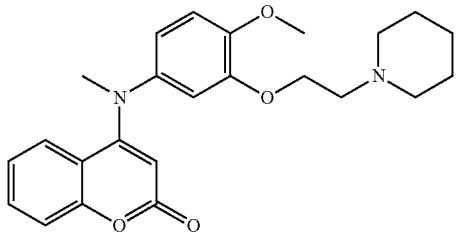

Under protection of nitrogen gas, dissolve intermediate 15a and N,N-diisopropyl ethylamine in anhydrous dichloromethane, add chloroethyl piperidine hydrochloride in batches while stirring in an ice bath. Then, increase to room temperature to stir overnight. On the next day, remove organic solvent, and carry out flash column chromatography with petroleum ether: ethyl acetate of 3:1 for separation of residual substrate to obtain a light yellow solid, with a yield of 53%.

Embodiment 52: Preparation of 4-(N-methyl-N-(4-methoxy-3-(2-pyrrole ethoxy)-benzene)-amino) Coumarin (COUM-52)

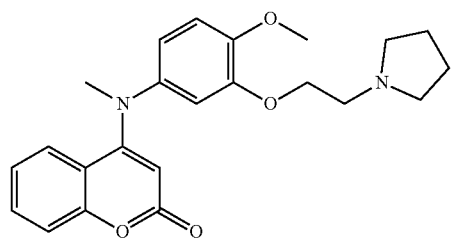

Under protection of nitrogen gas, dissolve intermediate 15a and N,N-diisopropyl ethylamine in anhydrous dichloromethane, add chloroethyl pyrrole hydrochloride in batches while stirring in an ice bath. Then, increase to room temperature to stir overnight. On the next day, remove organic solvent, and carry out flash column chromatography with petroleum ether: ethyl acetate of 3:1 for separation of residual substrate to obtain a light yellow solid, with a yield of 53%.

Embodiment 53: Preparation of 4-(N-methyl-N-(4-methoxy-3-((4-ethylbenzene) methoxycarbonyl)-benzene)-amino) Coumarin (COUM-53)

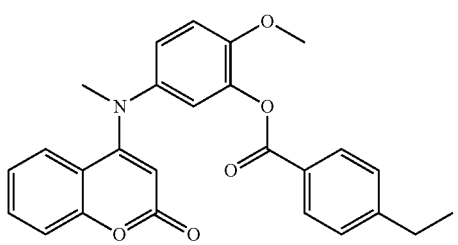

Under protection of nitrogen gas, dissolve intermediate 15a and N,N-diisopropyl ethylamine in anhydrous dichloromethane, slowly dropwise add dichloromethane solution containing 4-ethylbenzoyl chloride while stirring in an ice bath. Then, increase to room temperature to stir overnight. On the next day, remove organic solvent, and carry out flash column chromatography with petroleum ether: ethyl acetate of 6:1 for separation of residual substrate to obtain a light yellow solid, with a yield of 80%.

$^1$H NMR (400 MHz, CDCl$_3$) δ 8.10 (d, J=7.9 Hz, 2H), 7.34 (ddd, J=23.4, 15.4, 8.0 Hz, 4H), 7.08 (d, J=8.2 Hz, 1H), 7.03 (s, 1H), 6.99-6.90 (m, 3H), 5.87 (s, 1H), 3.81 (s, 3H), 3.38 (s, 3H), 2.74 (q, J=7.6 Hz, 2H), 1.28 (t, J=7.6 Hz, 3H). MS (ESI, m/z): 430.2367 [M+H]$^+$.

Embodiment 54: Preparation of 4-(N-methyl-N-(4-methoxy-3-methanesulfonate-benzene)-amino) Coumarin (COUM-54)

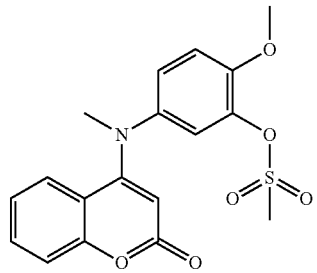

Under protection of nitrogen gas, dissolve intermediate 15a and N,N-diisopropyl ethylamine in anhydrous dichloromethane, slowly dropwise add dichloromethane solution containing methanesulfonyl chloride while stirring in an ice bath. Then, increase to room temperature to stir overnight. On the next day, remove organic solvent, and carry out flash column chromatography with petroleum ether: ethyl acetate of 6:1 for separation of residual substrate to obtain a light yellow solid, with a yield of 86%.

$^1$H NMR (400 MHz, CDCl$_3$) δ 7.37 (t, J=7.3 Hz, 1H), 7.30 (d, J=8.2 Hz, 1H), 7.16 (d, J=2.1 Hz, 1H), 7.02-6.88 (m, 4H), 5.90 (s, 1H), 3.90 (s, 3H), 3.37 (s, 3H), 3.19 (s, 3H). MS (ESI, m/z): 376.1383 [M+H]$^+$.

Embodiment 55: Preparation of 4-(N-methyl-N-(4-methoxy-3-(4-methyl benzene) methanesulfonate-benzene)-amino) Coumarin (COUM-55)

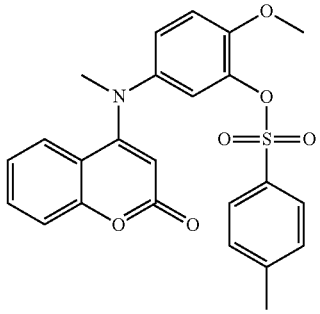

Under protection of nitrogen gas, dissolve intermediate 15a (4-(N-methyl-N-(3-hydroxyl-4-methoxybenzene)-amino) coumarin) and N,N-diisopropyl ethylamine in anhydrous dichloromethane, slowly dropwise add dichloromethane solution containing 4-toluenesulfonyl chloride while stirring in an ice bath. Then, increase to room temperature to stir overnight. On the next day, remove organic solvent, and carry out flash column chromatography with petroleum ether: ethyl acetate of 6:1 for separation of residual substrate to obtain a light yellow solid, with a yield of 82%.

$^1$H NMR (400 MHz, CDCl$_3$) δ 7.79 (dd, J=8.7, 5.0 Hz, 2H), 7.41 (t, J=7.4 Hz, 1H), 7.33 (d, J=8.2 Hz, 1H), 7.16 (t, J=8.4 Hz, 2H), 7.01~6.90 (m, 4H), 6.81 (d, J=8.6 Hz, 1H), 5.87 (s, 1H), 3.62 (s, 3H), 3.34 (s, 3H), 2.65 (s, 3H).

Embodiment 56: Preparation of 4-(N-methyl-N-(4-methoxy-3-(4-fluorobenzene) methanesulfonate-benzene)-amino) Coumarin (COUM-56)

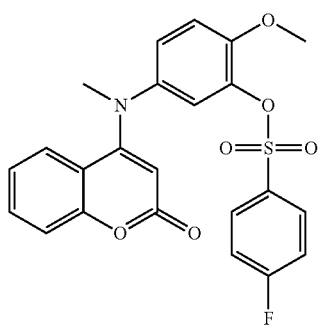

Under protection of nitrogen gas, dissolve intermediate 15a (4-(N-methyl-N-(3-hydroxyl-4-methoxybenzene)-amino) coumarin) and N,N-diisopropyl ethylamine in anhydrous dichloromethane, slowly dropwise add dichloromethane solution containing 4-fluorobenzenesulfonyl chloride while stirring in an ice bath. Then, increase to room temperature to stir overnight. On the next day, remove organic solvent, and carry out flash column chromatography with petroleum ether: ethyl acetate of 6:1 for separation of residual substrate to obtain a light yellow solid, with a yield of 82%.

$^1$H NMR (400 MHz, CDCl$_3$) δ 7.79 (dd, J=8.7, 5.0 Hz, 2H), 7.41 (t, J=7.4 Hz, 1H), 7.33 (d, J=8.2 Hz, 1H), 7.16 (t, J=8.4 Hz, 2H), 7.01~6.90 (m, 4H), 6.81 (d, J=8.6 Hz, 1H), 5.87 (s, 1H), 3.62 (s, 3H), 3.34 (s, 3H). MS (ESI, m/z): 456.1704 [M+H]$^+$.

Embodiment 57: Preparation of 4-(N-methyl-N-(4-methoxy-3-alkenyl propionate-benzene)-amino) Coumarin (COUM-57)

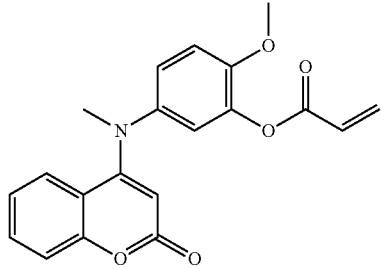

Under protection of nitrogen gas, dissolve intermediate 15a and N,N-diisopropyl ethylamine in anhydrous dichloromethane, slowly dropwise add dichloromethane solution containing acryloyl chloride while stirring in an ice bath. Then, increase to room temperature to stir overnight. On the next day, remove organic solvent, and carry out flash column chromatography with petroleum ether: ethyl acetate of 6:1 for separation of residual substrate to obtain a light yellow solid, with a yield of 81%.

$^1$H NMR (400 MHz, CDCl$_3$) δ 7.36 (t, J=7.6 Hz, 1H), 7.29 (d, J=8.2 Hz, 1H), 7.02 (t, J=8.8 Hz, 1H), 6.93 (d, J=10.8 Hz, 4H), 6.61 (d, J=17.3 Hz, 1H), 6.32 (dd, J=17.3, 10.5 Hz, 1H), 6.03 (d, J=10.5 Hz, 1H), 5.86 (s, 1H), 3.83 (s, 3H), 3.37 (s, 3H). MS (ESI, m/z): 352.1173 [M+H]$^+$.

Embodiment 58: Preparation of 4-(N-methyl-N-(4-methoxy-3-ethoxy-benzene)-amino) Coumarin (COUM-58)

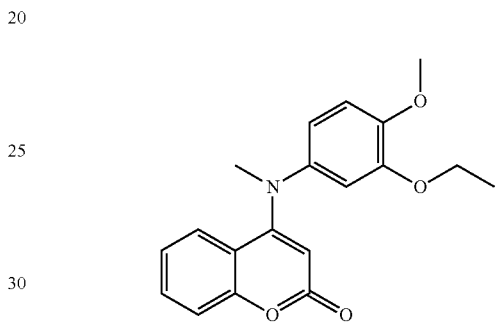

Under protection of nitrogen gas, dissolve intermediate 15a and N,N-diisopropyl ethylamine in anhydrous dichloromethane, slowly dropwise add dichloromethane solution containing iodoethane while stirring in an ice bath. Then, increase to room temperature to stir overnight. On the next day, remove organic solvent, and carry out flash column chromatography with petroleum ether: ethyl acetate of 6:1 for separation of residual substrate to obtain a light yellow solid, with a yield of 81%.

$^1$H NMR (400 MHz, CDCl$_3$) δ 7.36 (t, J=7.6 Hz, 1H), 7.29 (d, J=8.7 Hz, 1H), 7.03 (d, J=8.0 Hz, 1H), 6.95~6.88 (m, 2H), 6.85 (s, 2H), 5.85 (s, 1H), 4.13 (m, 2H), 3.81 (s, 3H), 3.35 (s, 3H), 1.41 (m, 3H). MS (ESI, m/z): 326.4 [M+H]$^+$.

Embodiment 59: Preparation of 4-(N-methyl-N-(4-methoxy-3-pivalate-benzene)-amino) Coumarin (COUM-59)

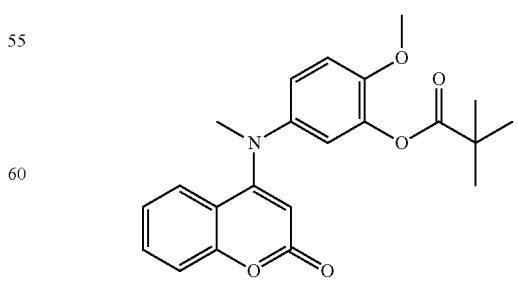

Under protection of nitrogen gas, dissolve intermediate 15a and N,N-diisopropyl ethylamine in anhydrous dichloromethane, slowly dropwise add dichloromethane solution containing tert-butylacetyl chloride while stirring in an ice bath. Then, increase to room temperature to stir overnight. On the next day, remove organic solvent, and carry out flash column chromatography with petroleum ether: ethyl acetate of 6:1 for separation of residual substrate to obtain a light yellow solid, with a yield of 84%.

¹H NMR (400 MHz, CDCl₃) δ 7.36 (t, J=7.6 Hz, 1H), 7.29 (d, J=8.7 Hz, 1H), 7.03 (d, J=8.0 Hz, 1H), 6.95~6.88 (m, 2H), 6.85 (s, 2H), 5.85 (s, 1H), 3.81 (s, 3H), 3.35 (s, 3H), 1.36 (s, 9H). MS (ESI, m/z): 382.4 [M+H]⁺.

Embodiment 60: Preparation of 4-(N-methyl-N-(4-methoxy-3-(2-chloroethyl carbonyloxy)-benzene)-amino) Coumarin (COUM-60)

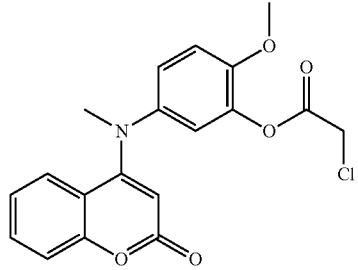

Under protection of nitrogen gas, dissolve intermediate 15a and N,N-diisopropyl ethylamine in anhydrous dichloromethane, slowly dropwise add dichloromethane solution containing chloroacetyl chloride while stirring in an ice bath. Then, increase to room temperature to stir overnight. On the next day, remove organic solvent, and carry out flash column chromatography with petroleum ether: ethyl acetate of 6:1 for separation of residual substrate to obtain a light yellow solid, with a yield of 84%.

¹H NMR (400 MHz, CDCl₃) δ 7.36 (d, J=8.0 Hz, 1H), 7.29 (d, J=8.2 Hz, 1H), 7.0-36.88 (m, 5H), 5.88 (s, 1H), 4.32 (s, 2H), 3.84 (s, 3H), 3.36 (s, 3H). MS (ESI, m/z): 396.6 [M+Na]⁺.

Embodiment 61: Preparation of 4-(N-methyl-N-(4-methoxy-3-(furan-2-yl-methoxycarbonyl)-benzene)-amino) Coumarin (COUM-61)

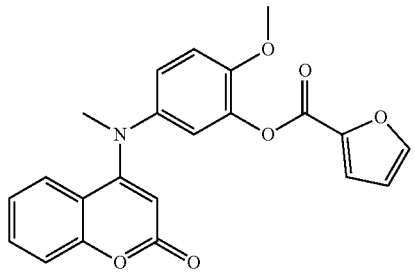

Under protection of nitrogen gas, dissolve intermediate 15a (4-(N-methyl-N-(3-hydroxyl-4-methoxybenzene)-amino) coumarin) and N,N-diisopropyl ethylamine in anhydrous dichloromethane, slowly dropwise add dichloromethane solution containing furan-2-acyl chloride while stirring in an ice bath. Then, increase to room temperature to stir overnight. On the next day, remove organic solvent, and carry out flash column chromatography with petroleum ether: ethyl acetate of 6:1 for separation of residual substrate to obtain a light yellow solid, with a yield of 84%.

¹H NMR (400 MHz, CDCl₃) δ 7.68 (m, 1H), 7.38 (m, 2H), 7.29 (d, J=8.4 Hz, 1H), 7.07~7.01 (m, 2H), 6.93 (m, 3H), 6.60 (d, J=1.7 Hz, 1H), 5.87 (s, 1H), 3.83 (s, 3H), 3.38 (s, 3H). MS (ESI, m/z): 414.2 [M+Na]⁺.

Embodiment 62: Preparation of 4-(N-methyl-N-(4-methoxy-3-(3-chlorophenyl-methoxycarbonyl)-benzene)-amino) Coumarin (COUM-62)

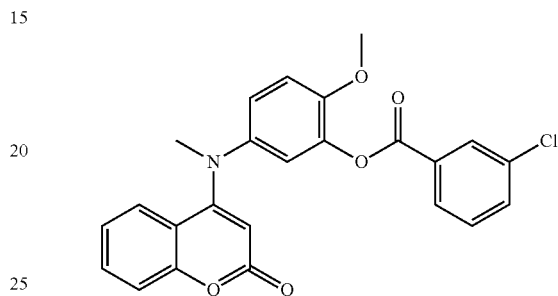

Under protection of nitrogen gas, dissolve intermediate 15a and N,N-diisopropyl ethylamine in anhydrous dichloromethane, slowly dropwise add dichloromethane solution containing 3-chlorobenzoyl chloride while stirring in an ice bath. Then, increase to room temperature to stir overnight. On the next day, remove organic solvent, and carry out flash column chromatography with petroleum ether: ethyl acetate of 6:1 for separation of residual substrate to obtain a light yellow solid, with a yield of 83%.

¹H NMR (400 MHz, CDCl₃) δ 8.17 (s, 1H), 8.07 (d, J=7.6 Hz, 1H), 7.61 (d, J=8.2 Hz, 1H), 7.46 (t, J=7.9 Hz, 1H), 7.38 (t, J=7.5 Hz, 1H), 7.30 (d, J=8.4 Hz, 1H), 7.07 (d, J=8.2 Hz, 1H), 7.01 (s, 1H), 6.99~6.92 (m, 3H), 5.88 (s, 1H), 3.83 (s, 3H), 3.39 (s, 3H). MS (ESI, m/z): 458.5[M+Na]⁺.

Embodiment 63: Preparation of 4-(N-methyl-N-(4-methoxy-3-(2-methylphenyl-methoxycarbonyl)-benzene)-amino) Coumarin (COUM-63)

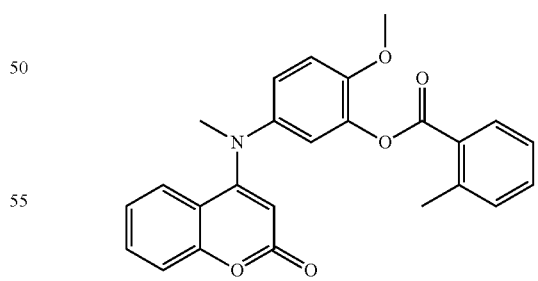

Under protection of nitrogen gas, dissolve intermediate 15a (4-(N-methyl-N-(3-hydroxyl-4-methoxybenzene)-amino) coumarin) and N,N-diisopropyl ethylamine in anhydrous dichloromethane, slowly dropwise add dichloromethane solution containing 2-Methyl benzoyl chloride while stirring in an ice bath. Then, increase to room temperature to stir overnight. On the next day, remove organic solvent, and carry out flash column chromatography with petroleum ether: ethyl acetate of 6:1 for separation of residual substrate to obtain a light yellow solid, with a yield of 81%.

$^1$H NMR (400 MHz, CDCl$_3$) δ 8.14 (d, J=7.8 Hz, 1H), 7.48 (t, J=7.5 Hz, 1H), 7.37 (t, J=7.7 Hz, 1H), 7.30 (t, J=8.1 Hz, 3H), 7.08 (d, J=8.1 Hz, 1H), 7.02 (s, 1H), 6.98-6.91 (m, 3H), 5.88 (s, 1H), 3.84 (s, 3H), 3.39 (s, 3H), 2.66 (s, 3H).

Embodiment 64: Preparation of 4-(N-methyl-N-(4-methoxy-3-(thiophene-2-yl-methoxycarbonyl)-benzene)-amino) Coumarin (COUM-64)

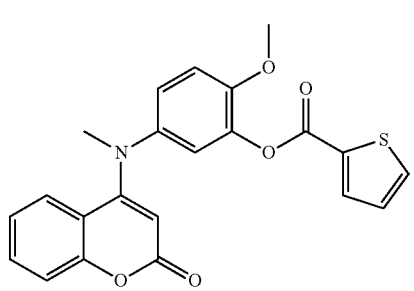 [SMILES: COc1ccc(N(C)c2cc(=O)oc3ccccc23)cc1OC(=O)c1cccs1]

Under protection of nitrogen gas, dissolve intermediate 15a (4-(N-methyl-N-(3-hydroxyl-4-methoxybenzene)-amino) coumarin) and N,N-diisopropyl ethylamine in anhydrous dichloromethane, slowly dropwise add dichloromethane solution containing thiophene-2-formyl chloride while stirring in an ice bath. Then, increase to room temperature to stir overnight. On the next day, remove organic solvent, and carry out flash column chromatography with petroleum ether: ethyl acetate of 6:1 for separation of residual substrate to obtain a light yellow solid, with a yield of 81%.

$^1$H NMR (400 MHz, CDCl$_3$) δ 7.68 (d, J=4.9 Hz, 1H), 7.47~7.37 (m, 2H), 7.32 (d, J=8.2 Hz, 1H), 7.08~7.01 (m, 1H), 6.97 (m, 3H), 6.85 (m, 2H), 5.85 (s, 1H), 3.70 (s, 3H), 3.32 (s, 3H).

Embodiment 65: Preparation of 4-(N-methyl-N-(4-methoxy-3-(4-(methoxyphenyl)-methoxycarbonyl)-benzene)-amino) Coumarin (COUM-65)

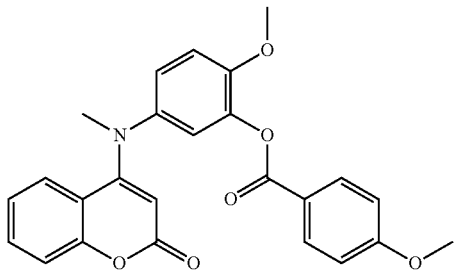 [SMILES: COc1ccc(C(=O)Oc2cc(N(C)c3cc(=O)oc4ccccc34)ccc2OC)cc1]

Under protection of nitrogen gas, dissolve intermediate 15a and N,N-diisopropyl ethylamine in anhydrous dichloromethane, slowly dropwise add dichloromethane solution containing 4-methoxybenzoyl chloride while stirring in an ice bath. Then, increase to room temperature to stir overnight. On the next day, remove organic solvent, and carry out flash column chromatography with petroleum ether: ethyl acetate of 6:1 for separation of residual substrate to obtain a light yellow solid, with a yield of 81%.

$^1$H NMR (400 MHz, CDCl$_3$) δ 8.14 (d, J=8.8 Hz, 2H), 7.37 (t, J=7.6 Hz, 1H), 7.29 (d, J=8.2 Hz, 1H), 7.11~6.89 (m, 8H), 5.87 (s, 1H), 3.90 (s, 3H), 3.82 (s, 3H), 3.38 (s, 3H). MS (ESI, m/z): 454.4 [M+Na]$^+$.

Embodiment 66: Preparation of 4-(N-methyl-N-(4-methoxy-3-amylcarbonyloxy-benzene)-amino) Coumarin (COUM-66)

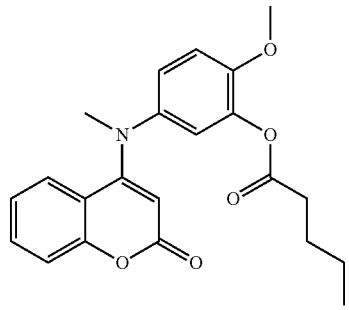 [SMILES: CCCCC(=O)Oc1cc(N(C)c2cc(=O)oc3ccccc23)ccc1OC]

Under protection of nitrogen gas, dissolve intermediate 15a and N,N-diisopropyl ethylamine in anhydrous dichloromethane, slowly dropwise add dichloromethane solution containing n-valeryl chloride while stirring in an ice bath. Then, increase to room temperature to stir overnight. On the next day, remove organic solvent, and carry out flash column chromatography with petroleum ether: ethyl acetate of 6:1 for separation of residual substrate to obtain a light yellow solid, with a yield of 87%.

$^1$H NMR (400 MHz, CDCl$_3$) δ 7.36 (t, J=7.6 Hz, 1H), 7.28 (d, J=9.3 Hz, 1H), 7.01 (d, J=8.2 Hz, 1H), 6.94~6.86 (m, 4H), 5.85 (s, 1H), 3.83 (d, J=7.2 Hz, 3H), 3.36 (s, 3H), 2.56 (t, J=7.5 Hz, 2H), 1.78~1.70 (m, 2H), 1.45 (dd, J=15.0, 7.4 Hz, 2H), 0.96 (t, J=7.3 Hz, 3H). MS (ESI, m/z): 404.6 [M+Na]$^+$.

Embodiment 67: Preparation of 4-(N-methyl-N-(4-methoxy-3-propylcarbonyloxy-benzene)-amino) Coumarin (COUM-67)

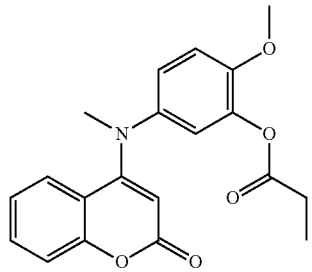 [SMILES: CCC(=O)Oc1cc(N(C)c2cc(=O)oc3ccccc23)ccc1OC]

Under protection of nitrogen gas, dissolve intermediate 15a and N,N-diisopropyl ethylamine in anhydrous dichloromethane, slowly dropwise add dichloromethane solution containing propionyl chloride while stirring in an ice bath. Then, increase to room temperature to stir overnight. On the next day, remove organic solvent, and carry out flash column chromatography with petroleum ether: ethyl acetate of 6:1 for separation of residual substrate to obtain a light yellow solid, with a yield of 87%.

¹H NMR (400 MHz, DMSO) δ 7.48~7.42 (m, 1H), 7.33 (d, J=8.2 Hz, 1H), 7.12~7.04 (m, 3H), 7.02~6.94 (m, 2H), 5.87 (s, 1H), 3.76 (s, 3H), 3.32 (s, 3H), 2.54 (dd, J=14.1, 6.6 Hz, 2H), 1.10 (t, J=7.5 Hz, 3H). MS (ESI, m/z): 376.2 [M+Na]⁺.

Embodiment 68: Preparation of 4-(N-methyl-N-(4-methoxy-3-(2-bromoethyl carbonyloxy)-benzene)-amino) Coumarin (COUM-68)

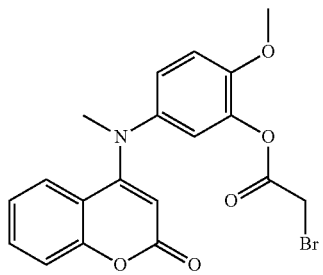 [SMILES: COc1ccc(N(C)c2cc(=O)oc3ccccc23)cc1OC(=O)CBr]

Under protection of nitrogen gas, dissolve intermediate 15a (4-(N-methyl-N-(3-hydroxyl-4-methoxybenzene)-amino) coumarin) and N,N-diisopropyl ethylamine in anhydrous dichloromethane, slowly dropwise add dichloromethane solution containing bromoacetyl bromide while stirring in an ice bath. Then, increase to room temperature to stir overnight. On the next day, remove organic solvent, and carry out flash column chromatography with petroleum ether: ethyl acetate of 6:1 for separation of residual substrate to obtain a light yellow solid, with a yield of 86%.

¹H NMR (400 MHz, DMSO) δ 7.50~7.42 (m, 1H), 7.33 (d, J=8.3 Hz, 1H), 7.08 (s, 1H), 6.98 (d, J=8.4 Hz, 2H), 5.89 (s, 1H), 4.41 (s, 2H), 3.78 (s, 3H). MS (ESI, m/z): 440.3, 442.3 [M+Na]⁺.

Embodiment 69: Preparation of 4-(N-methyl-N-(4-methoxy-3-(2-methyl-allylcarbonyloxy)-benzene)-amino) Coumarin (COUM-69)

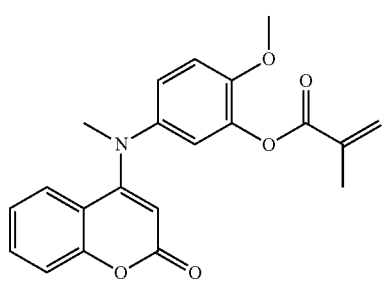 [SMILES: C=C(C)C(=O)Oc1cc(N(C)c2cc(=O)oc3ccccc23)ccc1OC]

Under protection of nitrogen gas, dissolve intermediate 15a (4-(N-methyl-N-(3-hydroxyl-4-methoxybenzene)-amino) coumarin) and N,N-diisopropyl ethylamine in anhydrous dichloromethane, slowly dropwise add dichloromethane solution containing 2-methacryloyl chloride while stirring in an ice bath. Then, increase to room temperature to stir overnight. On the next day, remove organic solvent, and carry out flash column chromatography with petroleum ether: ethyl acetate of 6:1 for separation of residual substrate to obtain a light yellow solid, with a yield of 85%.

¹H NMR (400 MHz, CDCl₃) δ 7.36 (t, J=7.7 Hz, 1H), 7.28 (d, J=10.5 Hz, 1H), 7.0-96.85 (m, 5H), 6.35 (s, 1H), 5.86 (s, 1H), 5.77 (s, 1H), 3.81 (d, J=9.2 Hz, 3H), 3.36 (s, 3H), 2.06 (s, 3H). MS (ESI, m/z): 388.5 [M+Na]⁺, 753.3 [2M+Na]⁺.

Embodiment 70: Preparation of 4-(N-methyl-N-(4-methoxy-3-(3-methylbut-2-ene) carbonyloxy) benzene)-amino) Coumarin (COUM-70)

Under protection of nitrogen gas, dissolve intermediate 15a and N,N-diisopropyl ethylamine in anhydrous dichloromethane, slowly dropwise add dichloromethane solution containing 3-methylbut-2-enoyl chloride while stirring in an ice bath. Then, increase to room temperature to stir overnight. On the next day, remove organic solvent, and carry out flash column chromatography with petroleum ether: ethyl acetate of 6:1 for separation of residual substrate to obtain a light yellow solid, with a yield of 81%.

¹H NMR (400 MHz, CDCl₃) δ 7.35 (t, J=7.7 Hz, 1H), 7.28 (d, J=8.0 Hz, 1H), 7.02 (t, J=8.9 Hz, 1H), 6.90 (d, J=14.3 Hz, 4H), 5.93 (s, 1H), 5.85 (s, 1H), 3.83 (s, 3H), 3.36 (s, 3H), 2.22 (s, 3H), 1.99 (s, 3H). MS (ESI, m/z): 402.8 [M+Na]⁺.

Embodiment 71: Preparation of 4-(N-methyl-N-(4-methoxy-3-(but-2-ene-carbonyloxy-) benzene)-amino) Coumarin (COUM-71)

Under protection of nitrogen gas, dissolve intermediate 15a and N,N-diisopropyl ethylamine in anhydrous dichloromethane, slowly dropwise add dichloromethane solution containing but-2-enoyl chloride while stirring in an ice bath. Then, increase to room temperature to stir overnight. On the next day, remove organic solvent, and carry out flash column chromatography with petroleum ether: ethyl acetate of 6:1 for separation of residual substrate to obtain a light yellow solid, with a yield of 91%.

¹H NMR (400 MHz, CDCl₃) δ 7.36 (t, J=7.2 Hz, 1H), 7.28 (d, J=9.3 Hz, 1H), 7.19 (dq, J=13.9, 6.9 Hz, 1H), 7.03

(d, J=8.2 Hz, 1H), 6.92 (dd, J=7.2, 6.1 Hz, 4H), 6.05 (dd, J=15.5, 1.4 Hz, 1H), 5.85 (s, 1H), 3.82 (s, 3H), 3.36 (s, 3H), 1.97 (dd, J=6.9, 1.2 Hz, 3H). MS (ESI, m/z): 388.5 [M+Na]+.

Embodiment 72: Preparation of 4-(N-methyl-N-(4-methoxy-3-(cyclopropyl-carbonyloxy) benzene)-amino) Coumarin (COUM-72)

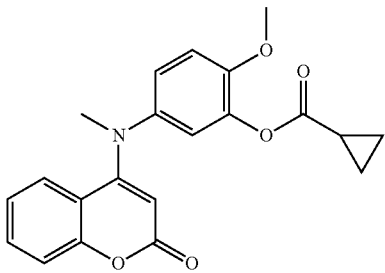 [SMILES: COc1ccc(N(C)c2cc(=O)oc3ccccc23)cc1OC(=O)C1CC1]

Under protection of nitrogen gas, dissolve intermediate 15a and N,N-diisopropyl ethylamine in anhydrous dichloromethane, slowly dropwise add dichloromethane solution containing cyclopropylformyl chloride while stirring in an ice bath. Then, increase to room temperature to stir overnight. On the next day, remove organic solvent, and carry out flash column chromatography with petroleum ether: ethyl acetate of 6:1 for separation of residual substrate to obtain a light yellow solid, with a yield of 89%.

$^1$H NMR (400 MHz, CDCl$_3$) δ 7.38~7.27 (m, 2H), 7.01 (d, J=8.1 Hz, 1H), 6.89 (d, J=12.3 Hz, 4H), 5.85 (s, 1H), 3.83 (s, 3H), 3.35 (s, 3H), 1.90~1.78 (m, 1H), 1.22-1.14 (m, 2H), 1.09~0.98 (m, 2H). MS (ESI, m/z): 388.5 [M+Na]+.

Embodiment 73: Preparation of 4-(N-methyl-N-(4-methoxy-3-(cyclopentyl-carbonyloxy) benzene)-amino) Coumarin (COUM-73)

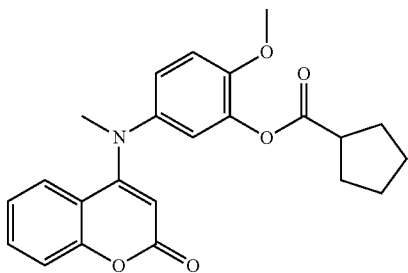 [SMILES: COc1ccc(N(C)c2cc(=O)oc3ccccc23)cc1OC(=O)C1CCCC1]

Under protection of nitrogen gas, dissolve intermediate 15a and N,N-diisopropyl ethylamine in anhydrous dichloromethane, slowly dropwise add dichloromethane solution containing cyclopropylformyl chloride while stirring in an ice bath. Then, increase to room temperature to stir overnight. On the next day, remove organic solvent, and carry out flash column chromatography with petroleum ether: ethyl acetate of 6:1 for separation of residual substrate to obtain a light yellow solid, with a yield of 89%.

Embodiment 74: Preparation of 4-(N-methyl-N-(4-methoxy-3-(3-ethoxycarbonyl carbonyloxy) benzene)-amino) Coumarin (COUM-74)

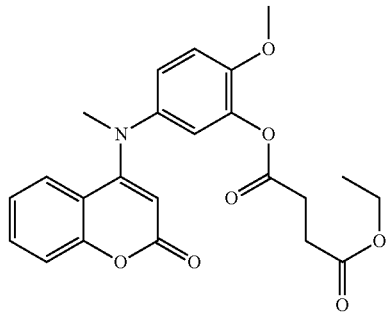 [SMILES: CCOC(=O)CCC(=O)Oc1cc(N(C)c2cc(=O)oc3ccccc23)ccc1OC]

Under protection of nitrogen gas, dissolve intermediate 15a and N,N-diisopropyl ethylamine in anhydrous dichloromethane, slowly dropwise add dichloromethane solution containing 3-ethoxycarbonyl propionyl chloride while stirring in an ice bath. Then, increase to room temperature to stir overnight. On the next day, remove organic solvent, and carry out flash column chromatography with petroleum ether: ethyl acetate of 6:1 for separation of residual substrate to obtain a light yellow solid, with a yield of 85%.

$^1$H NMR (400 MHz, DMSO) δ 7.44 (dd, J=10.4, 4.2 Hz, 1H), 7.33 (d, J=8.3 Hz, 1H), 7.16~7.05 (m, 2H), 6.98 (dd, J=14.1, 7.7 Hz, 3H), 5.87 (s, 1H), 4.13~3.96 (m, 3H), 3.75 (s, 3H), 3.33 (s, 3H), 2.79 (t, J=6.5 Hz, 2H), 2.61 (t, J=6.5 Hz, 2H), 1.17 (q, J=7.2 Hz, 2H). MS (ESI, m/z): 448.5 [M+Na]+.

Embodiment 75: Preparation of 4-(N-methyl-N-(4-methoxy-3-(hexane carbonyloxy) benzene)-amino) Coumarin (COUM-75)

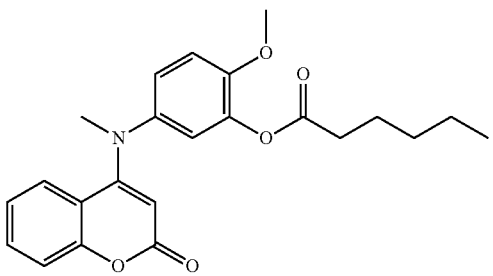 [SMILES: CCCCCC(=O)Oc1cc(N(C)c2cc(=O)oc3ccccc23)ccc1OC]

Under protection of nitrogen gas, dissolve intermediate 15a and N,N-diisopropyl ethylamine in anhydrous dichloromethane, slowly dropwise add dichloromethane solution containing n-hexanoyl chloride while stirring in an ice bath. Then, increase to room temperature to stir overnight. On the next day, remove organic solvent, and carry out flash column chromatography with petroleum ether: ethyl acetate of 6:1 for separation of residual substrate to obtain a light yellow solid, with a yield of 84%.

$^1$H NMR (400 MHz, CDCl$_3$) δ 7.38~7.33 (m, 1H), 7.28 (d, J=9.3 Hz, 1H), 7.04~6.99 (m, 1H), 6.95~6.85 (m, 4H), 5.85 (s, 1H), 3.82 (s, 3H), 3.36 (s, 3H), 2.55 (t, J=7.5 Hz, 2H), 1.80~1.70 (m, 2H), 1.44~1.33 (m, 4H), 0.92 (t, J=7.0 Hz, 3H).

Embodiment 76: Preparation of 4-(N-methyl-N-(4-methoxy-3-(decane carbonyloxy) benzene)-amino) Coumarin (COUM-76)

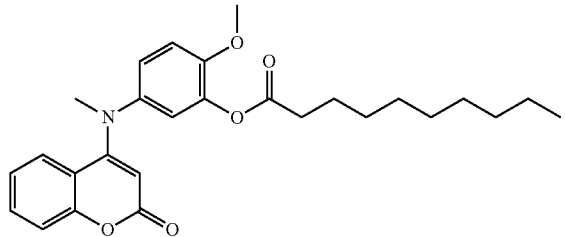 [SMILES: CCCCCCCCCC(=O)Oc1cc(N(C)c2cc(=O)oc3ccccc23)ccc1OC]

Under protection of nitrogen gas, dissolve intermediate 15a and N,N-diisopropyl ethylamine in anhydrous dichloromethane, slowly dropwise add dichloromethane solution containing n-decanoyl chloride while stirring in an ice bath. Then, increase to room temperature to stir overnight. On the next day, remove organic solvent, and carry out flash column chromatography with petroleum ether: ethyl acetate of 6:1 for separation of residual substrate to obtain a light yellow solid, with a yield of 64%.

$^1$H NMR (400 MHz, CDCl$_3$) δ 7.35 (t, J=7.4 Hz, 1H), 7.28 (d, J=7.8 Hz, 1H), 7.01 (d, J=8.1 Hz, 1H), 6.95~6.85 (m, 4H), 5.85 (s, 1H), 3.82 (s, 3H), 3.36 (s, 3H), 2.55 (t, J=7.4 Hz, 2H), 1.80~1.68 (m, 2H), 1.25 (dd, J=15.7, 8.4 Hz, 12H), 0.88 (t, J=6.5 Hz, 3H).

Embodiment 77: Preparation of 4-(N-methyl-N-(4-methoxy-3-((4-methoxycarbonyl)-carbonyloxy) benzene)-amino) Coumarin (COUM-77)

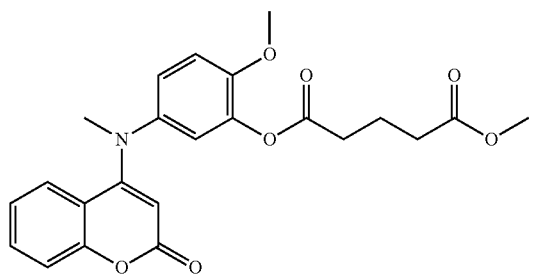 [SMILES: COC(=O)CCCC(=O)Oc1cc(N(C)c2cc(=O)oc3ccccc23)ccc1OC]

Under protection of nitrogen gas, dissolve intermediate 15a and N,N-diisopropyl ethylamine in anhydrous dichloromethane, slowly dropwise add dichloromethane solution containing 4-methoxycarbonyl butyryl chloride while stirring in an ice bath. Then, increase to room temperature to stir overnight. On the next day, remove organic solvent, and carry out flash column chromatography with petroleum ether: ethyl acetate of 6:1 for separation of residual substrate to obtain a light yellow solid, with a yield of 82%.

$^1$H NMR (400 MHz, CDCl$_3$) δ 7.36 (t, J=7.6 Hz, 1H), 7.28 (d, J=8.8 Hz, 1H), 7.01 (d, J=8.1 Hz, 1H), 6.96~6.85 (m, 4H), 5.86 (s, 1H), 3.82 (s, 3H), 3.69 (s, 3H), 3.36 (s, 3H), 2.64 (t, J=7.2 Hz, 2H), 2.47 (q, J=7.2 Hz, 2H), 2.11~2.03 (m, 2H). MS (ESI, m/z): 448.7 [M+Na]$^+$.

Embodiment 78: Preparation of 4-(N-methyl-N-(4-methoxy-3-(5-chloro-n-pentane carbonyloxy) benzene)-amino) Coumarin (COUM-78)

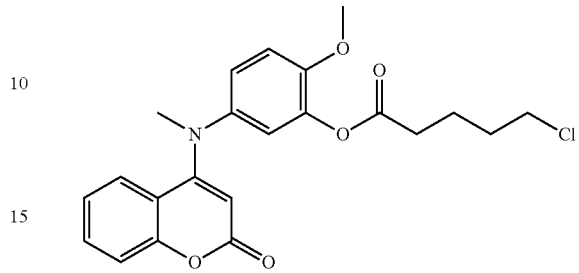

Under protection of nitrogen gas, dissolve intermediate 15a and N,N-diisopropyl ethylamine in anhydrous dichloromethane, slowly dropwise add dichloromethane solution containing 5-chlorovaleryl chloride while stirring in an ice bath. Then, increase to room temperature to stir overnight. On the next day, remove organic solvent, and carry out flash column chromatography with petroleum ether: ethyl acetate of 6:1 for separation of residual substrate to obtain a light yellow solid, with a yield of 84%.

$^1$H NMR (400 MHz, CDCl$_3$) δ 7.39~7.33 (m, 1H), 7.28 (dd, J=8.3, 1.1 Hz, 1H), 7.01 (dd, J=8.2, 1.3 Hz, 1H), 6.95~6.85 (m, 4H), 5.86 (s, 1H), 3.83 (s, 3H), 3.64~3.53 (m, 2H), 3.36 (s, 3H), 2.61 (dd, J=8.5, 5.1 Hz, 2H), 1.98~1.84 (m, 4H). MS (ESI, m/z): 438.3 [M+Na]$^+$.

Embodiment 79: Preparation of 4-(N-methyl-N-(4-methoxy-3-(3,3-dimethyl-butanecarbonyloxy) benzene)-amino) Coumarin (COUM-79)

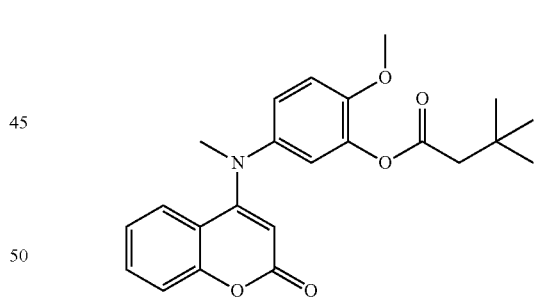

Under protection of nitrogen gas, dissolve intermediate 15a and N,N-diisopropyl ethylamine in anhydrous dichloromethane, slowly dropwise add dichloromethane solution containing pivaloyl chloride while stirring in an ice bath. Then, increase to room temperature to stir overnight. On the next day, remove organic solvent, and carry out flash column chromatography with petroleum ether: ethyl acetate of 6:1 for separation of residual substrate to obtain a light yellow solid, with a yield of 84%.

$^1$H NMR (400 MHz, CDCl$_3$) δ 7.4-07.32 (m, 1H), 7.28 (dd, J=9.1, 1.8 Hz, 1H), 7.02 (dd, J=8.3, 1.3 Hz, 1H), 6.95~6.85 (m, 4H), 5.85 (s, 1H), 3.82 (s, 3H), 3.36 (s, 3H), 2.44 (s, 2H), 1.13 (s, 9H).

Embodiment 80: Preparation of 4-(N-methyl-N-(4-methoxy-3-(pent-1-ene-carbonyloxy) benzene)-amino) Coumarin (COUM-80)

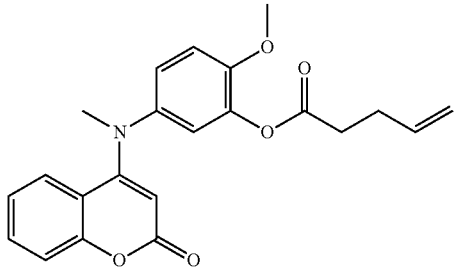 [SMILES: C=CCCC(=O)Oc1cc(N(C)c2cc(=O)oc3ccccc23)ccc1OC]

Under protection of nitrogen gas, dissolve intermediate 15a and N,N-diisopropyl ethylamine in anhydrous dichloromethane, slowly dropwise add dichloromethane solution containing pent-1-enoyl chloride while stirring in an ice bath. Then, increase to room temperature to stir overnight. On the next day, remove organic solvent, and carry out flash column chromatography with petroleum ether: ethyl acetate of 6:1 for separation of residual substrate to obtain a light yellow solid, with a yield of 76%.

$^1$H NMR (400 MHz, CDCl$_3$) δ 7.41~7.32 (m, 1H), 7.28 (d, J=7.9 Hz, 1H), 7.01 (d, J=8.2 Hz, 1H), 6.90 (dd, J=12.9, 7.2 Hz, 3H), 5.90 (ddd, J=17.4, 8.7, 4.5 Hz, 1H), 5.85 (d, J=3.9 Hz, 1H), 5.19~5.08 (m, 1H), 5.06 (d, J=10.2 Hz, 1H), 3.82 (s, 3H), 3.35 (s, 3H), 2.67 (t, J=7.4 Hz, 2H), 2.50 (dd, J=13.8, 6.7 Hz, 2H). MS (ESI, m/z): 380.2 [M+H]$^+$.

Embodiment 81: Preparation of 4-(N-methyl-N-(4-methoxy-3-(4-methyl-pent-3-ene-carbonyloxy) benzene)-amino) Coumarin (COUM-81)

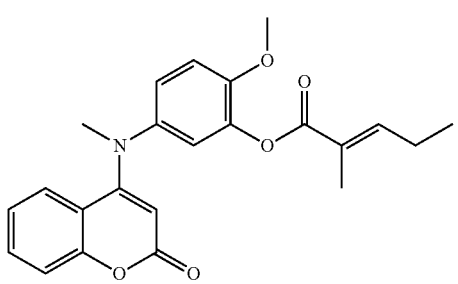 [SMILES: CC/C=C(\C)C(=O)Oc1cc(N(C)c2cc(=O)oc3ccccc23)ccc1OC]

Under protection of nitrogen gas, dissolve intermediate 15a and N,N-diisopropyl ethylamine in anhydrous dichloromethane, slowly dropwise add dichloromethane solution containing 4-methyl-pent-3-enoyl chloride while stirring in an ice bath. Then, increase to room temperature to stir overnight. On the next day, remove organic solvent, and carry out flash column chromatography with petroleum ether: ethyl acetate of 6:1 for separation of residual substrate to obtain a light yellow solid, with a yield of 76%.

$^1$H NMR (400 MHz, CDCl$_3$) δ 7.39~7.33 (m, 1H), 7.30~7.27 (m, 1H), 7.05 (dd, J=8.2, 1.2 Hz, 1H), 7.00 (dd, J=8.0, 6.7 Hz, 1H), 6.96~6.86 (m, 4H), 5.85 (s, 1H), 3.82 (s, 3H), 3.36 (s, 3H), 2.27 (p, J=7.4 Hz, 2H), 1.94 (s, 3H), 1.10 (t, J=7.6 Hz, 3H). MS (ESI, m/z): 394.2 [M+H]$^+$.

Embodiment 82: Preparation of 4-(N-methyl-N-(4-methoxy-3-(trans-hex-4-ene-carbonyloxy) benzene)-amino) Coumarin (COUM-82)

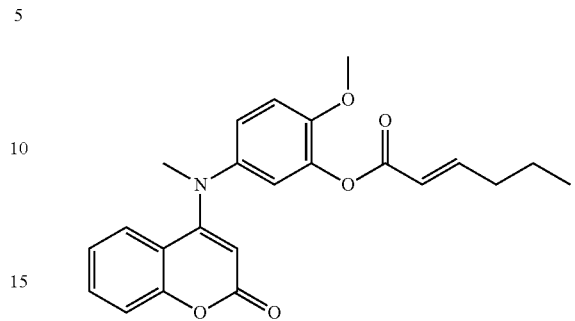

Under protection of nitrogen gas, dissolve intermediate 15a and N,N-diisopropyl ethylamine in anhydrous dichloromethane, slowly dropwise add dichloromethane solution containing trans-hex-4-enoyl chloride while stirring in an ice bath. Then, increase to room temperature to stir overnight. On the next day, remove organic solvent, and carry out flash column chromatography with petroleum ether: ethyl acetate of 6:1 for separation of residual substrate to obtain a light yellow solid, with a yield of 79%.

$^1$H NMR (400 MHz, CDCl$_3$) δ 7.3-97.32 (m, 1H), 7.28 (dd, J=8.3, 0.9 Hz, 1H), 7.18 (dt, J=15.6, 6.9 Hz, 1H), 7.03 (dd, J=8.2, 1.2 Hz, 1H), 6.91 (dd, J=9.7, 4.1 Hz, 4H), 6.02 (dt, J=15.6, 1.5 Hz, 1H), 5.85 (s, 1H), 3.83 (s, 3H), 3.36 (s, 3H), 2.33~2.19 (m, 2H), 1.53 (dt, J=14.7, 7.4 Hz, 2H), 0.97 (t, J=7.4 Hz, 3H).

Embodiment 83: Preparation of 4-(N-methyl-N-(4-methoxy-3-(Boc-glycine ester) benzene)-amino) Coumarin (COUM-83)

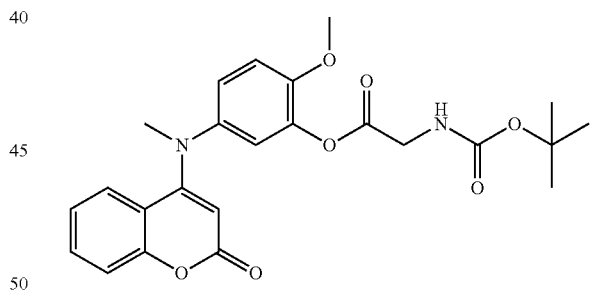

Under protection of nitrogen gas, dissolve intermediate 15a, EDCi (1-ethyl-(3-dimethylaminopropyl) carbodiimide hydrochloride) and DMAP (4-dimethylaminopyridine) in anhydrous dichloromethane, dropwise add dichloromethane solution containing Boc-glycine in an ice bath. Then, increase to room temperature for reaction overnight. On the next day, remove dichloromethane solution through rotary evaporation, dilute with large amount of water, and perform ethyl acetate extraction for three times. Combine organic phases, dry the organic phase with anhydrous sodium sulfate, remove organic solvent, and carry out flash column chromatography with petroleum ether: ethyl acetate of 3:1 for separation of residual substrate to obtain a white solid, with a yield of 59%.

$^1$H NMR (400 MHz, CDCl$_3$) δ 7.40~7.33 (m, 1H), 7.29 (dd, J=8.3, 1.1 Hz, 1H), 7.01 (dd, J=8.3, 1.4 Hz, 1H), 6.95-6.86 (m, 4H), 5.85 (d, J=14.1 Hz, 1H), 5.19 (s, 1H), 3.97 (d, J=3.9 Hz, 2H), 3.87 (d, J=6.2 Hz, 3H), 3.35 (d, J=6.6 Hz, 3H), 1.51 (d, J=11.0 Hz, 9H).

Embodiment 84: Preparation of 4-(N-methyl-N-(4-methoxy-3-(Boc-leucine) benzene) amino) Coumarin (COUM-84)

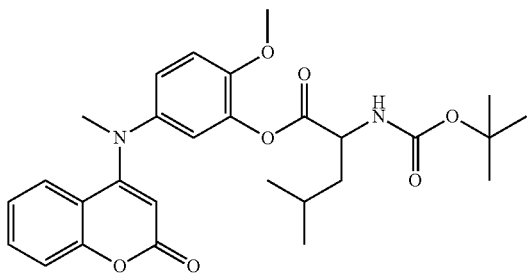 [SMILES: COc1ccc(N(C)c2cc(=O)oc3ccccc23)cc1OC(=O)C(CC(C)C)NC(=O)OC(C)(C)C]

Under protection of nitrogen gas, dissolve intermediate 15a, EDCi and DMAP in anhydrous dichloromethane, dropwise add dichloromethane solution containing Boc-leucine in an ice bath. Then, increase to room temperature for reaction overnight. On the next day, remove dichloromethane solution through rotary evaporation, dilute with large amount of water, and perform ethyl acetate extraction for three times. Combine organic phases, dry the organic phase with anhydrous sodium sulfate, remove organic solvent, and carry out flash column chromatography with petroleum ether: ethyl acetate of 3:1 for separation of residual substrate to obtain a white solid, with a yield of 58%.

$^1$H NMR (400 MHz, CDCl$_3$) δ 7.39~7.32 (m, 1H), 7.31~7.27 (m, 1H), 7.01 (dd, J=8.3, 1.3 Hz, 1H), 6.97~6.83 (m, 4H), 5.86 (s, 1H), 4.92 (d, J=8.6 Hz, 1H), 4.54 (s, 1H), 3.80 (s, 3H), 3.35 (s, 3H), 1.90~1.76 (m, 1H), 1.71~1.56 (m, 2H), 1.44 (s, 9H), 1.00 (d, J=6.3 Hz, 6H).

Embodiment 85: Preparation of 4-(N-methyl-N-(4-methoxy-3-(Boc-α-alanine) benzene) amino) Coumarin (COUM-85)

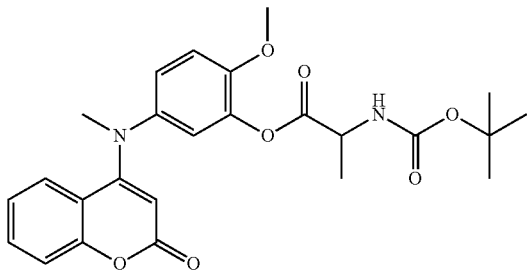 [SMILES: COc1ccc(N(C)c2cc(=O)oc3ccccc23)cc1OC(=O)C(C)NC(=O)OC(C)(C)C]

Under protection of nitrogen gas, dissolve intermediate 15a, EDCi and DMAP in anhydrous dichloromethane, dropwise add dichloromethane solution containing Boc-α-alanine in an ice bath. Then, increase to room temperature for reaction overnight. On the next day, remove dichloromethane solution through rotary evaporation, dilute with large amount of water, and perform ethyl acetate extraction for three times. Combine organic phases, dry the organic phase with anhydrous sodium sulfate, remove organic solvent, and carry out flash column chromatography with petroleum ether: ethyl acetate of 3:1 for separation of residual substrate to obtain a white solid, with a yield of 59%.

$^1$H NMR (400 MHz, CDCl$_3$) δ 7.40~7.33 (m, 1H), 7.29 (dd, J=8.3, 1.1 Hz, 1H), 7.01 (dd, J=8.3, 1.4 Hz, 1H), 6.95~6.86 (m, 4H), 5.85 (d, J=14.1 Hz, 1H), 5.19 (d, J=27.0 Hz, 1H), 3.87 (d, J=9.8 Hz, 3H), 3.53 (d, J=5.5 Hz, 1H), 3.35 (d, J=11.0 Hz, 3H), 1.58 (s, 3H), 1.45 (s, 9H).

Embodiment 86: Preparation of 4-(N-methyl-N-(4-methoxy-3-(Boc-methionine) benzene) amino) Coumarin (COUM-86)

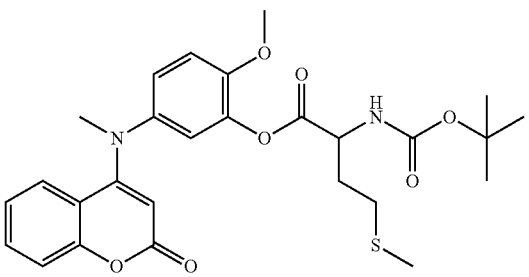 [SMILES: COc1ccc(N(C)c2cc(=O)oc3ccccc23)cc1OC(=O)C(CCSC)NC(=O)OC(C)(C)C]

Under protection of nitrogen gas, dissolve intermediate 15a, EDCi and DMAP in anhydrous dichloromethane, dropwise add dichloromethane solution containing Boc-α-alanine in an ice bath. Then, increase to room temperature for reaction overnight. On the next day, remove dichloromethane solution through rotary evaporation, dilute with large amount of water, and perform ethyl acetate extraction for three times. Combine organic phases, dry the organic phase with anhydrous sodium sulfate, remove organic solvent, and carry out flash column chromatography with petroleum ether: ethyl acetate of 3:1 for separation of residual substrate to obtain a white solid, with a yield of 59%.

$^1$H NMR (400 MHz, CDCl$_3$) δ 7.40~7.33 (m, 1H), 7.29 (dd, J=8.3, 1.1 Hz, 1H), 7.01 (dd, J=8.3, 1.4 Hz, 1H), 6.95~6.86 (m, 4H), 5.85 (d, J=14.1 Hz, 1H), 5.19 (d, J=27.0 Hz, 1H), 3.87 (d, J=9.8 Hz, 3H), 3.53 (d, J=5.5 Hz, 1H), 3.35 (d, J=11.0 Hz, 3H), 2.60 (m, 2H), 2.18 (m, 2H), 2.07 (s, 3H), 1.45 (s, 9H).

Embodiment 87: Preparation of 4-(N-methyl-N-(4-methoxy-3-amino-benzene)-amino) Coumarin (COUM-87)

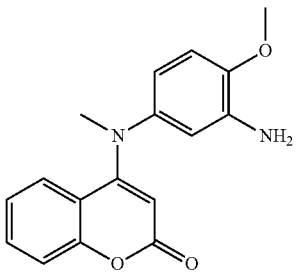 [SMILES: COc1ccc(N(C)c2cc(=O)oc3ccccc23)cc1N]

Under protection of nitrogen gas, dissolve intermediate 18 (4-methoxy-N$^1$-methyl-1,3-diamine benzene) and intermediate 10 (4-bromo-coumarin) in N,N-dimethyl formamide (DMF), dropwise add 2 equivalents of diisopropyl ethylamine for reaction under 100° C. overnight. Dilute the reaction substrate with large amount of water and perform ethyl acetate extraction. Remove organic solvent through rotary evaporation and push the substrate through flash column (mobile phase is petroleum ether and ethyl acetate with a ratio of 4:1) to obtain a light yellow solid, with a yield of 78%.

$^1$H NMR (400 MHz, DMSO) δ 7.47~7.39 (m, 1H), 7.30 (dd, J=8.2, 0.8 Hz, 1H), 7.10 (dd, J=8.2, 1.3 Hz, 1H), 7.01~6.95 (m, 1H), 6.77 (d, J=8.5 Hz, 1H), 6.45 (d, J=2.6 Hz, 1H), 6.37 (dd, J=8.4, 2.6 Hz, 1H), 5.75 (s, 1H), 4.90 (s, 2H), 3.76 (s, 3H), 3.28 (s, 3H). MS (ESI, m/z): 297.2 [M+H]$^+$.

Embodiment 88: Preparation of 4-(N-methyl-N-(4-methoxy-3-(3-ethoxycarbonyl carbonylamino) benzene)-amino) Coumarin (COUM-88)

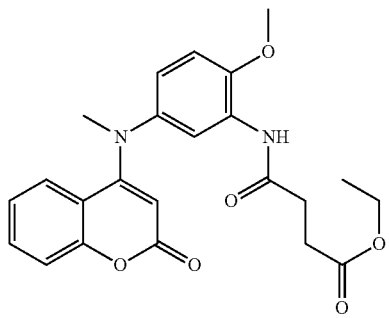 [SMILES: CCOC(=O)CCC(=O)Nc1cc(N(C)c2cc(=O)oc3ccccc23)ccc1OC]

Under protection of nitrogen gas, dissolve intermediate 19a (4-(N-methyl-N-(4-methoxyl-3-amino-benzene)-amino) coumarin) and N,N-diisopropyl ethylamine in anhydrous dichloromethane, slowly dropwise add dichloromethane solution containing 3-ethoxycarbonyl propionyl chloride while stirring in an ice bath. Then, increase to room temperature to stir overnight. On the next day, remove organic solvent, and carry out flash column chromatography with petroleum ether: ethyl acetate of 3:1 for separation of residual substrate to obtain a light yellow solid, with a yield of 84%.

$^1$H NMR (400 MHz, CDCl$_3$) δ 8.46 (d, J=2.3 Hz, 1H), 8.02 (s, 1H), 7.36~7.30 (m, 1H), 7.27 (d, J=2.3 Hz, 1H), 7.03 (dd, J=8.2, 1.1 Hz, 1H), 6.92-6.82 (m, 1H), 6.71 (d, J=8.6 Hz, 1H), 6.56 (dd, J=8.6, 2.6 Hz, 1H), 5.83 (s, 1H), 4.17 (p, J=7.3 Hz, 2H), 3.88 (s, 3H), 3.35 (s, 3H), 2.74 (s, 4H), 1.28 (t, J=7.1 Hz, 3H). MS (ESI, m/z): 447.1 [M+Na]$^+$.

Embodiment 89: Preparation of 4-(N-methyl-N-(4-methoxy-3-((4-methoxycarbonyl)-carbonylamino) phenyl)-amino) Coumarin (COUM-89)

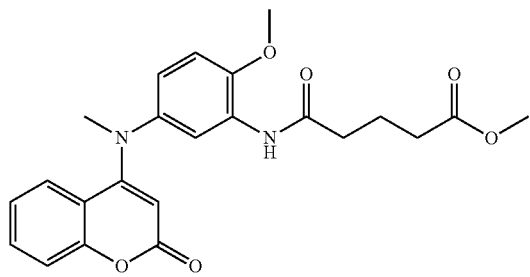 [SMILES: COC(=O)CCCC(=O)Nc1cc(N(C)c2cc(=O)oc3ccccc23)ccc1OC]

Under protection of nitrogen gas, dissolve intermediate 19a and N,N-diisopropyl ethylamine in anhydrous dichloromethane, slowly dropwise add dichloromethane solution containing 4-methoxycarbonyl butyryl chloride while stirring in an ice bath. Then, increase to room temperature to stir overnight. On the next day, remove organic solvent, and carry out flash column chromatography with petroleum ether: ethyl acetate of 3:1 for separation of residual substrate to obtain a light yellow solid, with a yield of 82%.

$^1$H NMR (400 MHz, CDCl$_3$) δ 8.48 (s, 1H), 7.87 (s, 1H), 7.38~7.29 (m, 1H), 7.27 (d, J=4.3 Hz, 1H), 7.03 (t, J=10.1 Hz, 1H), 6.86 (t, J=7.5 Hz, 1H), 6.71 (d, J=8.7 Hz, 1H), 6.56 (dd, J=8.6, 2.6 Hz, 1H), 5.83 (s, 1H), 3.88 (s, 3H), 3.70 (s, 3H), 3.36 (s, 3H), 2.49 (dt, J=14.5, 7.2 Hz, 4H), 2.11~2.03 (m, 2H). MS (ESI, m/z): 447.1 [M+Na]$^+$.

Embodiment 90: Preparation of 4-(N-methyl-N-(4-methoxy-3-(hexane carbonylamino) phenyl)-amino) Coumarin (COUM-90)

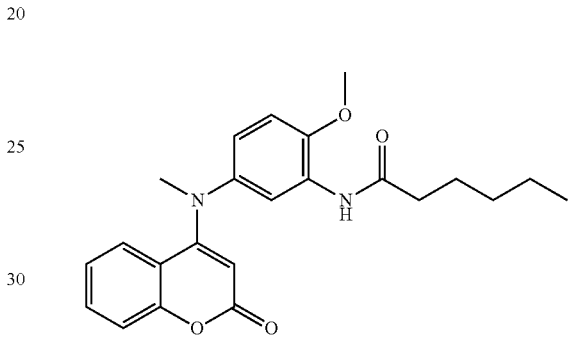

Under protection of nitrogen gas, dissolve intermediate 19a and N,N-diisopropyl ethylamine in anhydrous dichloromethane, slowly dropwise add dichloromethane solution containing hexanoyl chloride while stirring in an ice bath. Then, increase to room temperature to stir overnight. On the next day, remove organic solvent, and carry out flash column chromatography with petroleum ether: ethyl acetate of 3:1 for separation of residual substrate to obtain a light yellow solid, with a yield of 86%.

$^1$H NMR (400 MHz, CDCl$_3$) δ 8.51 (d, J=2.3 Hz, 1H), 7.83 (s, 1H), 7.33 (t, J=7.6 Hz, 1H), 7.27 (d, J=4.9 Hz, 1H), 7.05 (d, J=7.4 Hz, 1H), 6.86 (t, J=7.1 Hz, 1H), 6.71 (d, J=8.6 Hz, 1H), 6.55 (dd, J=8.6, 2.5 Hz, 1H), 5.83 (s, 1H), 3.88 (s, 3H), 3.38 (m, 2H), 2.40 (m, 2H), 1.80~1.69 (m, 2H), 1.42~1.33 (m, 4H), 0.93 (t, J=6.9 Hz, 3H). MS (ESI, m/z): 417.1 [M+Na]$^+$.

Embodiment 91: Preparation of 4-(N-methyl-N-(4-methoxy-3-(decane carbonylamino) phenyl)-amino) Coumarin (COUM-91)

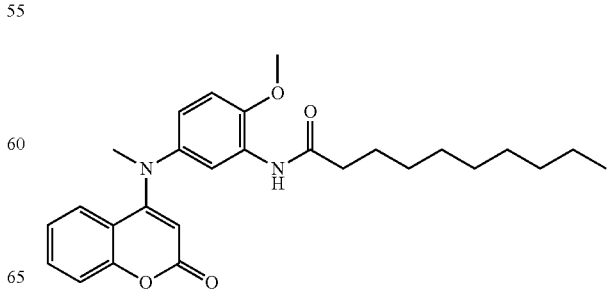

Under protection of nitrogen gas, dissolve intermediate 19a and N,N-diisopropyl ethylamine in anhydrous dichloromethane, slowly dropwise add dichloromethane solution containing decanoyl chloride while stirring in an ice bath. Then, increase to room temperature to stir overnight. On the next day, remove organic solvent, and carry out flash column chromatography with petroleum ether: ethyl acetate of 3:1 for separation of residual substrate to obtain a light yellow solid, with a yield of 84%.

$^1$H NMR (400 MHz, CDCl$_3$) δ 8.51 (d, J=2.5 Hz, 1H), 7.83 (s, 1H), 7.36~7.30 (m, 1H), 7.29~7.27 (m, 1H), 7.05 (dd, J=8.2, 1.1 Hz, 1H), 6.91~6.81 (m, 1H), 6.71 (d, J=8.6 Hz, 1H), 6.55 (dd, J=8.6, 2.6 Hz, 1H), 5.83 (s, 1H), 3.88 (s, 3H), 3.36 (s, 3H), 2.42 (t, J=7.6 Hz, 2H), 1.75 (dd, J=14.6, 7.4 Hz, 2H), 1.64~1.00 (m, 24H), 0.88 (t, J=6.8 Hz, 3H). MS (ESI, m/z): 473.4 [M+Na]$^+$.

Embodiment 92: Preparation of 4-(N-methyl-N-(4-methoxy-3-(5-chloro-n-pentane carbonylamino) phenyl)-amino) Coumarin (COUM-92)

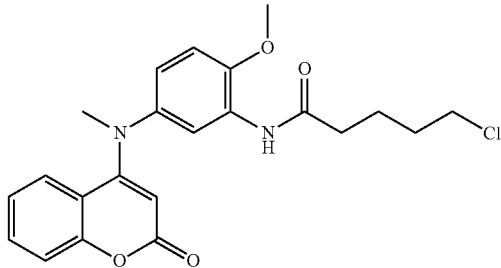 [SMILES: COc1ccc(N(C)c2cc(=O)oc3ccccc23)cc1NC(=O)CCCCCl]

Under protection of nitrogen gas, dissolve intermediate 19a and N,N-diisopropyl ethylamine in anhydrous dichloromethane, slowly dropwise add dichloromethane solution containing 5-chlorovaleryl chloride while stirring in an ice bath. Then, increase to room temperature to stir overnight. On the next day, remove organic solvent, and carry out flash column chromatography with petroleum ether: ethyl acetate of 3:1 for separation of residual substrate to obtain a light yellow solid, with a yield of 83%.

$^1$H NMR (400 MHz, CDCl$_3$) δ 8.48 (d, J=2.5 Hz, 1H), 7.83 (s, 1H), 7.33 (dd, J=11.1, 4.1 Hz, 1H), 7.28 (s, 1H), 7.07~7.01 (m, 1H), 6.91~6.81 (m, 1H), 6.72 (d, J=8.6 Hz, 1H), 6.57 (dd, J=8.6, 2.6 Hz, 1H), 5.83 (s, 1H), 3.88 (s, 3H), 3.64~3.55 (m, 2H), 3.36 (s, 3H), 2.46 (d, J=6.6 Hz, 2H), 1.95~1.83 (m, 4H). MS (ESI, m/z): 437.5 [M+Na]$^+$.

Embodiment 93: Preparation of 4-(N-methyl-N-(4-methoxy-3-(but-2-ene-carbonylamino-) phenyl)-amino) Coumarin (COUM-93)

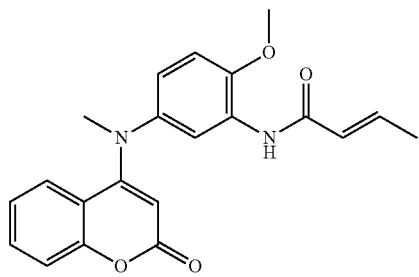

Under protection of nitrogen gas, dissolve intermediate 19a and N,N-diisopropyl ethylamine in anhydrous dichloromethane, slowly dropwise add dichloromethane solution containing but-2-enoyl chloride while stirring in an ice bath. Then, increase to room temperature to stir overnight. On the next day, remove organic solvent, and carry out flash column chromatography with petroleum ether: ethyl acetate of 3:1 for separation of residual substrate to obtain a light yellow solid, with a yield of 78%.

$^1$H NMR (400 MHz, CDCl$_3$) δ 8.58 (s, 1H), 7.83 (s, 1H), 7.36~7.29 (m, 1H), 7.27 (d, J=2.7 Hz, 1H), 7.08~6.95 (m, 2H), 6.85 (t, J=7.0 Hz, 1H), 6.72 (d, J=8.6 Hz, 1H), 6.57 (dd, J=8.6, 2.5 Hz, 1H), 6.01 (d, J=14.9 Hz, 1H), 5.84 (s, 1H), 3.88 (s, 3H), 3.37 (s, 3H), 1.94 (d, J=6.8 Hz, 3H). MS (ESI, m/z): 387.5 [M+Na]$^+$.

Embodiment 94: Preparation of 4-(N-methyl-N-(4-methoxy-3-(1-methyl ester-decane-oxy) phenyl)-amino) Coumarin (COUM-94)

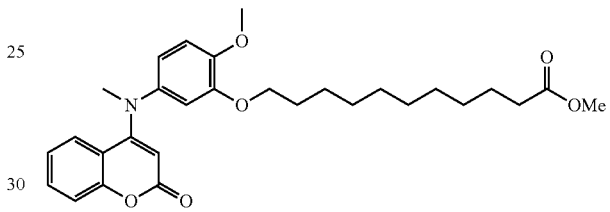

Under protection of nitrogen gas, dissolve intermediate 15a and N,N-diisopropyl ethylamine in anhydrous dichloromethane, slowly dropwise add dichloromethane solution containing methyl 11-bromo-undecylate while stirring in an ice bath. Then, increase to room temperature to stir overnight. On the next day, remove organic solvent, and carry out flash column chromatography with petroleum ether: ethyl acetate of 8:1 for separation of residual substrate to obtain a light yellow solid, with a yield of 83%.

$^1$H NMR (400 MHz, CDCl$_3$) δ 7.33 (dd, J=11.2, 4.1 Hz, 1H), 7.28 (d, J=5.2 Hz, 1H), 6.98 (d, J=8.3 Hz, 1H), 6.85 (dd, J=11.2, 4.2 Hz, 1H), 6.79 (d, J=8.4 Hz, 1H), 6.66~6.60 (m, 2H), 5.82 (s, 1H), 3.89 (dd, J=12.2, 5.3 Hz, 2H), 3.86 (s, 3H), 3.67 (s, 3H), 3.36 (s, 3H), 2.30 (t, J=7.5 Hz, 2H), 1.82~1.69 (m, 2H), 1.60 (d, J=7.2 Hz, 2H), 1.40 (m, 2H), 1.28 (s, 10H).

Embodiment 95: Preparation of 4-(N-methyl-N-(4-methoxy-3-(pent-1-ene-carbonylamino) phenyl)-amino) Coumarin (COUM-95)

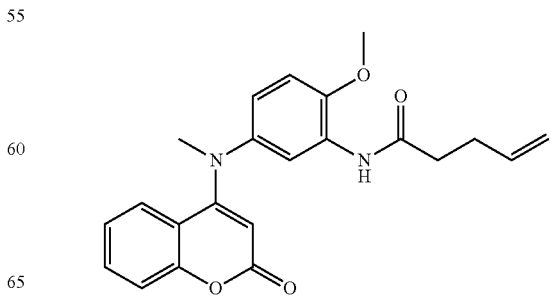

Under protection of nitrogen gas, dissolve intermediate 19a and N,N-diisopropyl ethylamine in anhydrous dichloromethane, slowly dropwise add dichloromethane solution containing pent-1-enoyl chloride while stirring in an ice bath. Then, increase to room temperature to stir overnight. On the next day, remove organic solvent, and carry out flash column chromatography with petroleum ether: ethyl acetate of 3:1 for separation of residual substrate to obtain a light yellow solid, with a yield of 83%.

¹H NMR (400 MHz, CDCl₃) δ 8.50 (d, J=2.1 Hz, 1H), 7.86 (s, 1H), 7.32 (dd, J=14.2, 7.2 Hz, 1H), 7.27 (d, J=5.1 Hz, 1H), 7.05 (d, J=8.3 Hz, 1H), 6.86 (t, J=7.6 Hz, 1H), 6.71 (d, J=8.6 Hz, 1H), 6.56 (dd, J=8.6, 2.4 Hz, 1H), 5.91 (ddd, J=16.9, 10.4, 6.1 Hz, 1H), 5.84 (s, 1H), 5.14 (d, J=16.6 Hz, 1H), 5.07 (d, J=10.3 Hz, 1H), 3.88 (s, 3H), 3.36 (s, 3H), 2.53 (d, J=10.9 Hz, 4H).

Embodiment 96: Preparation of 4-(N-methyl-N-(4-methoxy-3-(4-methoxy-pent-2-ene-carbonylamino) phenyl)-amino) Coumarin (COUM-96)

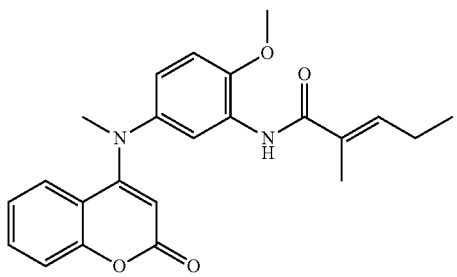 [SMILES: CC/C=C(\C)C(=O)Nc1cc(N(C)c2cc(=O)oc3ccccc23)ccc1OC]

Under protection of nitrogen gas, dissolve intermediate 19a and N,N-diisopropyl ethylamine in anhydrous dichloromethane, slowly dropwise add dichloromethane solution containing pent-1-enoyl chloride while stirring in an ice bath. Then, increase to room temperature to stir overnight. On the next day, remove organic solvent, and carry out flash column chromatography with petroleum ether: ethyl acetate of 3:1 for separation of residual substrate to obtain a light yellow solid, with a yield of 81%.

¹H NMR (400 MHz, CDCl₃) δ 8.51 (d, J=2.3 Hz, 1H), 7.83 (s, 1H), 7.33 (t, J=7.6 Hz, 1H), 7.27 (d, J=4.9 Hz, 1H), 7.05 (d, J=7.4 Hz, 1H), 6.86 (t, J=7.1 Hz, 1H), 6.71 (d, J=8.6 Hz, 1H), 6.55 (dd, J=8.6, 2.5 Hz, 1H), 6.34 (m, 1H), 5.83 (s, 1H), 3.88 (s, 3H), 2.34 (s, 3H), 2.02 (m, 2H), 1.01 (m, 3H).

Embodiment 97: Preparation of 4-(N-methyl-N-(4-methoxy-3-(cyclopentyl carbonylamino) phenyl)-amino) Coumarin (COUM-97)

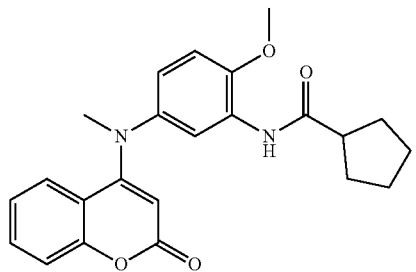 [SMILES: COc1ccc(N(C)c2cc(=O)oc3ccccc23)cc1NC(=O)C1CCCC1]

Under protection of nitrogen gas, dissolve intermediate 19a and N,N-diisopropyl ethylamine in anhydrous dichloromethane, slowly dropwise add dichloromethane solution containing cyclopentanecarbonyl chloride while stirring in an ice bath. Then, increase to room temperature to stir overnight. On the next day, remove organic solvent, and carry out flash column chromatography with petroleum ether: ethyl acetate of 3:1 for separation of residual substrate to obtain a light yellow solid, with a yield of 81%.

¹H NMR (400 MHz, CDCl₃) δ 8.51 (d, J=2.3 Hz, 1H), 7.83 (s, 1H), 7.33 (t, J=7.6 Hz, 1H), 7.27 (d, J=4.9 Hz, 1H), 7.05 (d, J=7.4 Hz, 1H), 6.86 (t, J=7.1 Hz, 1H), 6.71 (d, J=8.6 Hz, 1H), 6.55 (dd, J=8.6, 2.5 Hz, 1H), 5.83 (s, 1H), 3.88 (s, 3H), 2.61 (m, 1H), 1.76~1.68 (m, 8H).

Embodiment 98: Preparation of 4-(N-methyl-N-(4-methoxy-3-(1-carboxylic acid-propane carbonylamino-) phenyl)-amino) Coumarin (COUM-98)

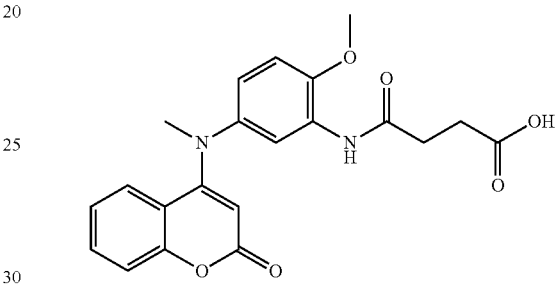

Under protection of nitrogen gas, dissolve intermediate compound 19a, EDCi and DMAP in anhydrous dichloromethane, dropwise add dichloromethane solution containing succinic anhydride in an ice bath. Then, increase to room temperature for reaction overnight. On the next day, remove dichloromethane solution through rotary evaporation, dilute with large amount of water, and perform ethyl acetate extraction for three times. Combine organic phases, dry the organic phase with anhydrous sodium sulfate, remove organic solvent, and carry out flash column chromatography with petroleum ether: ethyl acetate of 1:1 for separation of residual substrate to obtain a white solid, with a yield of 58%.

¹H NMR (400 MHz, CDCl₃) δ 8.43 (s, 1H), 8.02 (s, 1H), 7.36~7.30 (m, 1H), 7.27 (d, J=4.1 Hz, 1H), 7.03 (d, J=8.1 Hz, 1H), 6.86 (t, J=7.6 Hz, 1H), 6.72 (d, J=8.6 Hz, 1H), 6.58 (d, J=8.3 Hz, 1H), 5.85 (s, 1H), 3.88 (s, 3H), 3.35 (s, 3H), 2.81 (d, J=5.3 Hz, 2H), 2.77 (d, J=5.2 Hz, 2H).

Embodiment 99: Preparation of 4-(N-methyl-N-(4-methoxy-3-(Boc-β-alaninamide) phenyl)-amino) Coumarin (COUM-99)

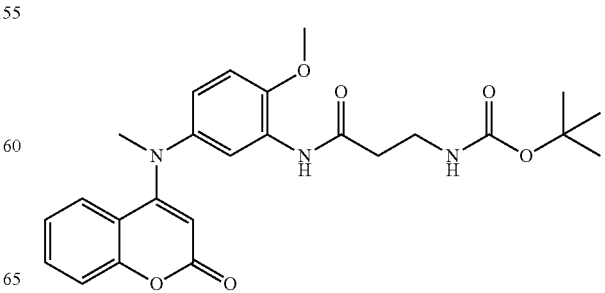

Under protection of nitrogen gas, dissolve intermediate compound 19a, EDCi and DMAP in anhydrous dichloromethane, dropwise add dichloromethane solution containing Boc-β-alanine in an ice bath. Then, increase to room temperature for reaction overnight. On the next day, remove dichloromethane solution through rotary evaporation, dilute with large amount of water, and perform ethyl acetate extraction for three times. Combine organic phases, dry the organic phase with anhydrous sodium sulfate, remove organic solvent, and carry out flash column chromatography with petroleum ether: ethyl acetate of 3:1 for separation of residual substrate to obtain a white solid, with a yield of 58%.

$^1$H NMR (400 MHz, CDCl$_3$) δ 8.43 (d, J=2.3 Hz, 1H), 7.86 (s, 1H), 7.33 (dd, J=11.1, 4.1 Hz, 1H), 7.30~7.27 (m, 1H), 7.03 (t, J=11.6 Hz, 1H), 6.87 (dd, J=11.1, 4.1 Hz, 1H), 6.73 (d, J=8.7 Hz, 1H), 6.59 (dd, J=8.6, 2.5 Hz, 1H), 5.84 (s, 1H), 5.13 (s, 1H), 3.87 (s, 3H), 3.53~3.46 (m, 2H), 3.36 (s, 3H), 2.65 (t, J=5.8 Hz, 2H), 1.45 (s, 9H).

Pharmacodynamic Studies

Embodiment 100: Tumor Cell Proliferation Inhibitory Activity Tests In Vitro

The coumarin derivatives in the Invention have significant pharmacological activities, such as anti-tumor and anti-vascular diseases. In order to provide evidence for the above features, tumor cell proliferation inhibitory activity tests were carried out for the compounds in the embodiments of the Invention.

1) Cell Line and Cell Culture

Human non-small cell lung cancer cell line NCI-H460, human small cell lung cancer cell line NCI-H446, human hepatocellular carcinoma cell strain HepG2, human colon carcinoma cell strain HCT116, human prostate cancer PC-3, human melanoma A375, colon carcinoma cell HCT-8, breast cancer cell MCF-7, ovarian cancer cell A2780s, drug-resistant ovarian cancer cell A2780/T, drug-resistant colon cancer cell HCT-8/T and doxorubicin-resistant breast cancer cell MCF-7/ADR are obtained from American Type Culture Collection (ATCC) and are cultured and preserved by the cell bank of State Key Laboratory of Biotherapy of Sichuan University. Above tumor cells are routinely cultured in DMEM culture medium containing 10% fetal bovine serum, 100 U·mL-1 penicillin and 100 mg·L-1 streptomycin, and in an incubator at 37° C. and with saturated humidity and 5% CO$_2$ concentration.

2) Apparatus

CO$_2$ incubator: ESCO CCL-170B-8 from Singapore. Digital inverted microscope: Olympus CKX31. Research-level upright microscope: Olympus BX51TRF. Microplate reader: M5 of Molecular Device from America. Normal temperature centrifuge: thermo SOROALLST16 made by Thermosicentific. Water purification system: FTPN09748 made by Millipore from America. Upright autoclave: MLS-3780 made by SANYO from Japan. Thermostatic water bath: DF-101S made by Yu Hua Instrument Co., Ltd. of Gongyi City. Superclean bench: ESCO Bilogical safety Cabinet, AC2-L1S1 Class II made by ESCO from Singapore. Vortex mixer: cel-866 made by Haimen Kylin-Bell Lab Instruments Co., Ltd. pH meter: DELTA320 made by METTLER TOLEDO. Weighing scale: LD5102 from Longteng Electronics Co., Ltd. Hygrothermograph: GJWS-A5 made by Wuqiang Hygrothermograph Manufacturing Center of Hengshui City, Hebei Province. Nitrogen container: CY50985-70 made by Thermo from America.

3) Cell Counting

Digest the in vitro cultured cells with 0.25% trypsin, blow gently and collect by centrifugation, 1200 g*3 min, resuspend the cells in fresh medium and dilute them to proper density. After mixing, draw a small amount of suspension on a hemocytometer and count through the inverted microscope. Record total number of cells in 4 big squares, get the average value and multiply it by 10$^4$ and then multiply the obtained value by the dilution factor to get cell density and multiply the cell density by total volume to get number of cells.

4) Inoculate In Vitro Cultured Cells in 96-Well Plate

After digesting the cells with 0.25% trypsin and centrifugation, add complete medium for suspension and count the cells with a hemocytometer. Fill diluted cell suspension in the 96-well plate with 1000-10000 cells per well and incubate it in CO$_2$ incubator overnight.

5) MTT Test

Select cells in logarithmic phase, digest them with 0.25% trypsin, adjust concentration of cell suspension with complete medium, inoculate the cells into the 96-well plate at 1000-10000 cells per well, 200 µL per well, incubate in an incubator at 37° C. and with 5% CO$_2$ concentration for 24 h. Replace with new medium containing various concentrations of compounds to be tested for the test group and replace with fresh medium with equal volume for the control group, each group is arranged with 5 parallel wells and incubated in an incubator at 37° C. and with 5% CO$_2$ concentration.

Discard the supernatant after 72 hours, add 200 µL freshly prepared serum-free medium containing 0.2 mg/mL MTT into each well, continue to incubate at 37° C. for 1-4 hours, then stop incubation, carefully remove the culture supernatant in the wells and add 200 uL DMSO (dimethyl sulfoxide), oscillate with a miniature ultrasonic oscillator for 15-20 minutes to make the crystal fully dissolved and mixed. Determine OD values using a microplate reader at 570 nm with a reference wavelength of 450 nm.

6) Data Processing

Calculate the growth inhibition rate for tumor cells under the drug concentration gradient with the following formula: relative growth inhibition rate for tumor cells (%)=(1-OD of test group/OD of control group)×100%.

Draw curves based on the growth inhibition rate for tumor cells of the same sample with different concentrations to get dose-response curve, so as to calculate IC$_{50}$. Repeat each test for 3 times, measure IC$_{50}$ (µM) or nanomolor concentration (nM) of compounds in different tumor cells.

7) Test Results

Table 1 is a list of ranges of IC$_{50}$ (µM) of compounds for hepatocellular carcinoma cell HEPG2 and colon carcinoma cell HCT116. In which "+" indicates IC$_{50}$>5 uM, "++" indicates 100 nM<IC$_{50}$<5 µM, "+++" indicates 10 nM<IC$_{50}$<100 nM and "++++" indicates 0.01<IC$_{50}$<10 nM.

The structural formula of MPC-6827 in Table 1 is

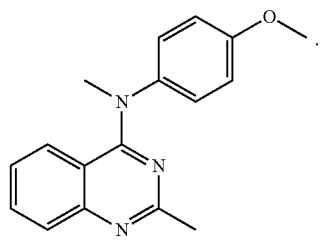 [SMILES: COc1ccc(N(C)c2nc(C)nc3ccccc23)cc1]

TABLE 1

IC$_{50}$ of compounds for tumor cells

| Compounds | Activity | | | | | |
|---|---|---|---|---|---|---|
| | HEPG2 | HCT116 | H460 | MCF-7 | PC-3 | A375 |
| MPC-6827 | ++++ | ++++ | ++++ | ++++ | ++++ | ++++ |
| COUM-1 | + | + | + | + | + | + |
| COUM-2 | + | + | + | + | + | + |
| COUM-3 | + | + | + | + | + | + |
| COUM-4 | + | + | + | + | + | + |
| COUM-5 | + | + | + | + | + | + |
| COUM-6 | + | + | + | + | + | + |
| COUM-7 | + | + | + | + | + | + |
| COUM-8 | + | + | + | + | + | + |
| COUM-9 | + | + | + | + | + | + |
| COUM-10 | + | + | + | + | + | + |
| COUM-11 | + | + | + | + | + | + |
| COUM-12 | + | + | + | + | + | + |
| COUM-13 | + | + | + | + | + | + |
| COUM-14 | + | + | + | + | + | + |
| COUM-15 | + | + | + | + | + | + |
| COUM-16 | + | + | + | + | + | + |
| COUM-17 | + | + | + | + | + | + |
| COUM-18 | + | + | + | + | + | + |
| COUM-19 | + | + | + | + | + | + |
| COUM-20 | + | + | + | + | + | + |
| COUM-21 | + | + | + | + | + | + |
| COUM-22 | + | + | + | + | + | + |
| COUM-23 | + | + | + | + | + | + |
| COUM-24 | + | + | + | + | + | + |
| COUM-25 | + | + | + | + | + | + |
| COUM-26 | + | + | + | + | + | + |
| COUM-27 | + | + | + | + | + | + |
| COUM-28 | + | + | + | + | + | + |
| COUM-29 | + | + | + | + | + | + |
| COUM-30 | + | + | + | + | + | + |
| COUM-31 | + | + | + | + | + | + |
| COUM-32 | + | + | + | + | + | + |
| COUM-33 | + | + | + | + | + | + |
| COUM-34 | + | + | + | + | + | + |
| COUM-35 | + | + | + | + | + | + |
| COUM-36 | + | + | + | + | + | + |
| COUM-37 | ++ | ++ | ++ | ++ | ++ | ++ |
| COUM-38 | ++ | ++ | ++ | ++ | ++ | ++ |
| COUM-39 | ++ | ++ | ++ | ++ | ++ | ++ |
| COUM-40 | +++ | +++ | +++ | +++ | +++ | +++ |
| COUM-41 | +++ | +++ | +++ | +++ | +++ | +++ |
| COUM-42 | +++ | +++ | +++ | +++ | +++ | +++ |
| COUM-43 | +++ | +++ | +++ | +++ | +++ | +++ |
| COUM-44 | +++ | +++ | +++ | +++ | +++ | +++ |
| COUM-45 | +++ | +++ | +++ | +++ | +++ | +++ |
| COUM-46 | ++++ | ++++ | ++++ | ++++ | ++++ | ++++ |
| COUM-47 | +++ | +++ | +++ | +++ | +++ | +++ |
| COUM-48 | ++++ | ++++ | ++++ | ++++ | ++++ | ++++ |
| COUM-49 | ++ | ++ | ++ | ++ | ++ | ++ |
| COUM-50 | +++ | +++ | +++ | +++ | +++ | +++ |
| COUM-51 | + | + | + | + | + | + |
| COUM-52 | ++ | ++ | ++ | ++ | ++ | ++ |
| COUM-53 | ++ | ++ | ++ | ++ | ++ | ++ |
| COUM-54 | ++ | ++ | ++ | ++ | ++ | ++ |
| COUM-55 | ++ | ++ | ++ | ++ | ++ | ++ |
| COUM-56 | ++ | ++ | ++ | ++ | ++ | ++ |
| COUM-57 | +++ | +++ | +++ | +++ | +++ | +++ |
| COUM-58 | + | + | + | + | + | + |
| COUM-59 | ++ | ++ | ++ | ++ | ++ | ++ |
| COUM-60 | ++ | ++ | ++ | ++ | ++ | ++ |
| COUM-61 | ++ | ++ | ++ | ++ | ++ | ++ |
| COUM-62 | ++ | ++ | ++ | ++ | ++ | ++ |
| COUM-63 | ++ | ++ | ++ | ++ | ++ | ++ |
| COUM-64 | + | + | + | + | + | + |
| COUM-65 | +++ | +++ | +++ | +++ | +++ | +++ |
| COUM-66 | +++ | +++ | +++ | +++ | +++ | +++ |
| COUM-67 | +++ | +++ | +++ | +++ | +++ | +++ |
| COUM-68 | ++++ | ++++ | ++++ | ++++ | ++++ | ++++ |
| COUM-69 | ++++ | ++++ | ++++ | ++++ | ++++ | ++++ |
| COUM-70 | ++++ | ++++ | ++++ | ++++ | ++++ | ++++ |
| COUM-71 | ++++ | ++++ | ++++ | ++++ | ++++ | ++++ |
| COUM-72 | ++++ | ++++ | ++++ | ++++ | ++++ | ++++ |
| COUM-73 | ++++ | ++++ | ++++ | ++++ | ++++ | ++++ |
| COUM-74 | ++++ | ++++ | ++++ | ++++ | ++++ | ++++ |
| COUM-75 | ++++ | ++++ | ++++ | ++++ | ++++ | ++++ |
| COUM-76 | ++++ | ++++ | ++++ | ++++ | ++++ | ++++ |
| COUM-77 | ++++ | ++++ | ++++ | ++++ | ++++ | ++++ |
| COUM-78 | +++ | +++ | +++ | +++ | +++ | +++ |
| COUM-79 | ++++ | ++++ | ++++ | ++++ | ++++ | ++++ |
| COUM-80 | ++++ | ++++ | ++++ | ++++ | ++++ | ++++ |
| COUM-81 | ++++ | ++++ | ++++ | ++++ | ++++ | ++++ |
| COUM-82 | + | + | + | + | + | + |
| COUM-83 | ++ | ++ | ++ | ++ | ++ | ++ |
| COUM-84 | +++ | +++ | +++ | +++ | +++ | +++ |
| COUM-85 | ++ | ++ | ++ | ++ | ++ | ++ |
| COUM-86 | ++ | ++ | ++ | ++ | ++ | ++ |
| COUM-87 | ++++ | ++++ | ++++ | ++++ | ++++ | ++++ |
| COUM-88 | +++ | +++ | +++ | +++ | +++ | +++ |
| COUM-89 | +++ | +++ | +++ | +++ | +++ | +++ |
| COUM-90 | +++ | +++ | +++ | +++ | +++ | +++ |
| COUM-91 | ++ | ++ | ++ | ++ | ++ | ++ |
| COUM-92 | +++ | +++ | +++ | +++ | +++ | +++ |
| COUM-93 | ++ | ++ | ++ | ++ | ++ | ++ |
| COUM-94 | + | + | + | + | + | + |
| COUM-95 | +++ | +++ | +++ | +++ | +++ | +++ |
| COUM-96 | +++ | +++ | +++ | +++ | +++ | +++ |
| COUM-97 | ++ | ++ | ++ | ++ | ++ | ++ |
| COUM-98 | ++ | ++ | ++ | ++ | ++ | ++ |
| COUM-99 | ++++ | ++++ | ++++ | ++++ | ++++ | ++++ |

It can be concluded from Table 1 that plural compounds in the Table 1 exhibit good anti-tumor cell proliferation activities. Wherein, the compounds COUM-46, COUM-48, COUM-57, COUM-68, COUM-69, COUM-70, COUM-71, COUM-72, COUM-73, COUM-74, COUM-75, COUM-76, COUM-77, COUM-78, COUM-79, COUM-80, COUM-81, COUM-87, COUM-88, COUM-89, COUM-90, COUM-91, COUM-92, COUM-93, COUM-96, etc., have the best anti-tumor activity, with IC$_{50}$ values between 0.01-10 nM. Activity of some compounds under the Invention has exceeded that of MPC6827, taxol, vincristine, colchicine and other positive drugs.

TABLE 2

IC$_{50}$ (nM) of compounds for sensitive and drug-resistant tumor cells

| IC$_{50}$/nM | A2780S | A2780/T |
|---|---|---|
| MPC6827 | 3.162 ± 0.034 | 4.113 ± 0.062 |
| COUM-71 | 2.184 ± 0.018 | 24.630 ± 0.431 |
| COUM-73 | 1.678 ± 0.075 | 3.343 ± 0.101 |
| COUM-75 | 1.185 ± 0.046 | 2.153 ± 0.140 |
| COUM-76 | 2.164 ± 0.043 | 3.171 ± 0.121 |
| COUM-77 | 1.102 ± 0.001 | 6.110 ± 0.010 |
| COUM-79 | 0.113 ± 0.005 | 0.722 ± 0.151 |
| COUM-80 | 0.416 ± 0.013 | 3.101 ± 0.333 |
| COUM-46 | 2.005 ± 0.047 | 3.174 ± 0.073 |
| COUM-87 | 1.981 ± 0.060 | 2.132 ± 0.023 |
| COUM-96 | 219.90 ± 11.1 | 310.1 ± 19.85 |
| COUM-99 | 115.6 ± 52.09 | 121.1 ± 61.07 |
| COUM-95 | 56.83 ± 3.90 | 57.11 ± 4.342 |
| COUM-89 | 257.2 ± 16.7 | 281.1 ± 20.10 |
| COUM-90 | 387.11 ± 29.21 | 399.1 ± 30.13 |
| COUM-69 | 4.72 ± 0.302 | 5.231 ± 0.212 |
| COUM-70 | 30.76 ± 3.160 | 31.119 ± 3.52 |
| COUM-48 | 4.030 ± 0.752 | 4.321 ± 0.764 |
| COUM-57 | 29.12 ± 1.168 | 32.346 ± 1.21 |
| COUM-68 | 3.112 ± 0.430 | 3.853 ± 0.562 |
| COUM-91 | 296.18 ± 18.3 | 311.1 ± 14.27 |
| COUM-92 | 33.67 ± 12.34 | 61.13 ± 12.90 |
| COUM-81 | 4.312 ± 0.019 | 6.129 ± 0.013 |

TABLE 2-continued

IC$_{50}$ (nM) of compounds for sensitive and drug-resistant tumor cells

| | | |
|---|---|---|
| Taxol | 58.09 ± 24.10 | 8115.100 ± 185 |
| Vincristin | 22.45 ± 2.68 | 476.24 ± 76.14 |
| Colchicine | 30.81 ± 9.875 | 491.13 ± 39.02 |

| IC$_{50}$/nM | MCF-7 | MCF-7/ADR |
|---|---|---|
| MPC6827 | 0.581 ± 0.004 | 0.699 ± 0.053 |
| COUM-71 | 0.380 ± 0.008 | 0.801 ± 0.102 |
| COUM-80 | 0.358 ± 0.242 | 0.919 ± 0.163 |
| COUM-95 | 96.980 ± 5.887 | 111.010 ± 50.324 |
| COUM-87 | 4.910 ± 0.018 | 7.782 ± 0.736 |
| COUM-92 | 54.690 ± 3.915 | 188.576 ± 14.831 |
| COUM-81 | 4.440 ± 0.344 | 9.745 ± 0.836 |
| Taxol | 32.270 ± 19.46 | 9.153 ± 56.19 (μM) |
| Vincristin | 54.740 ± 527.6 | 5.846 ± 1.39 (μM) |
| Colchicine | 64.130 ± 9.188 | 6.005 ± 3.100 (μM) |

| IC$_{50}$/nM | HCT-8 | HCT-8/V |
|---|---|---|
| MPC6827 | 3.117 ± 0.066 | 3.748 ± 0.131 |
| COUM-71 | 0.732 ± 0.023 | 1.935 ± 0.944 |
| COUM-80 | 0.987 ± 0.004 | 1.986 ± 0.036 |
| COUM-95 | 58.726 ± 2.278 | 231.200 ± 135.60 |
| COUM-87 | 2.765 ± 0.823 | 6.234 ± 58.355 |
| COUM-92 | 32.873 ± 11.76 | 46.760 ± 4.392 |
| COUM-81 | 7.123 ± 0.182 | 18.890 ± 5.983 |
| Taxol | 36.987 ± 23.87 | 0.189 ± 0.052 (μM) |
| Vincristin | 14.771 ± 3.15 | 0.023 ± 0.004 (μM) |
| Colchicine | 29.718 ± 9.269 | 0.144 ± 0.032 (μM) |

Table 2 shows that plural compounds not only have strong anti-proliferation activity for ovarian cancer cell A2780s, colon carcinoma cell HCT-8 and breast cancer cell MCF-7, but also exhibit good anti-proliferation activity for taxol-resistant ovarian cancer cell A2780/T, taxol-resistant colon cancer cell HCT-8/T and doxorubicin-resistant breast cancer cell MCF-7/ADR. Wherein, the compounds COUM-71, COUM-80, COUM-87 and COUM-81 all demonstrate better activity compared with taxol, vincristin and colchicine.

Embodiment 101: Depolymerization of Some Compounds on Microtubule by Application of Immunofluorescence Technique 1) Test method Place round coverslips into 6-well plate, plate hepatocellular carcinoma cell HepG2 in the 6-well plate and make the cells adhere to the round coverslips. Apply 200 nM colchicine and 300 nM taxol as positive control drugs, respectively apply DMSO of three concentrations or of equal volume for MPC-6827, COUM-87, COUM-92, COUM-95, COUM-71, COUM-76, COUM-79, COUM-81 and COUM-83 compounds to be tested to treat the cells for 16 h; remove cell culture liquid, wash with PBS (phosphate buffer) once and then apply 4% paraformaldehyde for fixation at room temperature for 15 min; wash with cold PBS once; apply PBS containing 0.5% tritonX-100 to wells at room temperature for 10 min; apply blocking buffer to block at room temperature for 30 min; incubate anti β-tubulin primary antibodies under moisturized condition, incubate at room temperature for 1 h, wash with PBS for 3 times; incubate 488-labeled goat anti-mouse secondary antibodies (purchased from Beijing Zhongshan Golden Bridge Biotechnology) for 45 min; apply DAPI (4',6-diamidino-2-phenylindole) fluid to stain at room temperature for 5 min in the dark; wash with PBS for three times; place round coverslips on slides, apply anti-quenching agent to seal the slides, and then use Axiovert200 inverted fluorescence microscope of Zeiss to observe inhibition of compounds to microtubule.

2) Test Results

Figure 2:
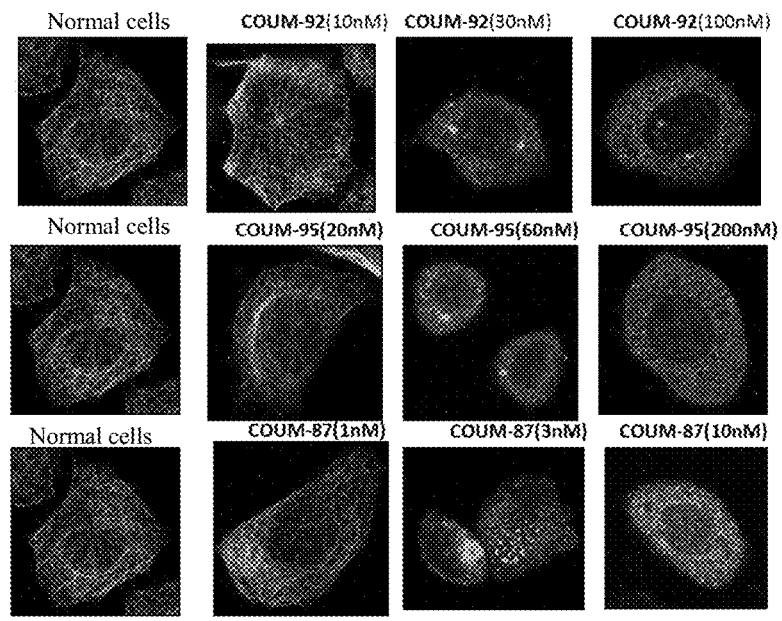
FIG. 2 Depolymerization of some compounds on microtubule.

FIG. 1 and FIG. 2 show that in the DMSO control group, the microtubule has natural structures in order, while in the MPC-6827 group of positive drugs, the microtubule fails to form orderly filamentous structures due to inhibited polymerization, with apparent appearance of scattered and uniform distribution in cellular outline. Compounds COUM-79, COUM-81, COUM-87, COUM-92 and COUM-95 in the Patent all demonstrate improved capability to inhibit polymerization of microtubule as concentration increases. Especially for COUM-79, COUM-81 and COUM-87, in circumstance of 1 nM concentration, only some filamentous structures can be observed, when the concentration increases to 3 nM, the microtubule structures are completely damaged, demonstrating stronger depolymerization than MPC-6827. These all demonstrate that the compounds are able to inhibit polymerization of microtubules.

Embodiment 102: Pharmacodynamics in Tumor Models of In Vivo Tumor-Bearing Mice

1) Compounds: 9 compounds including COUM-87, COUM-89, COUM-92, COUM-95, COUM-71, COUM-76, COUM-77, COUM-80 and COUM-83.

2) Experimental Animals and Culture Medium

BALB/c nude mice of SPF level (Balb/C nu/nu) and white mice, female, 4-6 weeks old, 18-22 g, purchased from Beijing Huafukang Bioscience Co., Inc., license No.: SOCK (J) 2009-0004 and SCXX (J) 2014-0004, raised in the animal laboratory of SPF level.

Modified RPMI 1640 medium is provided by HyClone. For batch No. of NWE 0416 with specification of 500 mL, the expiry date is May 31, 2012; for batch No. of NYG0920 with specification of 500 mL, the expiry date is Jul. 31, 2014; for batch No. of NZG1176 with specification of 500 mL, the expiry date is Jul. 31, 2015; and for batch No. of NZG1177 with specification of 500 mL, the expiry date is Jul. 31, 2015. All preserved under 2-8° C.

DMEM culture medium is provided by HyClone with batch No. of NZB1077, specification of 500 mL, expiry date of Feb. 28, 2015 and is preserved under 2-8° C.

3) Cell Culture

Culture human lung carcinoma H460 and mouse colon carcinoma C26 cell in RPMI 1640 medium (by HyClone), which contains 10% fetal bovine serum (by Hohhot Caoyuan Lvye Bioengineering Material Co., Ltd.) and 100 U/mL penicillin and streptomycin. Select cells in logarithmic phase, digest them with 0.25% trypsin and count, and dilute single-cell suspension with fetal bovine serum-free culture medium to $1 \times 10^7$ or $6 \times 10^7$ cells/mL for standby.

4) Inoculation, Grouping and Treatment

Collect tumor cells under aseptic conditions, adjust cell density to $5 \times 10^7$ cells/mL with sterilized physiological saline, subcutaneously inoculate 0.2 mL into armpit and back of nude mice, remove the tumor when it grew to 1 cm diameter under aseptic conditions, slice it into 1 mm×1 mm tumor blocks and evenly and subcutaneously inoculate it into armpit and back of nude mice for subculture. Remove the tumor under aseptic conditions after 2 subcultures and when it grew to 1 cm diameter, slice it into 1 mm×1 mm tumor blocks and evenly and subcutaneously inoculate it into armpit and back of nude mice. Conduct random grouping of animals after 7 days when the tumor grew to 100-300 mm$^3$ and perform tail intravenous injection (i.v.) once per two days, with dosages and administration methods shown in Table 3 and Table 4.

TABLE 3

Grouping for the test treating colon carcinoma C26

| Compounds | Dosage (mg/kg) | Administration method | Administration frequency |
|---|---|---|---|
| Physiological saline | — | — | — |
| MPC-6827 | 5 | i.v. | Once/two days |
| COUM-87 | 5 | i.v. | Once/two days |
| COUM-89 | 5 | i.v. | Once/two days |
| COUM-92 | 5 | i.v. | Once/two days |
| COUM-95 | 5 | i.v. | Once/two days |
| COUM-71 | 5 | i.v. | Once/two days |
| COUM-76 | 5 | i.v. | Once/two days |
| COUM-77 | 5 | i.v. | Once/two days |
| COUM-80 | 5 | i.v. | Once/two days |
| COUM-83 | 5 | i.v. | Once/two days |

TABLE 4

Grouping for the test treating lung carcinoma H460

| Compounds | Dosage (mg/kg) | Administration method | Administration frequency |
|---|---|---|---|
| Physiological saline | — | — | — |
| MPC6827 | 2.5 | i.v.. | Once/two days |
| COUM-87 | 10 | i.v. | Once/two days |
| COUM-92 | 10 | i.v. | Once/two days |
| COUM-95 | 10 | i.v. | Once/two days |
| COUM-87 hydrochloride | 10 | i.v. | Once/two days |
| COUM-71 | 10 | i.v. | Once/two days |
| COUM-76 | 10 | i.v. | Once/two days |
| COUM-79 | 10 | i.v. | Once/two days |
| COUM-81 | 10 | i.v. | Once/two days |
| COUM-83 | 10 | i.v. | Once/two days |

5) Indicators and Effect Evaluation Standards (1) Tumor volume (TV), relative tumor volume (RTV) and relative tumor proliferation rate: measure long diameter and short diameter of tumor in every two days using a vernier caliper or ruler with 1/50 mm precision and dynamically observe anti-tumor effects of tested drugs.

Formula for calculating tumor volume (TV) is: TV (mm3) =a×b$^2$×π/6; wherein a and b stand for long diameter and short diameter respectively.

Calculate relative tumor volume (RTV) based on the measured results with formula: RTV=Vt/V0, wherein V0 stands for the measured TV of each group at the time of being grouped for administration (i.e. d0) and Vt stands for the TV value of each group for every measurement.

The indicator used to evaluate anti-tumor activity is the relative tumor proliferation rate T/C (%), with the calculating formula as following:

$$T/C(\%) = \frac{TRTV}{CRTV} 100\%$$

TRTV: relative tumor volume of treated group; CRTV: relative tumor volume of negative control group.

Evaluation standard of curative effects: T/C (%)>60, ineffective; T/C (%)≤60 and P<0.05 after statistics processing, effective.

(2) Measurement of Tumor Weight and Calculation of Tumor Inhibition Rate (%)

Kill the animal at the end of treatment, dissect and remove the tumor, weigh the tumor and take a picture. The tumor inhibition rate (%) is calculated as the following formula:

$$\text{Tumor inhibition rate (inhibitiong rate of tumor growth, \%)} = \frac{\text{Average tumor weight of negative control group(g)} - \text{average tumor weight of treated group(g)}}{\text{Average tumor weight of negative control group((g)}} 100\%$$

Evaluation standard of curative effects: tumor inhibition rate (i.e. inhibition rate of tumor growth)<40%, ineffective; tumor inhibition rate>40% and P<0.05 after statistics processing, effective.

6) Test Results

TABLE 5

Influence of compounds to the weight of subcutaneously transplanted mouse colon carcinoma C26 and the tumor inhibition rate

| | Average tumor weight (g) | Tumor inhibition rate (%) | P | t test |
|---|---|---|---|---|
| Physiological saline | 2.46 | | | 0.83 |
| MPC-6827 | 0.525 | 78.66 | <0.001 | 0.27 |
| COUM-87 | 0.45 | 81.70 | <0.001 | 0.15 |
| COUM-89 | 1.99 | 19.12 | 0.05 | 0.84 |
| COUM-92 | 0.98 | 60.26 | <0.001 | 0.35 |
| COUM-95 | 0.68 | 72.26 | <0.001 | 0.26 |
| COUM-71 | 1.58 | 35.77 | ns | 0.68 |
| COUM-76 | 1.64 | 33.18 | ns | 0.40 |
| COUM-77 | 1.82 | 26.12 | ns | 0.91 |
| COUM-80 | 2.00 | 18.60 | ns | 0.56 |
| COUM-83 | 1.74 | 29.12 | ns | 0.95 |

Figure 3A:
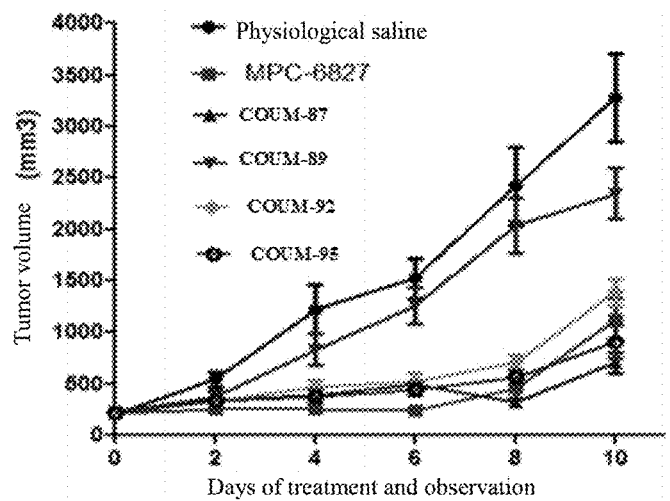
FIGS. 3A and 3B Curve diagrams, of tumor growth on C26 colon carcinoma model of compounds.
Figure 3B:
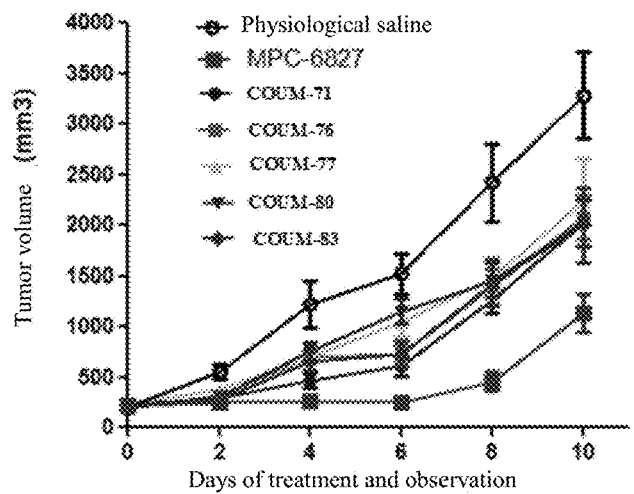

It can be concluded from FIGS. 3A and 3B and Table 5 that representative compounds such as COUM-87, COUM-92 and COUM-95 and positive drug MPC-6827 all demonstrate good anti-tumor activity on the mouse colon carcinoma model. Inhibition rate of the representative compounds for the colon carcinoma C26 model are respectively 81.70%, 60.26% and 72.66%, and the mice did not show significant changes in weight during the treatment. Although the positive drug MPC-6827 has an inhibition rate of 78.66%, but in the treatment, mice had significant drops in weight and even died. This indicates that toxicity of the compounds in the Invention is lower than the positive drug MPC-6827 and has better anti-tumor effects.

TABLE 6

Influence of compounds to the weight of subcutaneous human lung carcinoma H460 in nude mice and the tumor inhibition rate

| | Average tumor weight (g) | Tumor inhibition rate (%) | Standard deviation | t test |
|---|---|---|---|---|
| Physiological saline | 2.01 | | 0.56 | |
| COUM-87 | 0.61 | 69.88 | 0.28 | 0.14 |
| COUM-92 | 0.42 | 79.12 | 0.10 | 0.64 |

TABLE 6-continued

Influence of compounds to the weight of subcutaneous human lung carcinoma H460 in nude mice and the tumor inhibition rate

| | Average tumor weight (g) | Tumor inhibition rate (%) | Standard deviation | t test |
|---|---|---|---|---|
| COUM-95 | 0.47 | 76.64 | 0.13 | 0.39 |
| COUM-87 hydrochloride | 0.60 | 70.37 | 0.13 | 0.05 |
| COUM-71 | 0.98 | 51.53 | 0.41 | 0.01 |
| COUM-76 | 1.00 | 50.12 | 0.28 | 0.16 |
| COUM-79 | 0.93 | 53.74 | 0.33 | 0.04 |
| COUM-81 | 0.79 | 60.70 | 0.24 | 0.05 |
| COUM-83 | 1.05 | 48.05 | 0.39 | 0.01 |

Figure 4:
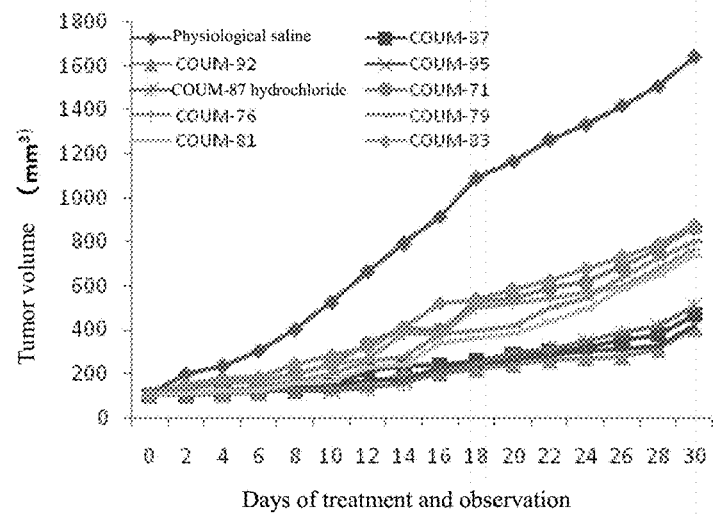
FIG. 4 Curve diagram of tumor growth on H460 lung carcinoma model of compounds.

FIG. 4 and Table 6 show the anti-tumor activity of plural representative compounds based on the human lung carcinoma H460 model. As shown in FIG. 4 and Table 6, the test results show that compared with the bland control group, the compounds COUM-87, COUM-92, COUM-95, COUM-71, COUM-76, COUM-79, COUM-81, COUM-83 and COUM-87 hydrochloride with intravenous administration of 10 mg/kg has a tumor inhibition rate higher than 40% on the human lung carcinoma H460 model and all demonstrate good treatment effects. Wherein, compounds COUM-87, COUM-92 and COUM-95 respectively has a tumor inhibition rate of 69.88%, 79.12% and 76.64%, exhibiting better anti-tumor effects. Compared with the blank control group, no significant changes in weight were observed during the treatment by applying the above compounds, indicating relatively small toxicity.

Embodiment 103: Pharmacodynamics in Tumor Models of Tumor-Bearing Nude Mice for Human Ovarian Cancer Cell A2780S and Taxol-Resistant Cell A2780/Taxol 1) Compounds: COUM-87 Citrate and COUM-92
2) Experimental Animals and Culture Medium BALB/c nude mice of SPF level (Balb/C nu/nu) and white mice, female, 4-6 weeks old, 18-22 g, purchased from Beijing Huafukang Bioscience Co., Inc., license No.: SCXK (J) 2014-0012. Test condition: animal house of SPF level, use permit No. of experiment animals: SYXK (J) 2015-0023

Modified RPMI 1640 medium is provided by HyClone. For batch No. of NWE 0416 with specification of 500 mL, the expiry date is May 31, 2012; for batch No. of NYG0920 with specification of 500 mL, the expiry date is Jul. 31, 2014; for batch No. of NZG1176 with specification of 500 mL, the expiry date is Jul. 31, 2015; and for batch No. of NZG1177 with specification of 500 mL, the expiry date is Jul. 31, 2015. All preserved under 2-8° C.

DMEM culture medium is provided by HyClone with batch No. of NZB1077, specification of 500 mL, expiry date of Feb. 28, 2015 and is preserved under 2-8° C.

3) Cell Culture

Culture human ovarian cancer cell A2780S and taxol-resistant ovarian cancer cell A2780/Taxol in RPMI 1640 medium (by HyClone), which contains 10% fetal bovine serum (by Hohhot Caoyuan Lvye Bioengineering Material Co., Ltd.) and 100 U/mL penicillin and streptomycin. Select cells in logarithmic phase, digest them with 0.25% trypsin and count, and dilute single-cell suspension with fetal bovine serum-free culture medium to $1 \times 10^7$ or $6 \times 10^7$ cells/mL for standby.

4) Inoculation, grouping and treatment: collect human ovarian cancer cell A2780S and taxol-resistant ovarian cancer cell A2780/Taxol under aseptic conditions, adjust cell density to $5 \times 10^7$ cells/mL with sterilized physiological saline, subcutaneously inoculate 0.1 mL into armpit and back of nude mice, remove the tumor when it grew to 1 cm diameter under aseptic conditions, slice it into 1 mm×1 mm tumor blocks and evenly and subcutaneously inoculate it into armpit and back of nude mice for subculture. Conduct random grouping of animals after 12 days when the tumor grew to 100-300 $mm^3$ and perform administration. Inject physiological saline for blank control group at 0.2 mL/mouse through tail intravenous injection, once per two days; inject MPC6827 for MPC6827 group at 5 mg/kg through tail intravenous injection, once per seven days; inject taxol for taxol group at 10 mg/kg through intraperitoneal administration, once per two days and at 30 mg/kg through intraperitoneal administration, once per seven days; inject COUM-87 citrate and COUM-92 at 2.5, 5 and 10 mg/kg through tail intravenous injection, once per two days and at 20 mg/kg through tail intravenous injection, once per seven days. Weigh the mouse and measure length and width of tumor using a vernier caliper in every two days, perform cervical dislocation for the nude mice after 20 days of drug administration, remove the tumor tissues, weigh and take a picture. Calculate tumor inhibition rate (%) eventually to evaluate anti-tumor effects. Table 7 is a list of curative effects of compounds for ovarian cancer cells A2780s and A2780T.

TABLE 7

Summary of curative effects for ovarian cancer cells A2780s and A2780T

| Tumor model | Compounds | Administration description | | | Death rate | Mouse weight (g) | |
|---|---|---|---|---|---|---|---|
| | | Dosage mg/kg | Frequency | Method | | Initial | Final |
| A2780s | Blank control group | — | Once/two days | Intravenous | 0/6 | 20.7 ± 0.7 | 23.6 ± 0.6 |
| | COUM 87 citrate | 2.5 | Once/two days | Intravenous | 0/6 | 21.0 ± 1.0 | 21.8 ± 0.5 |
| | COUM-87 citrate | 5 | Once/two days | Intravenous | 0/6 | 21.0 ± 0.7 | 22.1 ± 0.2 |
| | COUM-87 citrate | 10 | Once/two days | Intravenous | 0/6 | 20.8 ± 0.7 | 21.8 ± 0.4 |
| | COUM-92 | 2.5 | Once/two days | Intravenous | 0/6 | 21.2 ± 0.8 | 23.3 ± 0.7 |
| | COUM-92 | 5 | Once/two days | Intravenous | 0/6 | 21.4 ± 1.2 | 23.0 ± 0.5 |
| | COUM-92 | 10 | Once/two days | Intravenous | 0/6 | 20.9 ± 0.5 | 22.6 ± 0.6 |

TABLE 7-continued

Summary of curative effects for ovarian cancer cells A2780s and A2780T

|  |  |  |  |  |  |  |  |
|---|---|---|---|---|---|---|---|
|  | Taxol | 30 | Once/seven days | Intraperitoneal | 0/6 | 21.0 ± 0.7 | 18.2 ± 0.4 |
| A2780/T | Blank control group | — | Once/two days | Intravenous | 0/6 | 20.3 ± 0.7 | 21.5 ± 0.5 |
|  | COUM-87 citrate | 2.5 | Once/two days | Intravenous | 0/6 | 20.3 ± 1.1 | 22.2 ± 0.9 |
|  | COUM-87 citrate | 5 | Once/two days | Intravenous | 0/6 | 20.7 ± 0.9 | 21.2 ± 0.6 |
|  | COUM-87 citrate | 10 | Once/two days | Intravenous | 0/6 | 20.0 ± 0.6 | 20.4 ± 0.4 |
|  | COUM-92 | 2.5 | Once/two days | Intravenous | 0/6 | 20.2 ± 0.4 | 20.5 ± 0.9 |
|  | COUM-92 | 5 | Once/two days | Intravenous | 0/6 | 20.3 ± 0.7 | 21.1 ± 0.9 |
|  | COUM-92 | 10 | Once/two days | Intravenous | 0/6 | 20.3 ± 0.4 | 20.4 ± 1.0 |
|  | Taxol | 30 | Once/seven days | Intraperitoneal | 0/6 | 20.3 ± 0.8 | 19.4 ± 1.0 |

| Tumor model | Compounds | Tumor volume (mm³) Initial | Tumor volume (mm³) Final | T/C (%) | Tumor weight (g) X ± SD | Inhibition rate % |
|---|---|---|---|---|---|---|
| A2780s | Blank control group | 148.0 | 1512.5 | NA[b] | 1.64 ± 0.25 | NA |
|  | COUM 87 citrate | 137.0 ± 17.8 | 260.7 ± 45.3 [c] | 18.6 | 0.25 ± 0.10 [c] | 85.0 |
|  | COUM-87 citrate | 136.1 ± 25.9 | 203.6 ± 32.7 [c] | 14.6 | 0.22 ± 0.04 [c] | 86.6 |
|  | COUM-87 citrate | 138.3 ± 21.8 | 153.7 ± 28.4 [c] | 10.9 | 0.21 ± 0.03 [c] | 87.5 |
|  | COUM-92 | 143.4 ± 13.4 | 312.7 ± 254.2 [c] | 21.3 | 0.39 ± 0.35 [c] | 76.52 |
|  | COUM-92 | 140.3 ± 20.5 | 208.2 ± 15.4 [c] | 14.5 | 0.25 ± 0.04 [c] | 85.06 |
|  | COUM-92 | 139.0 ± 23.2 | 162.4 ± 41.1 [c] | 11.4 | 0.18 ± 0.06 [c] | 88.82 |
|  | Taxol | 138.1 ± 25.6 | 184.8 ± 26.6 [c] | 13.1 | 0.28 ± 0.07 [c] | 82.9 |
| A2780/T | Blank control group | 155.1 ± 17.8 | 1237.4 ± 571.9 | NA | 1.27 ± 0.68 | NA |
|  | COUM-87 citrate | 153.2 ± 18.8 | 371.0 ± 183.1[b] | 30.34 | 0.36 ± 0.20 | 72.1 |
|  | COUM-87 citrate | 161.9 ± 19.2 | 274.3 ± 56.1 [c] | 21.23 | 0.21 ± 0.06 | 83.9 |
|  | COUM-87 citrate | 149.6 ± 13.4 | 243.6 ± 57.1 [c] | 20.41 | 0.17 ± 0.08 | 86.9 |
|  | COUM-92 | 152.0 ± 15.3 | 509.6 ± 401.4[a] | 42.00 | 0.52 ± 0.19[a] | 59.19 |
|  | COUM-92 | 149.7 ± 17.2 | 321.4 ± 159.6[b] | 26.90 | 0.28 ± 0.12[b] | 77.95 |
|  | COUM-92 | 158.5 ± 19.0 | 265.4 ± 86.2[b] | 20.98 | 0.22 ± 0.06[b] | 82.68 |
|  | Taxol | 155.6 ± 20.6 | 936.4 ± 347.9 | 75.4 | 0.79 ± 0.41 | 37.7 |

Table 7 shows that compounds COUM-87 citrate and COUM-92 can inhibit tumor growth in a dose-dependent manner, with better anti-tumor activity than taxol. In the treatment, weight of mice did not have significant changes, while weight in taxol group dropped about 2 g in average, demonstrating lower toxicity of compounds COUM-87 citrate and COUM-92 when compared with taxol.

Embodiment 104: Activity of Compounds to Inhibit Polymerization of Tubulin

Test Method:

Apply sterile water to prepare 100×GTP solution (100 mM concentration, GTP powders purchased from Dalian Meilun Biotech Co., Ltd.) on the day of test.

The tubulin is purchased from cytoskeleton and is preserved at −80° C. Put it on the ice, apply precooled microtubule polymerization buffer (Genaral Tubulin Buffer containing 80 mM piperazine-1,4-diethanesulphonate, 2 mM magnesium chloride, 0.5 mM ethylene glycol bis(2-aminoethylether) tetraacetic acid, pH 6.9) to dissolve the tubulin, mix on the ice and leave it for 30 min to 1 h to completely depolymerize the tubulin; meanwhile preheat the 96-well plate for the test in the microplate reader, adjust the temperature to 37° C. for the whole course and properly set up the microplate reader: dynamic readings (kinetic mode), measurement for absorbance at 340 nm, test duration as 30-60 min and one reading per 1 min; then balance some General Tubulin Buffer to the room temperature.

Transfer tubulin to the precooled EP tube for centrifugation at 13,000 rpm under 4° C. for 20 min, take the supernatant and put it on the ice. Apply Bradford test for protein quantification, add microtubule polymerization buffer based on the quantification results to adjust the concentration of tubulin to 2 mg/mL.

Mix the compound to be tested with concentration of 10 times of the test concentration into the 100 μL general tubulin buffer preheated to the room temperature to produce 10× solution of the compound to be tested. Prepare DMSO of equal volume ratio for the control group. Observe the compound, after the compound dissolved well and no separating-out occurred, take out the preheat 96-well plate from the microplate reader, quickly add 10 μL corresponding 10× solution in the compound for each test group, and then put the 96-well plate back to the microplate reader for incubation at 37° C.

Add 100×GTP solution into tubulin solution till the final concentration reached 1 mM, and mix rapidly.

Take out the 96-well plate from the microplate reader, quickly add 90 μL tubulin into each well (air bubbles should be prevented in adding the sample).

Rapidly put the 96-well plate into the microplate reader and start reading.

Figure 5A:
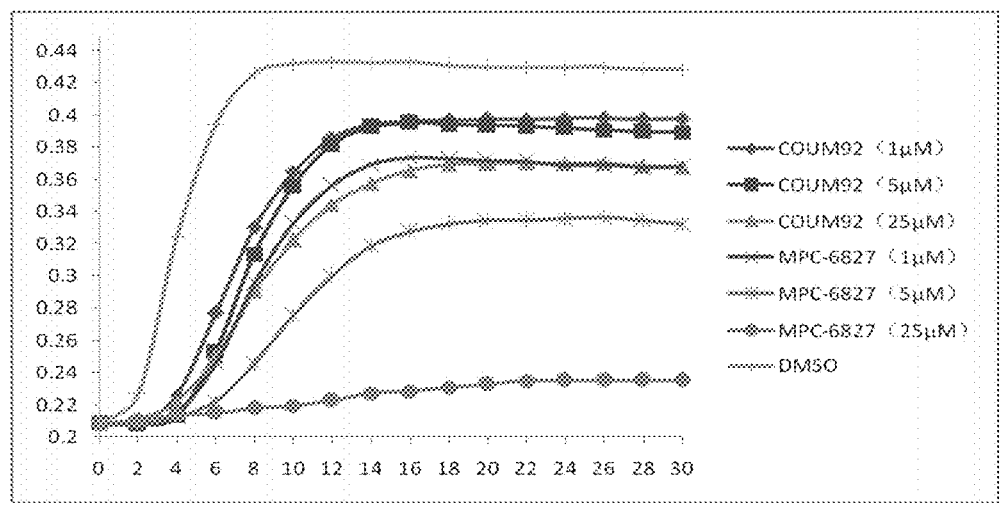
FIGS. 5A and 5B Curves of microtubule polymerization in vitro. The degree of microtubule polymerization is reflected by applying a microplate reader to monitor the absorbance at 340 nm wavelength under 37° C.
Figure 5B:
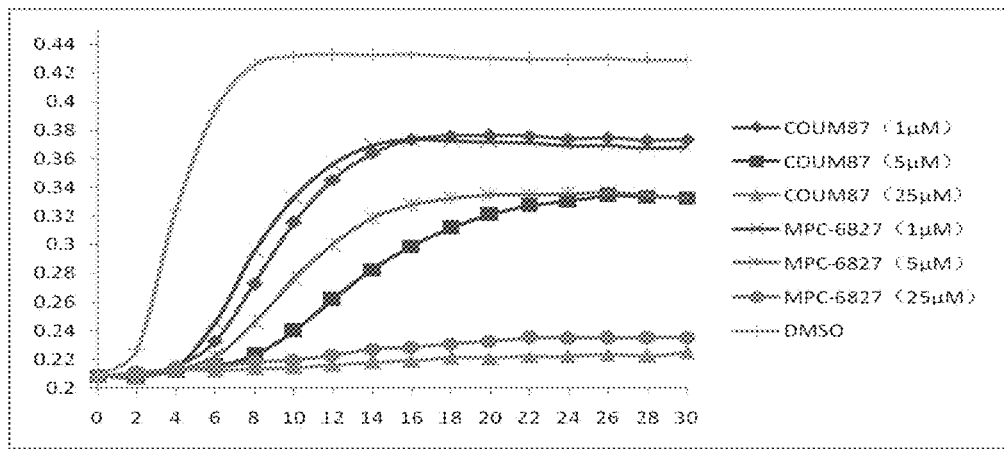
Figure 6A:
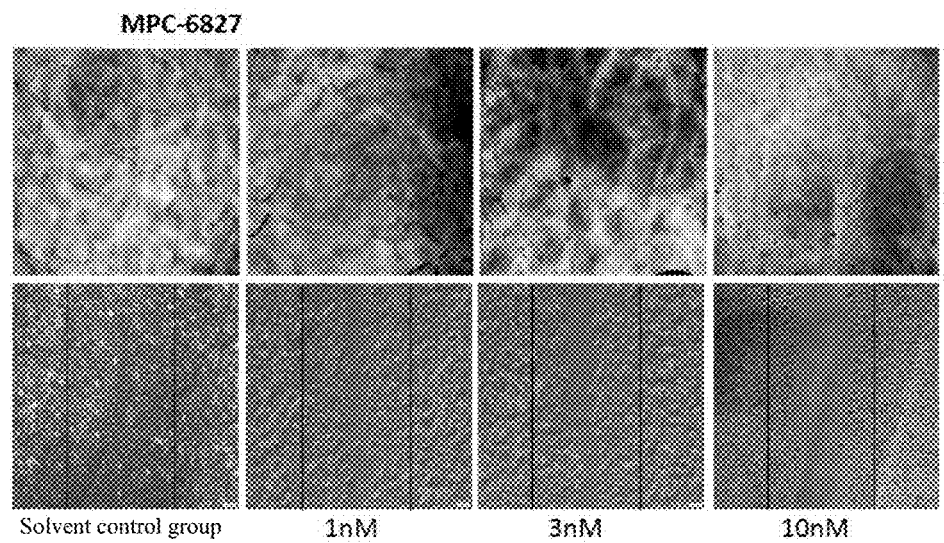
FIGS. 6A, 6B, 6C, 6D and 6E Wound healing test and angiogenesis test. Wound healing test and angiogenesis test based on HUVECs are carried out to prove the anti-angiogenic activity of the compounds of the Invention.
Figure 6B:
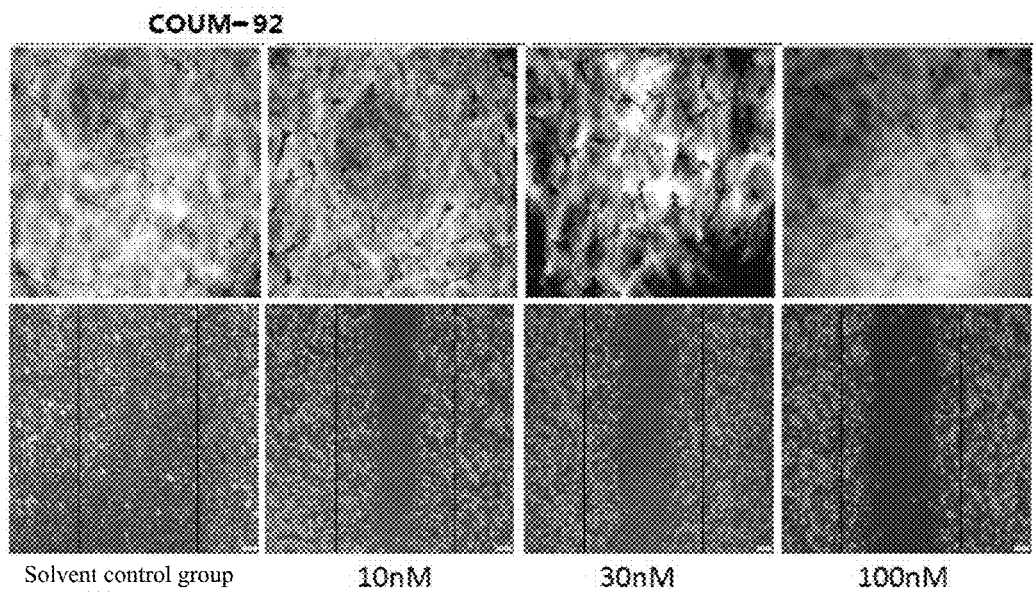
Figure 6C:
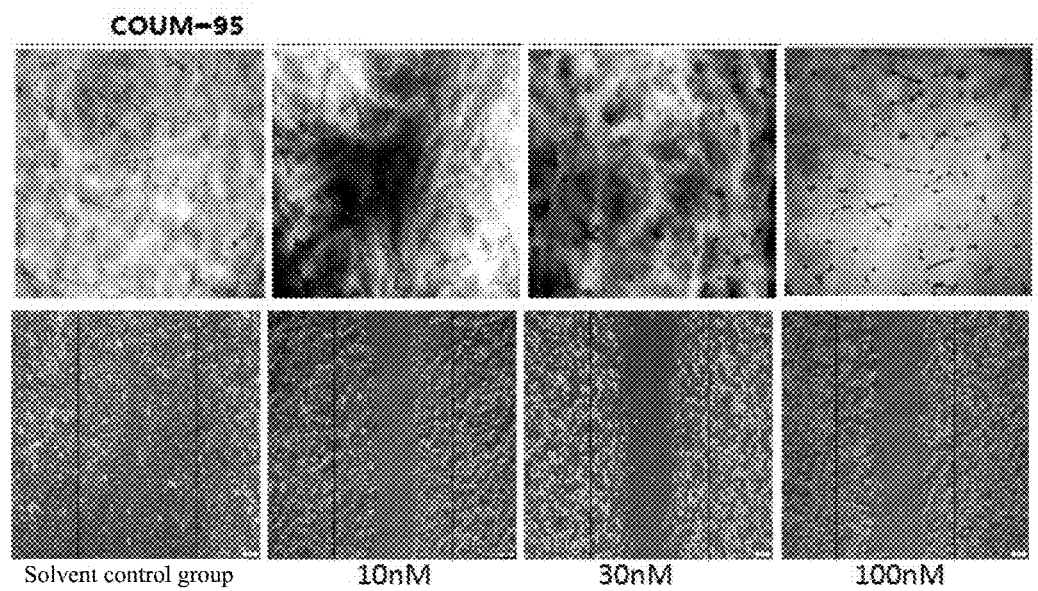
Figure 6D:
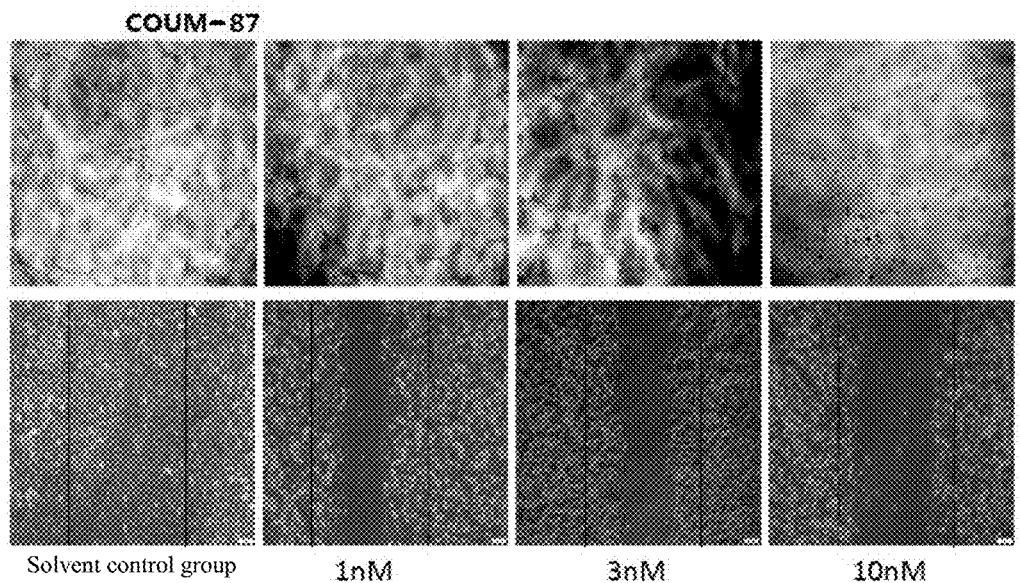
Figure 6E:
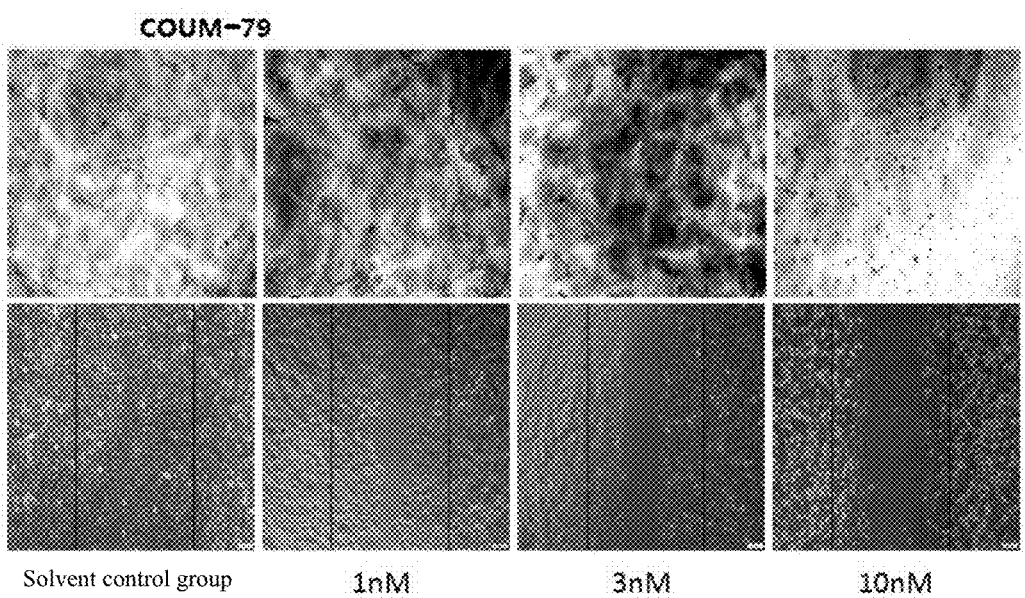

It can be concluded from FIGS. 5A and 5B that, like positive drugs, compounds COUM-87 and COUM-92 can inhibit polymerization of tubulin in vitro in a dose-dependent manner, and the compounds have comparative inhibition effects compared with MPC6827 when with 5 μM concentration, demonstrating that COUM-87 and COUM-92 compounds have strong activity to inhibit polymerization of microtubule.

Embodiment 105: Anti-Angiogenic Activity In Vitro of Compounds

Microtubule inhibitors acting on the colchicine binding site often destroy the blood vessels related to the tumor. That's because this kind of compounds are regarded to have a dual mechanism to kill both the tumor cells and the vascular endothelial cells related to the tumor. The influence of compounds to microtubules will lead to morphological changes of endothelial cells. We've observed the anti-angiogenic activity in vitro of 8a by applying cultured human umbilical vein endothelial cells (HUVECs).

Culture methods to isolate HUVECs:

Obtain neonate umbilical cords from clinical sources after being approved by relevant authorities, put them into sterile PBS solution, provide ice bags at the external to keep them under low temperature, and return to the clean bench to operate. Insert a blunt needle into the human umbilical vein and wash with sterile PBS solution for multiple times until cleaning up the tainted blood. Clamp the lower end of the cord with surgical clamps, add collagenase with 1 mg/mL concentration (purchased from Roche) for digestion for 15 to 20 minutes at room temperature and shake the cord up and down at intervals. After digestion, open the surgical clamp at the lower end, let the digestive solution flow into a 50 mL centrifuge tube and wash the cord for 2-3 times with sterile PBS solution. Centrifuge the collected solution for 3 minutes at 1500 rpm. Discard the supernatant, resuspend cells with EBM-2 medium (purchased from lonza) containing various growth factors and incubate them in an incubator at constant temperature of 37° C. with 5% $CO_2$ concentration.

(1) Test Method: Wound Healing Test on HUVECs

Collect HUVECs between the 3rd to 7th subculture generations and plate them in the 6-well plate. When the cells were about to form a confluent monolayer of cells, change the medium into a serum-free medium to starve the cells for 6 h. Scratch the cells with a sterile pipette tip of middle size, wash with sterile PBS for two times, change back into the EBM-2 medium containing various growth factors to continue culturing and add compounds at different concentrations simultaneously. Then place it immediately under the microscope for imaging as the 0 h group. The migration duration for cells is 24 h. When time was over, apply 4% paraformaldehyde for fixation and then put it under the microscope for imaging. Randomly select 3 different microscopic fields for each group to count number of the migrated cells.

(2) Angiogenesis Test on HUVECs

Place Matrigel (purchased from Becton Dickinson (BD)) at 4° C. and make it in liquid state; precool the pipette tip, 96-well plate and EP tube to be used in the test.

Add Matrigel into the 96-well plate at 50 μL/well and incubate it in an incubator at 37° C. with $CO_2$ concentration for 45 min to make it solidify. Collect HUVECs between the 3rd to 7th subculture generations and plate them in the 96-well plate with preplated Matrigel at 10,000 cells/well, and add compounds at different concentrations simultaneously. After 8 h, apply 4% paraformaldehyde for fixation and put it under the microscope for imaging. Randomly select 3 different microscopic fields for each group to count number of the cavity structures formed.

The wound healing test and angiogenesis test were carried out on HUVECs. As shown in FIG. 6A-6E, in the wound healing test, after 24 h of cells migration, the scratched HUVECs in the solvent control group show strong migration activity compared with the initial scratch. While like MPC-6827, the compounds COUM-92, COUM-95, COUM-87 and COUM-79 all inhibit migration of HUVECs in a dose-dependent manner. The compounds COUM-92, COUM-95 and COUM-87 completely inhibit migration of HUVECs at a maximum test concentration of 10 nM. In the angiogenesis test, after 8 h treatment, the cells in the solvent control group form into tubular structures well, while like MPC-6827, the compounds COUM-92, COUM-95, COUM-87 and COUM-79 all inhibit angiogenesis of HUVECs in a dose-dependent manner. HUVECs are in completely scattered forms with high concentrations of the compounds. The series of tests related to vessels demonstrate that the above compounds have anti-angiogenic activity.

Besides strong anti-tumor activity, the compounds of the Invention also have $IC_{50}$ values for plural tumor cell strains between 0.01-5 nM, better inhibition to microtubule polymerization, diversified biological activities and low toxicity and good solubility.

The invention claimed is:

1. A 4-substituted coumarin derivative with a structural formula as shown in Formula I:

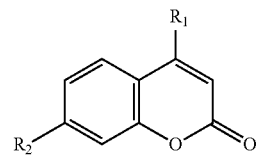

wherein:
$R_1$ is

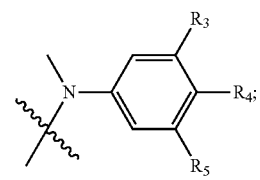

$R_2$ is C1-C8 alkoxy, —H,

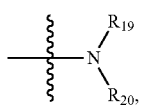

C1-C8 alkyl, halogen or C3-C8 cycloalkyl;

R$_3$-R$_5$ are each independently —H, C1-C8 alkoxy, C1-C8 alkyl, halogen, C3-C8 cycloalkyl,

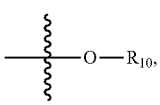

C2-C8 alkenyl, C1-C8 alkyl substituted by halogen, —NH$_2$ or

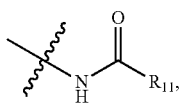

and are not —H at the same time;

R$_{10}$ is

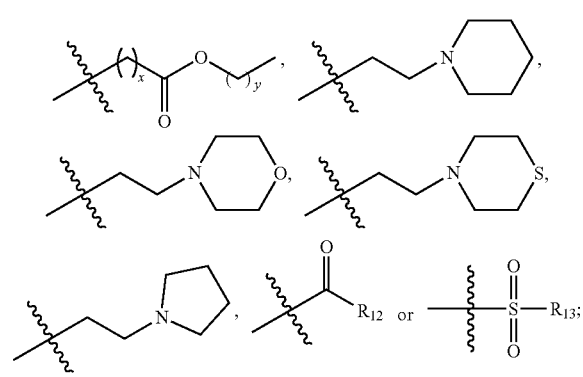

x=1-4, y=1-4;

R$_{11}$ is C1-C10 alkyl,

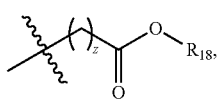

C2-C8 alkenyl, C1-C8 alkyl substituted by halogen, C3-C8 cycloalkyl,

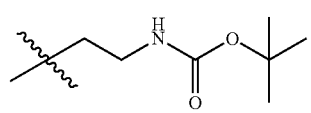 [SMILES: *CCNC(=O)OC(C)(C)C]

or —NH$_2$; z=1-10;

R$_{12}$ is C1-C10 alkyl,

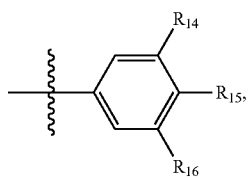

halogen, C2-C8 alkenyl, C1-C8 alkyl substituted by halogen, C3-C8 cycloalkyl,

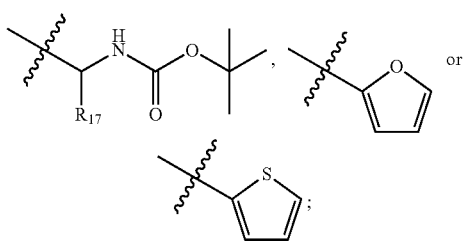

R$_{13}$ is C1-C8 alkyl, phenyl substituted by C1-C8 alkyl or phenyl substituted by halogen;

R$_{14}$-R$_{16}$ are each independently C1-C8 alkyl, halogen, —H, C1-C8 alkoxy or —NH$_2$, and are not —H at the same time;

R$_{17}$ is C1-C8 alkyl, halogen, —H or

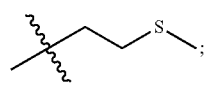

R$_{18}$ is C1-C8 alkyl, halogen or —H; and

R$_{19}$ and R$_{20}$ are each independently C1-C8 alkyl, halogen or —H.

2. The 4-substituted coumarin derivative according to claim 1, wherein:

R$_2$ is C1-C4 alkoxy, —H,

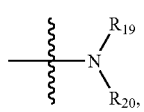

C1-C4 alkyl, halogen or C3-C8 cycloalkyl;

R$_3$-R$_5$ are each independently —H, C1-C4 alkoxy, C1-C4 alkyl, halogen, C3-C8 cycloalkyl,

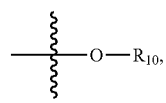

C2-C4 alkenyl, C1-C4 alkyl substituted by halogen, —NH$_2$ or

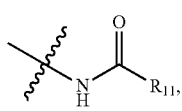

and are not —H at the same time;
R$_{11}$ is C1-C10 alkyl,

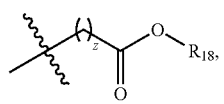

C2-C8 alkenyl, C1-C4 alkyl substituted by halogen, C3-C8 cycloalkyl,

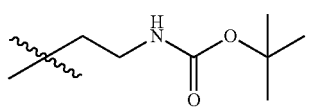 [SMILES: *CCNC(=O)OC(C)(C)C]

or —NH$_2$; z=1-10;
R$_{12}$ is C1-C10 alkyl,

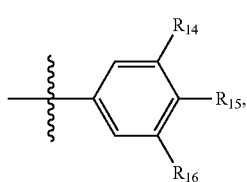

halogen, C2-C8 alkenyl, C1-C4 alkyl substituted by halogen, C3-C8 cycloalkyl,

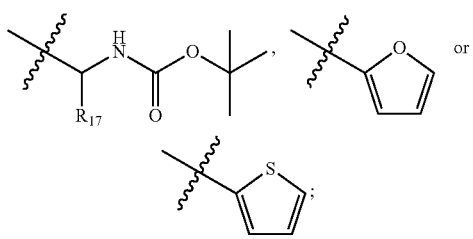

R$_{13}$ is C1-C4 alkyl, phenyl substituted by C1-C4 alkyl or phenyl substituted by halogen;
R$_{14}$-R$_{16}$ are each independently C1-C4alkyl, halogen, —H, C1-C4 alkoxy or —NH$_2$, and are not —H at the same time;
R$_{17}$ is C1-C4 alkyl, halogen, —H or

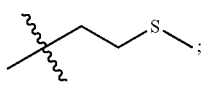

R$_{18}$ is C1-C4 alkyl, halogen or —H; and
R$_{19}$ and R$_{20}$ are each independently C1-C4alkyl, halogen or —H.
3. The 4-substituted coumarin derivative according to claim 1, wherein:
R$_2$ is C1-C4 alkoxy, —H,

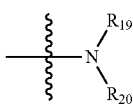

or C1-C4 alkyl;
R$_3$-R$_5$ are each independently —H, C1-C4alkoxy, C1-C4 alkyl, halogen, C3-C8 cycloalkyl,

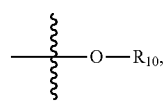

C2-C4 alkenyl, C1-C4 alkyl substituted by halogen, —NH$_2$ or

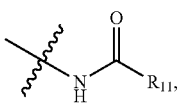

and are not —H at the same time;
R$_{11}$ is C1-C10 alkyl,

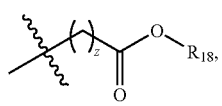

C2-C8 alkenyl, C1-C4 alkyl substituted by halogen, C3-C8 cycloalkyl,

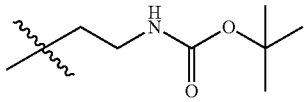 [SMILES: *CCNC(=O)OC(C)(C)C]

or —NH$_2$; z=1-10;
R$_{12}$ is C1-C10 alkyl,

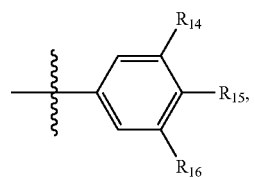

halogen, C2-C8 alkenyl, C1-C4 alkyl substituted by halogen, C3-C8 cycloalkyl,

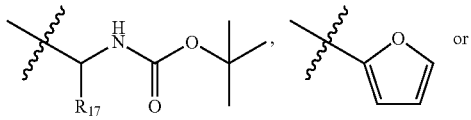

-continued

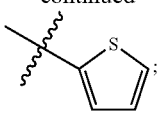

R$_{13}$ is C1-C4 alkyl, phenyl substituted by C1-C4 alkyl or phenyl substituted by halogen;

R$_{14}$-R$_{16}$ are each independently C1-C4alkyl, halogen, —H, C1-C4 alkoxy or —NH$_2$, and are not —H at the same time;

R$_{17}$ is C1-C4 alkyl, halogen, —H or

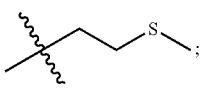 [SMILES: *CCSC]

R$_{18}$ is C1-C4 alkyl, halogen or —H; and

R$_{19}$ and R$_{20}$ are each independently C1-C4alkyl, halogen or —H.

4. The 4-substituted coumarin derivative according to claim 3, wherein R$_2$ is C1-C4 alkoxy, —H or

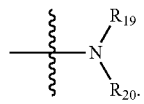

5. The 4-substituted coumarin derivative according to claim 1, wherein R$_2$ is C1-C4 alkoxy, —H or

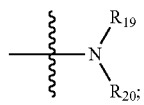

R$_3$-R$_5$ are each independently —H, C1-C4 alkoxy, C1-C4 alkyl, halogen, C3-C8 cycloalkyl,

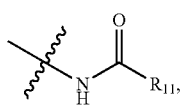

—NH$_2$ or

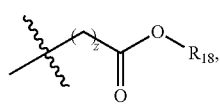

and are not —H at the same time;

R$_{11}$ is C1-C10 alkyl,

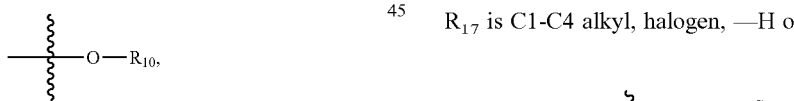

C2-C8 alkenyl, C1-C4 alkyl substituted by halogen, C3-C8 cycloalkyl,

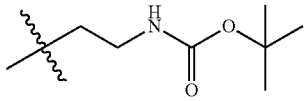 [SMILES: *CCNC(=O)OC(C)(C)C]

or —NH$_2$; z=1-10;

R$_{12}$ is C1-C10 alkyl,

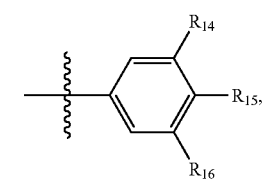

halogen, C2-C8 alkenyl, C1-C4 alkyl substituted by halogen, C3-C8 cycloalkyl,

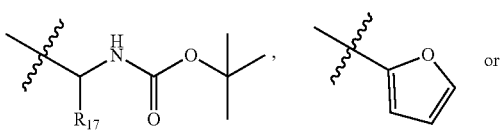

R$_{13}$ is C1-C4 alkyl, phenyl substituted by C1-C4 alkyl or phenyl substituted by halogen;

R$_{14}$-R$_{16}$ are each independently C1-C4alkyl, halogen, —H, C1-C4 alkoxy or —NH$_2$, and are not —H at the same time;

R$_{17}$ is C1-C4 alkyl, halogen, —H or

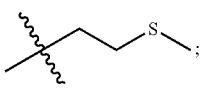 [SMILES: *CCSC]

R$_{18}$ is C1-C4 alkyl, halogen or —H; and

R$_{19}$ and R$_{20}$ are each independently C1-C4alkyl, halogen or —H.

6. The 4-substituted coumarin derivative according to claim 5, wherein R$_3$-R$_5$ are each independently —H, C1-C4 alkoxy,

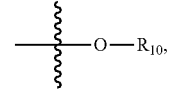

—NH₂ or

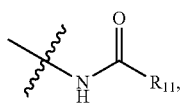

and are not —H at the same time.

7. The 4-substituted coumarin derivative according to claim 1, wherein:

R₂ is C1-C4 alkoxy, —H or

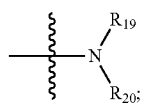

R₃-R₅ are each independently —H, C1-C4 alkoxy,

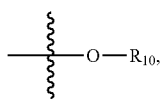

—NH₂ or

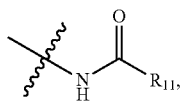

and are not —H at the same time;

R₁₁ is C1-C10 alkyl,

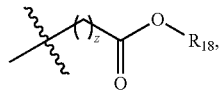

C2-C8 alkenyl, C1-C4 alkyl substituted by halogen, C3-C8 cycloalkyl,

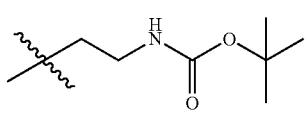 [SMILES: *CCNC(=O)OC(C)(C)C]

or —NH₂; z=1-10;

R₁₂ is C1-C10 alkyl,

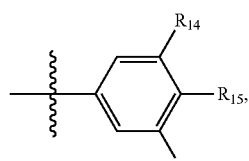

halogen, C2-C8 alkenyl, C1-C4 alkyl substituted by halogen, C3-C8 cycloalkyl,

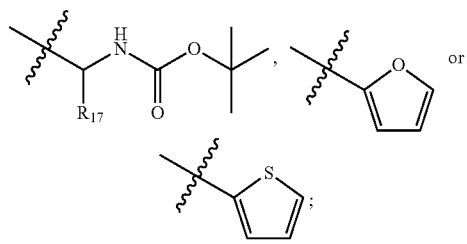

R₁₃ is C1-C4 alkyl, phenyl substituted by C1-C4 alkyl or phenyl substituted by halogen;

R₁₄-R₁₆ are each independently C1-C4 alkyl, halogen, —H, C1-C4 alkoxy or —NH₂, and are not —H at the same time;

R₁₇ is C1-C4 alkyl, halogen, —H or

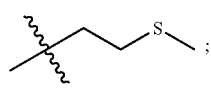

R₁₈ is C1-C4 alkyl, halogen or —H; and

R₁₉ and R₂₀ are each independently C1-C4alkyl, halogen or —H.

8. The 4-substituted coumarin derivative according to claim 1, wherein:

R₂ is C1-C4 alkoxy, —H or

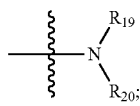

R₃-R₅ are each independently —H, C1-C4 alkoxy,

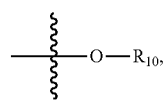

—NH₂ or

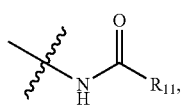

and are not —H at the same time;

R₁₀ is

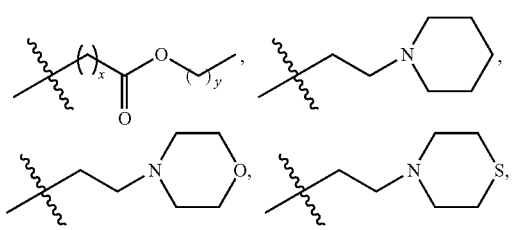

-continued

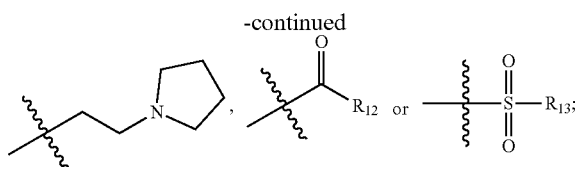

x=1-2, y=1-2;
R$_{11}$ is C1-C10 alkyl,

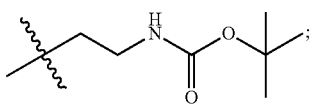

C2-C8 alkenyl, C1-C4 alkyl substituted by halogen, C3-C8 cycloalkyl or

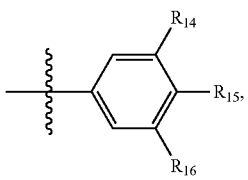

z=1-10;
R$_{12}$ is C1-C10 alkyl,

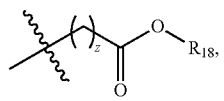

halogen, C2-C8 alkenyl, C1-C4 alkyl substituted by halogen, C3-C8 cycloalkyl,

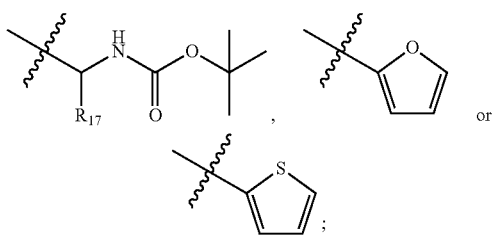

R$_{13}$ is C1-C4 alkyl, phenyl substituted by C1-C4 alkyl or phenyl substituted by halogen;
R$_{14}$-R$_{16}$ are each independently C1-C4alkyl, halogen, —H or C1-C4 alkoxy, and are not —H at the same time;
R$_{17}$ is C1-C4 alkyl, —H or

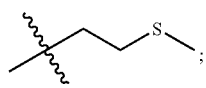

R$_{18}$ is C1-C4 alkyl or —H; and
R$_{19}$ and R$_{20}$ are each independently C1-C4alkyl or —H.

9. The 4-substituted coumarin derivative according to claim 1, wherein the structural formula of the coumarin derivative is shown in Formula III below when R$_1$ is

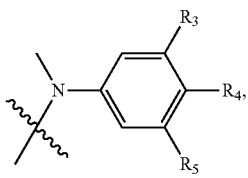

R$_3$ is-H, R$_4$ is methoxyl and R$_5$ is

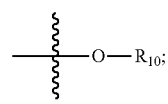

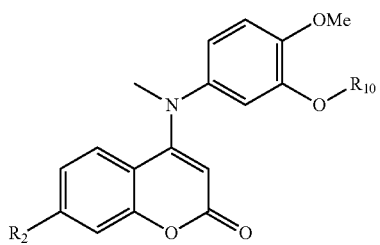

wherein:
R$_2$ is C1-C4 alkoxy, —H,

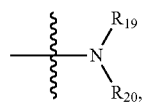

C1-C4 alkyl, halogen or C3-C8 cycloalkyl;
R$_{12}$ is C1-C10 alkyl,

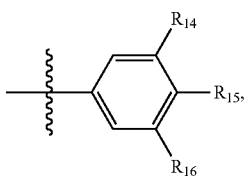

halogen, C2-C8 alkenyl, C1-C4 alkyl substituted by halogen, C3-C8 cycloalkyl,

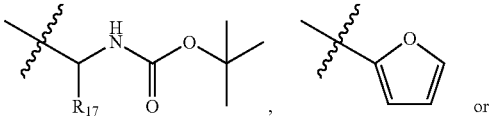

-continued

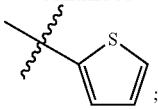;

$R_{13}$ is C1-C4 alkyl, phenyl substituted by C1-C4 alkyl or phenyl substituted by halogen;

$R_{14}$-$R_{16}$ are each independently C1-C4 alkyl, halogen, —H, C1-C4 alkoxy or —NH$_2$, and are not —H at the same time; and $R_{17}$ is C1-C4 alkyl, halogen, —H or

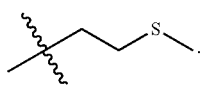 [SMILES: *CCSC].

10. The 4-substituted coumarin derivative according to claim 9, wherein $R_2$ is C1-C4 alkoxy, —H or

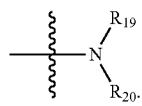.

11. The 4-substituted coumarin derivative according to claim 10, wherein:

$R_{10}$ is

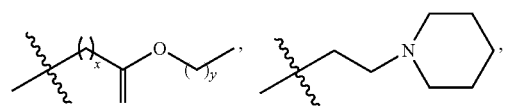

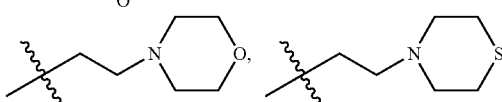

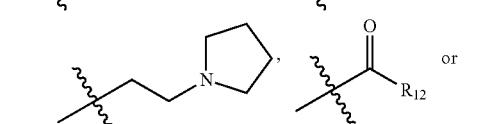

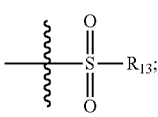

x=1-2, y=1-2;

$R_{14}$-$R_{16}$ are each independently C1-C4 alkyl, halogen, —H or C1-C4 alkoxy, and are not —H at the same time; and $R_{17}$ is C1-C4 alkyl, —H or

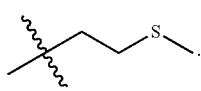 [SMILES: *CCSC].

12. The 4-substituted coumarin derivative according to claim 1, wherein the structural formula of the coumarin derivative is shown in Formula IV when $R_1$ is

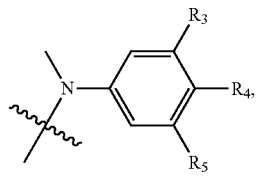

$R_3$ is —H, $R_4$ is methoxyl and $R_5$ is

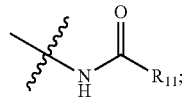;

IV

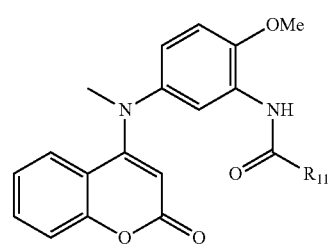

wherein:

$R_{11}$ is C1-C10 alkyl,

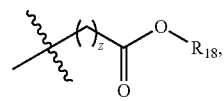

C2-C8 alkenyl, C1-C4 alkyl substituted by halogen, C3-C8 cycloalkyl,

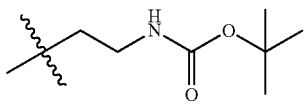 [SMILES: *CCNC(=O)OC(C)(C)C]

or —NH$_2$; z=1-10; and $R_{18}$ is C1-C4 alkyl, halogen or —H.

13. The 4-substituted coumarin derivative according to claim 12, wherein $R_{11}$ is C1-C10 alkyl,

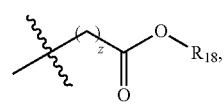

C2-C8 alkenyl, C1-C4 alkyl substituted by halogen, C3-C8 cycloalkyl or

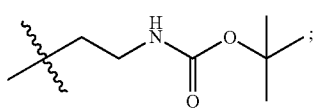 [SMILES: *CCNC(=O)OC(C)(C)C]
z=1-10.
14. The 4-substituted coumarin derivative according to claim 13, wherein $R_{18}$ is C1-C4 alkyl or —H.
15. A 4-substituted coumarin derivative with a structural formula selected from the group consisting of:
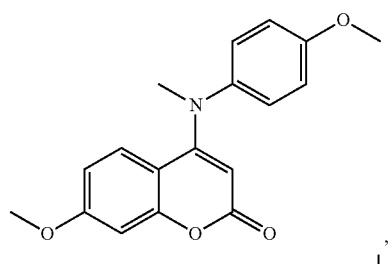
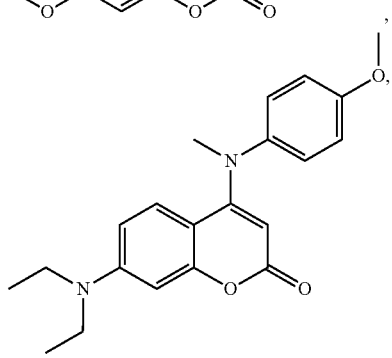
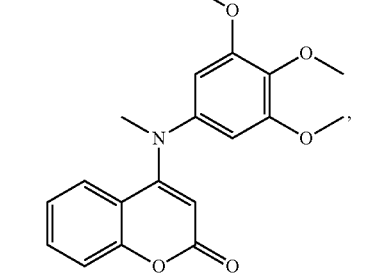
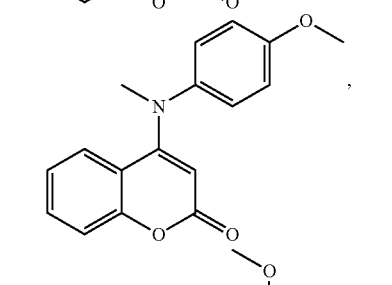
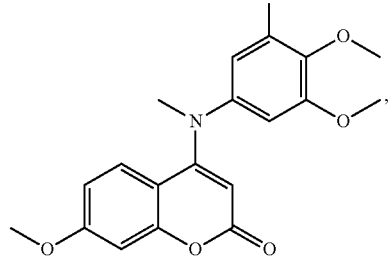
-continued
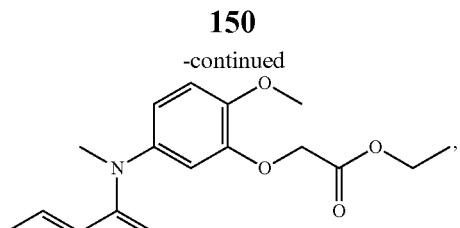
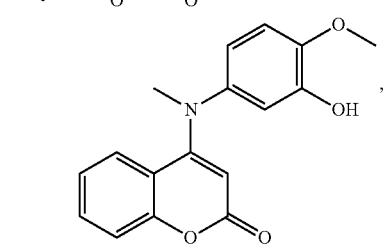
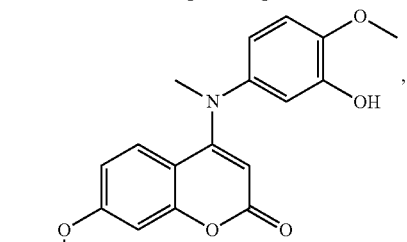
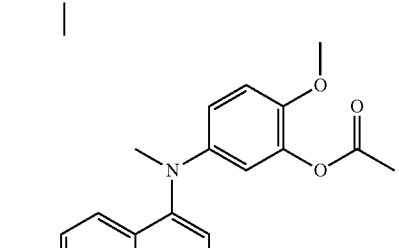
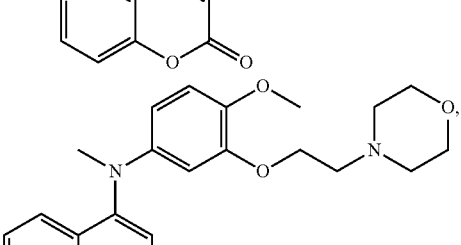
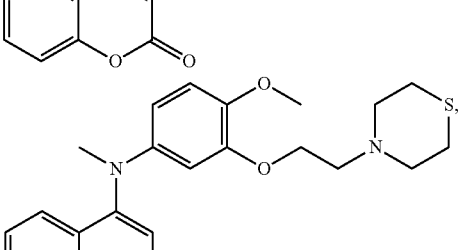
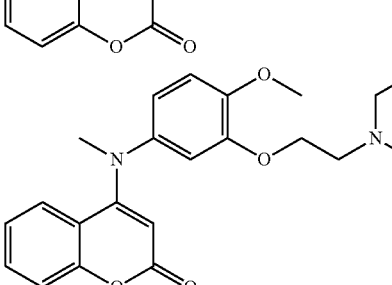

151
-continued
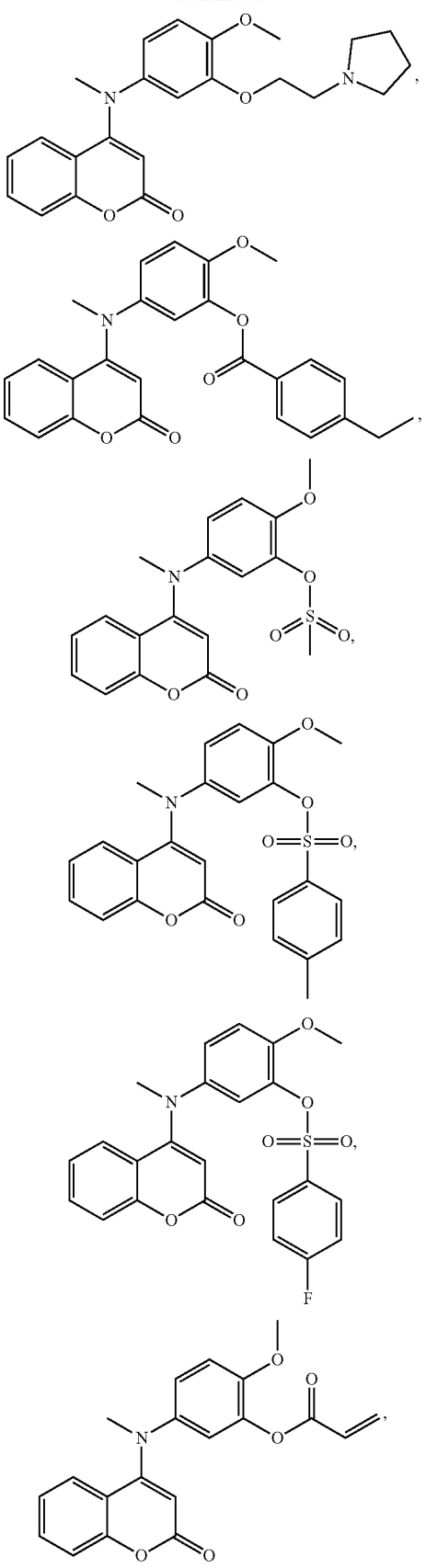
152
-continued
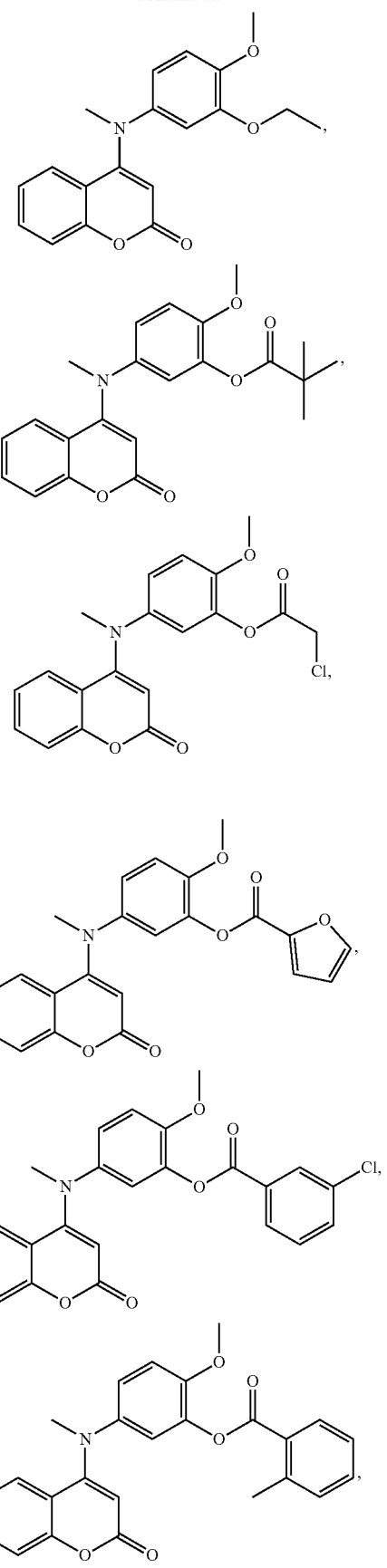

153
-continued
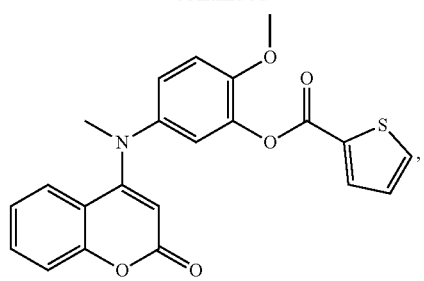
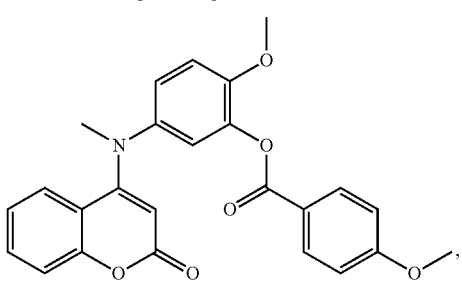
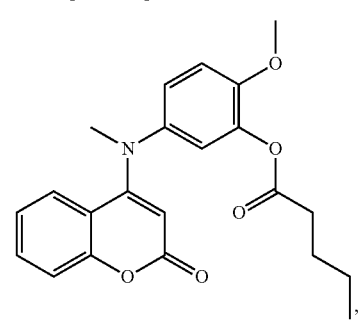
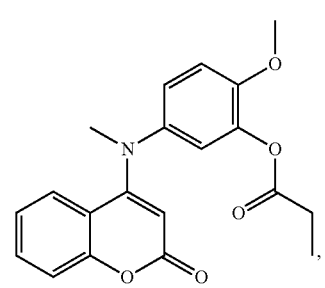
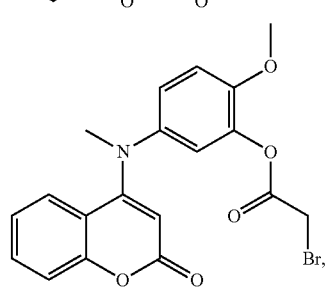
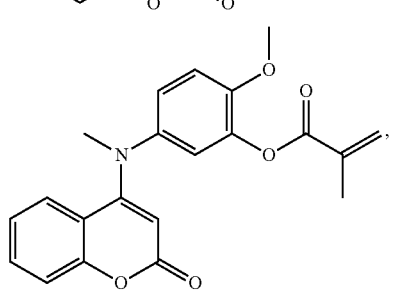
154
-continued
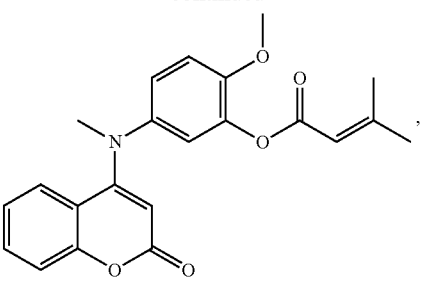
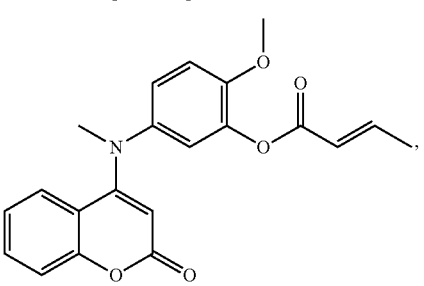
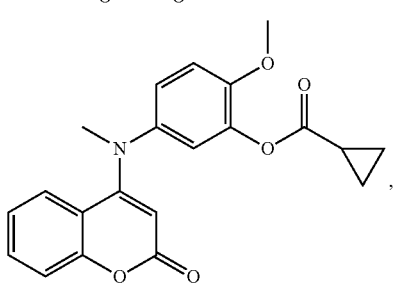
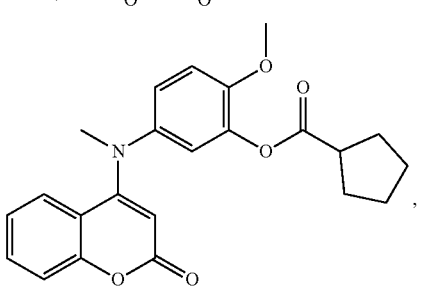
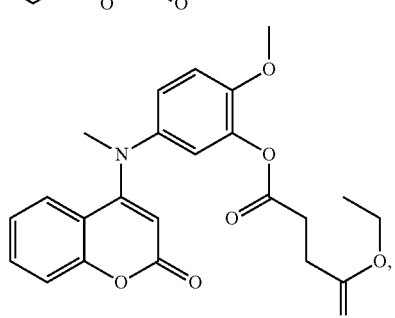
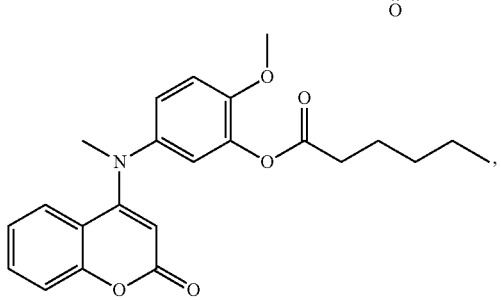

155
-continued
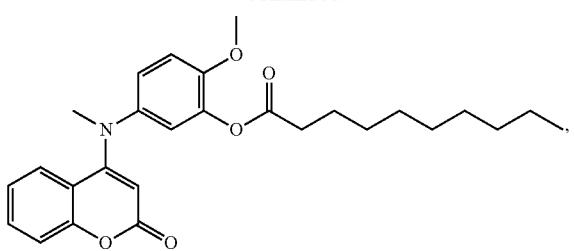
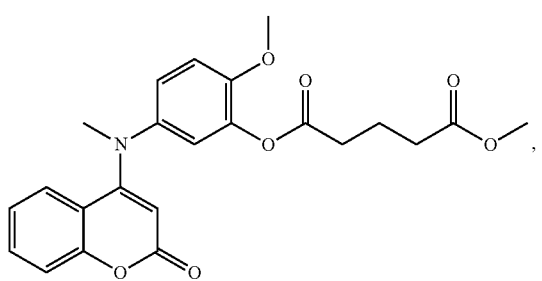
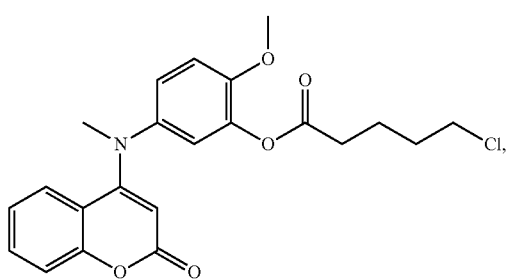
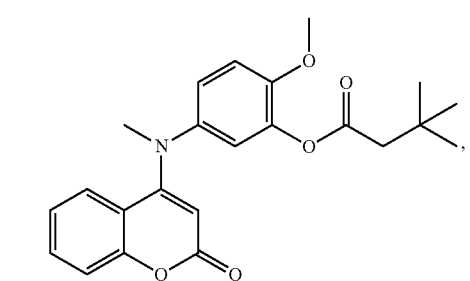
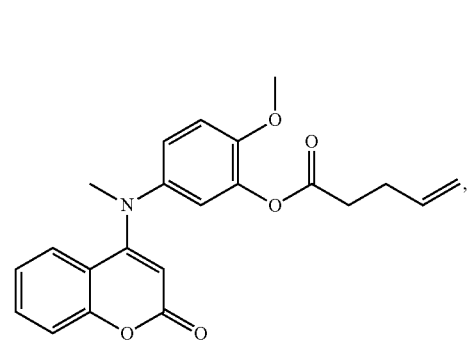
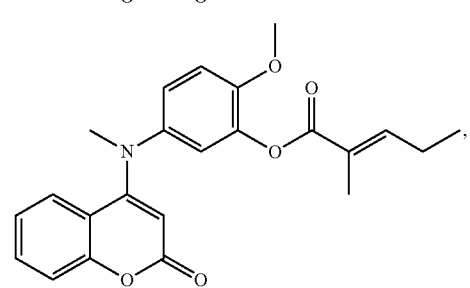
156
-continued
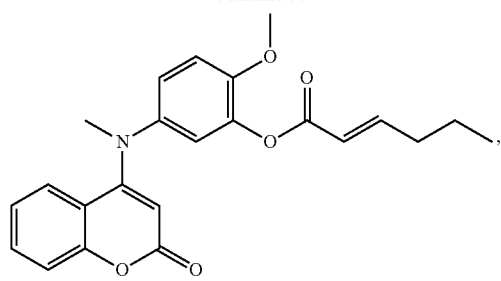
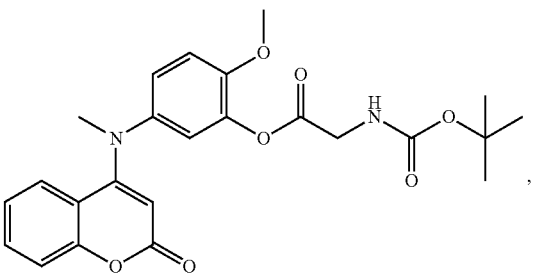
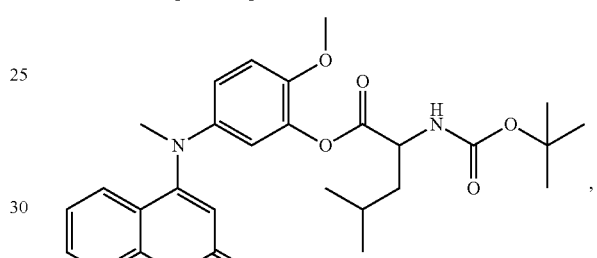
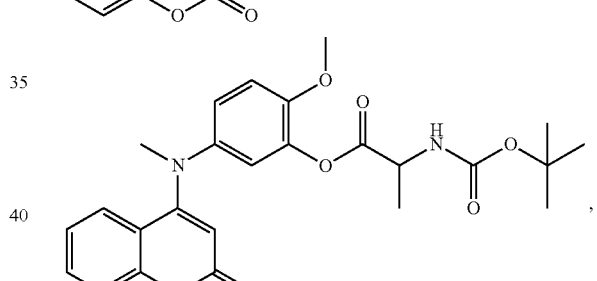
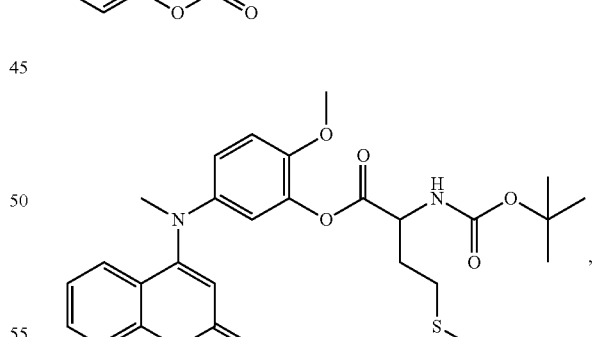
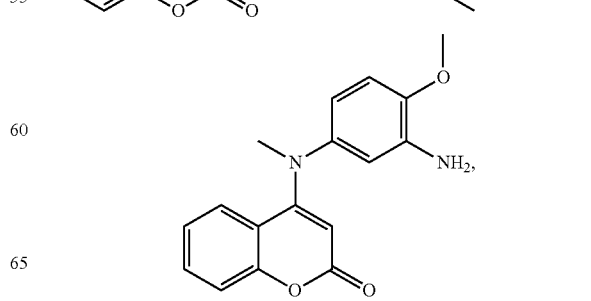

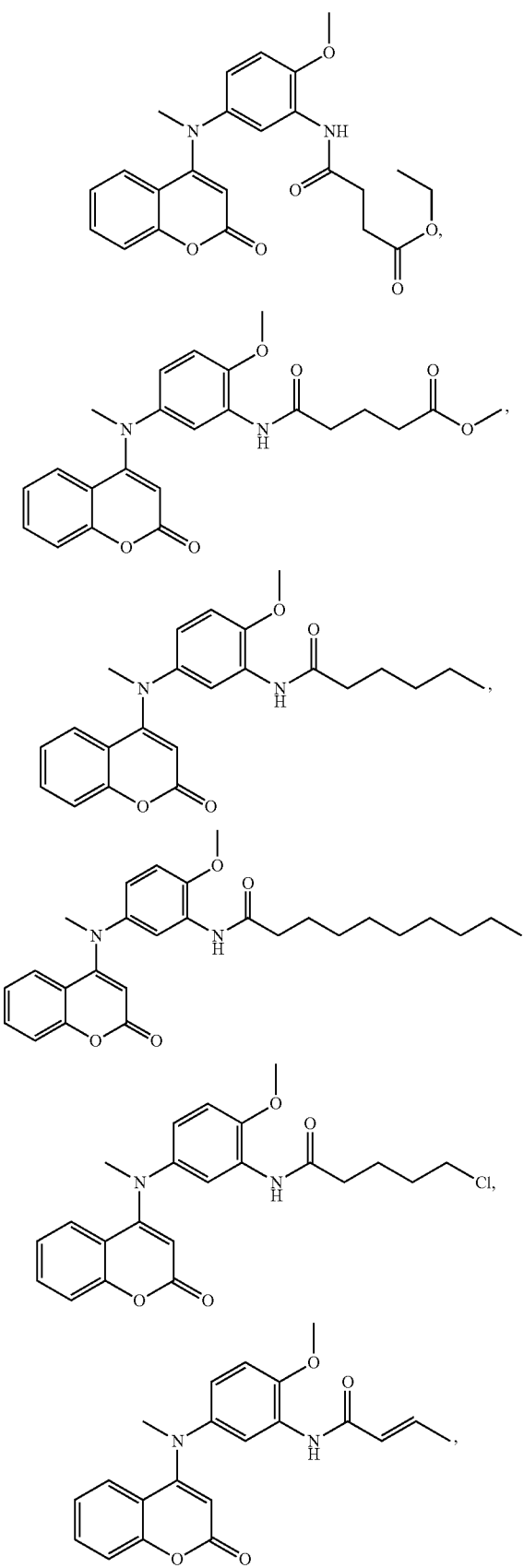
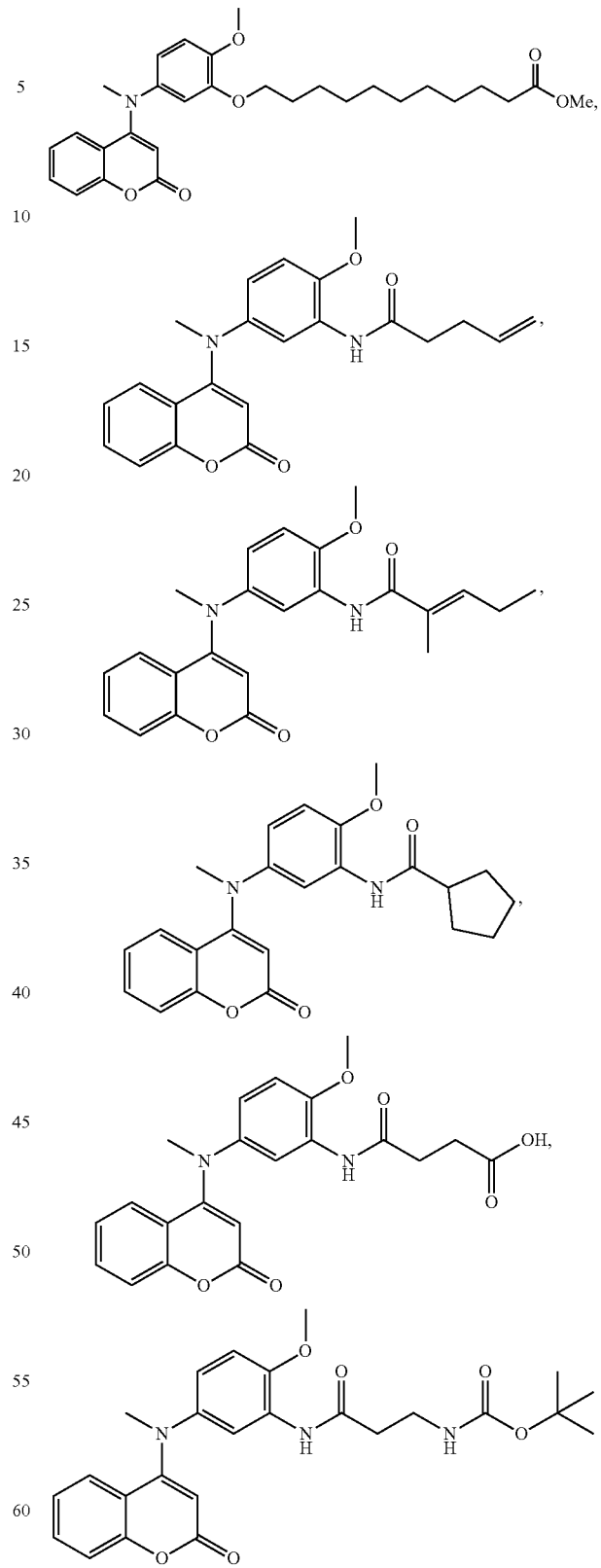
and salts thereof.
16. A pharmaceutically acceptable salt of the 4-substituted coumarin derivative according to claim 1.

17. A drug composition comprising the 4-substituted coumarin derivative according to claim 1 or a salt thereof as an active ingredient, plus a pharmaceutically acceptable carrier.

18. The drug composition of claim 17, which is a pharmaceutically acceptable preparation selected from the group consisting of tablets, oral agents, suppositories, dripping pills, infusion solutions, injection solutions, freeze-dried powders for injections, capsules, aerosols, dispersible tablets, ointments, sustained-release/controlled-release preparations and nano preparations.

19. The 4-substituted coumarin derivative of claim 1, a salt thereof or a drug composition thereof, which is effective to treat a tumor associated with leukemia, ovarian cancer, prostate cancer, testicular cancer, melanoma, pancreatic cancer, lymphoma, breast cancer, gastric cancer, brain cancer, lung cancer, liver cancer or colon cancer.

20. The 4-substituted coumarin derivative of claim 1, a salt thereof or a drug composition thereof, which is effective to inhibit proliferation of drug-sensitive and drug-resistant tumor cells.

21. The 4-substituted coumarin derivative of claim 1, a salt thereof or a drug composition thereof, which is effective to treat inflammations.

* * * * *

UNITED STATES PATENT AND TRADEMARK OFFICE
CERTIFICATE OF CORRECTION

PATENT NO. : 10,544,134 B2
APPLICATION NO. : 15/761885
DATED : January 28, 2020
INVENTOR(S) : Lijuan Chen and Yuquan Wei It is certified that error appears in the above-identified patent and that said Letters Patent is hereby corrected as shown below:

On the Title Page

Item (30), replace the foreign application priority number "2015 1 0618234" with the following:
-- 2015 1 0618234.7 --.

Signed and Sealed this
Twenty-sixth Day of May, 2020

Andrei Iancu
*Director of the United States Patent and Trademark Office*